(12) United States Patent
Tilson et al.

(10) Patent No.: US 11,697,005 B2
(45) Date of Patent: Jul. 11, 2023

(54) INFLATABLE MEDICAL DEVICES

(71) Applicant: LOMA VISTA MEDICAL, INC., Tempe, AZ (US)

(72) Inventors: Alexander Quillin Tilson, Burlingame, CA (US); Mark Christopher Scheeff, San Francisco, CA (US); Roland J. Downs, Mesa, AZ (US); Christopher Michael Adams, Tempe, AZ (US); Jon Michael Holweger, Queen Creek, AZ (US)

(73) Assignee: LOMA VISTA MEDICAL, INC., Franklin Lakes, NJ (US)

( * ) Notice: Subject to any disclaimer, the term of this patent is extended or adjusted under 35 U.S.C. 154(b) by 1013 days.

(21) Appl. No.: 16/419,225

(22) Filed: May 22, 2019

(65) Prior Publication Data

US 2019/0269892 A1 Sep. 5, 2019

Related U.S. Application Data

(63) Continuation of application No. 15/344,066, filed on Nov. 4, 2016, now abandoned, which is a (Continued)

(51) Int. Cl.
*A61M 29/00* (2006.01)
*A61M 29/02* (2006.01)
(Continued)

(52) U.S. Cl.
CPC ......... *A61M 29/02* (2013.01); *A61B 17/8816* (2013.01); *A61B 17/8827* (2013.01);
(Continued)

(58) Field of Classification Search
CPC .............. A61M 29/02; A61M 25/0147; A61M 25/1002; A61M 25/1029; A61M 25/1027;
(Continued)

(56) References Cited

U.S. PATENT DOCUMENTS 4,141,364 A 2/1979 Schultze
4,230,119 A 10/1980 Blum
(Continued)

FOREIGN PATENT DOCUMENTS

EP 0775500 A1 5/1997
EP 2241284 B1 9/2012
(Continued)

OTHER PUBLICATIONS

English Machine Translation of FR2331995A2 dated Jun. 17, 1977.
(Continued)

*Primary Examiner* — Steven O Douglas
(74) *Attorney, Agent, or Firm* — Dickinson Wright PLLC; Andrew D. Dorisio

(57) ABSTRACT

Inflatable medical devices and methods for making and using the same are disclosed. The inflatable medical devices can be medical balloons. The balloons can be configured to have a through-lumen or no through-lumen and a wide variety of geometries. The device can have a high-strength, non-compliant, fiber-reinforced, multi-layered wall. The inflatable medical device can be used for angioplasty, kyphoplasty, percutaneous aortic valve replacement, or other procedures described herein.

21 Claims, 132 Drawing Sheets

Related U.S. Application Data continuation of application No. 12/477,077, filed on Jun. 2, 2009, now Pat. No. 9,504,811.

(60) Provisional application No. 61/205,866, filed on Jan. 22, 2009, provisional application No. 61/105,385, filed on Oct. 14, 2008, provisional application No. 61/086,739, filed on Aug. 6, 2008, provisional application No. 61/057,986, filed on Jun. 2, 2008.

(51) Int. Cl.
| | |
|---|---|
| *A61B 17/88* | (2006.01) |
| *A61M 25/01* | (2006.01) |
| *A61M 25/10* | (2013.01) |
| B29C 41/04 | (2006.01) |
| B29C 41/14 | (2006.01) |
| A61F 5/00 | (2006.01) |

(52) U.S. Cl.
CPC ...... *A61B 17/8833* (2013.01); *A61B 17/8855* (2013.01); *A61M 25/0147* (2013.01); *A61M 25/1002* (2013.01); *A61M 25/1029* (2013.01); A61F 5/0036 (2013.01); A61M 25/1027 (2013.01); A61M 2025/1031 (2013.01); A61M 2025/1072 (2013.01); A61M 2025/1075 (2013.01); A61M 2025/1086 (2013.01); A61M 2025/1088 (2013.01); A61M 2025/1093 (2013.01); A61M 2210/02 (2013.01); A61M 2210/125 (2013.01); B29C 41/04 (2013.01); B29C 41/14 (2013.01); Y10T 156/108 (2015.01); Y10T 156/1028 (2015.01)

(58) Field of Classification Search
CPC .. A61M 2025/1031; A61M 2025/1072; A61M 2025/1075; A61M 2025/1086; A61M 2025/1088; A61M 2025/1093; A61M 2210/02; A61M 2210/125; A61M 2025/1097; A61B 17/8816; A61B 17/8827; A61B 17/8833; A61B 17/8855; A61B 2017/00783; A61F 5/0036; B29C 41/04; B29C 41/14; Y10T 156/1028; Y10T 156/108
See application file for complete search history.

(56) References Cited

U.S. PATENT DOCUMENTS

| | | | |
|---|---|---|---|
| 4,399,809 A | | 8/1983 | Baro et al. |
| 4,787,388 A | * | 11/1988 | Hofmann .......... A61M 25/1002 604/913 |
| 4,878,495 A | | 11/1989 | Grayzel |
| 4,917,667 A | * | 4/1990 | Jackson ............ A61M 25/0075 604/103 |
| 5,002,531 A | | 3/1991 | Bonzel |
| 5,261,878 A | * | 11/1993 | Galindo ............ A61M 25/1011 604/103.1 |
| 5,295,960 A | | 3/1994 | Alishmad et al. |
| 5,308,356 A | | 5/1994 | Blackshear, Jr. et al. |
| 5,330,528 A | | 6/1994 | Lazim |
| 5,352,199 A | | 10/1994 | Tower |
| 5,370,685 A | | 12/1994 | Stevens |
| 5,403,280 A | | 4/1995 | Wang |
| 5,425,714 A | * | 6/1995 | Johnson ................ A61M 25/10 604/523 |
| 5,437,638 A | | 8/1995 | Bowman |
| 5,458,575 A | | 10/1995 | Wang |
| 5,501,667 A | | 3/1996 | Verduin, Jr. |
| 5,645,529 A | | 7/1997 | Fagan et al. |
| 5,658,311 A | | 8/1997 | Baden |
| 5,704,913 A | | 1/1998 | Abele et al. |
| 5,797,948 A | | 8/1998 | Dunham |
| 5,947,924 A | | 9/1999 | Liprie |
| 5,985,307 A | | 11/1999 | Hanson et al. |
| 6,010,480 A | | 1/2000 | Abele et al. |
| 6,068,611 A | | 5/2000 | Loffler et al. |
| 6,369,039 B1 | | 4/2002 | Palasis et al. |
| 6,488,653 B1 | | 12/2002 | Lombardo |
| 6,632,196 B1 | | 10/2003 | Houser |
| 6,652,568 B1 | | 11/2003 | Becker et al. |
| 6,911,017 B2 | | 6/2005 | Lee et al. |
| 7,329,236 B2 | | 2/2008 | Kesten et al. |
| 7,887,557 B2 | | 2/2011 | Kelley et al. |
| 8,038,598 B2 | | 10/2011 | Khachi |
| 9,504,807 B2 | | 11/2016 | Drasler et al. |
| 2001/0047196 A1 | | 11/2001 | Ginsburg et al. |
| 2002/0049409 A1 | | 4/2002 | Noda et al. |
| 2002/0098307 A1 | | 7/2002 | Schwartz et al. |
| 2004/0082965 A1 | | 4/2004 | Beckam |
| 2005/0209629 A1 | | 9/2005 | Kerr et al. |
| 2006/0058867 A1 | | 3/2006 | Thistle et al. |
| 2006/0085022 A1 | * | 4/2006 | Hayes ..................... A61F 2/958 606/192 |
| 2006/0189960 A1 | | 8/2006 | Kesten et al. |
| 2007/0225800 A1 | | 9/2007 | Sahatjian et al. |
| 2008/0021495 A1 | | 1/2008 | Lee et al. |
| 2008/0077165 A1 | | 3/2008 | Murphy |
| 2008/0097374 A1 | * | 4/2008 | Korleski ............. A61B 17/8855 604/103.1 |
| 2009/0082609 A1 | | 3/2009 | Condado |
| 2009/0299327 A1 | | 12/2009 | Tilson et al. |
| 2010/0234875 A1 | | 9/2010 | Allex et al. |

FOREIGN PATENT DOCUMENTS

| | | |
|---|---|---|
| FR | 2331995 A2 | 6/1977 |
| JP | 2003117002 A | 4/2003 |
| WO | 9625971 A1 | 8/1996 |
| WO | 9927989 A1 | 6/1999 |
| WO | 2008021006 A2 | 2/2008 |
| WO | 2008021006 A3 | 8/2008 |
| WO | 2010027998 A1 | 3/2010 |

OTHER PUBLICATIONS

English Machine Translation of JP2003117002A dated Apr. 22, 2003.

Seifeddin S.El-Jack Md, Suwatchai Pornratanarangsi, Md, John A. Ormiston, Md, and Mark W.I. Webster, Md, Stenting Coronary Trifurcation Lesions:Is 'Menage a Tois' the Solution?, Catheterization and Cardiovascular Interventions, Mar. 2006, pp. 372-376; vol. 67, Issue 3, 2006 Wiley-Liss, Inc.

Robert B. Escalera, II Md, Thaddeus J. Chase PhD, Pe, and Carl Y. Owada, Md,FACC,Triple-Ballon Pulmonary Valvuloplasty: An Advantageous Technique for Percutaneous Repair of Pulmonary Valve Stenosis in the Large Pediatric and Adult Patients , Catheterization and Cardiovascular Interventions, 2005, pp. 446-451; vol. 66, 2005 Wiley-Liss, Inc.

Gregg M. Gaylord, Md, William F. Pritchard, Md, Vincent P. Chuang, Md, William J. Casarella, Md, Perry Sprawl, Md, The Geometry of Triple-Balloon Dilation, RSNA Radiology, Feb. 1988, pp. 541-545, vol. 166 No. 2, http:/pubs.rsna.org/doi/10.1148/radiology.166.2.2962228.

Richard L. Lindsey, Jr., Md, Justin Saporito, Md, Paul C. Kieist, Md, and Yaser Kalash, Md., Triple Balloon-on-a-Wire or "Menage a Trois" Coronary Angioplasty, Catheterization and Cardiovascular Diagnosis, Jan. 1993, pp. 76-79, vol. 28 Issue1, 1993 Wiley-Liss, Inc.

Bernhard Meier, Beat Friedli, and Ingrid Oberhansli, Trefoil balloon for aortic valvuloplasty, Br Heart J, 1986, pp. 292-293, vol. 56.

Paul H. Pevsner, Micro-Balloon Catheter for Superselective Angiography and Therapeutic Occusion, Department of Radiology, Medical College of Virginia, Richmond, Virginia, Feb. 1977, pp. 225-230, vol./Issue 128, Am J Roentgenol.

Shih-Horng Su, Robert Y.N. Chao, Charles L. Landau, Kevin D. Nelson, Richard B. Timmons, Robert S. Meidell, and Robert C.

(56) References Cited

OTHER PUBLICATIONS

Eberhart, Expandable Bioresorbable Endovascular Stent I. Fabrication and Properties, Annals of Biomedical Engineering, 2003, pp. 667-677, vol. 31.

Y. Tuggeman, L. Bloch, K. Suleiman, and T. Rosenfield, Balloon Mitral Valvuloplasty, Journal of the Israel Medical Association, Sep. 1996, pp. 151-156, vol. 131, No. 5-6.

M.Tynan, Balloon angioplasty in congenital heart disease, HERZ, Apr. 1988, pp. 59-70.

B. Meier, B. Friedli, L. Von Segesser, Valvuloplasty with trefoil and bifoil balloons and the long sheath technique, HERZ, Feb. 1988, No. 1, pp. 1-13.

USPTO, Final Office Action dated Jan. 8, 2016; U.S. Appl. No. 14/123,596; Richard K. Elton.

USPTO, Examiner's Answer to Appeal Brief dated Sep. 12, 2016; U.S. Appl. No. 14/123,596; Richard K. Elton.

USPTO, Office Action dated Dec. 31, 2018 for U.S. Appl. No. 15/344,066, filed Nov. 4, 2016.

\* cited by examiner

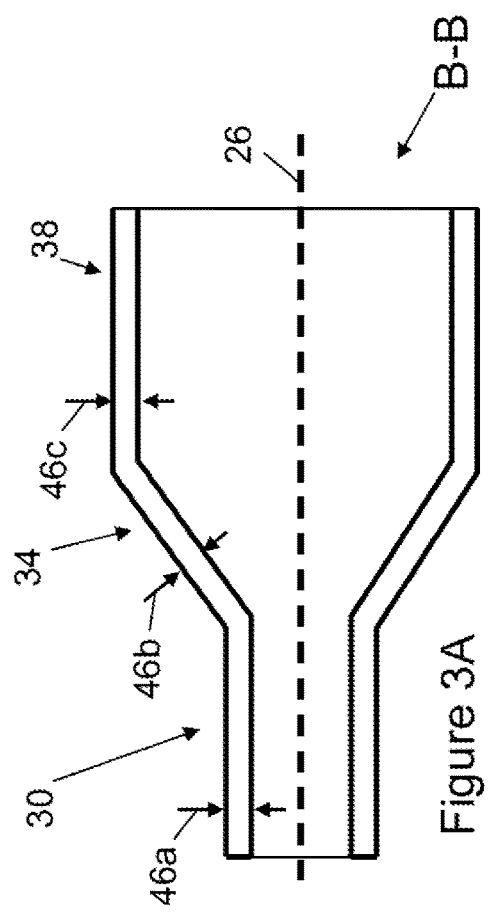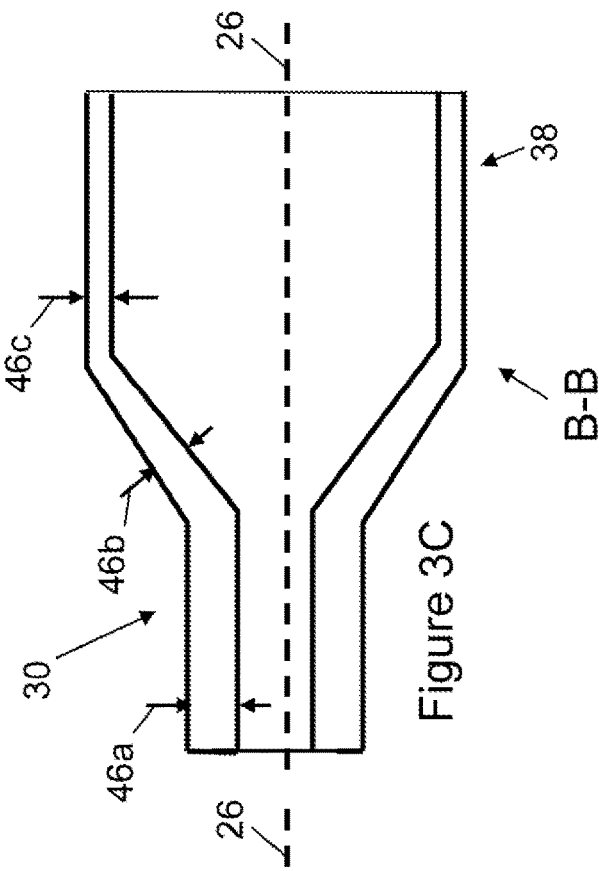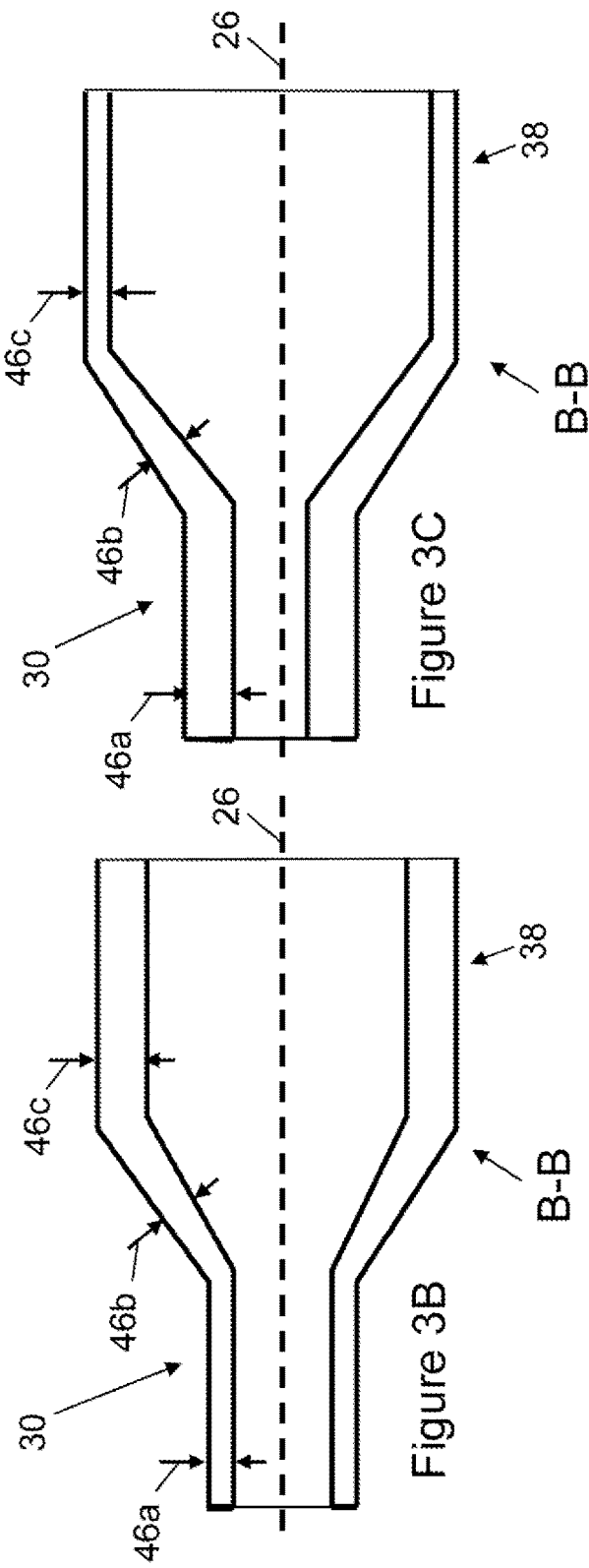

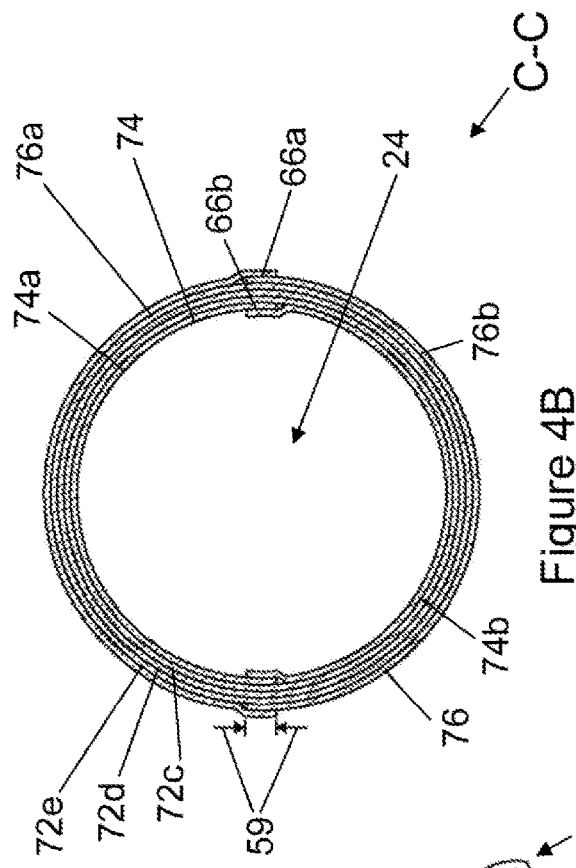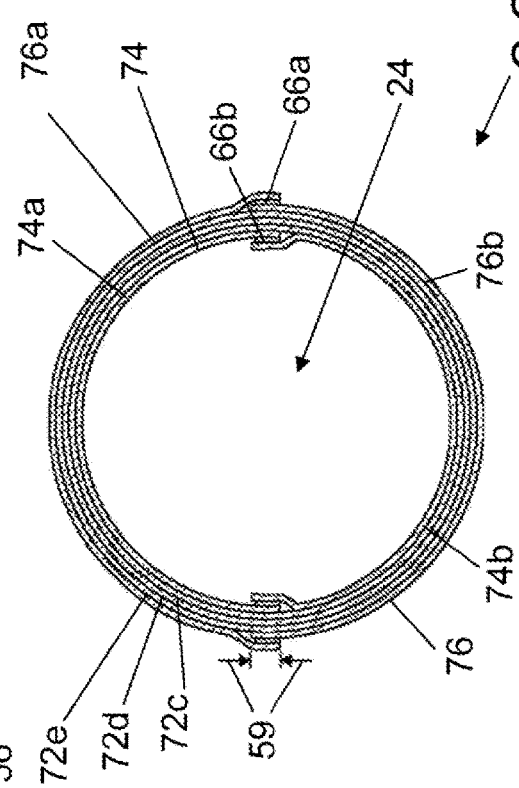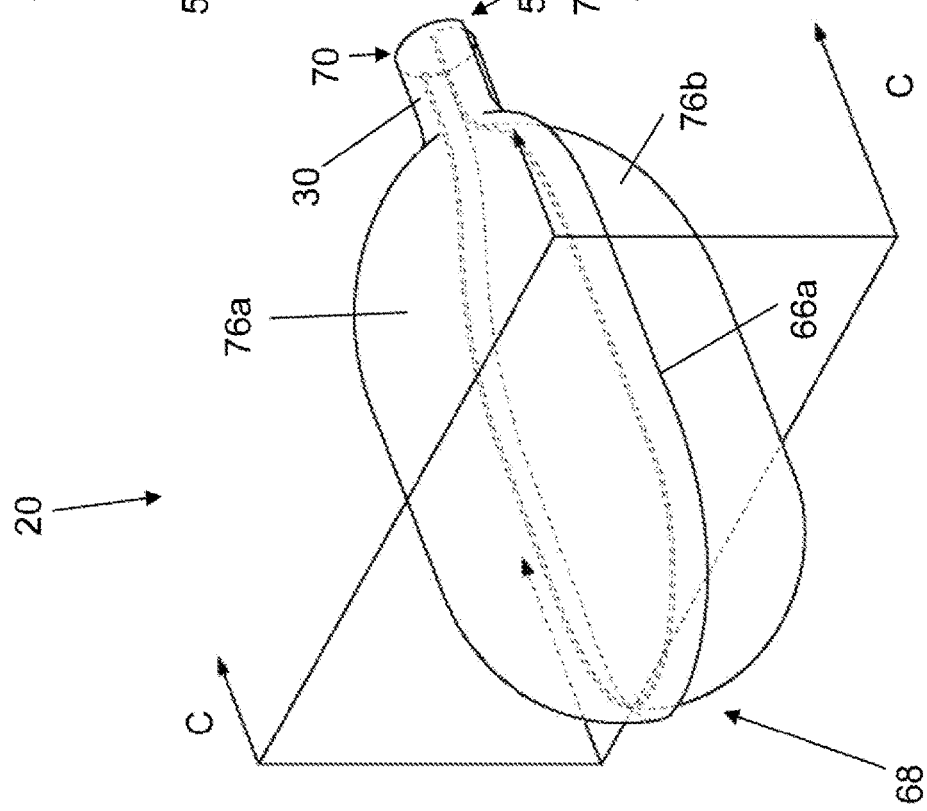

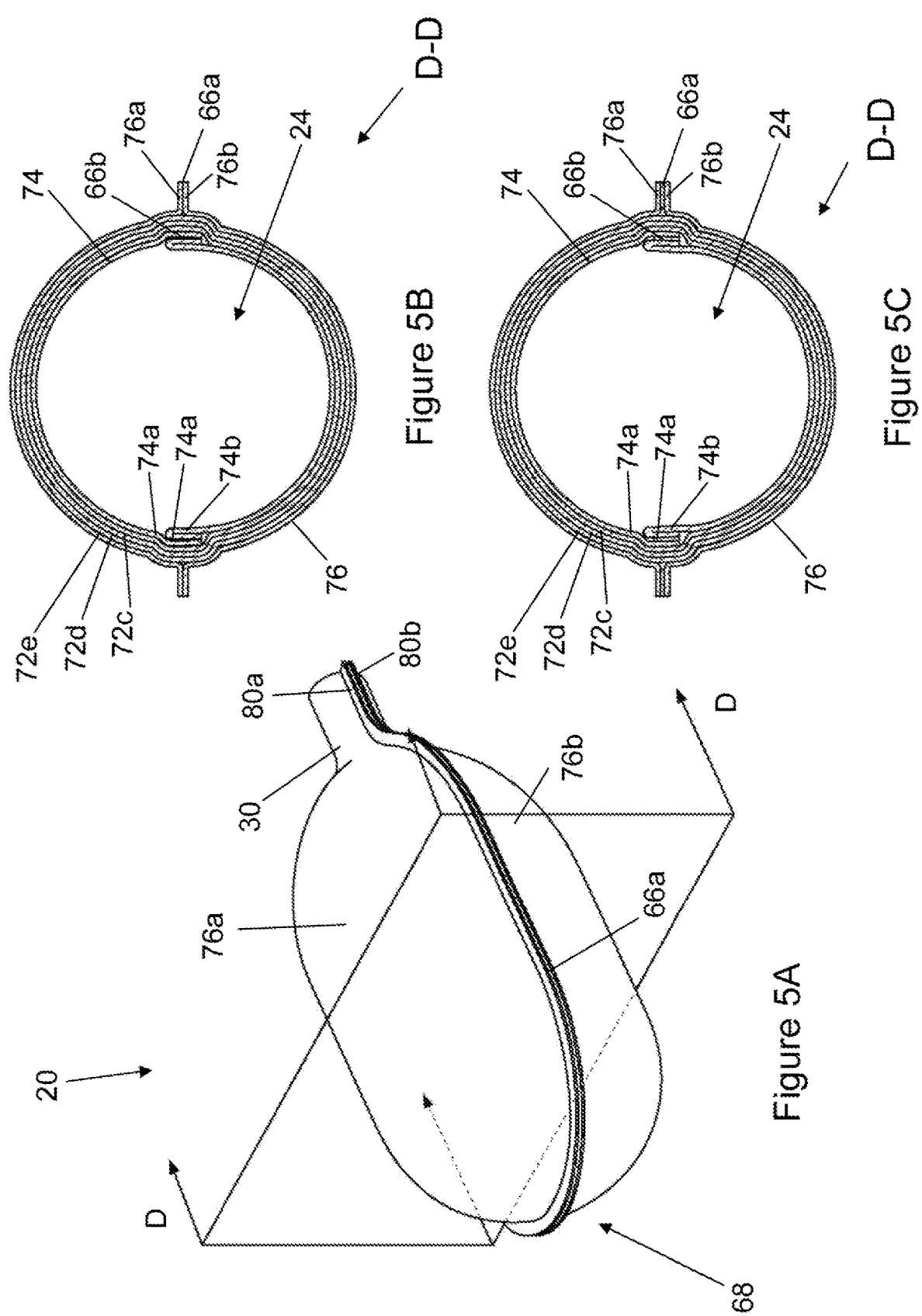

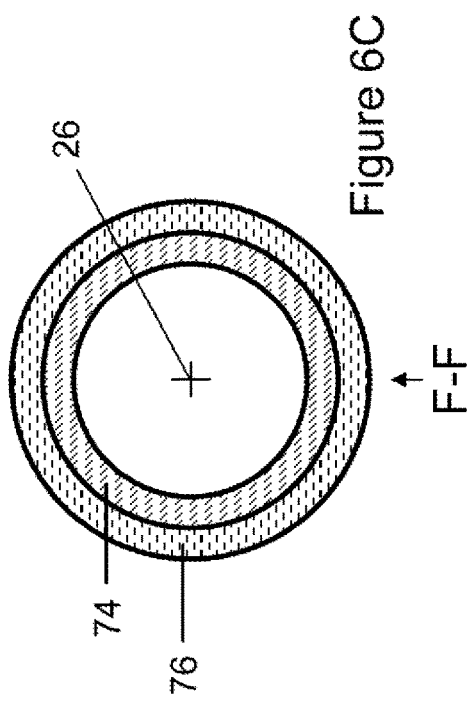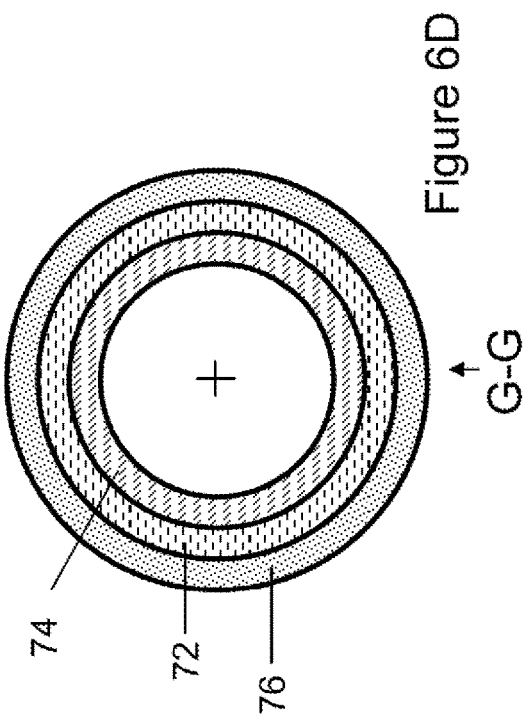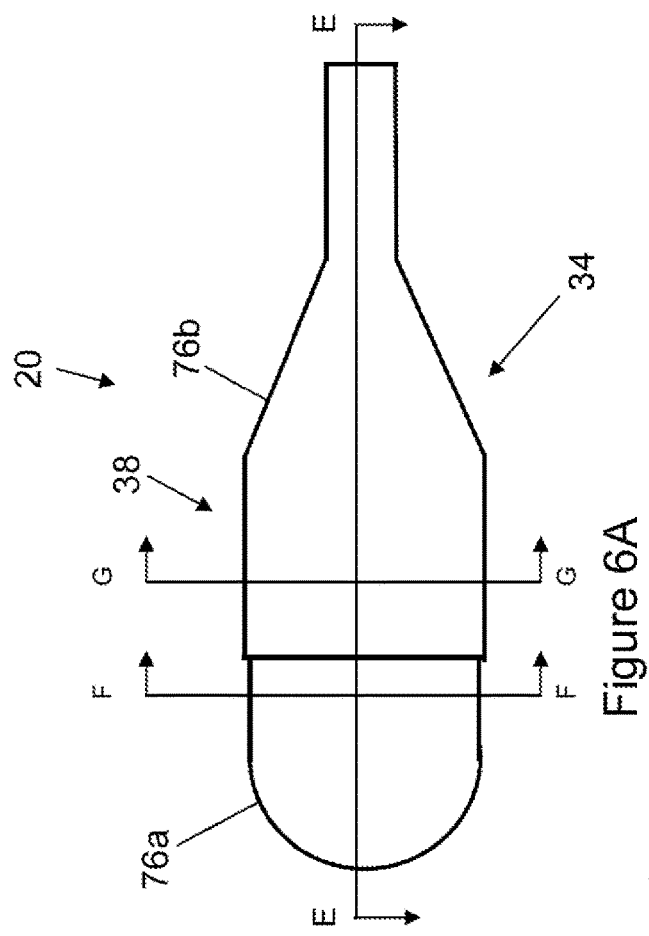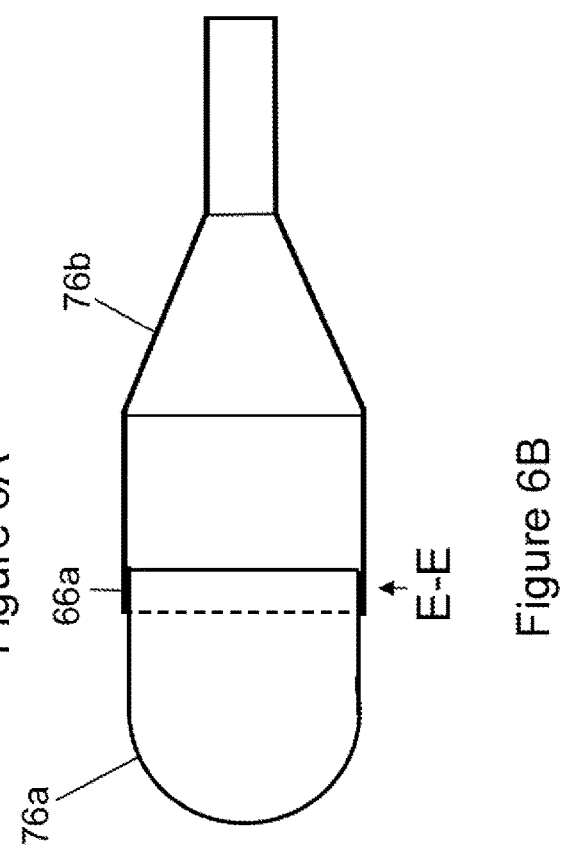

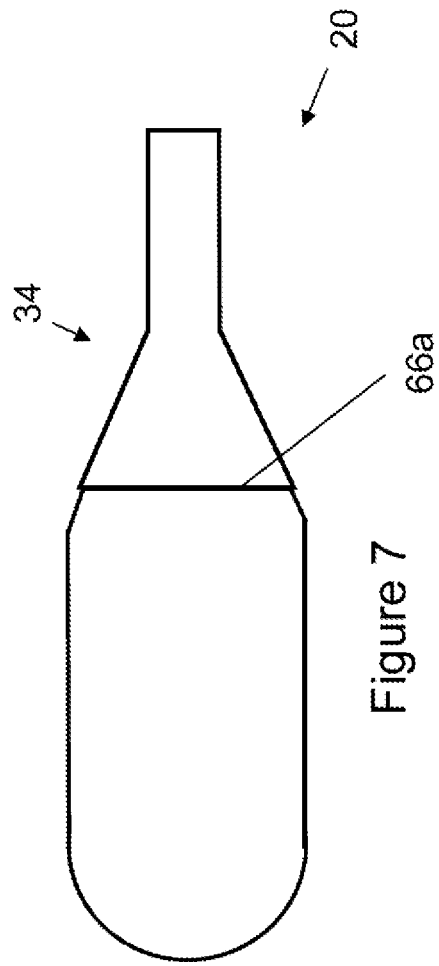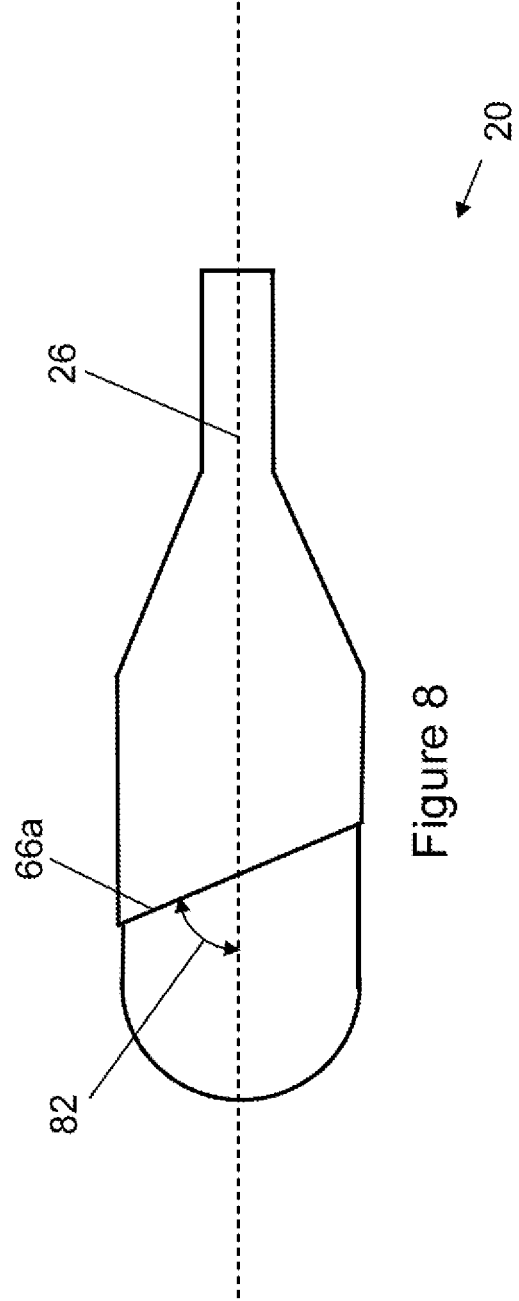

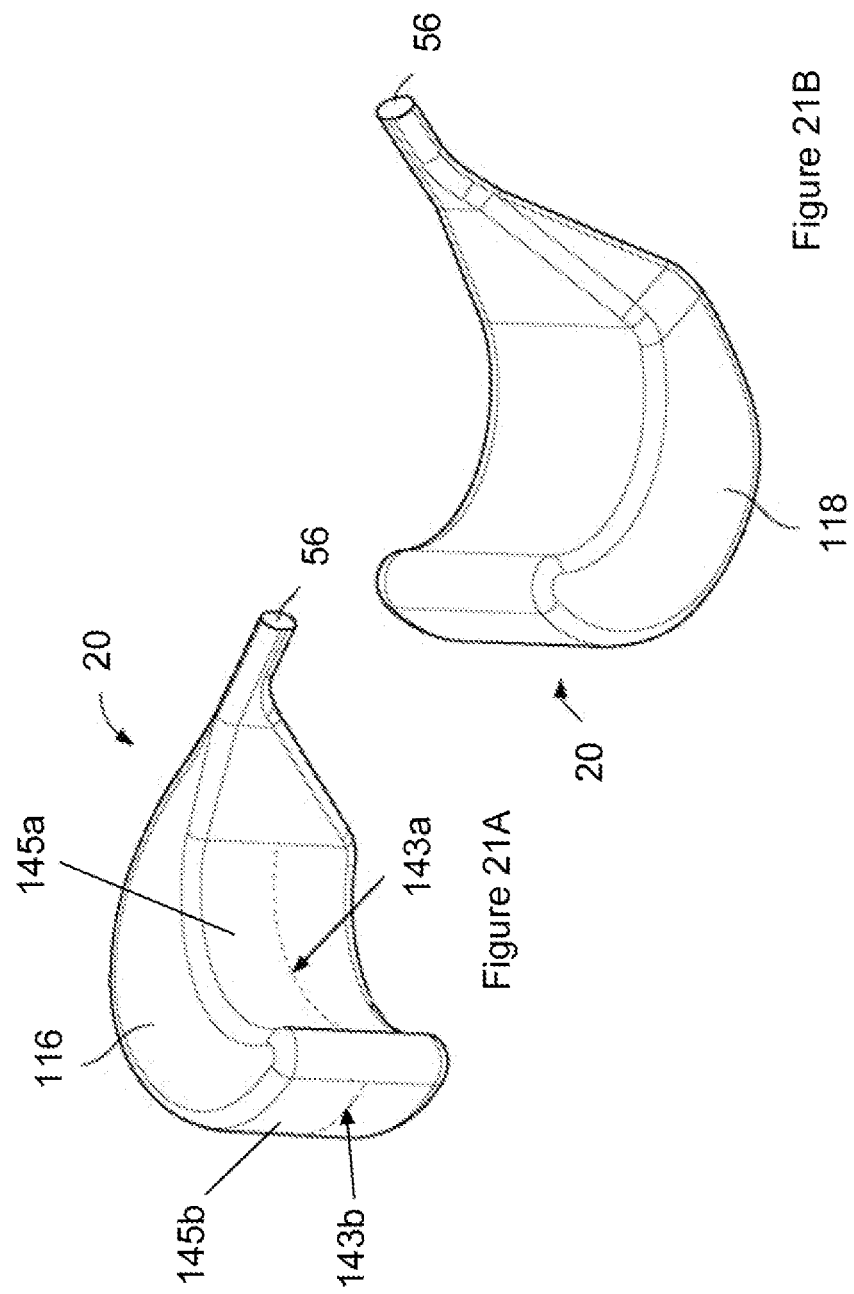

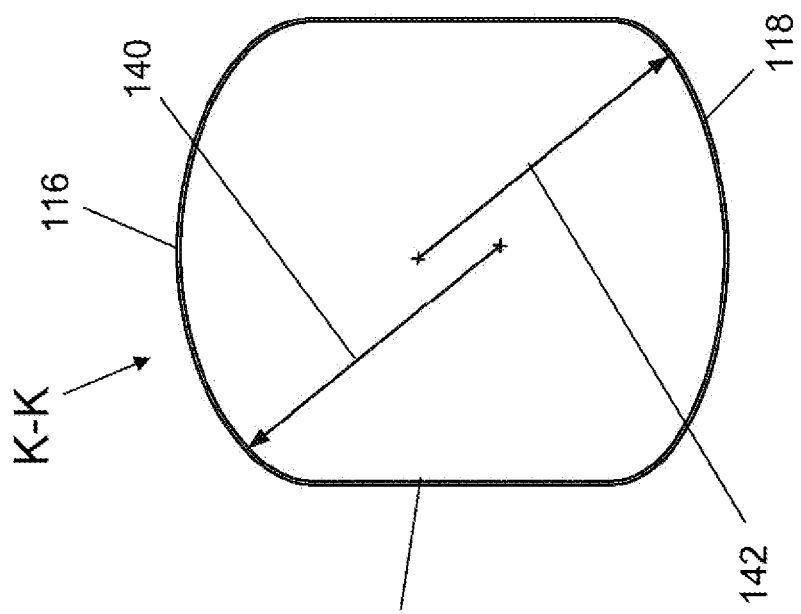
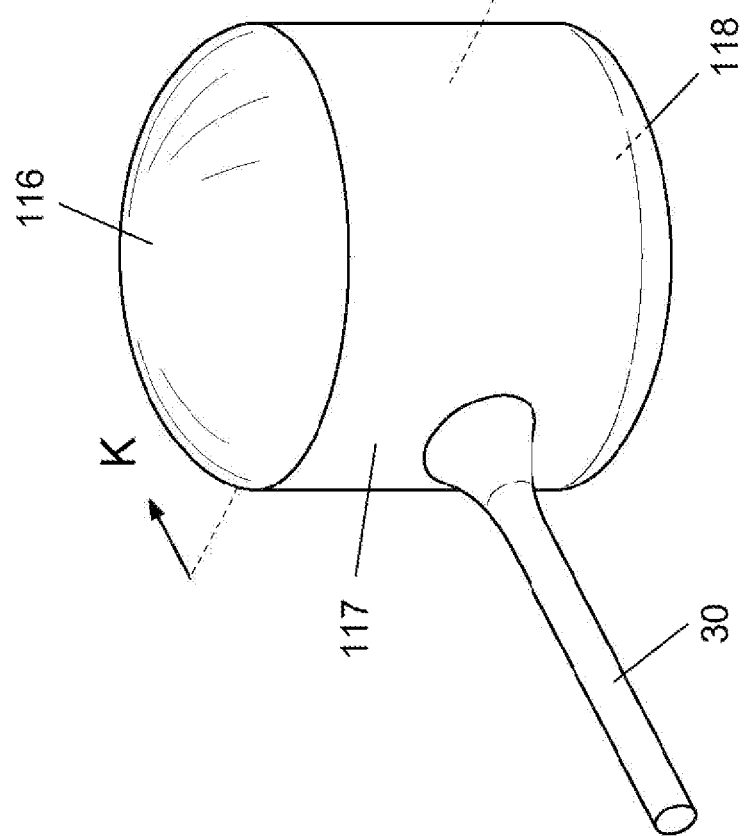
Figure 22B
Figure 22A

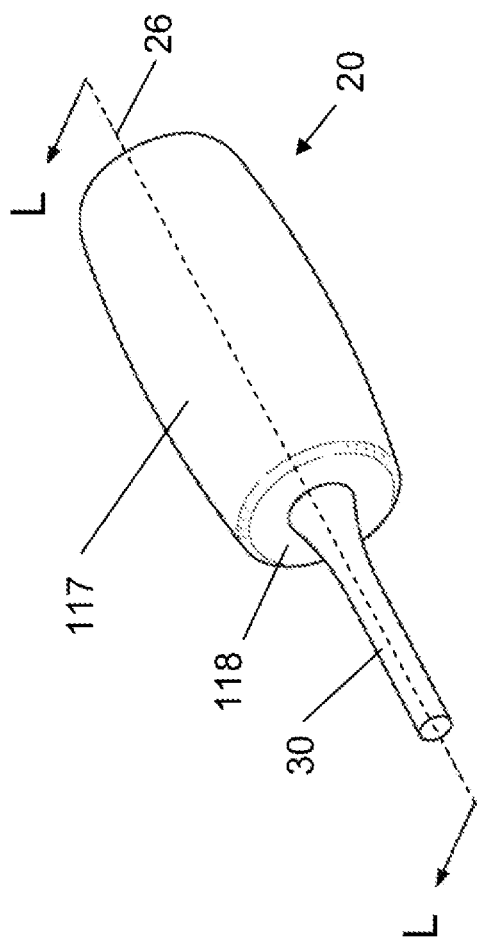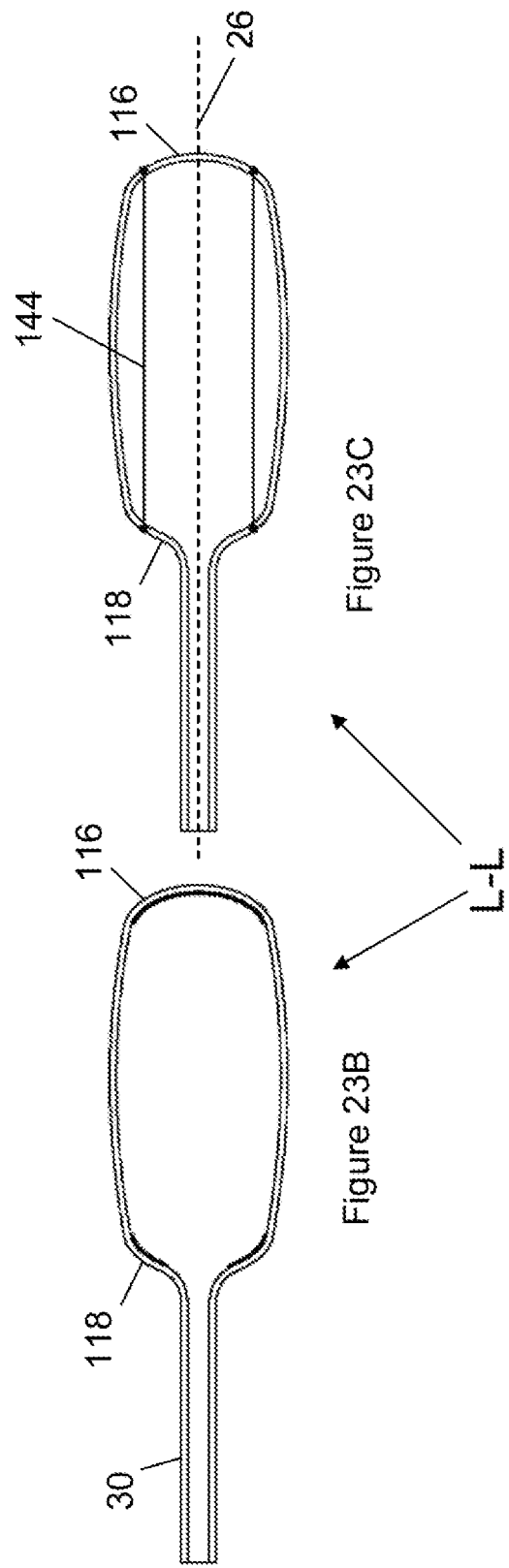

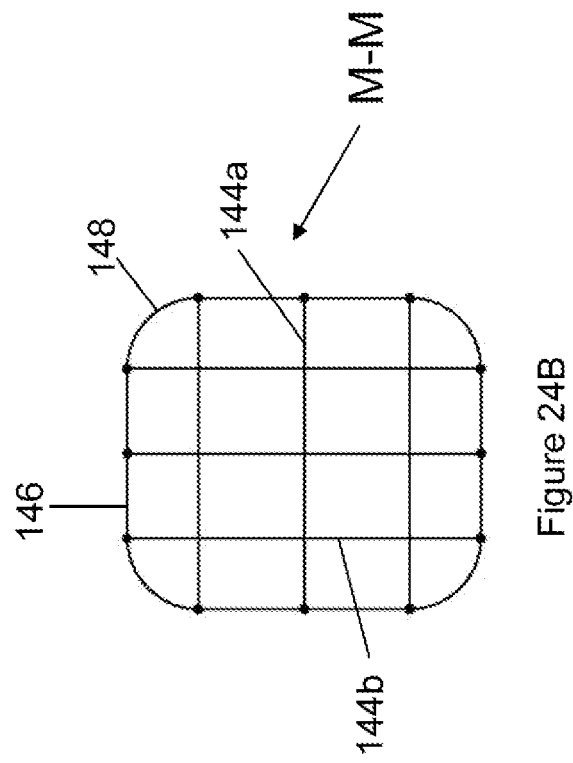
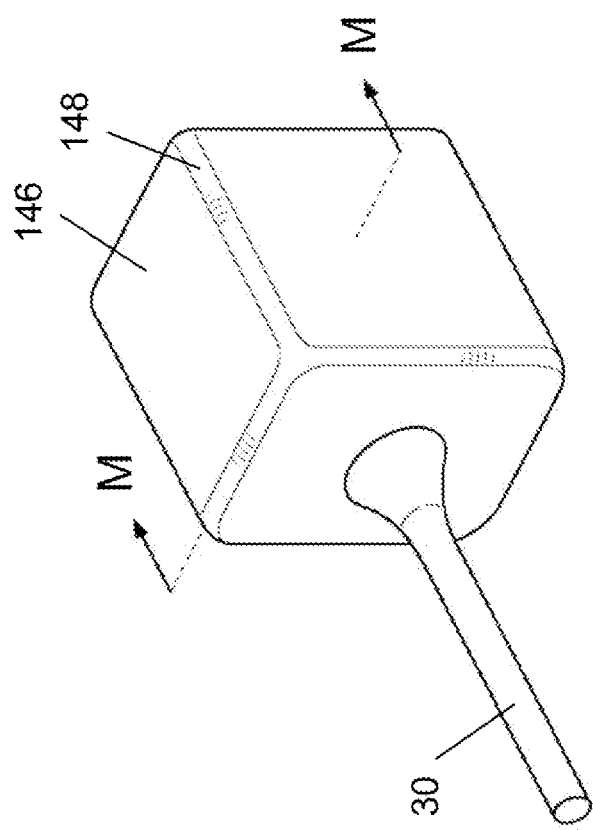
Figure 24B
Figure 24A

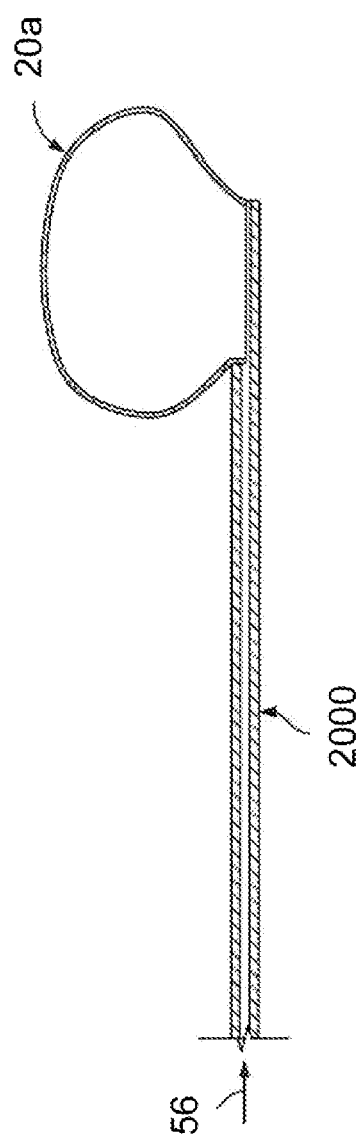
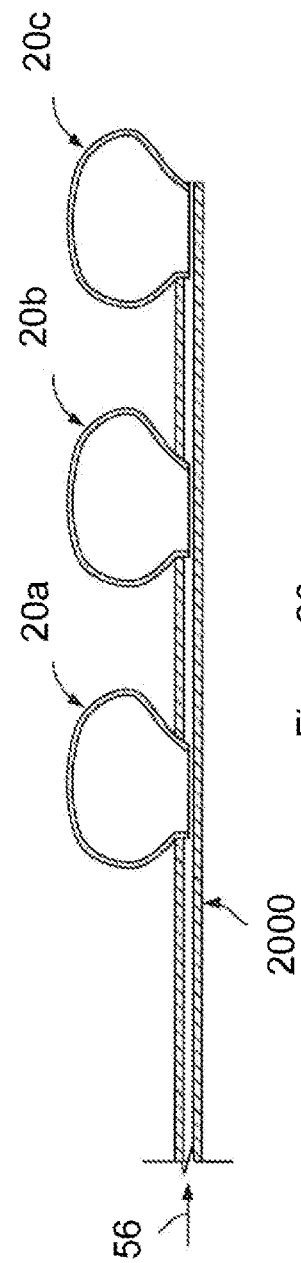

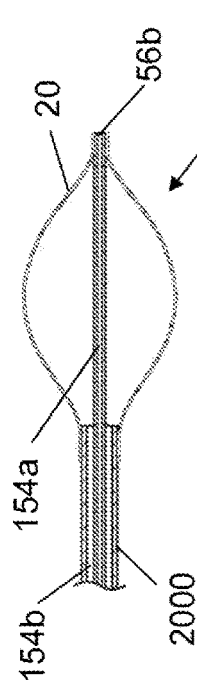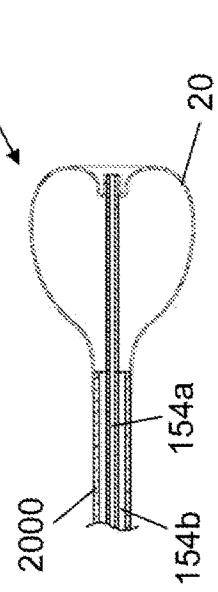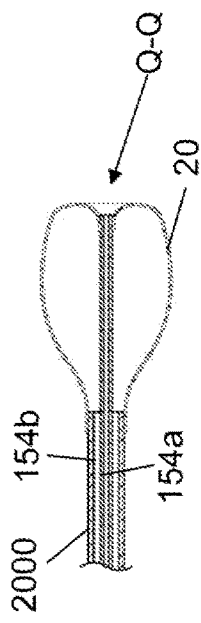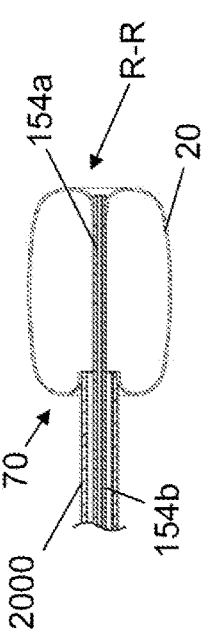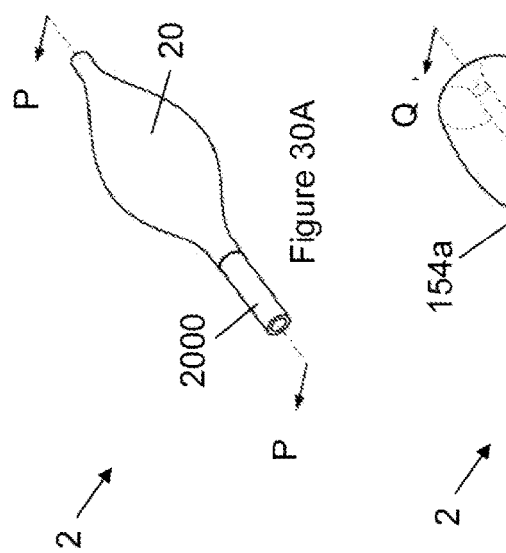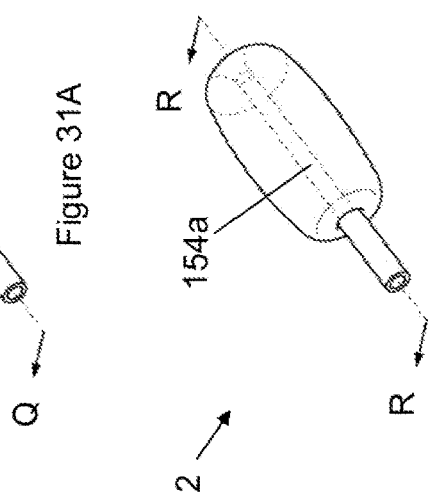

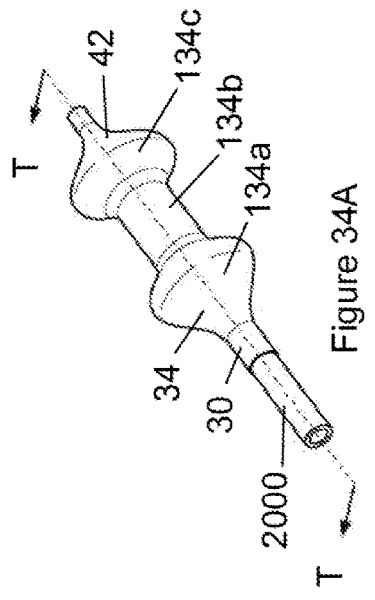
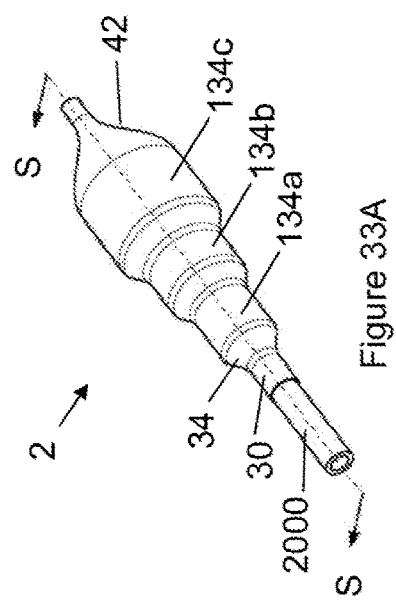
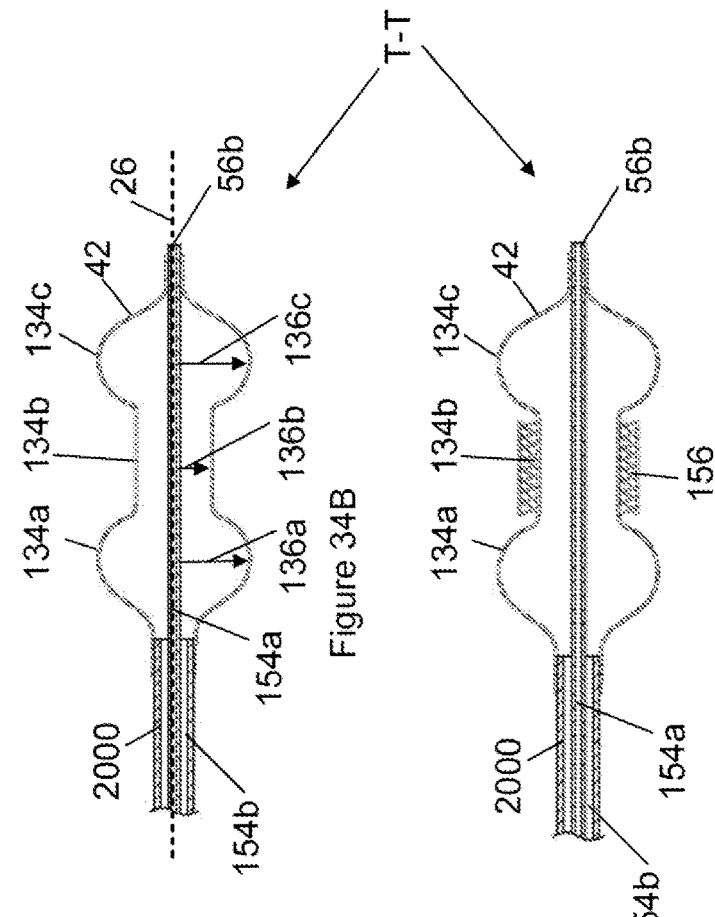

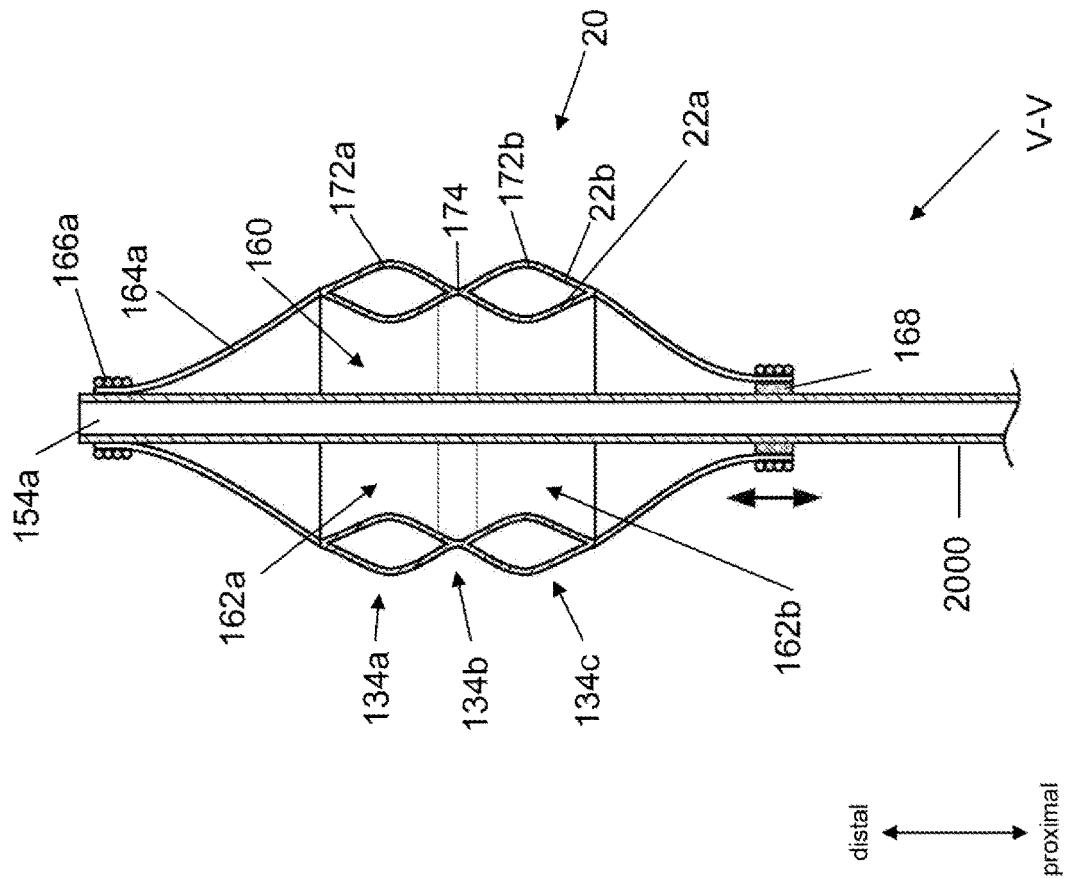
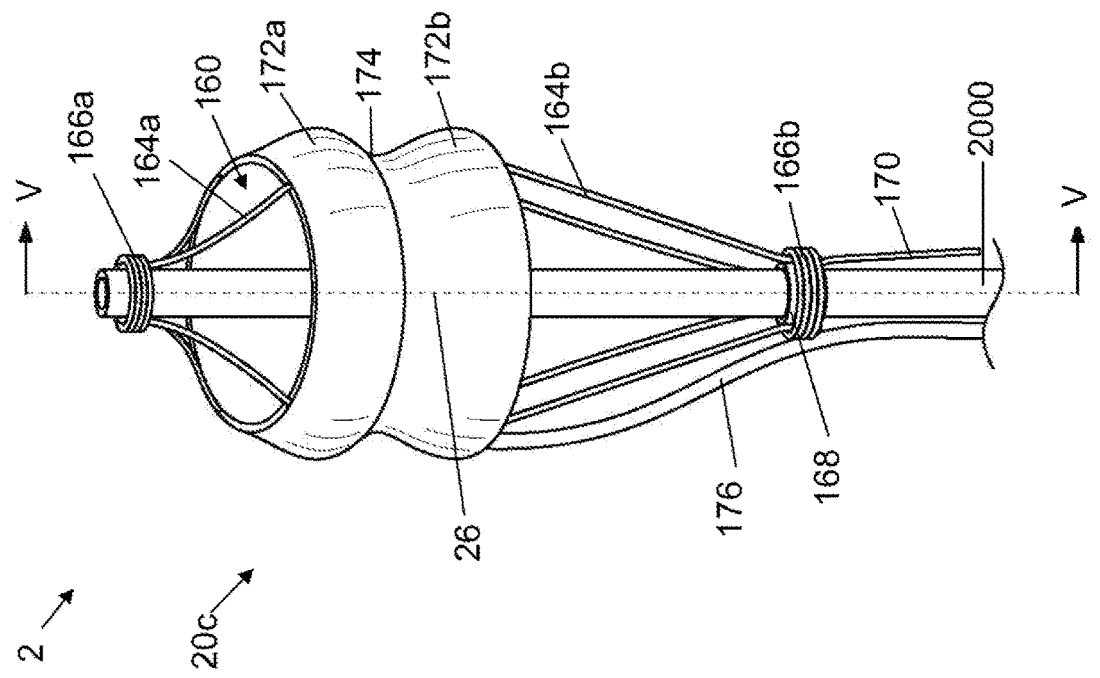
Figure 36B
Figure 36A

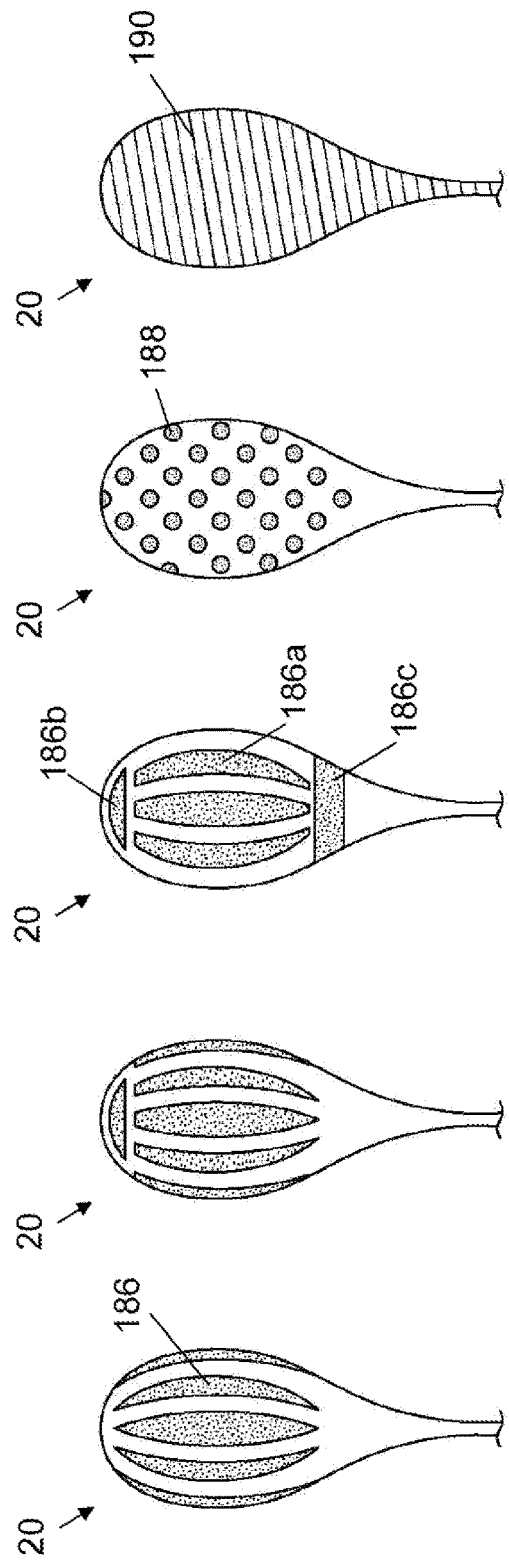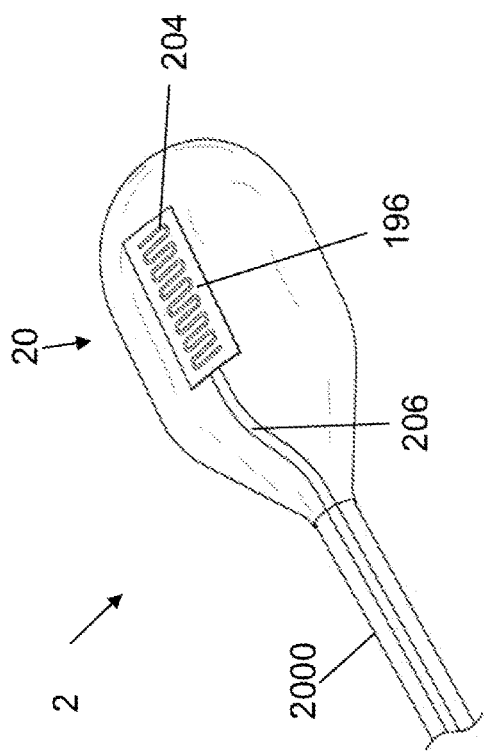

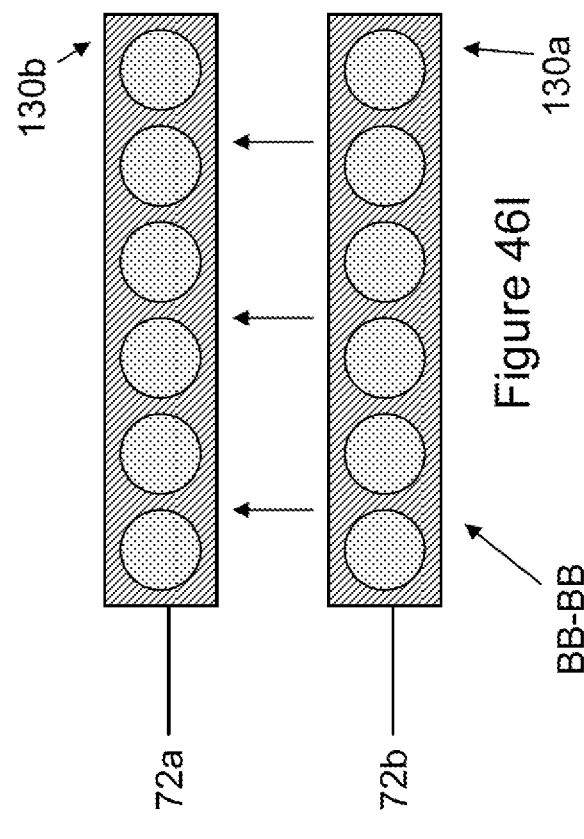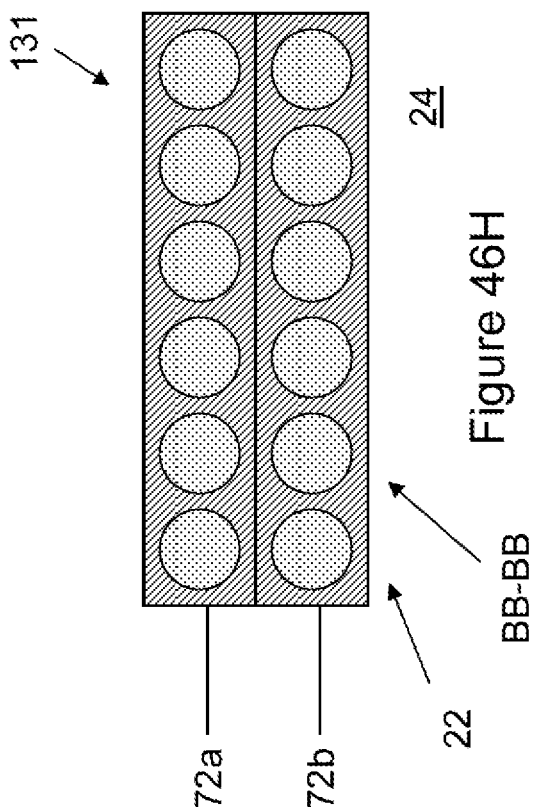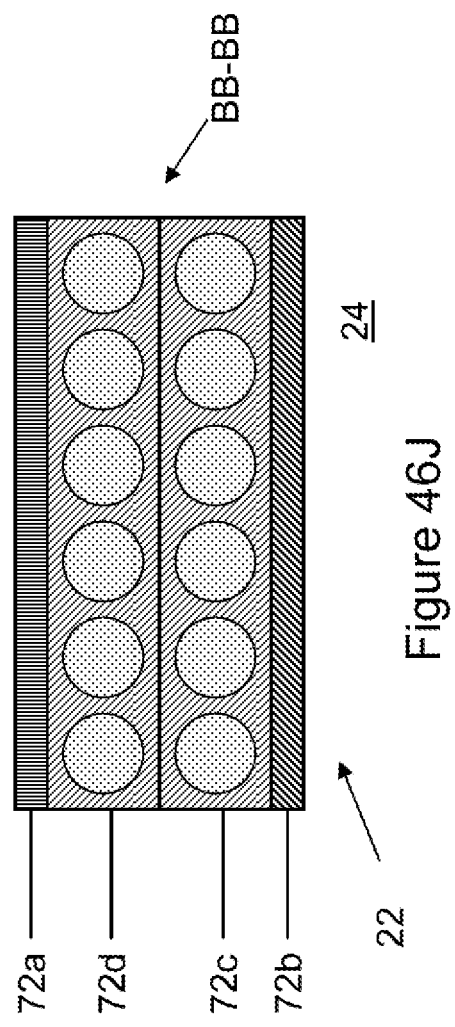

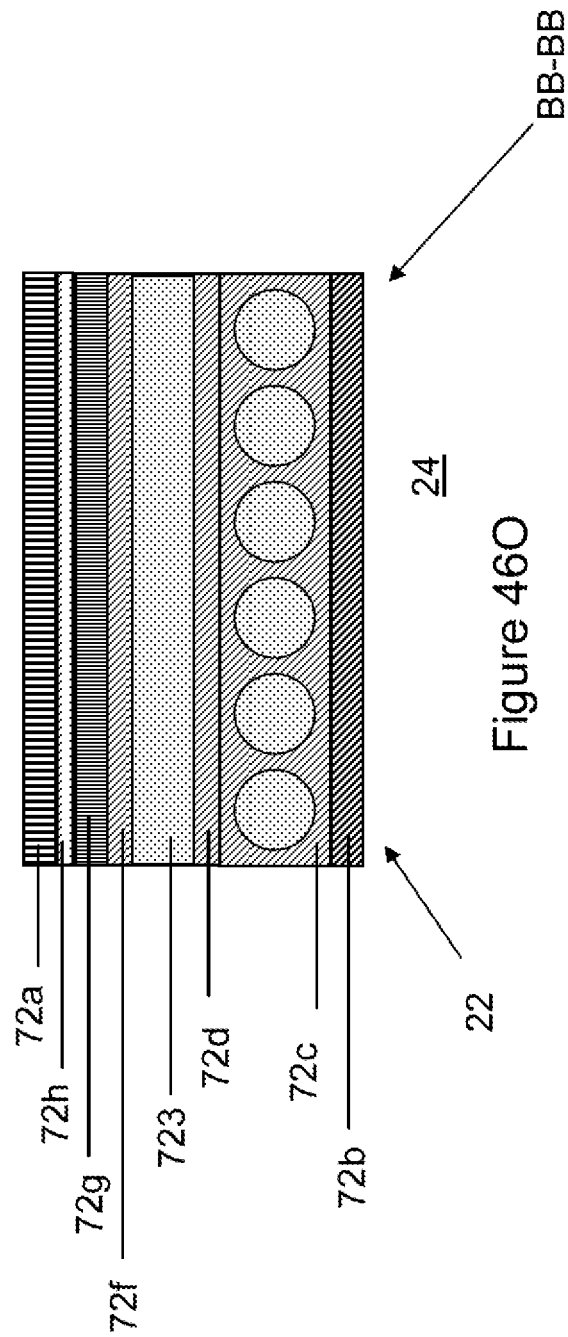

Film Materials

| Type | Sample Manufacturer or Supplier |
|---|---|
| Co-Polyamide | Deerfield Urethane, USA |
| Co-Polyester | Deerfield Urethane, USA |
| ECTFE | Saint-Gobain, France |
| FEP (Fluoroethylene-propylene) | DuPont, USA |
| Kapton | DuPont, USA |
| HDPE | Dow Chemical, USA |
| LDPE | Lyondell Chemical, USA |
| Mylar / PET (Polyethylene Terephthalate) / Polyester | DuPont, USA |
| Nylon | Honeywell, USA |
| PEEK | Victrex, UK |
| PEN (Polyethylene Naphthalate) | DuPont, USA |
| Tedlar (PVF) | DuPont, USA |
| Thermoplastic Polyurethane (TPU) | Deerfield Urethane, USA |
| Vectran (LCP (Liquid Crystal Polymer)) | Hoechst-Celanese, USA |
| Solef | Solvay, Italy |

Figure 47

Reinforcement material

| Type | Sample Manufacturer or Supplier |
|---|---|
| Vectran | Hoechst-Celanese, USA |
| PBO | Dow Chemical, USA |
| Spectra | Allied Signal, USA |
| Conex | Teijin, Japan |
| Dyneema | Teijin, Japan |
| Technora | Teijin, Japan |
| Dacron | DuPont, USA |
| Polyester | Hoechst-Celanese, USA |
| Compet | Allied Signal, USA |
| Nylon | DuPont, USA |
| PEEK | ICI-Fiberite, USA |
| PPS | Phillips Petroleum, USA |
| Boron Fiber | AVCO-Textron, USA |
| Ceramic Fiber | AVCO-Textron, USA |
| Kevlar | DuPont, USA |
| Inorganic Carbon/Carbon Fiber | Hercules Inc., USA |
| Inorganic Silicon/high strength fiberglass | Owens Corning Fiber, USA |
| Organic Polymer/Aramid | DuPont, USA |
| Twaron | Teijin, Japan |

Figure 48

Adhesive and Matrix Materials

| Type | Sample Manufacturer or Supplier |
|---|---|
| Urethanes | Hysol, USA |
| Polyesters | Thiokol, USA |
| Silicones | Dow Chemical, USA |
| Polypropylene | Honam Petrochemical, South Korea |
| Polyolefins | INEOS, UK |
| ULDPE, VLDPE, LDPE | ExxonMobil, USA |
| Nylon | Ashley Polymers, USA |
| Epoxies | Hysol, USA |
| Pebax | Arkema, USA |
| Tefzel | Dupont, USA |
| EVA | Dupont, USA |
| Solef | Solvay, Italy |

Figure 49

| Properties | Eutectics | | | | | Non-Eutectics | | | |
|---|---|---|---|---|---|---|---|---|---|
| | Low 117 | Low 136 | Low 158 | Low 255 | Low 281 | Low 158-190 | Low 217-440 | Low 281-338 |
| Melting Temperature (°F) | 117 | 136 | 158 | 255 | 281 | 165 | 240 | 302 |
| Range °F | 117-117 | 136 | 158-158 | 255-255 | 281-281 | 158-190 | 217-440 | 281-338 |
| Yield Temp °F | 117 | 136 | 158 | 255 | 281 | 162.5 | 240 | 302 |
| Range °C | 47 - 47 | 58 - 58 | 70 - 70 | 124 - 124 | 138 - 138 | 70 - 88 | 103 - 227 | 138 - 170 |
| Yield Temp °C | 47 | 58 | 70 | 124 | 138 | 72 | 116 | 150 |
| Tensile Strength Lbs/In² | 5400 | 6300 | 5990 | 6400 | 8000 | 5400 | 13000 | 8000 |
| %Elongation in slow Loading | 1.5 | 50 | 200 | 60-70 | 200 | 220 | <1% | 200 |
| Brinell Hardness No. | 12 | 14 | 9.2 | 10.2 | 22 | 9 | 19 | 22 |

Figure 52

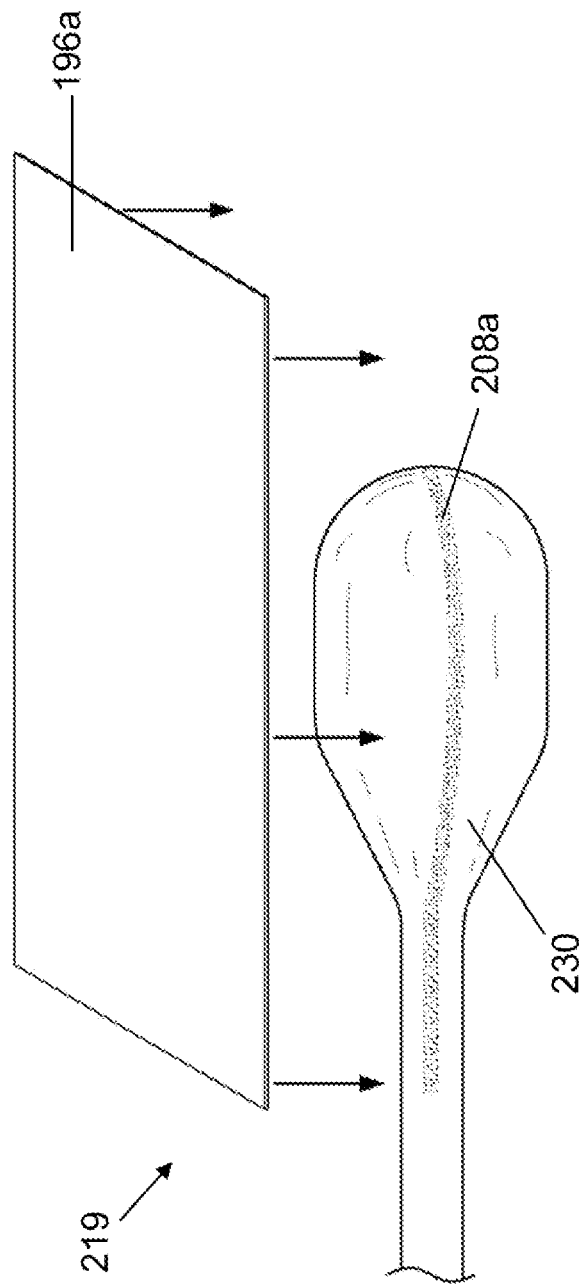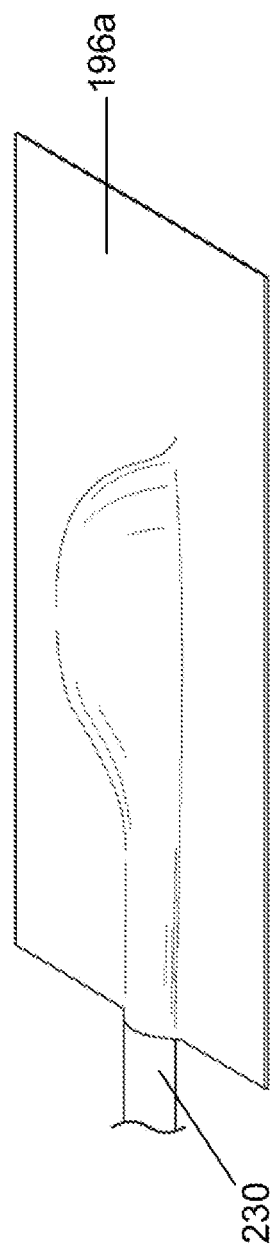

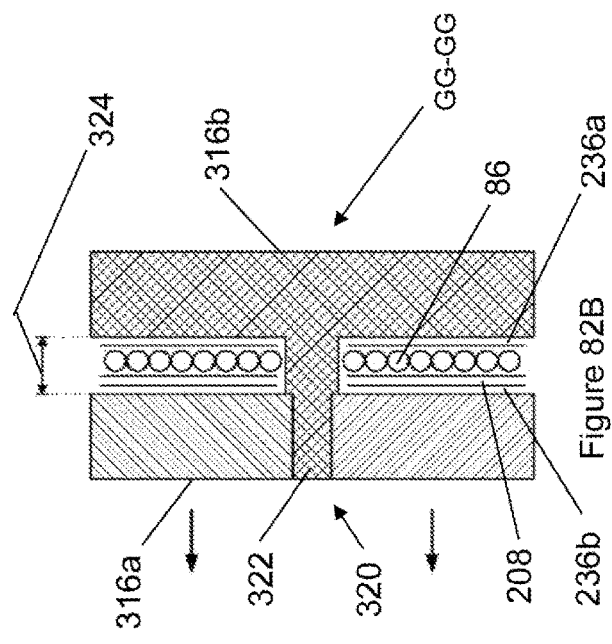
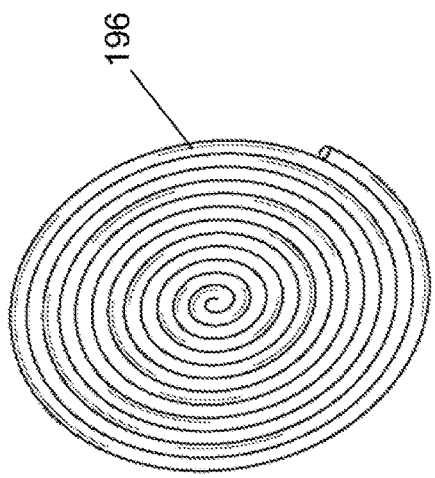
Figure 82B
Figure 83
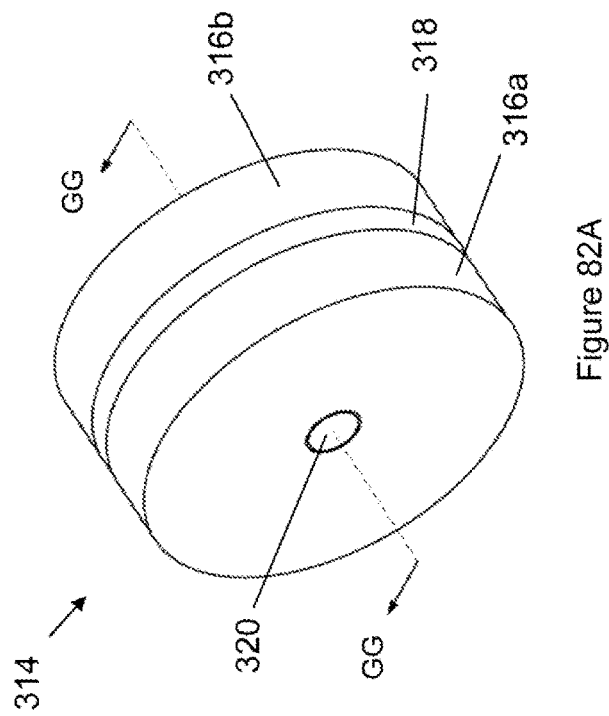
Figure 82A

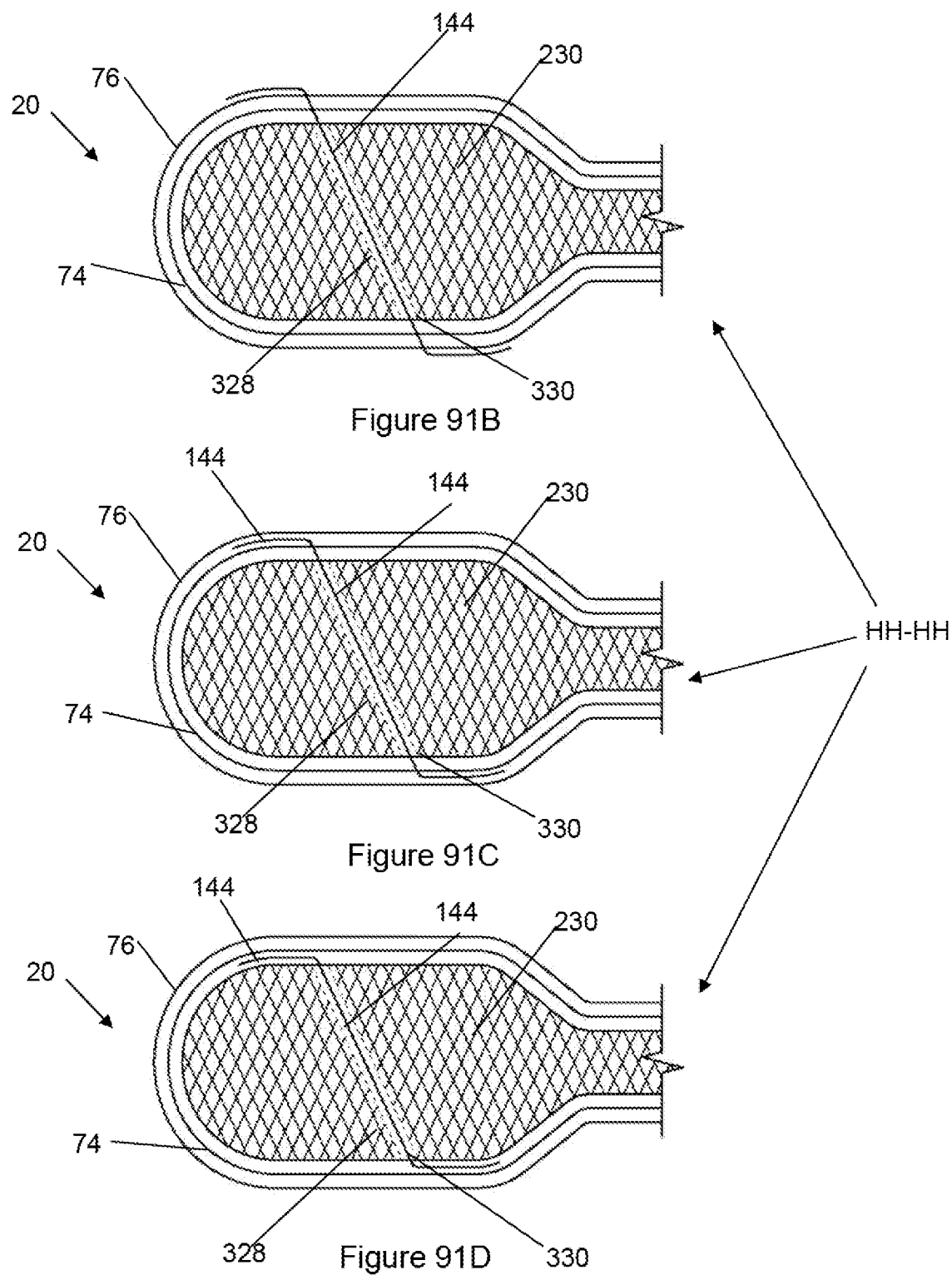

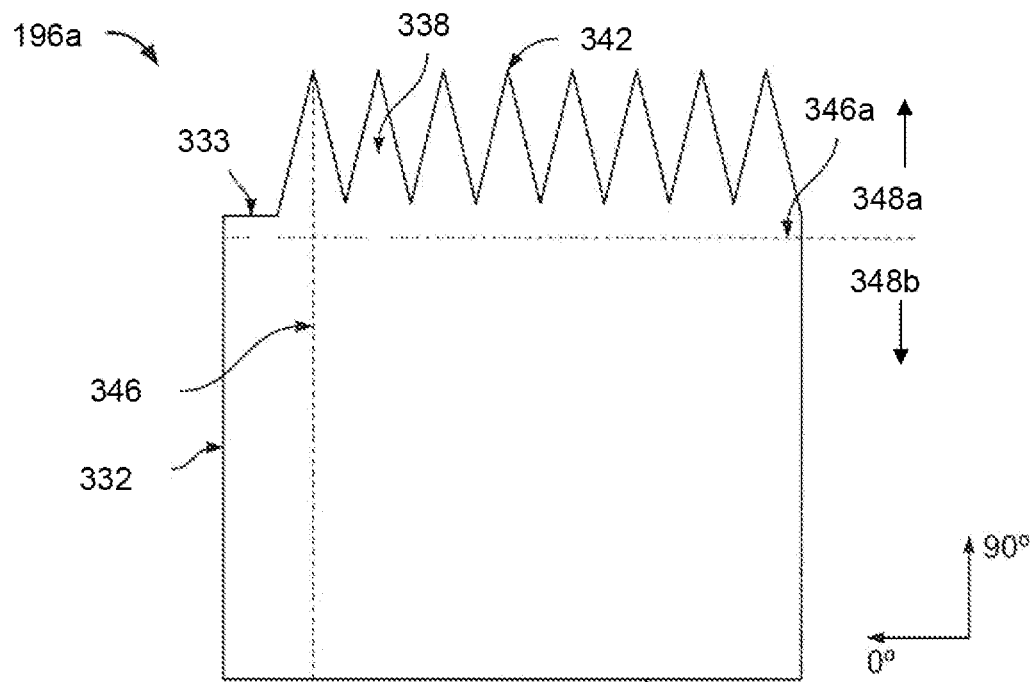
Figure 95
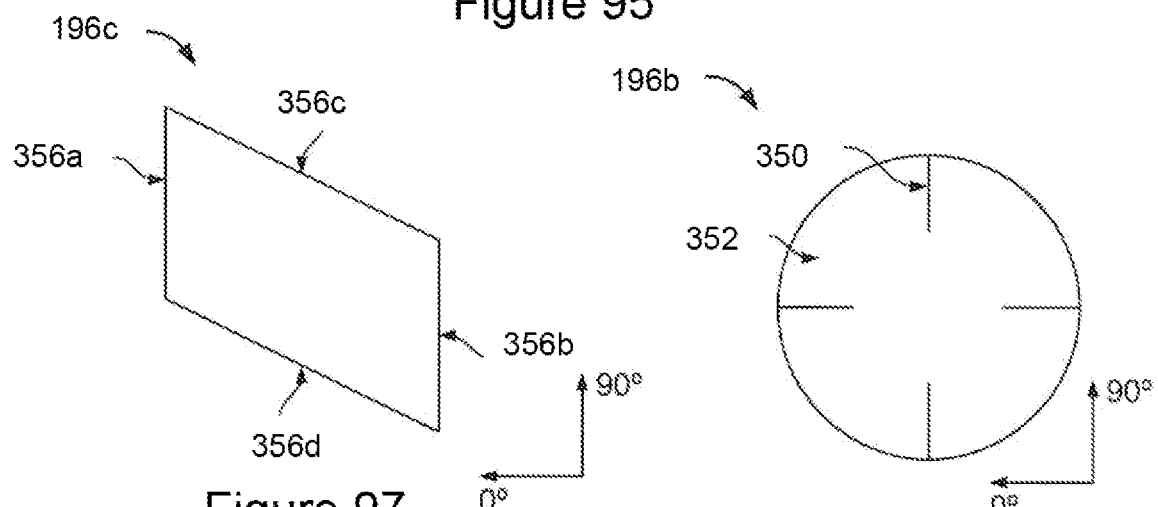
Figure 97
Figure 96
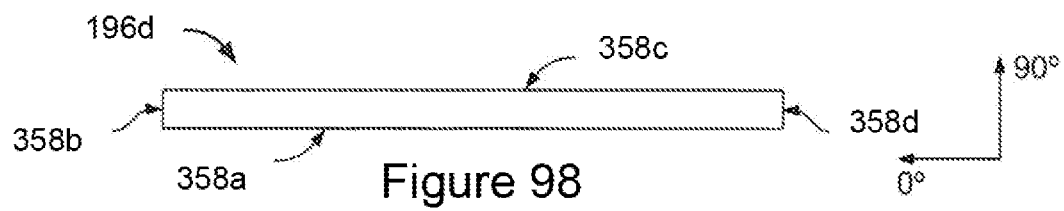
Figure 98

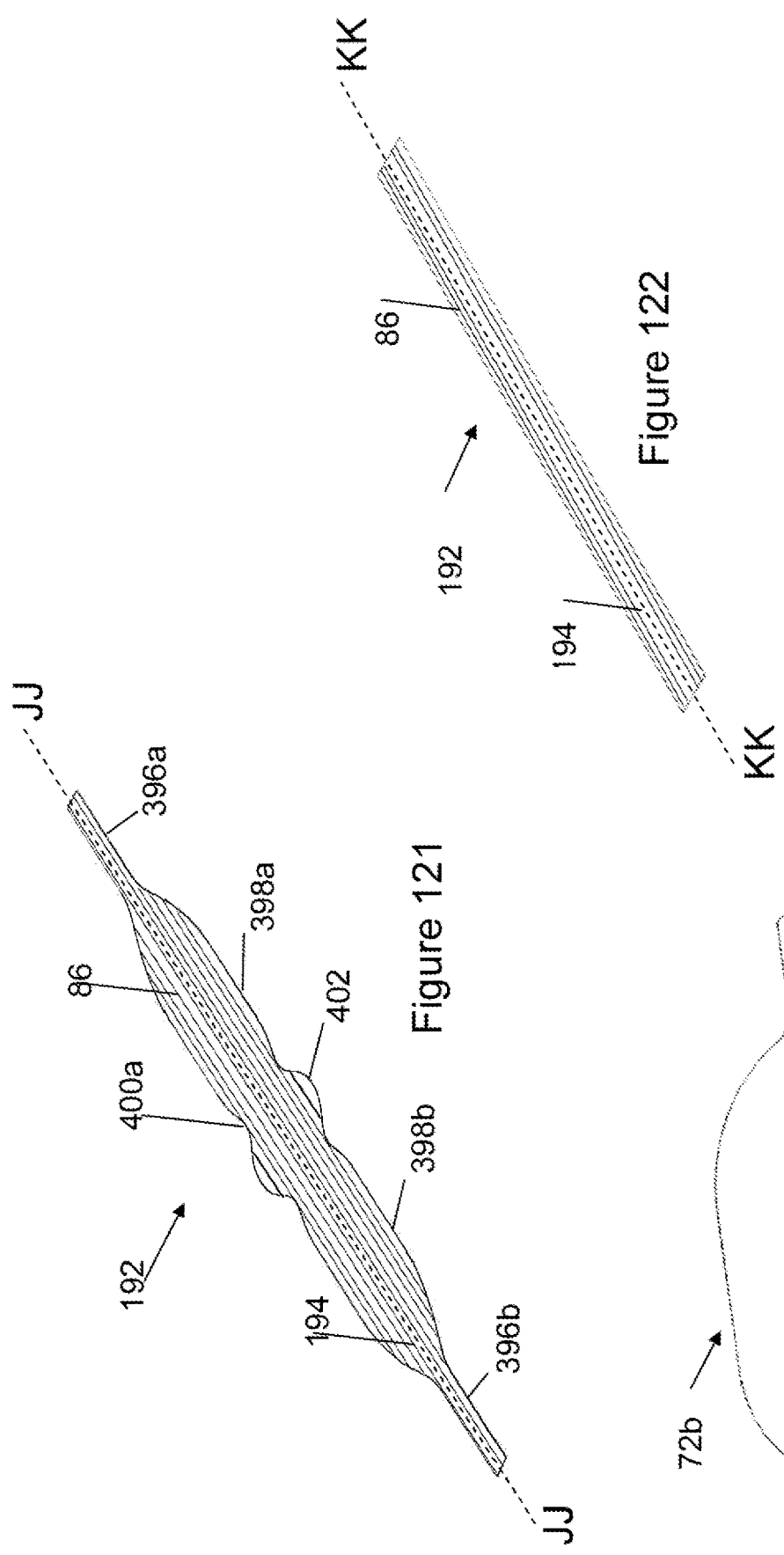
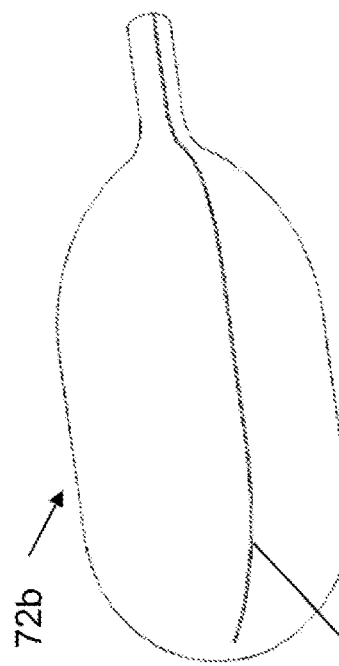

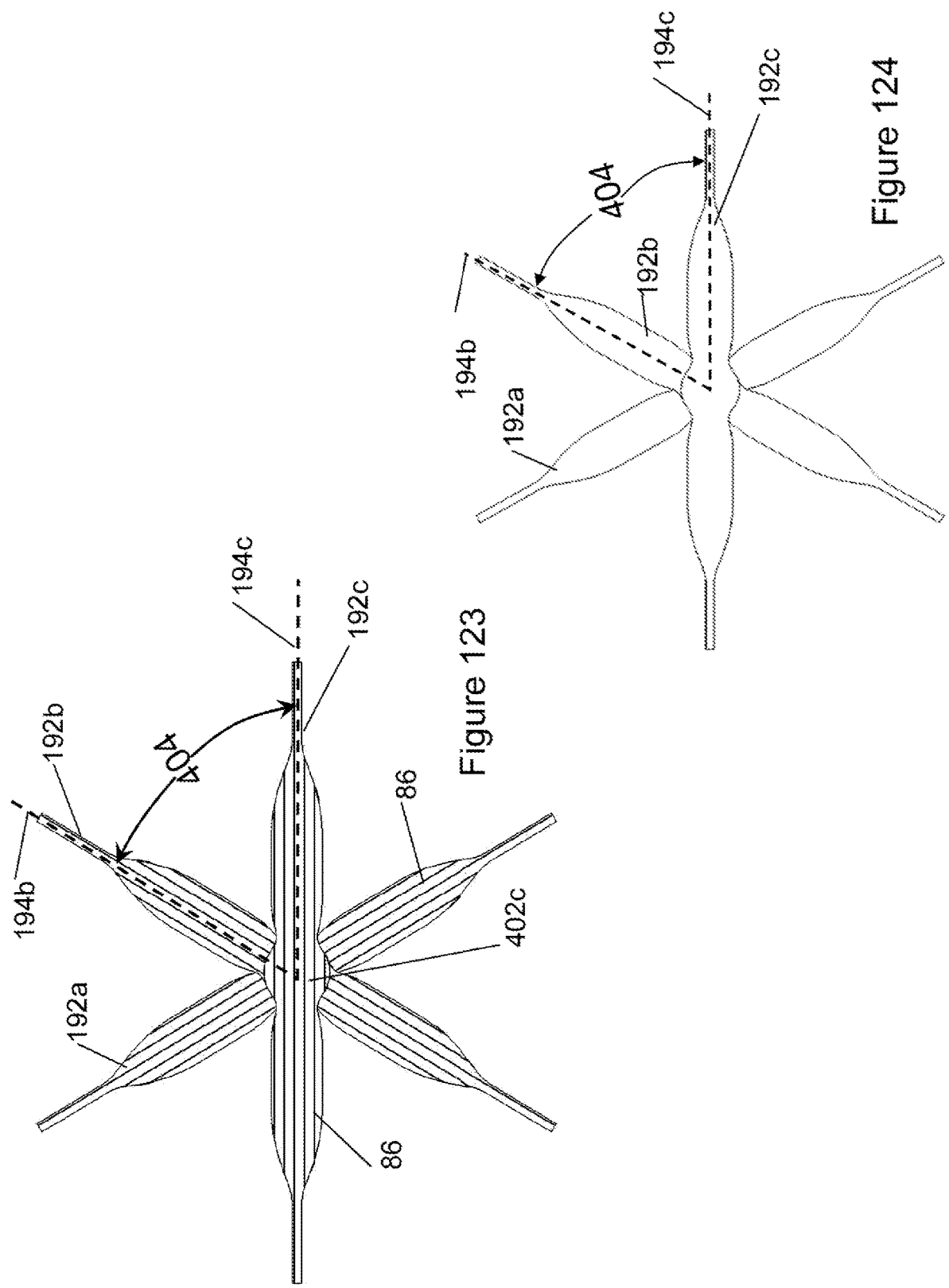

NOT INVENTION

NOT INVENTION

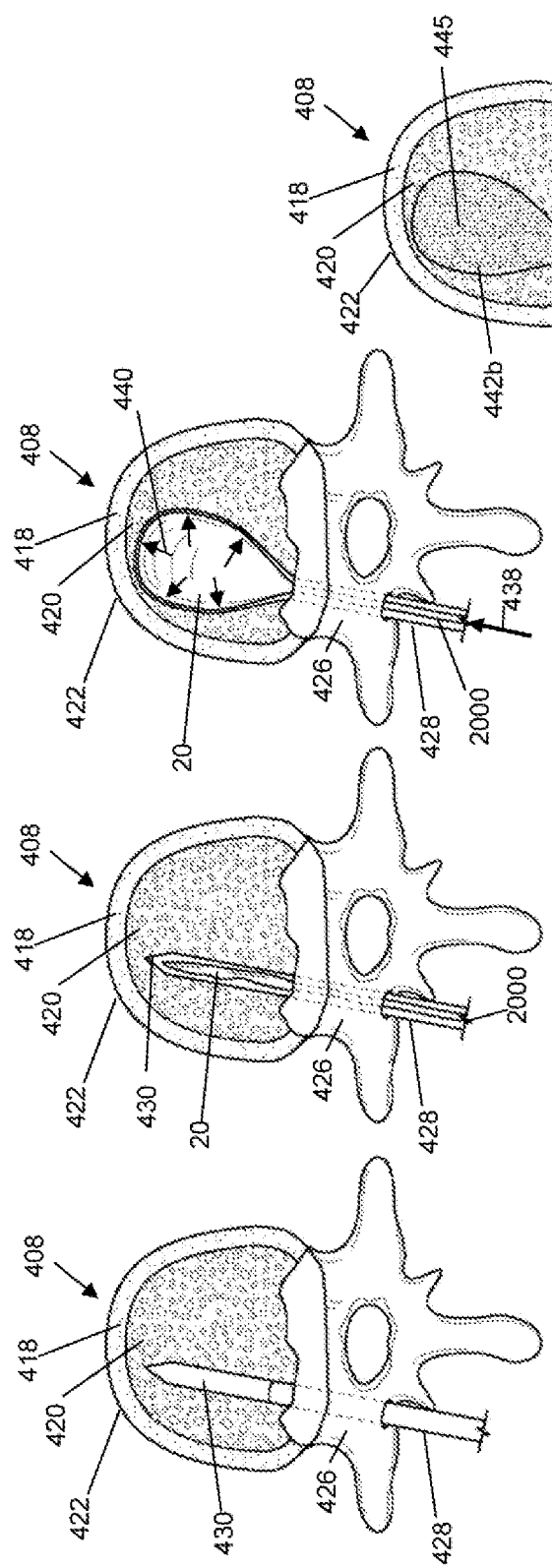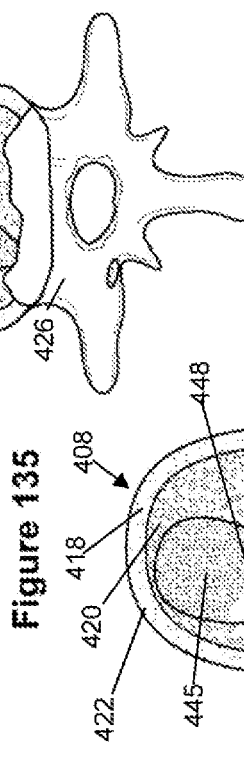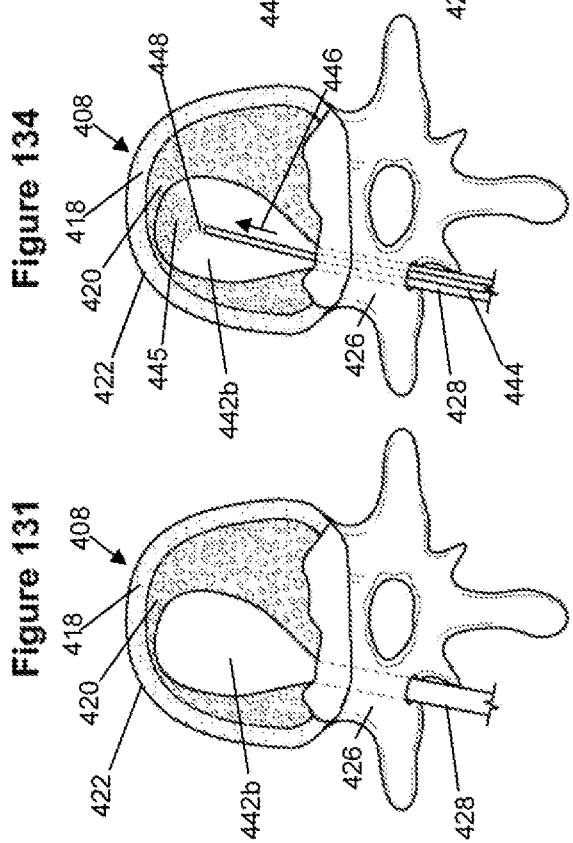

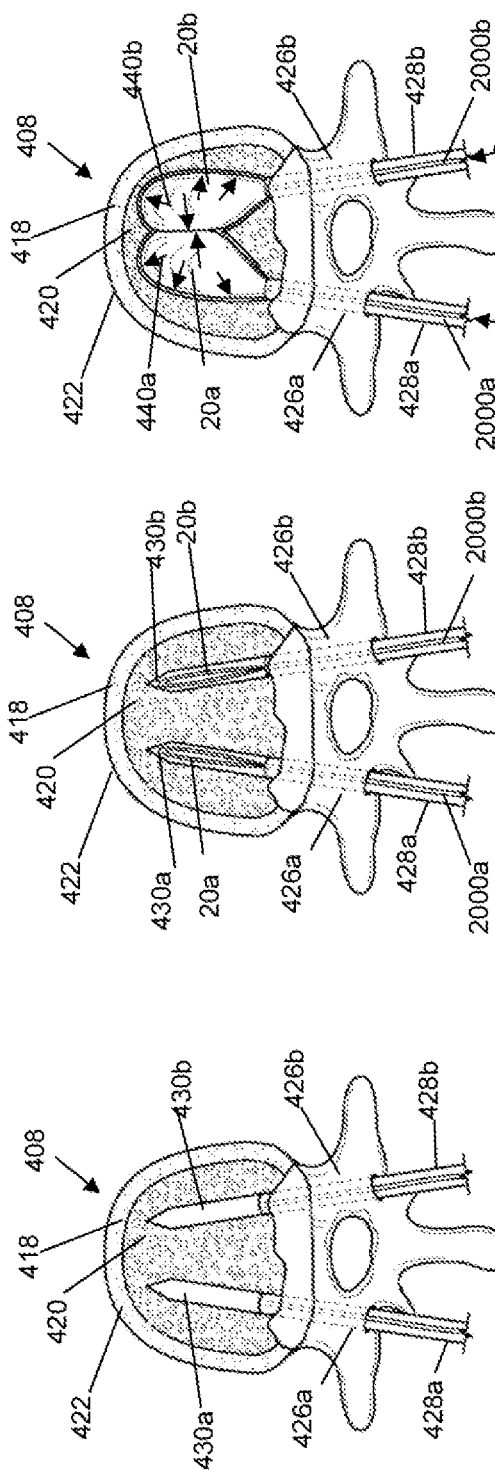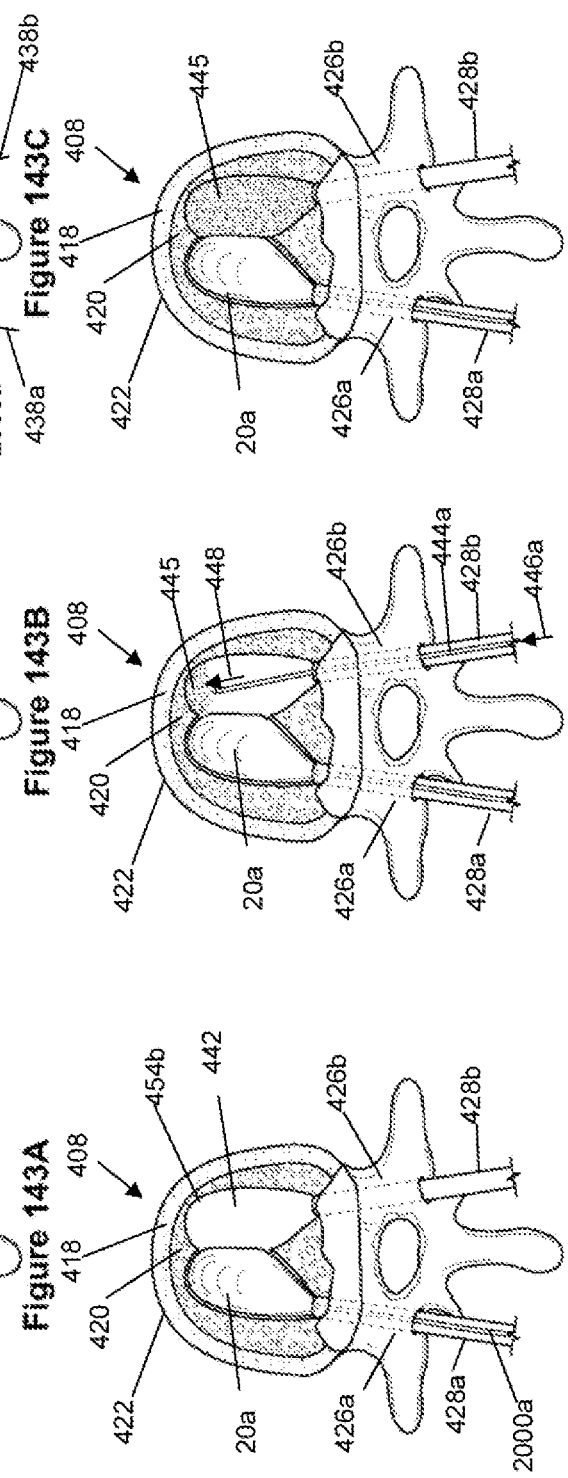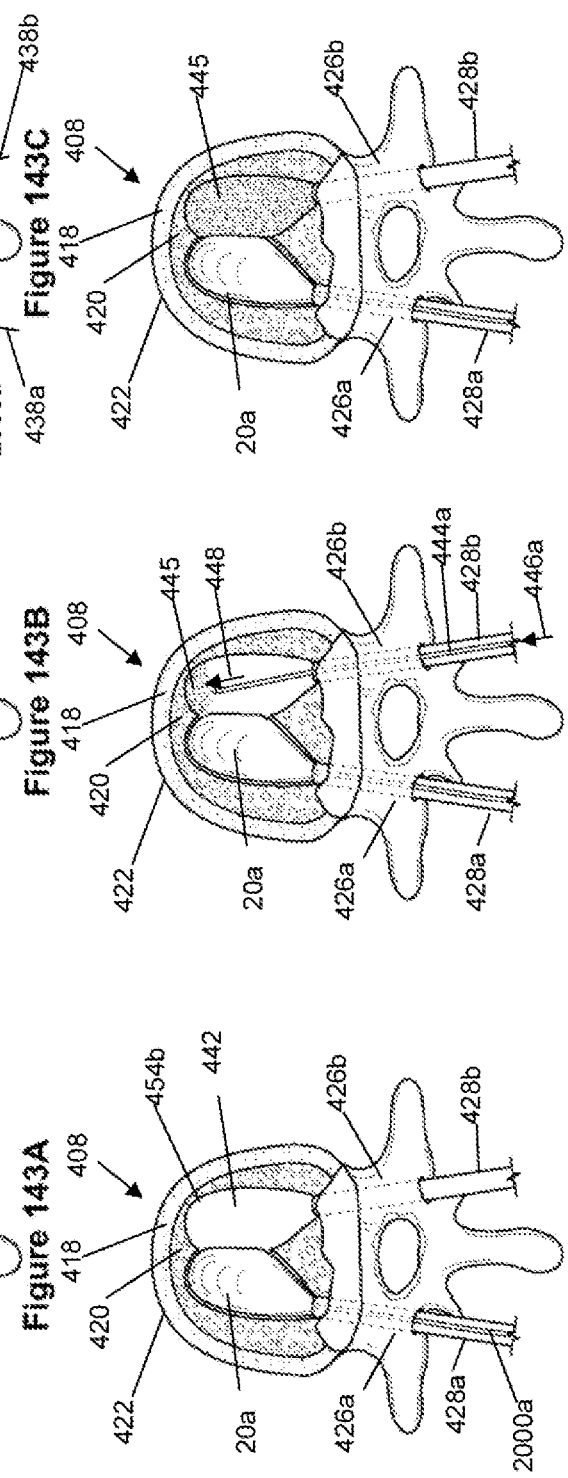

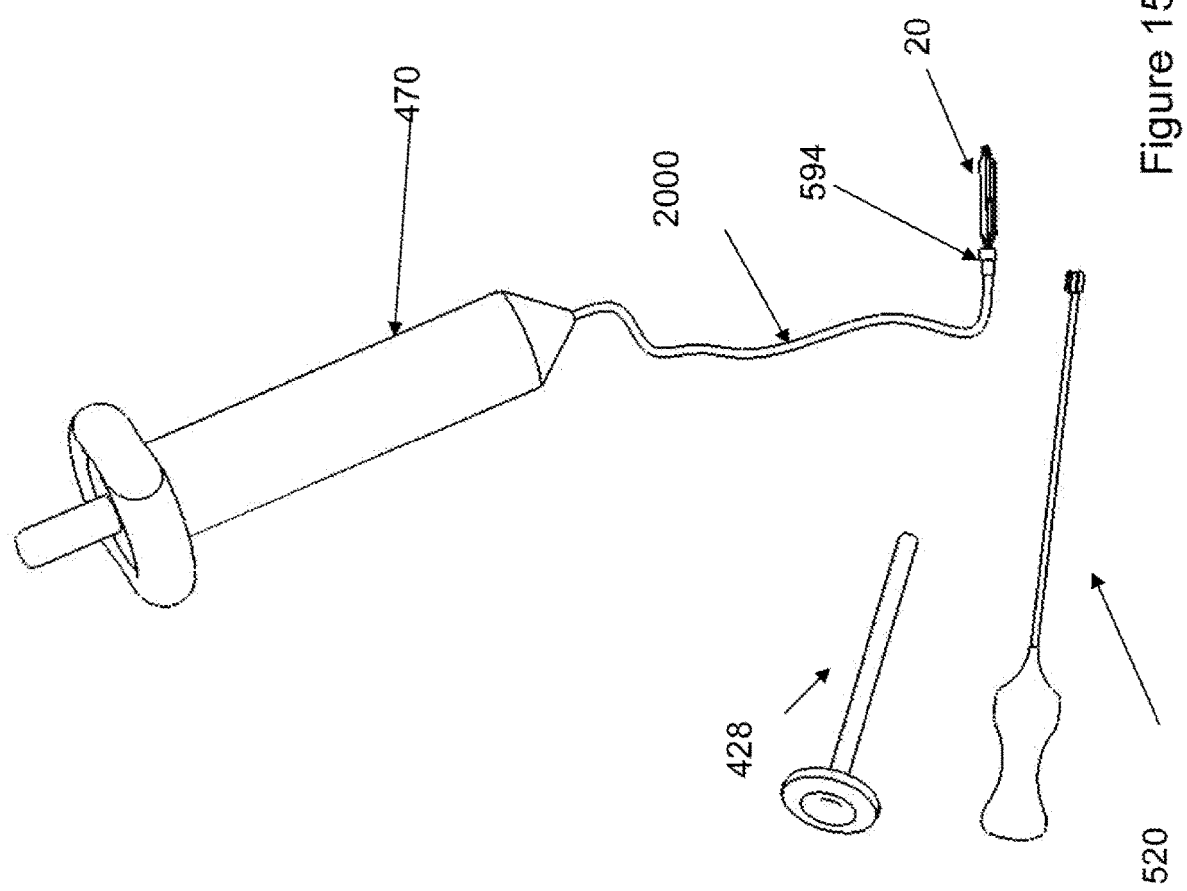

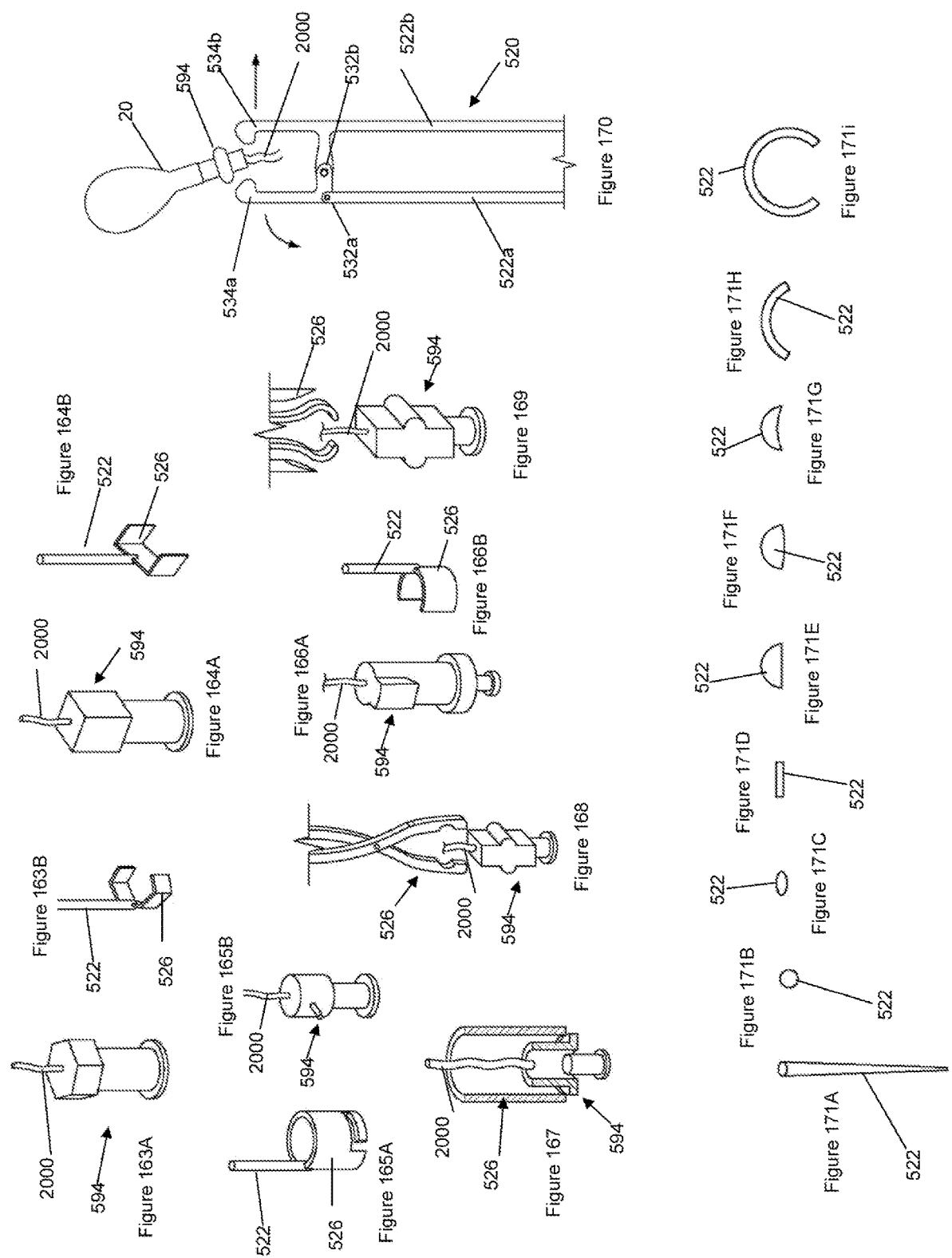

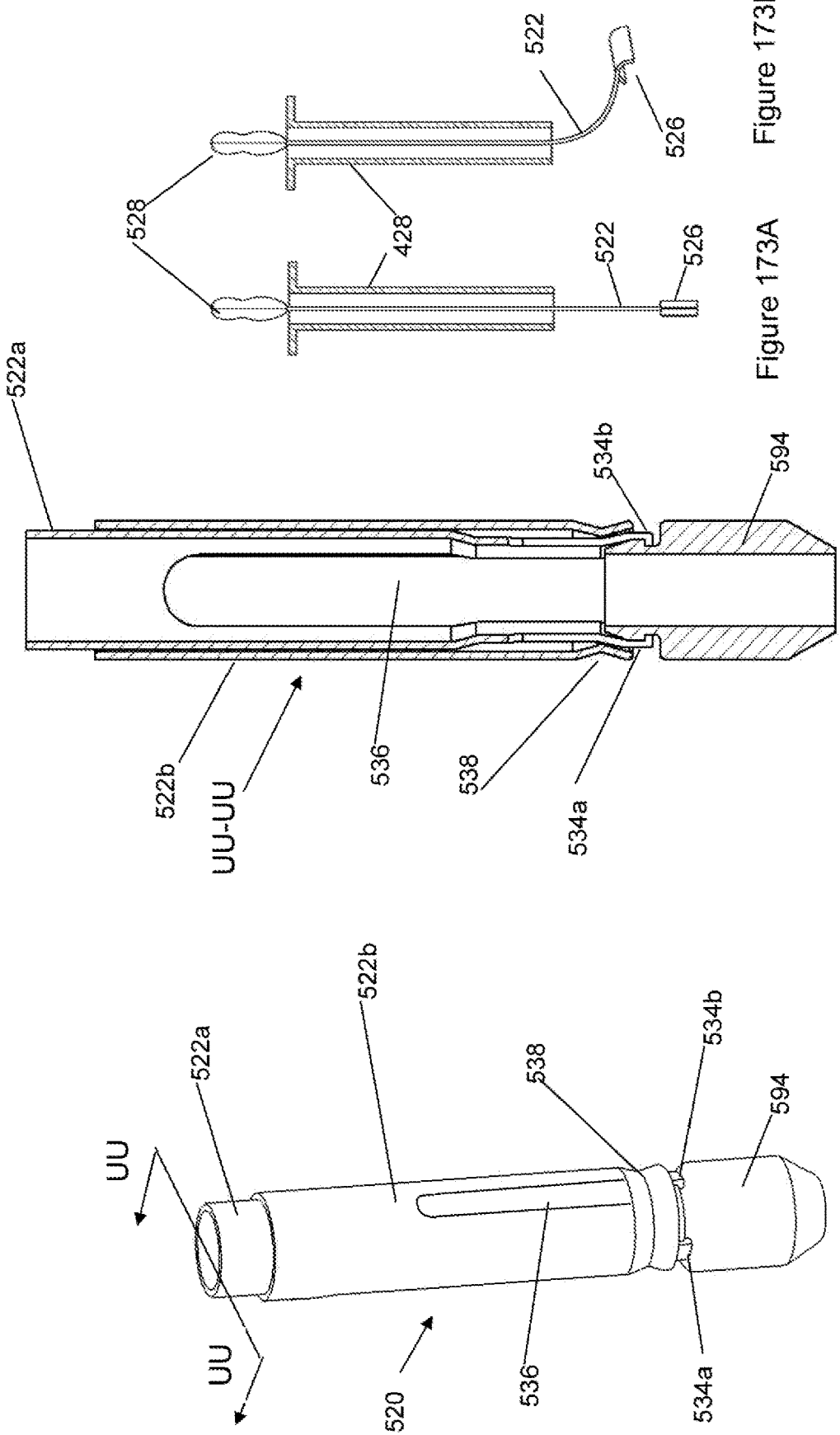

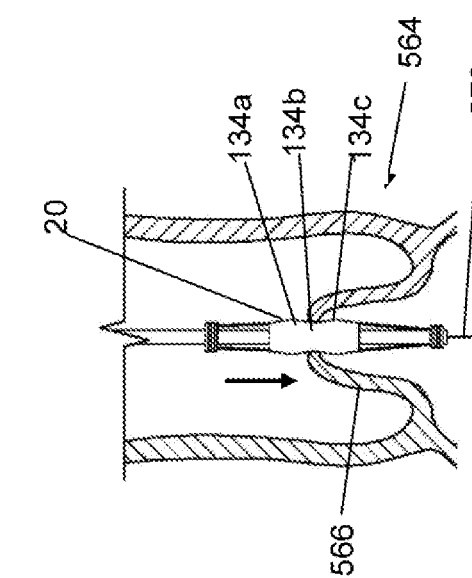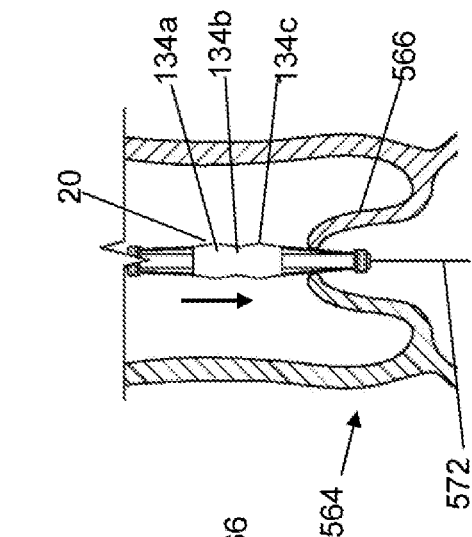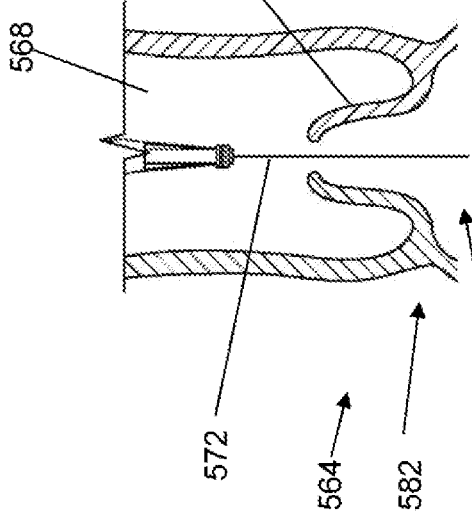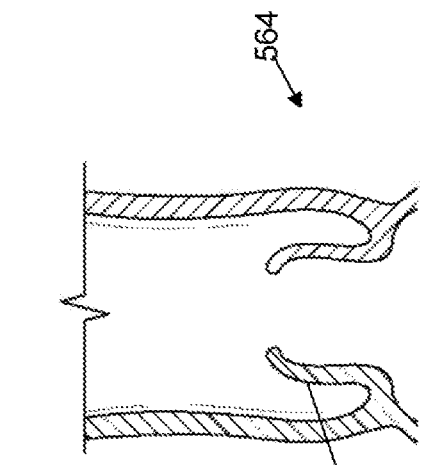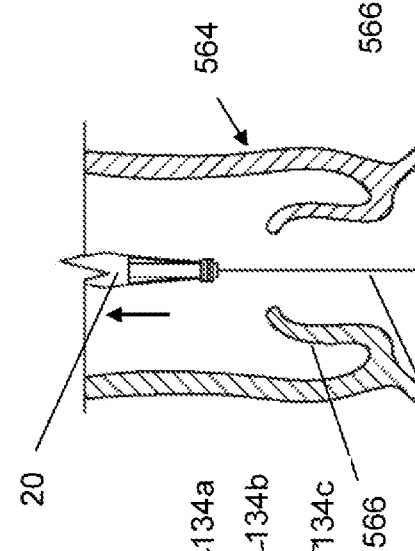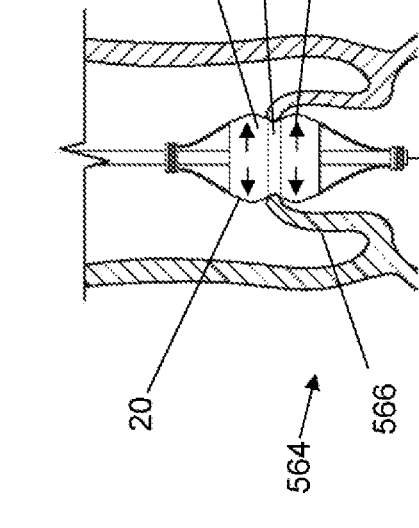

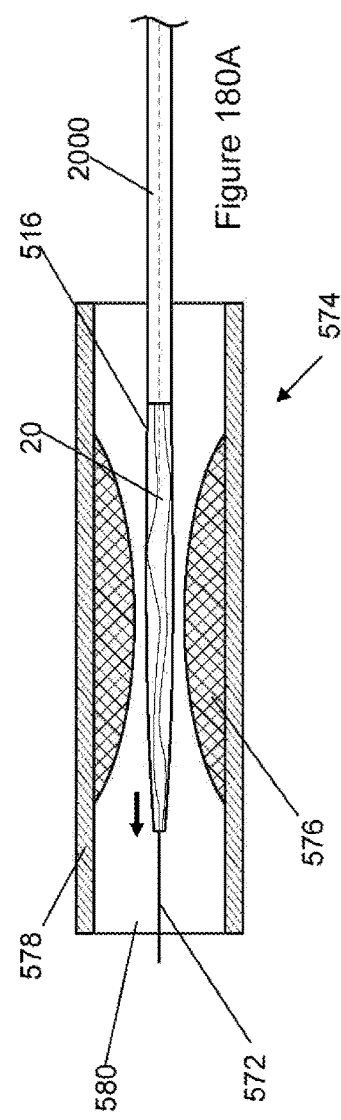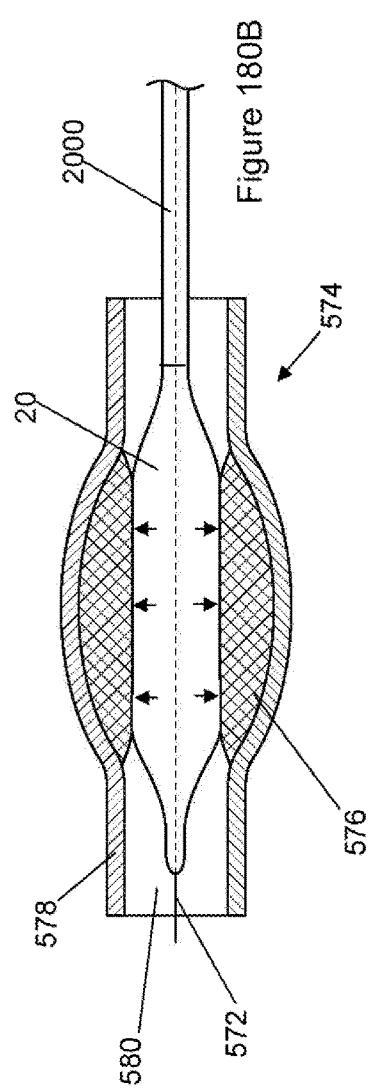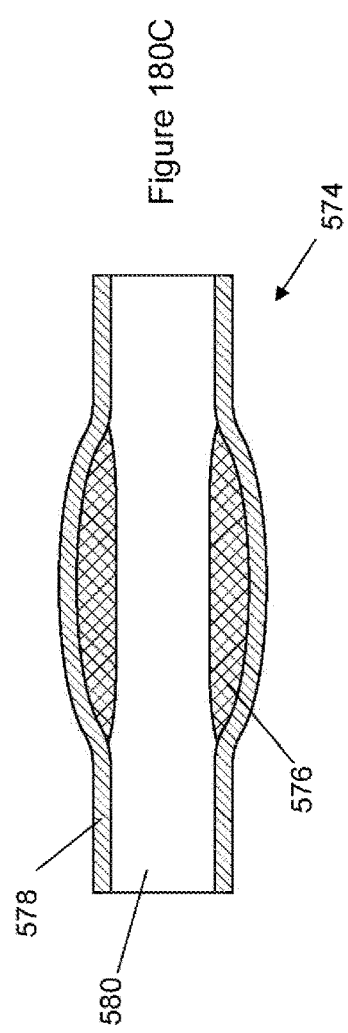

INFLATABLE MEDICAL DEVICES

CROSS-REFERENCE TO RELATED APPLICATIONS

This application claims priority to U.S. Provisional Application Nos. 61/057,986, filed 2 Jun. 2008; 61/086,739, filed 6 Aug. 2008; 61/105,385, filed 14 Oct. 2008; and 61/205,866, filed 22 Jan. 2009 which are incorporated by reference herein in their entireties. This application is a continuation of U.S. patent application Ser. No. 15/344,066 filed on Nov. 4, 2016, which is a continuation of U.S. application Ser. No. 12/477,077, filed Jun. 2, 2009, which are incorporated herein by reference.

BACKGROUND OF THE INVENTION

1. Field of the Invention

This invention relates to inflatable structures for use in medicine and other applications, and methods of manufacture and use of the same.

2. Description of the Related Art

Inflatable structures, such as balloons, are widely used in medical procedures. A balloon is inserted, typically on the end of a catheter, until the balloon reaches the area of interest. Adding pressure to the balloon causes the balloon to inflate. In one variation of use, the balloon creates a space inside the body when the balloon inflates.

Balloons may be used to move plaque away from the center of a vascular lumen toward the vasculature walls, such as during an angioplasty or a peripheral vasculature procedure. During this procedure, a balloon tipped catheter is placed in a vascular obstruction. As the balloon is inflated, the vessel constriction is dilated, resulting in improved blood flow.

Optionally, the balloon may have a stent placed over it. The balloon expands the stent in order to create a scaffold structure that keeps the vessel from constricting after the balloon is removed. Stents are used throughout the body, including the coronaries, other portions of the vasculature, the GI tract, the biliary ducts and the urinary and gynecologic tracts.

High pressure balloons may be used to expand constrictions in bone, such as in the sinuses in sinuplasty.

Balloons may be designed to make space in bone. After an osteoporotic compression or trauma-induced fracture in a vertebral body, a balloon can be inserted into the vertebral body through a working channel such as a cannula. The balloon is then inflated, creating a void in the bone. The balloon is withdrawn and bone cement is injected to internally stabilize the fracture. This procedure may be referred to as Kyphoplasty.

Sometimes the vasculature has a narrowing that is calcified, which can create a particularly difficult obstruction for dilation. As the vessel is increasingly narrowed, it can become what is known as a CTO (Chronic Total Occlusion). CTOs can be difficult to pass through with a device such as a guidewire or catheter and can be difficult to dilate or open. The balloon used to open a CTO is ideally resistant to puncture and operates at a very high pressure.

Balloons can have structures attached to their surface. These structures can include blades or stiffening rods. These structures may slice a vessel open. These structures may apply pressure to the inside of a vessel in order to expand the vessel.

Balloons can be used to locally deliver captured volumes of a radioactive substance. The procedure may be known as brachytherapy.

Balloons can be used to intentionally obstruct vessels. Stenting of the carotids serves to treat atherosclerotic carotid vessels. Stenting of the carotids may be less invasive than an endarterectomy. Stenting of the carotids may release a stream of debris that can travel to the brain, causing strokes. Expanding a balloon in the carotid artery above the area of treatment can prevent this debris movement to the brain, thereby reducing the potential for adverse complications.

Balloons may be used to position and deploy arterial grafts that repair aneurysms.

A balloon may deliver targeted drugs in the body by isolating a space for treatment.

A balloon may deliver targeted drugs in the body by having many tiny holes in the balloon wall. The holes in the balloon wall may allow the drug to slowly flow into the area surrounding the balloon.

Balloons may be used endoscopically to open up constrictions in the body, such as those in the esophageal tract, the urological tract, the biliary tract, the fallopian tubes, the carpal tunnel or esophagus, or other portions of the GI tract (the alimentary canal). A balloon may be used to expand constrictions in the urethra, including for Benign Prostate Hyperplasia (BPH).

Balloons may be used in the heart valves, including during Percutaneous Transvenous Mitral Valvuloplasty (PTMV) or Percutaneous Transvenous Mitral Balloon Commissurotomy (PTMC) or Mitral Annuloplasty. The balloons can be utilized to expand stenosed or calcifically-narrowed structures. The balloons can be utilized to expand valves to a tissue-opposed diameter.

A balloon may be used to affix a device inside the body. Another device may then use the balloon as a structure that the device can react against. The device may use this reaction force to move in the body. A balloon and a device may be used in the GI tract. A balloon and a device may be used during a Double Balloon Enteroscopy procedure, or during colonoscopy.

Balloons may be used to create space in the body or to move organs in body. Balloons can be used to manipulate organs along tissue planes.

The balloon may locate a cutting instrument in some ablative procedures. The balloon may position a diagnostic device.

An inflatable structure can be used to open space in tissue or to pull sclerotic structures apart, or to advance structures introduced herewithin to the body.

A balloon may be used to occupy a volumetric space for long periods of time, such as a device used to impart satiety at lower food volumes, as in Bariatric procedures.

A balloon can be used to create captured volumes that serve to transfer heat or cold. A balloon can provide small crossing profiles that then expand locally to create large volumes with high surface areas and intimate tissue contact. This is utilized in the prostate to treat BPH.

Balloons can be used as implants, creating an anatomical conforming structure advantageous to improved local fit.

Balloons have been suggested which seal against a lumen wall, then continue to dynamically seal as they are manipulated backwards or forwards. These balloons may be used in the GI tract. These balloons may be advanced forward or backward by pressure gradients on either side of the balloon.

Balloons may be used as pressure cuffs, such as those found in Lap-Band bariatric devices. By changing the pressure in the balloon, the inner diameter can grow or shrink. Changing the diameter alters clinical results.

Balloons may be elongated and used for movement through long lumens, including the GI tract.

Inflatable structures can be made into everting tubes, which have been utilized in gynecologic and urinary procedures, and have been suggested for GI procedures.

Two basic types of balloons are utilized: One is a high pressure, low-compliance balloon. The other is a lower pressure, high-compliance balloon.

High-compliance medical balloons are often composed of urethane, latex, silicone, PVC, Pebax, and other elastomers. As the pressure in a high-compliant balloon is increased, the balloon dimensions expand. Once the pressure is reduced, the high-compliance medical balloon may return to its original shape, or near its original shape. High-compliance medical balloons can easily expand several times in volume between zero inflation pressure and burst.

Traditional high-compliance medical balloons can be inadequate for many reasons. High-compliance, or highly elastic medical balloons typically cannot reach high pressures because their walls have a low tensile strength and their walls thin out as the balloon expands. In some instances, high-compliance medical balloons provide insufficient force to complete a procedure. Exceeding the rated pressure of a high-compliance medical balloon creates an excessive risk of balloon failure which can lead to serious complications for the patient.

High-compliance medical balloons also have poor shape control. As a high-compliance medical balloon expands, it may assume a shape dictated mostly by the particulars of the environment inside the patient rather than the clinical goals. In some cases, this can be contrary to what the medical practitioner desires. Many medical procedures are predicated on forming a particular balloon shape reliably.

High-compliance medical balloons often suffer from poor puncture resistance.

It is generally desirable that the medical balloon be able to enter and exit the body with as little trauma as possible. Therefore, a small deflated balloon profile is an important consideration in balloon design. This requirement favors materials with high strength to volume ratios. High-compliance medical balloons do not use materials that have outstanding strength to volume ratios.

In some cases, it is desirable that the medical balloon have a strong chemical resistance. For instance, a principal component of bone cement is methyl methacrylate, which readily degrades some elastomers, such as urethane. Therefore, many high-compliance medical balloons are not compatible with the introduction of aspects of the procedure that the high-compliance medical balloon is meant to support.

Low-compliance, high pressure medical balloons substantially retain their shape under comparatively high pressures. PET (polyethylene terephthalate) is the most common material for use in high pressure low-compliance balloons. PET is commonly used for high-performance angioplasty balloons. PET is stronger than other polymers, can be molded into a variety of shapes and can be made very thin (e.g., 5 μm to 50 μm (0.0002 in. to 0.002 in.)), thus giving these balloons a low profile.

Balloons made from PET walls are fragile and prone to tears. When pressed against a hard or sharp surface in the body, such as bone, PET balloons have poor puncture resistance. PET is very stiff so balloons made from PET may be difficult to pack or fold into a small diameter or with good trackability (i.e., the ability to slide and bend over a guidewire deployed through a tortuous vessel). In some applications, PET's chemical resistance can lead to unwanted adhesion, degradation or destruction of a PET balloon during a procedure.

Balloons made from PET, while stronger than most other balloons made from homogenous polymers, may still not be strong enough to hold pressures sufficient to complete certain medical procedures.

The PET in a balloon wall may be oriented during manufacture. However, the oriented PET may not have strength in all directions exactly proportionate to the expected load.

PET, like most low compliance balloons, is usually blow-molded. The blow molding process makes it difficult or impossible to create certain shapes. Blow molding can result in wall thicknesses in the balloon that do not match the material thicknesses to the expected load.

Nylon balloons are an alternative material for low-compliance, high pressure balloons. These balloons are typically weaker than PET balloons and so can contain less pressure. Nylon readily absorbs water, which can have an adverse affect on Nylon's material properties in some circumstances. Nylon has improved puncture resistance over PET and is more flexible than PET.

Low compliance fiber reinforced medical balloons have recently become commercially available for peripheral vascular procedures. High strength inelastic fibers are used as part of the low compliance fiber reinforced medical balloons to strengthen the walls of the balloon while further lowering strain rates. High strength inelastic fibers such as Kevlar, Vectran, Dyneema and carbon fiber all have strength to volume ratios that greatly exceed that of PET or Nylon. The high strength inelastic fibers are combined with a flexible adhesive and, optionally, one or more polymer walls to form a balloon.

Low compliance fiber reinforced medical balloons may suffer from several problems. These balloons may have a low volume ratio of high strength inelastic fiber to the total material volume in the balloon walls. It is reasonable to assume that a higher volume ratio of high strength inelastic fiber to the total material volume in the balloon walls would lead to a higher burst pressure for the same wall thickness.

Commercially available low compliance fiber reinforced medical balloons and the processes that produce them may only allow limited flexibility in the placement of the high strength inelastic fibers. For example, a process may result in fibers aligned along the axis of the balloon and fibers wrapped around the circumference. This limited choice of fiber orientation is not always the optimum way to orient the fibers for maximum strength. This limited choice of fiber orientation is not always the optimum way to orient fibers to resist puncture or ripping.

Commercially available low compliance fiber reinforced medical balloons and the processes that produce them may not allow for a large variety of different balloon shapes to be manufactured.

SUMMARY OF THE INVENTION

Medical inflatable devices for use in a biological body are disclosed. The device can have a balloon. The balloon can have a wall having an inner layer, a first middle layer, and an outer layer. The outer layer can be thinner than about 0.05 mm (0.002 in.), and the inner layer is thinner than about 0.05 mm (0.002 in.). The first middle layer can have a fiber. The outer layer can have a melt or decomposition temperature greater than about 200° Celsius.

The outer layer can be made from a thermoset material. The outer layer can be made from PEEK. The outer layer can be made from a polyamide. The outer layer can be MMA-resistant and/or MMA-releasing. An MMA-resistant layer can be substantially non-degrading when exposed to MMA, such as uncured MMA. An MMA-releasing layer can be substantially non-binding or non-adhering to MMA. The MMA-releasing layer can be pulled away and separated from cured MMA without binding to the MMA.

The first middle layer can be made from a resin. The inner layer can be thinner than about 0.01 mm (0.0004 in.), and the outer layer can be thinner than about 0.01 mm (0.0004 in.). The inner layer can be substantially air leak-proof.

The balloon can have a wall that can have an inner layer, a first middle layer, and an outer layer.

The outer layer can be thinner than about 0.05 mm (0.002 in.). The outer layer can have a thermoset material, such as PEEK. The outer layer can have a polyamide. The first middle layer can have a fiber and/or a resin.

The wall can have an air leak-proof inner layer and an MMA-resistant outer layer. The outer layer can be thinner than about 0.05 mm (0.002 in.), and the inner layer can be thinner than about 0.05 mm (0.002 in.).

The second layer can be radially inside the third layer, and the second layer can be radially outside the first layer. The third layer can make up the radial outermost surface of the wall. The wall can also have a fourth layer. The fourth layer can be radially inside the third layer. The fourth layer can be radially outside the first layer. The fourth layer can have a radiopaque material.

The wall can have a first layer, a second layer, a third layer, and a fourth layer. The first layer can be leak-proof and the fourth layer is MMA-resistant. The first layer can be radially inside of the second layer, the third layer, and the fourth layer. The fourth layer can be radially outside of the first layer, the second layer, and the third layer. One, two, or three layers can have resin and fiber in contact with the resin, for example the fiber can be embedded within the resin or in one side of the resin. The layers with the fiber can be MMA-resistant.

The wall can have a layer that can form at least one continuous seam around the balloon. The balloon can be substantially non-compliant or inelastic. The wall can be less than about 0.1 mm (0.004 in.) thick.

The balloon can have a longitudinal axis having a longitudinal axis length. The balloon can have a fiber having a fiber length. The fiber length can be about 175% to about 300% of the longitudinal axis length. The wall of the balloon can have a first layer and a second layer. The fiber can be in the second layer. The first layer can be on the radial inside of the fiber with respect to the balloon, and the first layer can be leak-proof, and/or MMA-resistant.

The balloon can have an inner diameter of more than about 2 mm, or about 13 mm (0.5 in.), or more than about 15 mm. The balloon can have a wall having a wall thickness of less than about 0.005 in., and a burst pressure greater than about 150 psi, more narrowly greater than about 3,400 kPa (500 psi). For example, the burst pressure of the balloon can be greater than about 2,100 kPa (300 psi).

The balloon can have a proximal terminal end and a distal terminal end. The balloon can have a closed distal terminal end, or no through-lumen. Having no through-lumen can include having no longitudinal through-lumen extending through the proximal terminal end and through the distal terminal end. The distal end of the balloon can be atraumatic, for example blunt.

The balloon can have a reinforcement fiber that can be in a matrix. The matrix can have a reinforcement fiber and a resin. The resin can be an adhesive. The fibers can be oriented longitudinally and/or around the distal end of the balloon. The fibers can cover (but not necessarily on the outer surface) greater than 50% of the area of the balloon wall. The matrix can have a thermoplastic material.

The balloon wall can have a first, second and/or more strips. The strips can have none, one or more reinforcement and/or radiopaque marker fibers. Each strip can have the same or a different number of fibers. The balloon can have a closed distal end. The first strip can overlay the second strip at the distal end. Additional strips can overlay the first and second strips at the distal end or elsewhere along the length of the balloon. The strips can intersect at a strip angle. The strip angle can be equal to or greater than about 30 or 45 degrees. For example, the strip angle can be about 60 degrees or about 90 degrees.

The first middle layer can have a radiopaque material and be substantially contiguous throughout the wall. For example, the first middle layer can have a metal foil. The first middle layer can have a radiopaque material in non-powder form. The first middle layer can have less than about 100 pieces of radiopaque material. The radiopaque material can covers (not necessarily on the top surface) at least about 30% of the area of the wall of the balloon. The first middle layer can have a first elongated member that can have a radiopaque material. For example, the elongate member can be a strip, such as the strip described herein.

The first middle layer can have a fiber. The second middle layer can have a radiopaque material. The first middle layer can be between the inner layer and the second middle layer.

The balloon wall can have a water-proof inner layer, a first middle layer that can have a fiber, a second middle layer that can have a radiopaque wire, and an outer layer. The fiber can be helically positioned or hoop or helically wrapped around the balloon wall.

The radially outer layer of the balloon wall can have a thickness of less than about 0.0005 in. and the radially outer layer can be resistant to degradation by MMA. The radially outer layer can be made from or coated with Teflon or PTFE. The MMA-resistant layer can have an MMA-resistant matrix and a fiber. The MMA-resistant matrix can have an adhesive. The balloon can be configured to deliver a radial pressure of about 2,800 kPa (400 psi).

The balloon can be shaped having a first side and a second side. The first side can be opposite the second side with respect to the balloon longitudinal axis. The first side can be substantially flat, and the second side can be substantially flat.

The balloon wall can have a wall thickness of equal to or less than about 0.3 mm, for example about 0.1 mm, and the balloon has an outer diameter less than or equal to about 13 mm, and the balloon has a burst pressure of equal to or greater than about 1000 kPa (150 psi).

The balloon wall can have a first layer that can have a reinforcement and/or marker fiber and a second layer that can have a resistive heating element, such as tantalum foil. The resistive heating element can be a wire helically configured around the balloon. The resistive heating element can be controlled by a controller configured to controllably deliver energy to the resistive heating element. The resistive heating material can be the elongated strip or in the elongated strip.

The wall can have a semi-rigid panel. The panel can be between an inner and outer layer of the wall. The panel can have a modulus of elasticity greater than about 1,000,000 and a thickness greater than about 0.0002 in. The panel can be a metal foil. The balloon can be pleated before use.

A method for making an inflatable device for use in a biological body is disclosed. The method can include forming a leak-proof member from solid film on a removable mandrel. The forming can occur at a temperature below 100° Celsius. the forming occurs without solvation of the film. The method can further include adhering the film to the mandrel, wherein adhering comprises adhering with a water-soluble tacking adhesive. The mandrel can be removed by dissolving the mandrel with water. Forming can include pressure-forming. (i.e., hydroforming with a fluid, even air).

The method can also include trimming the film. The thermoset film can have one or more fibers or no fiber. The film can be substantially anisotropically mechanically load-bearing. For example, the load-bearing properties of the film can be substantially unidirectional along the surface plane of the film.

A method for making the device is disclosed that can include adhering with a first bonding agent a first film to a mandrel, forming the first film on about the first half of mandrel, bonding with a second bonding agent the first film to a second film, forming the second film on about the second half of the mandrel, and dissolving the mandrel. Dissolving can include applying water to the mandrel. The first bonding agent can be water-soluble. The mandrel can be made from a sugar, a plastic, polylactic acid (PLA), polyvinylacetate, a water-soluble wax, or combinations thereof.

A method for making the device is disclosed that can include positioning a solid film on a mandrel and dissolving the mandrel with the solid film on the mandrel. Dissolving can include dissolving with water. The film can be watertight. The film can be configured as a flat piece of film before forming on the mandrel. The film can have a square or rectangular shape before forming on the mandrel.

Also disclosed is a method for making the device that can include creating a first hole that transects a mandrel, passing a fiber through the first hole, forming a layer of material on the mandrel, attaching the layer to the fiber, and dissolving the mandrel. Attaching can include attaching the fiber to the side of the layer against the mandrel, attaching the fiber to the side of the layer away from the mandrel, attaching the fiber to the inside of the layer, or combinations thereof.

A method for making the device is disclosed that can include applying fibers to a mandrel, applying an elastomeric resin to the fibers and bonding the fibers to the mandrel. Applying the fibers can include rotating the mandrel while feeding the length of the fibers from a location off the mandrel. The fibers or layer containing the fibers can be bonded to the mandrel or to an adjacent layer to prevent the fibers from slipping against the mandrel or adjacent layer. The mandrel can have an ovaloid shape.

A method for making the device is disclosed that can include applying a first layer of a material on a water-soluble mandrel and forming a thermoset film on the first layer. The method can be performed at a temperature from about 5 degrees Celsius to about 35 degrees Celsius, more narrowly from about 15° C. to about 30° C., for example at ambient or room temperature (e.g., about 18° C. to about 25.5° C.).

A method for making the device is disclosed that can include applying a first layer of a material on a madrel, bonding with a first bonding agent a first thermoset film to the first layer, forming the first thermoset film on about the first half of the first layer, bonding with a second bonding agent the first thermoset film to a second thermoset film, forming the second thermoset film on about the second half of the first layer, and dissolving the mandrel.

A method for making the device is disclosed that can include applying a first layer of a material on a mandrel, hydroforming an MMA-resistant film on the first layer; and dissolving the mandrel with water.

A method for using the device is disclosed that can include inserting the inflatable device adjacent to a target site, expanding the inflatable device to a pressure greater than about 350 kPa (51 psi), and delivering to the target site thermal energy generated in the wall of the inflatable device. Delivering the energy can include singeing or ablating tissue at the target site.

The balloon can be attached to a deployment tool having a deployment rod. The deployment rod can have a rod distal end. The deployment rod can be positioned at least partially inside the balloon when the balloon is in a deflated state. The deployment rod can be slidably adjustable with respect to the location of the proximal end of the balloon. The deployment rod can be in an extended position when the balloon is in the substantially deflated state. The deployment rod can be in a retracted position when the balloon is in the substantially inflated state. The rod distal end can be out of substantial contact with the balloon distal end when the balloon is in the substantially inflated state.

The rod distal end can be in contact with the balloon distal end when the balloon is in the substantially deflated state.

The deployment tool can have a fluid channel configured to deliver fluid to the balloon. When the deployment rod is in an extended position, the deployment rod can substantially obstruct the fluid channel. When the when the deployment rod is in a retracted position, the deployment rod can leave the fluid channel substantially unobstructed by the deployment rod retracting the deployment rod with respect to the balloon, wherein retracting comprises substantially unobstructing fluid delivery through the fluid channel. Further comprising delivering fluid to the balloon after retracting the deployment rod.

The deployment rod can be positioned at least partially inside the balloon when the balloon is in a deflated state. The deployment rod can be fixed with respect to the location of the proximal end of the balloon. The rod distal end can be substantially separate (i.e., not in substantial or any contact) with the balloon wall when the balloon is in the substantially inflated state. The rod distal end can be atraumatic. The rod distal end can have a curved surface facing the balloon distal end. The deployment rod can be stiffer than the balloon when the balloon is in a contracted state.

A method for using the device is disclosed that can include inserting a working channel through the biological body, delivering a first balloon through the working channel and positioning the first balloon at the target site. After the delivering the first balloon, the method can include delivering a second balloon through the working channel and positioning the second balloon at the target site while the first balloon is at the target site. The method can also include delivering an unsupported (i.e., in free air or about standard atmospheric pressure) pressure of greater than about 1400 kPa (200 psi) to the first and/or second balloon. The working channel can have an inner diameter less than about 5 mm. The working channel can have a distal port. The distal port can be positioned adjacent to, or at, the target site, such as the inside of a vertebral body. The second balloon can be inflated after or concurrent with inflating the first balloon.

The working channel can have an inner diameter less than about 5 mm. The first and second balloons can be attached to separate first and second deployment systems, respectively, enabling independent orientation and/or translation of the first balloon from the second balloon, or the first and second balloons can be attached to a single integral joint deployment system.

An inflatable device system is disclosed that can include a curved guide block, a drill, a trocar, a first balloon, a steering mechanism, and combinations thereof. A method for using the system can include positioning a guide block outside of the biological body and delivering a drill through the guide block. The method can include delivering the device through the guide block and into the biological body.

An inflatable device system is disclosed that can have a balloon, a reservoir, a fluid in the reservoir: and a sealed sterile package. The balloon, the reservoir and the fluid can be in the sealed sterile package.

An inflatable device kit is disclosed that can have a balloon having a fully inflated state having an inflated volume, a fluid channel having a fluid channel volume, a sealed reservoir, and a fluid in the reservoir. The fluid in the reservoir can have a fluid volume. The fluid volume can be within 10% of the sum of the inflated volume and the fluid channel volume.

A deployment tool for use with the inflatable device is disclosed that can have a fluid first channel having an incoming port. The fluid first channel can have a luer connector at the incoming port, a check valve and a swabbable valve. The swabbable valve can be adjacent to the luer connector. The check valve can be downstream from the luer connector.

An assembly for use in percutaneously treating a bone predisposed to fracture or to collapse, or that is fractured or collapsed, is disclosed. The assembly can have a cannula, a balloon, a catheter and a driving rod. The balloon can be insertable through the cannula into bone. The balloon can have a deflated condition which has a size for passage through the cannula for insertion into bone. The balloon can be inflated to a predetermined shape and size sufficient for compressing at least a portion of inner cancellous bone so as to form a cavity therein. The balloon can be restrained in the inflated condition to create said predetermined shape and size by having a wall that is thicker in selected portions than it is in other portions and/or by an internal restraint provided in or on the balloon wall and/or by an external restraint in or on the balloon wall. The outer diameter of the catheter can be smaller than the inner diameter of the cannula. The cannula can be adapted to not drive the deflated balloon through the cannula into the bone. The driving rod can releasably attach to the device. The driving rod can be adapted to drive the balloon through the cannula into the bone.

The catheter can have an elastomer and a fiber. The driving rod can have a shaft and a clasp at the distal end of the shaft.

A method for using the device is disclosed that includes inserting a balloon into the target site, inflating the balloon and injecting a load of bone cement into the target site. The load of bone cement can cure while in contact with the balloon. The balloon does not substantially degrade from contact with the load of bone cement. The balloon can have a fiber made from a substantially different material than the remainder of the balloon. Inserting can include inserting with a detachable driving rod. The method can include creating a void at the target site.

The balloon can be non-compliantly expanded. For example, the wall of the balloon can expand no more than about 2% to about 3% strain between the deflated state to the inflated state.

The device can be used to perform valvulopasty, annuloplasty, kyphoplasty, sinuplasty or angioplasty procedures. The device can be used to minimally invasively deliver and expand a vascular stent, graft or heart valve. The device can be used to expand constrictions in the urethra. The device can be used to dilate CTOs. The device can be used to temporarily or permanently occlude vessels, for example to isolate a space within a vessel to locally deliver drugs or to intentionally cause necrosis. The device can be used to deliver therapeutic and/or diagnostic drugs. The device can be used to deliver energy to warm, singe or ablate adjacent tissue. The device can be used as a radiopaque or echogenic marker. The device can be used during a balloon enteroscopy procedure or during colonoscopy. The device can be used to cut, tear, or otherwise rip tissue. The device can be implanted and inflated to create an anatomical feature, such as a breast implant.

BRIEF DESCRIPTION OF THE FIGURES

FIGS. 3A through 3C are cross-sectional views of a length of variations of the device.
FIG. 4A illustrates a variation of the device.
FIGS. 4B and 4C are variations of cross-section C-C of FIG. 4A.
FIG. 5A illustrates a variation of the device.
FIGS. 5B and 5C are variations of cross-section D-D of FIG. 5A.
FIG. 6A illustrates a variation of the device.
FIG. 6B is a variation of cross section E-E of the device of FIG. 6A.
FIG. 6C is a variation of cross section F-F of the device of FIG. 6A.
FIG. 6D is a variation of cross section G-G of the device of FIG. 6A.
FIGS. 7 and 8 illustrate variations of the device.
FIGS. 21A and 21B are top and bottom perspective views, respectively, of a variation of the device.
FIG. 22A illustrates a variation of the device.
FIG. 22B is a variation of cross-section K-K of FIG. 22A.
FIG. 23A illustrates a variation of the device.
FIGS. 23B and 23C are variations of cross-section L-L of FIG. 23A.
FIG. 24A illustrates a variation of the device.
FIG. 24B is a variation of cross-section M-M of FIG. 24A.

FIGS. 25 through 28 are cross-sectional views of variations of the device.

FIGS. 30A, 31A, 32A, 33A and 34A illustrate variations of the device.

FIGS. 30B; 30C; 31B; 32B; 33B; 34B and 34C are variations of cross-sectional views P-P through T-T respectively, of FIGS. 30A, 31A, 32A, 33A and 34A, respectively.

FIG. 36A illustrates a variation of the device.

FIG. 36B is a variation of cross-section V-V of FIG. 36A.

FIGS. 42A-42E are partial see-through views of variations of the device.

FIG. 45 illustrates a variation of the device.

FIGS. 47 through 49 are tables listing film materials, reinforcement materials, and adhesive and matrix materials, respectively.

FIG. 52 is a chart of material characteristics for variations of mandrel materials.

FIGS. 53 through 58 illustrate a variation of a method for manufacturing the device.

FIG. 82A illustrates a variation of a manufacturing tool.

FIG. 82B is a variation of cross-sectional view GG-GG of FIG. 82A.

FIG. 83 illustrates a variation of the fiber during a variation of a method for manufacturing the device.

FIGS. 95 through 100 illustrate variations of laminate sheets.

FIG. 120 illustrates a variation of a layer.

FIGS. 121 and 122 illustrate variations of elongated elements.

FIGS. 123 and 124 illustrate variations of three overlayed elongated elements.

FIGS. 131,134, 135, 137, 138, 139 and 140 are coronal cross-sectional views of a variation of a method of using a variation of the device in a vertebra.

FIGS. 143A through 143i are coronal cross-sectional views of a variation of a method of using a variation of the device in a vertebra.

FIG. 156 illustrates a variation of a system for using the device.

FIGS. 163A, 164A, 165A and 166A illustrate variations of the device.

FIGS. 163B, 164B, 165B and 166b illustrate variations of the distal ends of deployment or driving rods configured to interface with the devices of FIGS. 163A, 164A, 165A and 166A respectively.

FIGS. 167, 168 and 169 illustrate sectional views of variations of methods for using a deployment or driving rod with the device.

FIG. 170 illustrates a variation of a method for using a deployment or driving rod with the device.

FIG. 171A illustrates a variation of the shaft of the deployment rod.

FIGS. 171B through 171i are variations of cross-section of FIG. 171A.

FIG. 172A illustrates a variation of a method for using a deployment or driving rod with the device.

FIG. 172B is a variation of cross-sectional view UU-UU of FIG. 172A.

FIGS. 173A and 173B are cross sections of variations of methods of deployment.

FIGS. 178 through 179F illustrate a variation of a method for valvuloplasty.

FIGS. 180A through 180C illustrate a variation of a method for angioplasty.

DETAILED DESCRIPTION

Figure 1:
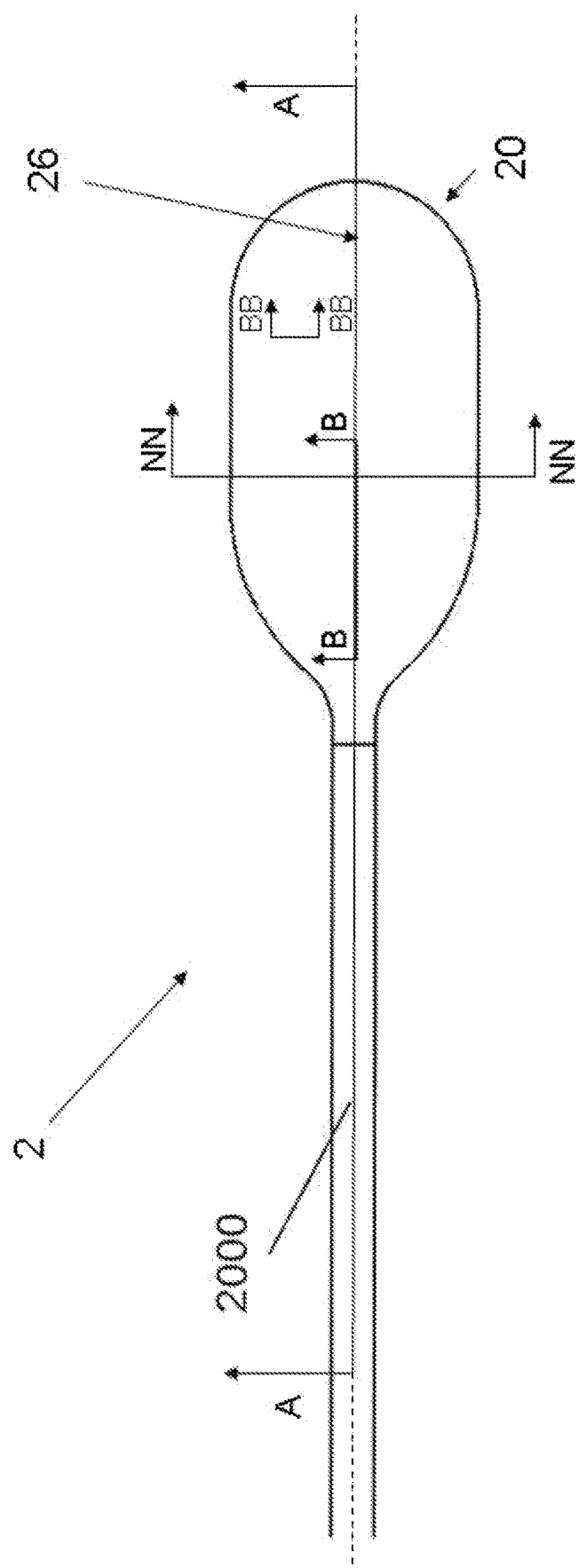
FIG. 1 illustrates a variation of the device.

FIG. 1 illustrates that a medical inflatable device 2 can have a balloon 20 and a hollow shaft 2000. An inflation system (shown herein) can be attached to the hollow shaft to deliver a fluid pressure through the hollow shaft and to the balloon. The balloon 20 can be resilient (i.e., elastic) or non-compliant (i.e., inelastic). The balloon 20 can have a balloon longitudinal axis 26. The balloon 20 can have a balloon wall 22. The balloon wall 22 can define a cavity having a balloon volume 24.

Figure 2:
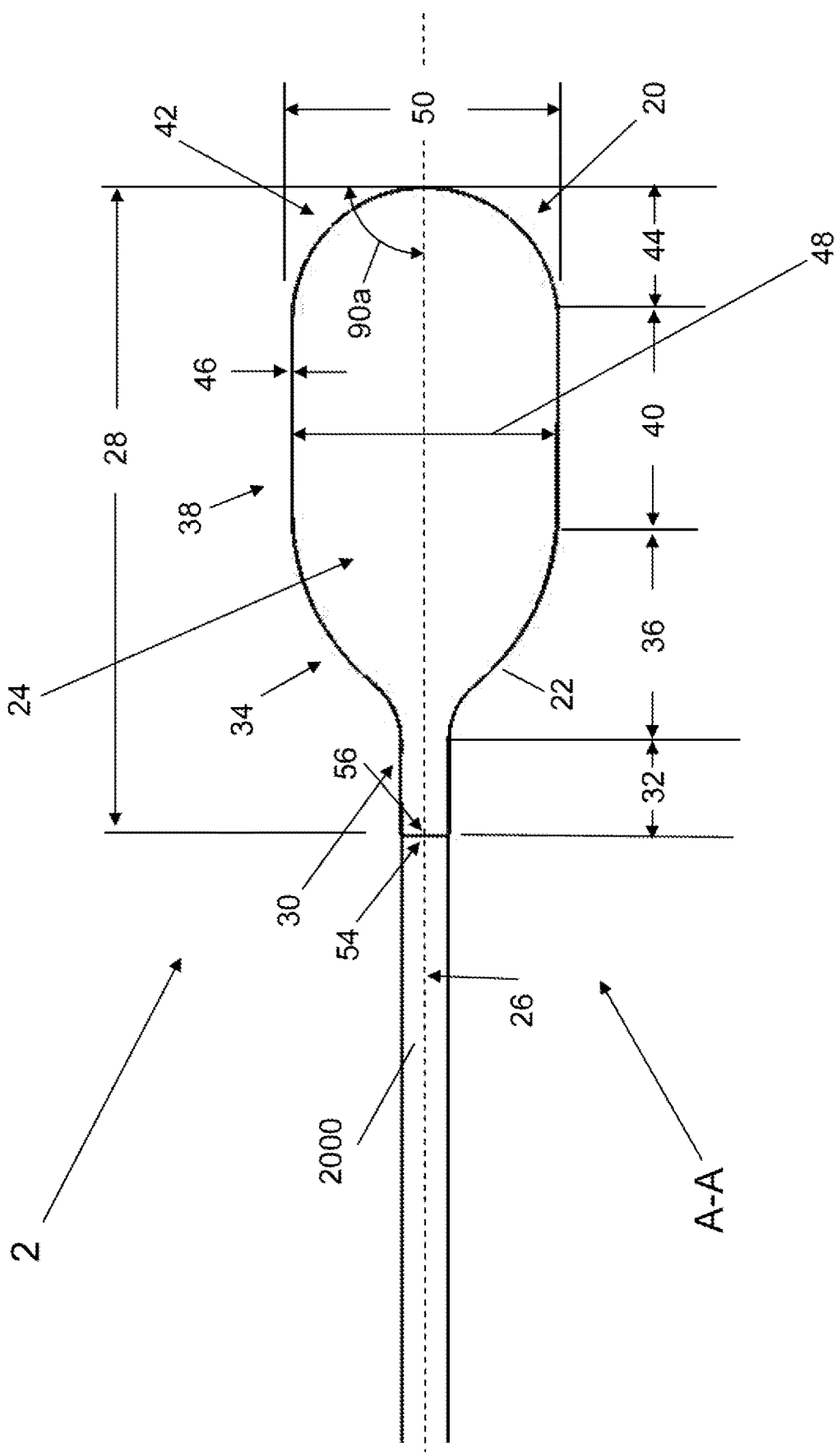
FIG. 2 illustrates a variation of cross section A-A of FIG. 1.

FIG. 2 illustrates that the balloon 20 can have balloon length 28. The balloon 20 can have a balloon proximal stem 30 having a balloon proximal stem length 32. The proximal stem length 32 can be from about 5 mm (0.2 in.) to about 15 mm (0.6 in.). The balloon can have a balloon proximal taper 34 having a balloon proximal taper length 36. The balloon proximal taper length 36 can be from about 0 mm (0 in.) to about 20 mm (0.8 in.), more narrowly from about 0 mm (0 in.) to about 15 mm (0.6 in.), yet more narrowly from about 5 mm (0.2 in.) to about 10 mm (0.4 in.) The balloon 20 can have a constant-diameter section 38 having a constant-diameter section length 40. The constant-diameter section length 40 can be from about 0 mm (0 in.) to about 15 mm (0.6 in.), more narrowly from about 0 mm (0 in.) to about 10 mm (0.4 in.). The balloon 20 can have a balloon distal taper 42 at the terminal distal end 68 or tip of the balloon 20. The distal taper 42 can have a distal taper length 44. The distal taper length 44 can be from about 0 mm (0 in.) to about 14 mm (0.55 in.), more narrowly from about 2 mm to about 9 mm.

The proximal and/or distal tapers 34 and/or 42 can have concave, convex and/or s-curves. For example, the proximal and/or distal tapers 34 and/or 42 can have continuously varying angles with respect to the balloon longitudinal axis 26.

The balloon 20 can have a wall thickness 46. The wall thickness 46 can be less than about 25 μm (0.98 mil). The wall thickness 46 can be from about 25 μm (0.98 mil) to about 250 μm (9.8 mil), more narrowly from about 50 μm (2 mil) to about 150 μm (5.9 mil), for example about 75 μm (3.0 mil) or about 100 μm (4 mil).

The balloon can have a balloon inner diameter 48 and a balloon outer diameter 50. The balloon outer diameter 50 can be measured perpendicular to the balloon longitudinal axis 26 at the widest point along the length of the balloon 20. The balloon outer diameter 50 can be from about 2 mm (0.08 in.) to about 50 mm (in.) for example about 17 mm (0.67 in.), 23 mm (0.91 in.), 3 mm (0.12 in.), or 6 mm (0.24 in.).

The balloon can have a radius (i.e., half the diameter), for example about 8.5 mm, and a distal taper length, for example about 8.5 mm. The ratio of the distal end length to the radius can be from about 2:1 to about 0:1, more preferably about 1:1 to about 0.25:1.

The balloon can have an unsupported burst pressure. The unsupported burst pressure is the pressure at which the balloon ruptures when inflated in free air without any external constraint on the walls at about 1 atm external pressure and about 20° C. temperature. The unsupported burst pressure can be greater than about 150 psi. For example, the unsupported burst pressure can be from about 1,400 kPa (200 psi) to about 10,000 MPa (1,500 psi). More narrowly, the burst pressure can be from about 3,500 kPa (500 psi) to about 6,000 kPa (900 psi). For example, the burst pressure can be about 3,500 kPa (500 psi), about 5,200 kPa (750 psi), about 7,000 (1.000 psi), about 10,000 kPa (1,500 psi), or higher than 10,000 kPa (1500 psi).

The balloon 20 can be non-compliant or inelastic. The balloon can have a failure strain of less than 0.30, more narrowly less than 0.20, more narrowly less than 0.10, yet more narrowly less than 0.05. A non-compliant balloon can have a failure strain of less than 0.30.

The failure strain of the balloon is the difference between the balloon outer diameter when the balloon is inflated to 100% of the burst pressure and the balloon outer diameter when the balloon is inflated to 5% of the burst pressure (i.e., to expand from a deflated state without stretching the wall material) divided by the 100% pressure diameter.

For example, the burst pressure of the balloon can be greater than about 3,500 kPa (500 psi) and have an outer diameter of about 17 mm and a wall thickness of less than about 100 µm with a failure strain of less than about 0.10, for example less than about 0.05.

The reinforced balloon wall may have a high tear strength as compared to traditional polymers. Tear strength can correlate to puncture strength and toughness. For example, in a Mod Mil-C-21189 10.2.4 tear test, a specimen is created. That specimen has a width, a height, and thickness. A slit is made in the sample parallel to the width, mid-way along its height. The slit is then pulled to initiate tear at the corners of the slit. The Mod Mil-C-21189 10.2.4 tear test gives resultant data in tensile pounds force (lbf). For the test to be meaningful as a comparison between two material samples, it should be done on a thickness-comparable basis. A nylon 12 balloon material at about 0.0055 in. thickness failed the test at a mean tensile load of 25 lbf. The balloon wall 22 of about 0005 in. failed at a mean tensile value of 134 lbf.

In an ASTM D-3039 tensile test, a nylon 12 material at 0.0055 in. thickness, failed at a mean tensile load of 22 lbf. The balloon wall 22 of about 0.005 in. failed at a mean tensile value of 222 lbf.

The balloon wall 22 can have one or more layers 72. The balloon 20 can have a leak-proof bladder 52. The bladder 52 can be fluid-tight, such as an air-tight, or saline tight, or a fluid porous bladder. The bladder 52 can be made of a urethane, a nylon, any material listed infra, or combinations thereof. The bladder 52 can be made from the radial innermost layer 72b of the balloon wall 22.

The bladder 52 can be fixedly or removably attached to the hollow shaft 2000, for example at the inside and/or outside diameter of hollow shaft 2000. The hollow shaft 2000 can be a flexible or rigid catheter. The hollow shaft 2000 can deliver pressurized fluid to the balloon volume 24.

Figure 29A:
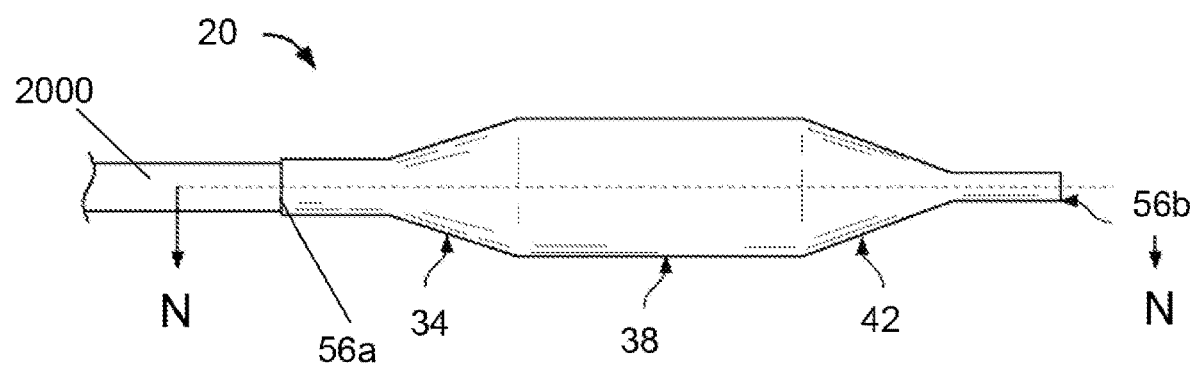
FIG. 29A illustrates a variation of the device.
Figure 29B:
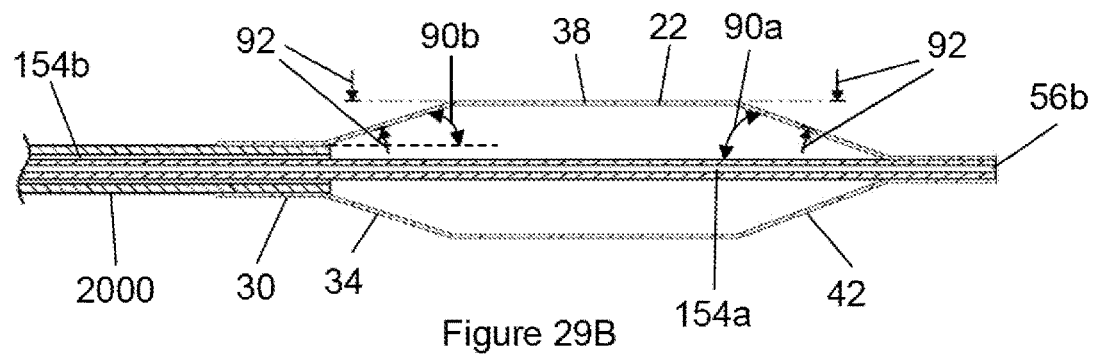
FIG. 29B is a variation of cross-section N-N of FIG. 29A.

The balloon 20 can have one or more balloon fluid ports 56. The hollow shaft 2000 can have a hollow shaft distal port 54. One of the balloon fluid ports 56 can attach to the hollow shaft distal port 54. The balloon 20 (as shown in FIGS. 29A and 29B) can have a balloon fluid first port 56a at a proximal end of the balloon 20 and a balloon fluid second port 56b at a distal end of the balloon 20. The fluid first port 56a can be in fluid communication with the balloon fluid second port 56b via a through lumen and/or the balloon volume 24. The balloon 20 can have a single balloon fluid port 56, two, three or more balloon fluid ports 56. The balloon 20 can have no through lumen. For example, the balloon 20 can have no longitudinal through-lumen extending through the proximal terminal end 70 and through the distal terminal end 68.

FIGS. 3A, 3B and 3C show cross sections of a balloon wall 22. FIG. 3A illustrates that a balloon 20 can have a constant or varying wall thicknesses 46 along the length of the balloon 20. A wall proximal stem thickness 46a can be substantially equal to a wall constant diameter section thickness 46c and the wall proximal taper thickness 46b.

FIG. 3B illustrates that the wall constant diameter section thickness 46c can be substantially greater than the wall proximal stem thickness 46a. The wall proximal taper thickness 46b can be less than the wall constant diameter section thickness 46c and greater than the wall proximal stem thickness 46a.

FIG. 3C illustrates that the wall proximal stem thickness 46a can substantially greater than the wall constant diameter section thickness 46c. The wall proximal taper thickness 46b can be less than the wall proximal stem thickness 46a and greater than the wall constant diameter section thickness 46c.

FIG. 4A illustrates that the balloon 20 can have a single balloon external seam 66a. The seam can extend partially, completely, or not at all through the depth of the wall thickness 46. The balloon external seam 66a can be a longitudinal seam. The balloon external scam 66a can extend from a first lateral side of the balloon 20 at the proximal terminal end 70 of the balloon 20, along the first lateral side of the balloon to the balloon distal terminal end 68. The balloon external seam 66a can wrap around the balloon distal terminal end 68a, extending around the distal end of the balloon 20 and returning on the second lateral side of the balloon 20.

The outer layer 72a of the balloon wall 22 can have an outer layer first panel 76a and an outer layer second panel 76b. The outer layer first panel 76a can cover from about 90° to about 270° of the balloon, as measured along the balloon longitudinal axis 26, for example about 185° of the balloon 20. The outer layer second panel 76b can cover from about 90° to about 270°, as measured along the balloon longitudinal axis 26, for example about 1850.

FIG. 4B illustrates that the balloon external seam 66a can be an overlayed seam or lap joint. The balloon external seam 66a can be flush against the side (i.e., having a substantially constant radius with respect to the balloon longitudinal axis 26) of the outer layer first panel 76a or outer layer second panel 76b. The outer layer first panel 76a can be radially outside of the outer layer second panel 76b where the outer layer first panel 76a overlaps the layer second panel 76b. The outer panels 76 may have an overlap length. The overlap length can be from about 0 mm (0 in.) to about 3 mm (0.1 in.), more narrowly from about 1 mm (0.04 in.) to about 2 mm (0.08 in.). The outer layer first panel 76a can be bonded or adhered (e.g., with epoxy or other adhesive) to the outer layer second panel 76b. The adhesive can be an epoxy.

The inner layer 72b can have a balloon inner seam 66b. The balloon inner seam 66b can join an inner layer first panel 74a and an inner layer second panel 74b. The inner seam 66b can have a similar structure to those described here for the balloon outer seam 66a, FIG. 4C illustrates that the outer layer first panel 76a can be fused, solvated to, glued, adhered to, welded to, or a combination thereof, with the outer layer second panel 76b at the outer seam 66a.

FIG. 5A illustrates that the balloon external seam 66a can be a flange joint. The layer first panel can have a seam first flange 80a around the perimeter of the outer layer first panel 76a. The outer layer second panel 76b can have a seam second flange 80b around the perimeter of the layer second panel. The seam first flange can attach to the seam second flange at the balloon external seam. The flange seam can extend radially away from the balloon longitudinal axis. The balloon external seam can be reinforced. The balloon external seam can be used to cut tissue during use in a biological target site.

FIG. 5B illustrates that the seam first flange can be bonded or adhered to the seam second flange in the flange joint. FIG. 5C illustrates that the layer first panel can be fused, solvated to, glued, adhered to, welded to, or a combination thereof, with the layer second panel in the flange joint.

FIG. 6A illustrates that the balloon external seam 66a can be a lateral or latitudinal seam. The balloon external seam can be in a plane perpendicular or substantially to the balloon longitudinal axis. The balloon can have one or more balloon external seams.

The outer layer first panel 76n can be at the distal end of the balloon 20. The outer layer second panel 76b can be at the proximal end of the balloon 20. The layer second panel can overlay the layer first panel at the balloon external seam.

FIG. 6B illustrates that the outer layer first panel can overlay the outer layer second panel at the balloon external seam 66a.

FIG. 6C illustrates that the balloon wall at a first length along the balloon can have a first layer and a second layer. The first layer can be a radially inner layer 72b, as measured from the balloon longitudinal axis. The second layer can be a radially outer layer 72a. Any of the layers 72 can be a laminate of fiber and resin. The resin can be an adhesive. The fiber and resin laminate can be a matrix of the fiber in the resin.

FIG. 6D illustrates that the balloon wall at a second length along the balloon can have first, second and third layers. The second layer can be a first middle layer 72c between the inner and outer layers. Any combination of the layers can be leak-proof, reinforced with one or more fibers, resistant and releasable from MMA, or combinations thereof. For example, the first layer can be leak-proof and form the bladder. The second layer can be reinforced with a fiber. The third layer can be MMA-resistant and/or MMA-releasing.

An MMA-resistant material can substantially maintain material strength and thickness when exposed to MMA bone cement in any stage of the MMA bone cement from mixing to curing. An MMA-releasable material can form no substantial bond with MMA.

FIG. 7 illustrates that the balloon external seam can be along the balloon at the proximal taper. The balloon external seams can be in the constant diameter section, the distal taper, the proximal taper, the proximal stem, or combinations thereof.

FIG. 8 illustrates that balloon external seam 66b can lie in a plane at a non-perpendicular angle to the balloon longitudinal axis 26. The plane in which the balloon external seam lies can form a seam angle 82 with the balloon longitudinal axis. The seam angle 82 can be from about 0° (i.e., a longitudinal seam) to about 90° (i.e., a latitudinal seam). More narrowly, the seam angle 82 can be from about 30° to about 60°. For example, the scam angle 82 can be about 00, about 30°, about 450, about 60°, or about 900.

Figure 9A:
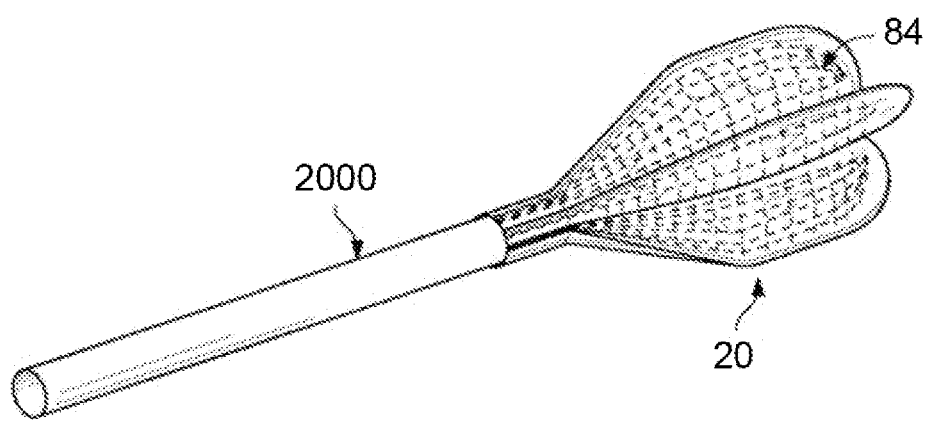
FIG. 9A illustrates a variation of the device in a deflated state.

FIG. 9A illustrates that the balloon 10 can be pleated to form flutes 84, for example four, five or six flutes 84, such as first flute 84a, second flute 84b. The flutes 84 can be made from accordion pleats, box pleats, cartridge pleats, fluted pleats, honeycomb pleats, knife pleats, rolled pleats, or combinations thereof. The pleating can be heat and/or pressure formed and/or the reinforcement fibers and/or panels can be oriented to form the flutes 84. The balloon 20 can be in a deflated configuration when the flutes 84 are shown.

Figure 9B:
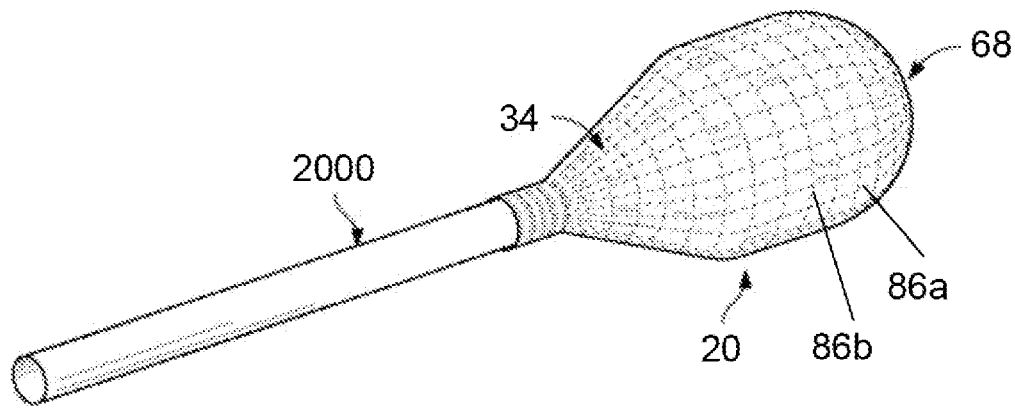
FIG. 9B illustrates a variation of the device in an inflated state.

FIG. 9B illustrates that the balloon 20 in an inflated configuration can push the pleated flutes out to form a substantially smooth outer surface. The balloon 20 can have reinforcement fibers 86. First or longitudinal reinforcement fibers 86a can be parallel with the balloon longitudinal axis 26. Second or latitudinal reinforcement fibers 86b can be perpendicular to the balloon longitudinal axis 26.

Figures 10A, 10B, 10C, 10D:
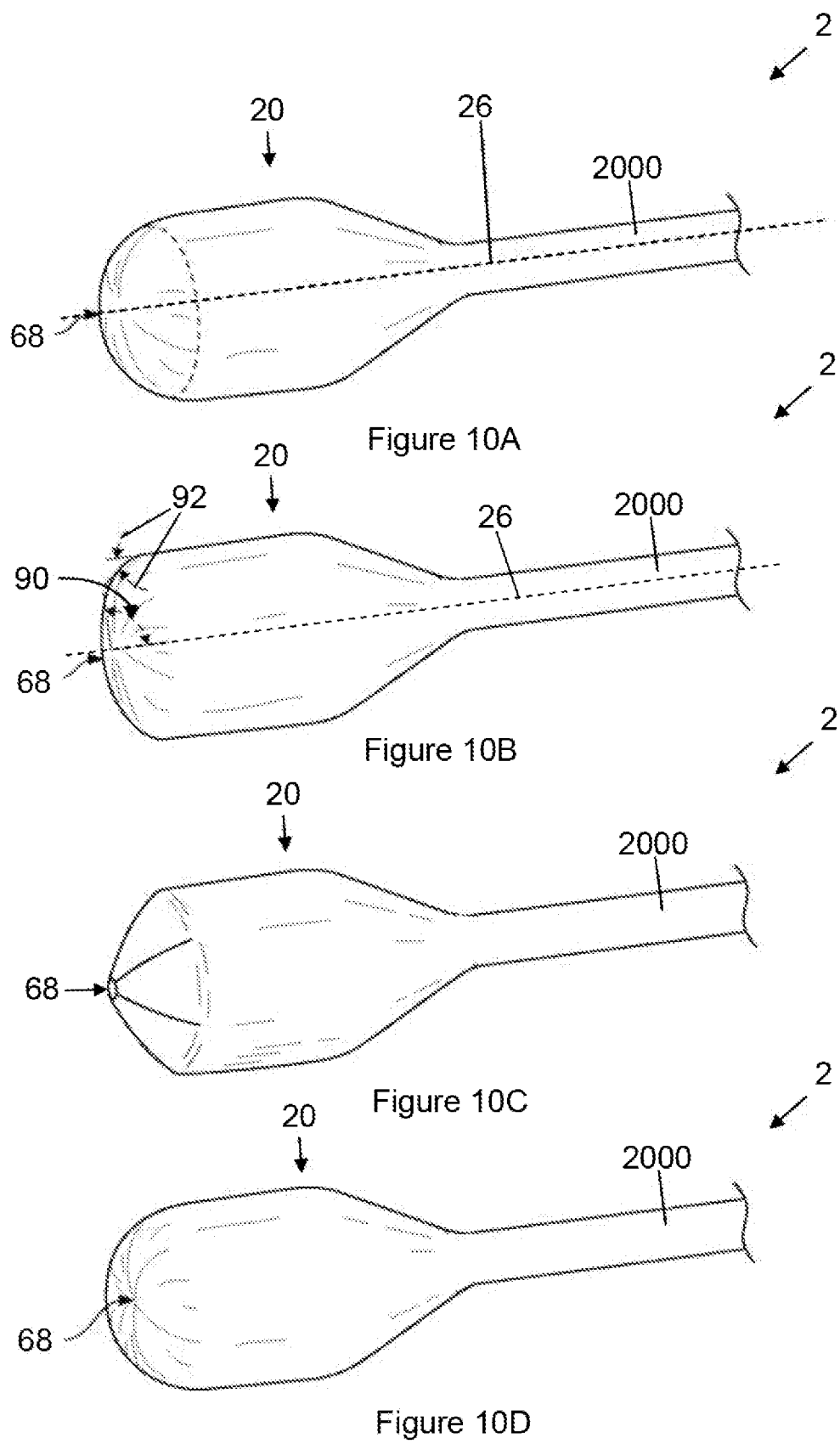
FIGS. 10A through 10D illustrate variations of the device.

The proximal end of the balloon can be bonded, glued, welded to, adhered, clamped, fused, or combinations thereof to the distal end of the hollow shaft. For example, a balloon cuff can apply a tension force between the proximal terminal end of the balloon and the distal end of the hollow shaft FIG. 10A illustrates that the balloon can have a blunt distal terminal end. The distal terminal end can be rounded. The distal taper can have a taper angle 90a measured from a perpendicular off the balloon longitudinal axis. The taper angle can be from about 00 to about 80°, more narrowly from about 2° to about 45°, yet more narrowly from about 5° to about 30°, for example about 0°, 10° or 15°.

FIG. 10B illustrates that the distal terminal end can be substantially flat. The taper angle of the balloon in FIG. 8B is lower than the taper angle of the balloon in FIG. 8A.

FIG. 10C illustrates that the distal terminal end can have facets. The facets can be angularly arranged around the balloon longitudinal axis.

FIG. 10D illustrates that the balloon distal terminal end can be configured to evert into the volume of the balloon. For example, the balloon distal terminal end can be hemitoroidal, for example with an inner diameter of about 0 mm (0 in.).

Figure 11A:
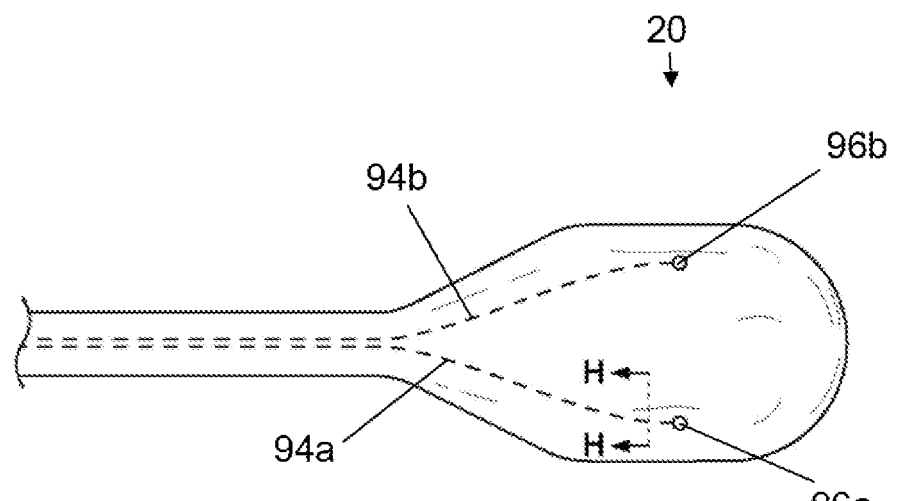
FIGS. 11A and 11B illustrate partially see-through variations of the device.

FIG. 11A illustrates that the balloon can have a first and/or second steering wires 94a and/or 94b. The first and second steering wires 94a and 94b can be evenly (about 180° apart) or unevenly (e.g., about 90° apart) spaced from each other with respect to the balloon longitudinal axis. The balloon can have third and/or fourth steering wires (not shown) evenly spaced along the balloon wall between the first and second steering wires.

The first steering wire 94a can be fixed to the balloon wall at a first wire terminal 96a. The second steering wire can be fixed to the balloon wall at a second wire terminal 96b. The wire terminals 96 can be located in the constant diameter section of the balloon, the proximal taper, the distal taper, or a combination thereof. The first wire terminal 96a can be located at the same or a different length along the balloon as the second wire terminal 96b.

The steering wires 96 can be slidably translatable with respect to the balloon 20, for example except at the terminal ends. Forces can be delivered to the steering wires 96 to angularly rotate or deflect the balloon 20 with respect to an attached member, such as a deployment rod or the hollow shaft.

Figure 11B:
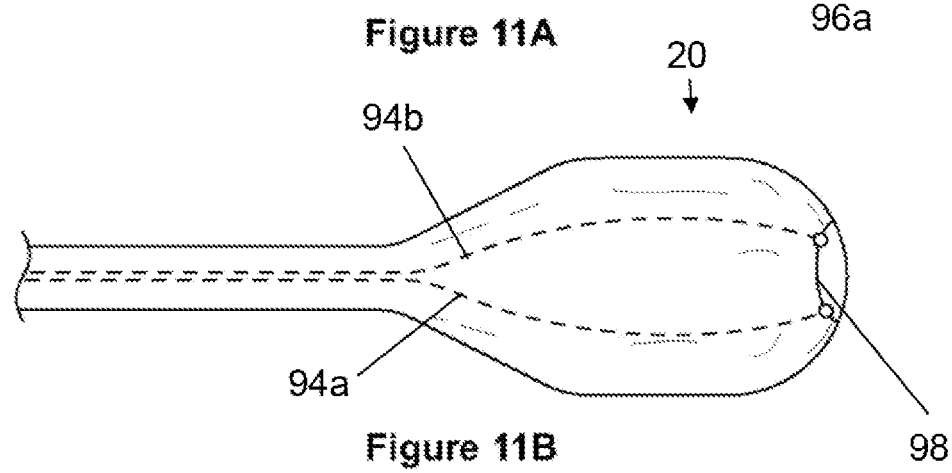

FIG. 11B illustrates that the balloon 20 can have a steering collar 98. The steering collar 98 can be rigid. The steering collar 98 can be a metal or plastic member embedded within or attached to the inside or outside of the balloon wall. The steering collar 98 can be a reinforced area of the balloon wall, for example, reinforced with additional reinforcement fibers. The wire terminals can be located on the steering collar. The steering wires can be fixed to the steering collar. The first steering wire can be fixed to a first steering collar. The second steering wire can be fixed to a second steering collar.

The steering collar can be located in the constant diameter section of the balloon, the proximal taper, the distal taper, or a combination thereof, for example if the balloon has the two or more steering collars and/or the steering collar is at a non-perpendicular angle to the balloon longitudinal axis.

Figures 11C, 11D, 11E, 11F:
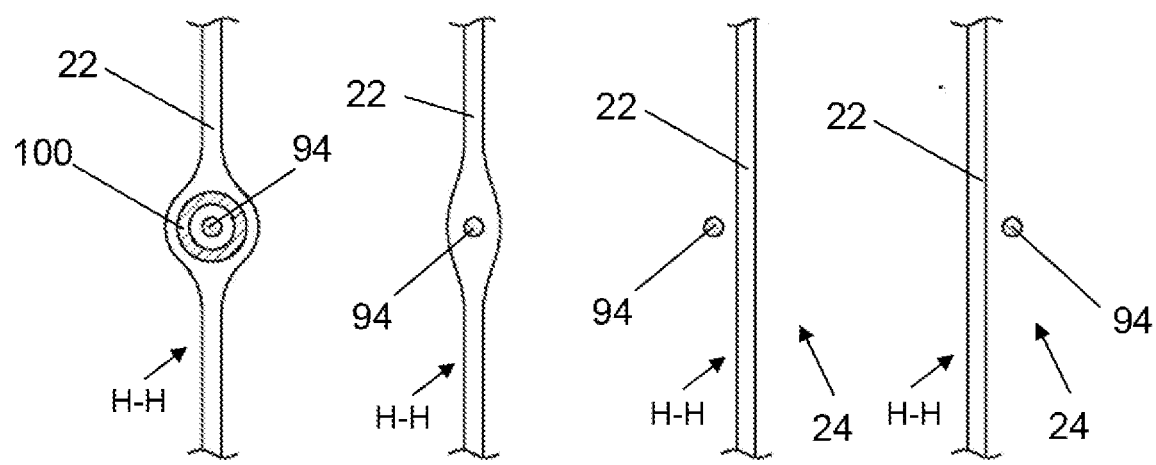
FIGS. 11C through 11F are variations of cross-section H-H of FIG. 11A.

FIG. 11C illustrates that the balloon can have a steering sheath 100. The steering wire 94 can slide within the steering sheath. The steering sheath 100 can be radially inside, radially outside, or embedded within (as shown) the balloon wall 22. The steering sheath 100 can be made from a low friction material and/or be coated with a low friction material, such as PTFE or Teflon.

FIG. 11D illustrates that the steering wire 94 can be located in the balloon wall 22, for example between the inner and outer layers 72b and 72a of the balloon wall 22. The balloon wall 22 can have no steering sheath or the steering sheath can end at a length before the wire terminal 98.

FIG. 11E illustrates that the steering wire can be on the outside of the balloon wall, opposite of the balloon volume. FIG. 11F illustrates that the steering wire can be on the inside of the balloon wall, within the balloon volume.

Figure 12:
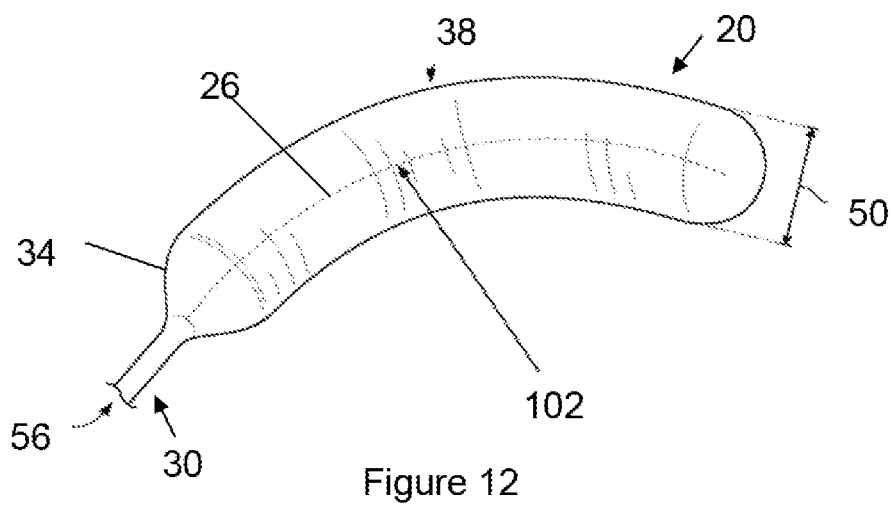
FIGS. 12 through 18 illustrate variations of the device.

FIG. 12 illustrates that the proximal stem, proximal taper, constant diameter section, distal taper, or combinations thereof can be curved. The balloon longitudinal axis can be straight or have a balloon radius of curvature 102. The balloon radius of curvature 102 can be from about 2 to about 50 mm, for example about 5 mm, about 8 mm, or about 30 mm.

Figure 13:
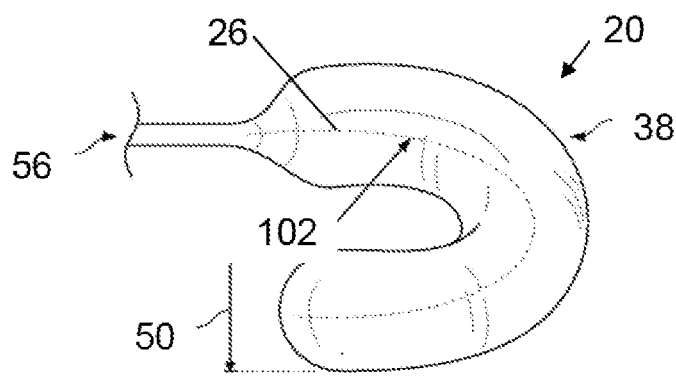
Figure 14:
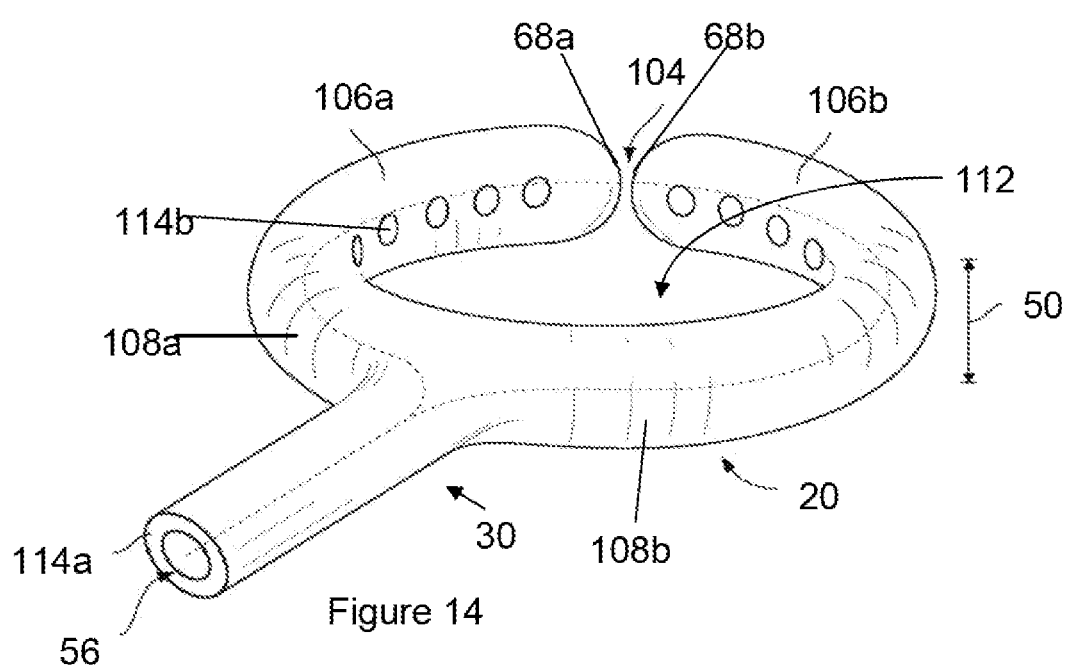

FIG. 13 illustrates that the balloon can have a C-shaped configuration. For example, the balloon radius of curvature can be from about 5 mm to about 40 mm for example about 15 mm FIG. 14 illustrates that the balloon can bifurcate into a first balloon branch 106a and a second balloon branch 106b. The first balloon branch 106a, second balloon branch 106b and proximal stem 30 can be coplanar (as shown) or not coplanar. Third, fourth or more balloon branches can extend from the proximal stem. The balloon branches 106 can be in fluid communication with the proximal stem 30 and other balloon branches 106. The balloon branches 106 can be inflated and deflated concurrently. The balloon branches 106 can be in fluid isolation from the other balloon branches 106. The balloon branches 106 can be inflated and deflated subsequent to the other balloon branches 106.

The proximal stem 30 can have a proximal stem longitudinal axis 110. The balloon first branch 106a and the balloon second branch 106b can be evenly separated (by about 180°) or unevenly separated (e.g., by about 90°) with respect to the proximal stem axis 110.

The balloon first branch 106a can have a first branch longitudinal axis 108a. The first branch longitudinal axis 108a can be straight or curved. The balloon second branch 106b can have a second branch longitudinal axis 108b. The second branch longitudinal axis 108b can be straight or curved. The balloon first branch 106a can have the same, the symmetric, or a different shape as the balloon second branch 106b. The balloon branches 106 can have symmetric c-shapes (as shown).

The balloon first branch 106a can have a balloon first distal terminal end 68a. The balloon second branch 106b can have a balloon second distal terminal end 68b. The balloon 20 can have a terminal end gap 104 between the first distal terminal end 68a and the second distal terminal end 68b.

The balloon wall can have a pressure input port in fluid communication with a pressure channel embedded in or attached to the outside or inside of the wall of the balloon. The port can be for inflating the balloon. The pressure can be delivered to the inner lumen 154a. The pressure can be and is conveyed with water.

The balloon wall can have a bone cement input port 114a. The bone cement input port 114a can be in fluid communication with a bone cement channel embedded in or attached to the outside or inside of the balloon wall 22, or as an outer lumen 154b (shown supra) within the balloon 20.

The balloon first and/or second branch can have one or more bone cement output ports 114b. The bone cement channel can be in fluid communication with the bone cement output ports 114b. The bone cement output ports can open to a contained area 112 defined by the first balloon branch and the second balloon branch. The bone cement output ports can open away from the contained area 112. The bone cement can be a bone cement or one or more liquid, gel or solid bone fillers with no cement properties.

Figure 15:
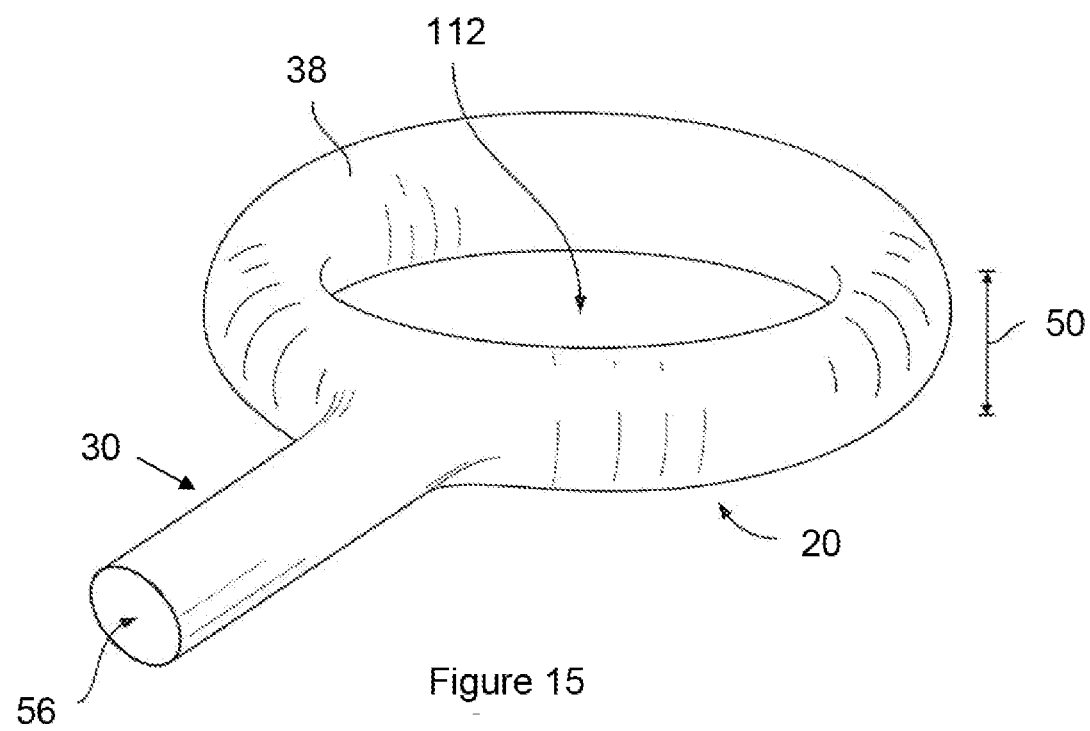

FIG. 15 illustrates that the balloon can have a substantially toroidal configuration. For example, the balloon can have no balloon terminal distal end. The proximal stem can attach to a toroidal constant diameter section. The toroid can define a circular contained area 112.

Figure 16:
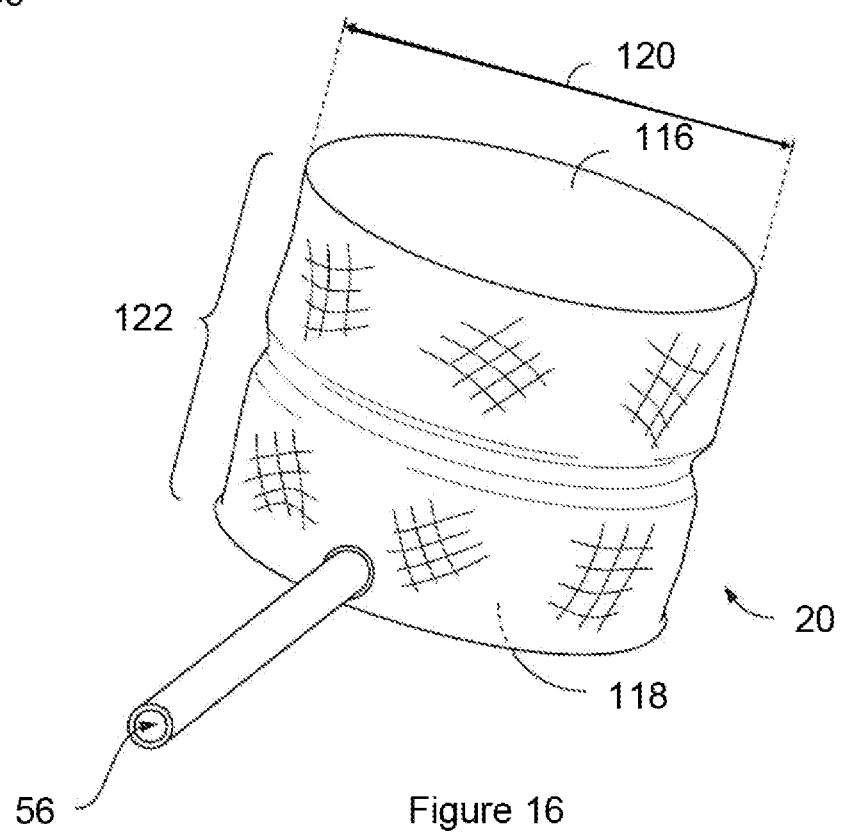

FIG. 16 illustrates that the balloon can have a substantially cylindrical configuration. The balloon can have a balloon top 116, balloon bottom 118 and a balloon pressure input port 56. During inflation, the balloon 20 can expand in the vertical direction. The balloon 20 can be folded in a contracted or deflated configuration. The ratio of balloon height 120 to balloon width 120 can be 1:3. For example, the balloon can form a disc. The ratio of balloon height 120 to balloon width 120 can be 1:1, for example the balloon can expand significantly in height during expansion. The balloon top 116 can be parallel to the balloon bottom 118. The balloon top 116 can be flat or tilted at about 10°, about 20°, or about 30° relative to the balloon bottom 118.

Figure 17:
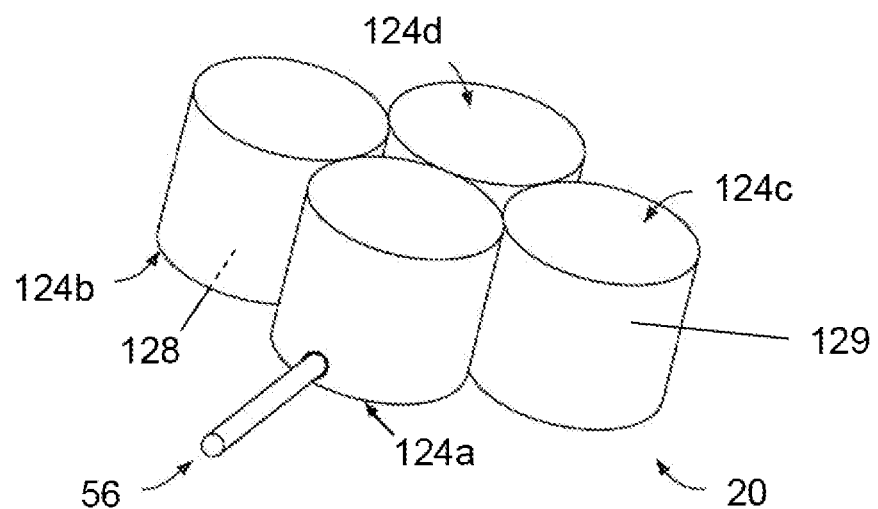

FIG. 17 illustrates that the balloon 20 can have balloon first, second, third and fourth segments 124a, 124b, 124c, and 124d. The balloon segments 124 can have cylindrical configurations. The balloon segments 124 can have segment sides 129, segment tops 126 and segment bottoms 128. The balloon segments 124 can be attached to the adjacent segments at the segment sides 129. The balloon segments 124 can be in fluid communication with each other and the proximal stem, for example by a common inflation lumen, or separately in fluid communication with proximal stem. The segments can be inflated concurrently, in combinations (e.g., the first and fourth segments concurrently, then the third and second segments), or sequentially.

The proximal stem shown herein can be substituted in variations for the hollow shaft and the hollow shaft can be substituted in variations for the proximal stem.

Figure 18:
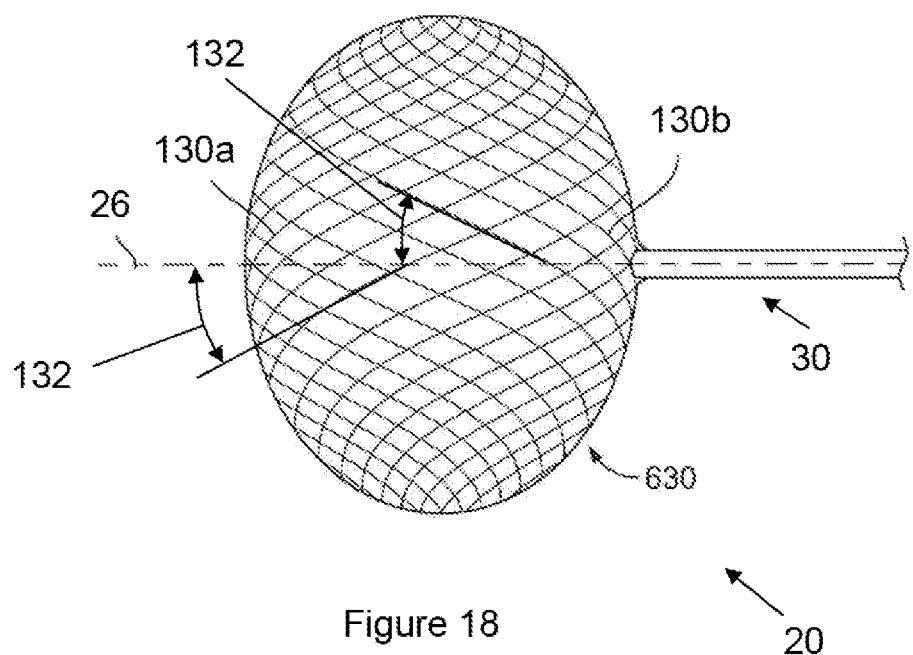

FIG. 18 illustrates that the balloon can have anisotropic compliance or elasticity characteristics across the balloon wall 22. For example, the balloon 20 can be less compliant or substantially non-compliant parallel to the balloon longitudinal axis, and more compliant perpendicular to the longitudinal axis.

The balloon wall 22 can have a first unidirectional fiber-reinforced laminate 130a oriented at a fiber angle 132 of about 15° relative to balloon the balloon longitudinal axis. The balloon wall 22 can have a second unidirectional fiber-reinforced laminate 130b oriented at a fiber angle 132 of about −15° relative to the balloon longitudinal axis. As the pressure inside the balloon increases, the diameter of the balloon adjacent to the balloon longitudinal axis can be substantially constant. As the pressure inside the balloon increases, the diameter of the balloon perpendicular to the longitudinal axis can substantially increase.

Figure 19A:
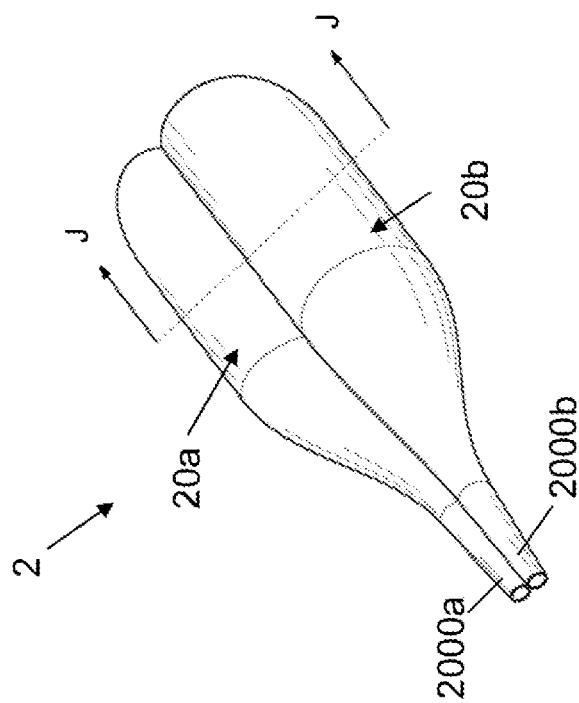
FIG. 19A illustrates a variation of the device.
Figure 19B:
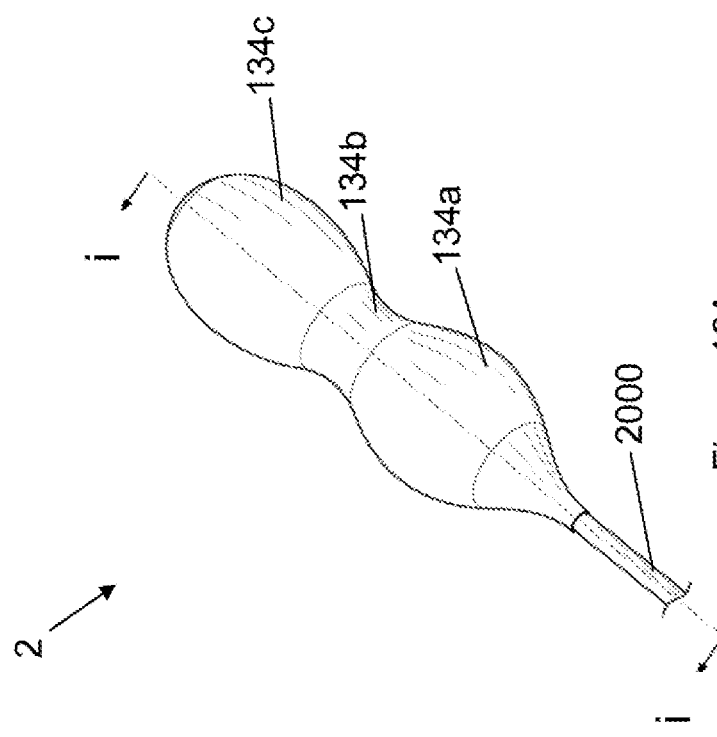
FIG. 19B is a variation of cross section i-i of FIG. 19A.

FIGS. 19A and 19B illustrate that the balloon can have a peanut configuration, like the balloon configuration shown in FIGS. H and H'.

Figure 20A:
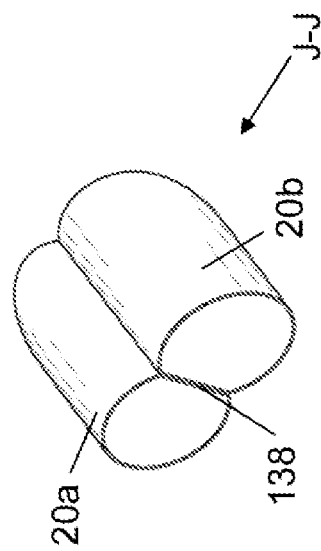
FIG. 20A illustrates a variation of the device.
Figure 20B:
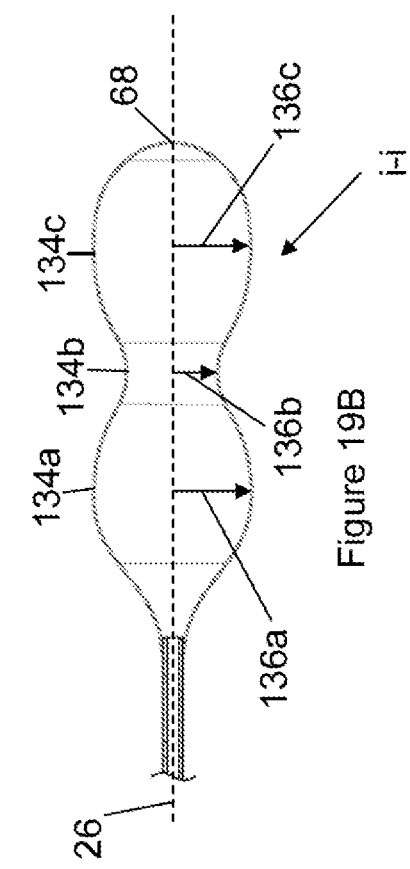
FIG. 20B is a variation of cross section JJ of FIG. 19A.

FIGS. 20A and 20B illustrate that a first balloon 20a can be bonded to a second balloon 20b. The first balloon 20a can be bonded to the second balloon 20b, for example along a bonded surface 138. The bonded surface 138 can be parallel with the balloon longitudinal axis.

FIGS. 21A and 21B illustrate that the balloon 20 can have a flat balloon top and/or flat balloon bottom 116 and/or 118. The balloon 20 can apply a uniform force across the balloon top and/or bottom 116 and/or 118 to the endplates of the vertebrae.

The balloon 20 can be shaped to follow the contours of the vertebral body. The balloon 20 can have a first lateral side 117a and a second lateral side 117b. The first lateral side 117a can have an inner radius of curvature. The second lateral side 117 can have an outer radius of curvature. The inner radius of curvature can be from about 5 mm to about 30 mm for example about 15 mm. The outer radius of curvature can be from about 5 mm to about 30 mm for example about 20 mm.

The inner radius of curvature side can face the posterior of the vertebral body. The outer radius of curvature side can face the anterior of the vertebral body.

FIGS. 22A and 22B illustrate that the balloon can have a substantially cylindrical configuration and that the balloon top and/or balloon bottom can curve when the balloon is in an expanded or inflated configuration. The balloon top can have a balloon top radius of curvature 140. The balloon bottom can have a balloon bottom radius of curvature 142. The balloon top radius of curvature 140 can be substantially equal to or different from the balloon bottom radius of curvature 142. The balloon top and/or balloon bottom can be reinforced, for example altering the respective radius of curvature. The balloon top or bottom radius of curvature 140 or 142 can be from about 250 mm to about 30 mm for example about 60 mm.

FIG. 23A illustrates that the balloon can have a cylindrical configuration oriented with the flat balloon top and flat balloon bottom facing parallel with the balloon longitudinal axis.

FIG. 23B illustrates that the balloon top and/or balloon bottom can be reinforced. For example, the balloon top and/or bottom can have vanes, hard plastic or metal (e.g., tantalum) discs, one, two or more layers of laminate compared to the wall of the balloon side, or combinations thereof.

FIG. 23C illustrates that one, two or more internal restraints 144 can be oriented longitudinally within the balloon. For example, the internal restraints 144 can be fixed to the balloon top and the balloon bottom.

FIG. 24A illustrates that the balloon can have a cube or three-dimensional rectangular configuration. The balloon can have six substantially flat balloon faces 146. The balloon faces 146 can be oriented at a right angle to the adjacent balloon faces 146. The balloon 20 can have a balloon edge 148 between adjacent faces.

FIG. 24B illustrates that the balloon 20 can have a one or more first internal restraints 144a. The first internal restraints 144a can be non-compliant fibers or wires fixed to opposing balloon faces. The first internal restraints 144a can be oriented vertically or latitudinally within the balloon. The balloon can have one or more second internal restraints 144b. The second internal restraints 144b can be oriented perpendicular to the first internal restraints 144a. The second internal restraints 144b can be oriented laterally or latitudinally within the balloon. The balloon can have one or more third internal restraints (not shown). The third internal restraints can be oriented perpendicular to the first and second internal restraints. The third internal restraints can be oriented longitudinally within the balloon. The restraints 144 can terminate on in the inside surface of the balloon wall 22, within the balloon wall 22 or on the outside of the balloon wall 22 (not shown).

Figure 25:
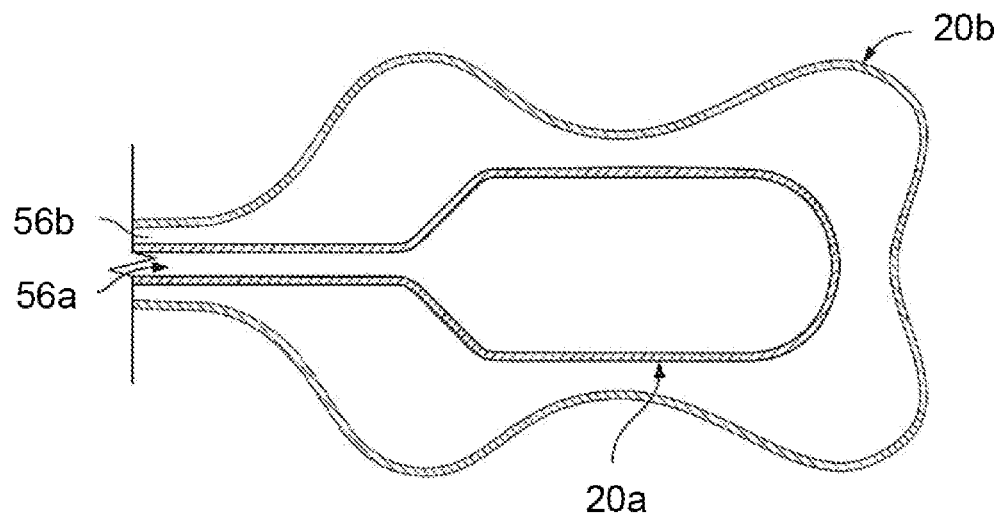

FIG. 25 illustrates that a first balloon 20a can be inflated though the first pressure inlet port 56. A second balloon 20b can surround the first balloon 20a. The second balloon 20b can be inflated though a second pressure inlet port 58. The first balloon 20a and the second balloon 20b can have different shapes when inflated. The first balloon 30a and the second balloon 30b may be inflated independently during a medical procedure. The first balloon 30a can be used to create an initial lumen in the body. The second balloon 30b can be used to shape or expand the initial lumen in the body.

Figure 26:
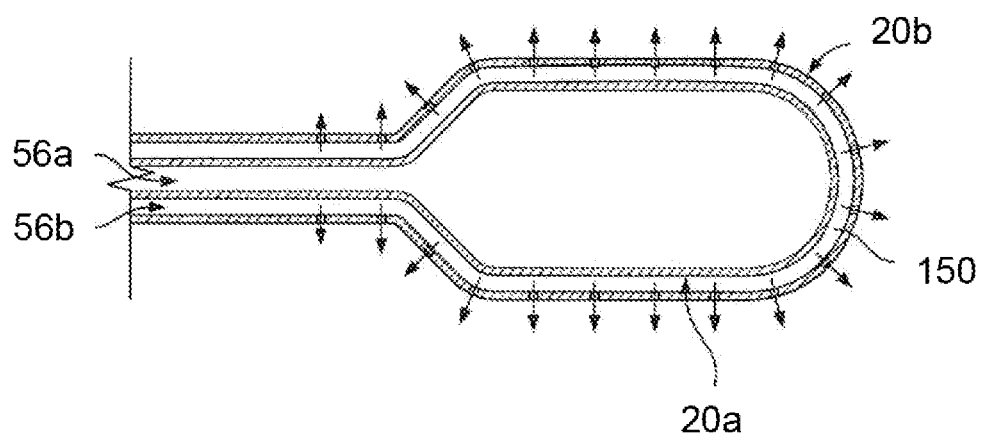

FIG. 26 illustrates that a first balloon 30a can be inflated though the first pressure inlet port 56a. The second balloon 30b can surround the first balloon 30a. The second balloon 20b can be separated from the first balloon 20a by an inter-balloon gap 150. The second balloon 20b can be in contact with the first balloon 20a (i.e., the inter-balloon gap 150 can be 0). The second balloon 30b can be inflated though the second pressure inlet port 58. The first balloon 20a and the second balloon 20b can have different shapes when inflated. The first balloon 20a and the second balloon 20b may be inflated independently during a medical procedure. The second balloon 20b can have holes in the balloon wall that leak inflation material during an inflation cycle. The second balloon 20b can be biocompatible. The inflation material can be bone cement. The bone cement can cure and leave the second balloon 20b implanted in the body. The first balloon 20a may be deflated and withdrawn before the bone cement cures.

FIG. 27 illustrates that the balloon 20 can extend from a lateral side of the hollow shaft 2000.

FIG. 28 illustrates that the balloons 20 can inflate from one lateral side of the hollow shaft 2000. Pressure is provided into the inflation lumen from the proximal end of the hollow shaft 2000. The balloons 20 may be of the same or different shapes. There may be two balloons 20 attached to the hollow shaft 2000. There may be four balloons 20 attached to the hollow shaft 2000.

FIGS. 29A and 29B illustrate that the balloon 20 can have a balloon first fluid port 56a at a first end and a balloon fluid second 56b port at a second end. The balloon 20 can have a distal stem 152 and a proximal stem. The balloon can have a longitudinal through lumen. The distal taper angle can be from about 0 to about 90°, more narrowly about 40° to about 15°, yet more narrowly about 30° to about 10°, for example about 22°. The proximal taper angle 90b can be from about 0 to about 90°, more narrowly about 40° to about 15°, yet more narrowly about 30° to about 10°, for example about 22°. The distal blunting angle 92 can be from about 0 to about 90°, more narrowly about 50° to about 85°, yet more narrowly about 60° to about 80°, for example about 68°. The distal blunting angle 92 can be about equivalent to the distal taper angle 90b.

FIGS. 30A and 30B illustrate that the balloon 20 can have a first segment 124a and a second segment 124b. The first segment 124a and the second segment 124b can be longitudinally concurrent. The distal end of the balloon wall can be attached to the distal end of the hollow shaft 2000 so the balloon wall 22 extends from the proximal side of the attachment.

FIG. 30C illustrates that the distal end of the balloon can be configured to extend distally past the attachment of the balloon to the hollow shaft, for example past the distal end of the hollow shaft. The shaft defining the inner lumen can translate in the longitudinal direction with respect to the hollow shaft 2000.

FIGS. 31A and 31B illustrates that the distal end of the balloon wall can be attached to the distal end of the hollow shaft so the balloon wall extends from the distal side of the attachment.

FIGS. 32A and 32B illustrates that the distal end of the balloon wall can be attached to the distal end of the hollow shaft so the balloon wall extends from the distal side of the attachment. The proximal terminal end of the balloon can overhang the outer hollow shaft.

FIGS. 33A and 33B illustrate that from the proximal end to the distal end, the balloon can have a proximal taper, a first step 134a, a first step taper, a second step 134b, a second step taper, a third step 134c, and a distal taper, or combinations thereof. The first step 134a can have a first step radius 136a. The second step 134b can have a second step radius 136b. The third step 134c can have a third step radius 136c. The first step radius 136a can be greater than or less than (as shown) the second step radius 136b. The second step radius 136b can be greater than or less than (as shown) the third step radius 136c. The first step radius 136a can be greater than or less than (as shown) the third step radius 136c.

During use, the increasing radii steps can be used to measure the target site and use the best size of balloon without having to remove the balloon from the patient and delivering a second balloon to the target site. For example, the balloon can sequentially dilate a stenotic vessel or valve with increasing known radii (e.g., instead of purely by feel) of dilation.

FIGS. 34A and 34B illustrate that the first step radius and the third step radius can be substantially equal. The second step radius can be less than the first step radius and the third step radius.

FIG. 34C illustrates that a radially expandable implant 156 can be removably attached to the balloon wall 22. For example, a stent, a percutaneous aortic heart valve, a replacement heart valve annulus, or combinations thereof, can be balloon-expandable and deformed into the second step before insertion of the balloon into the target site.

Figure 35A:
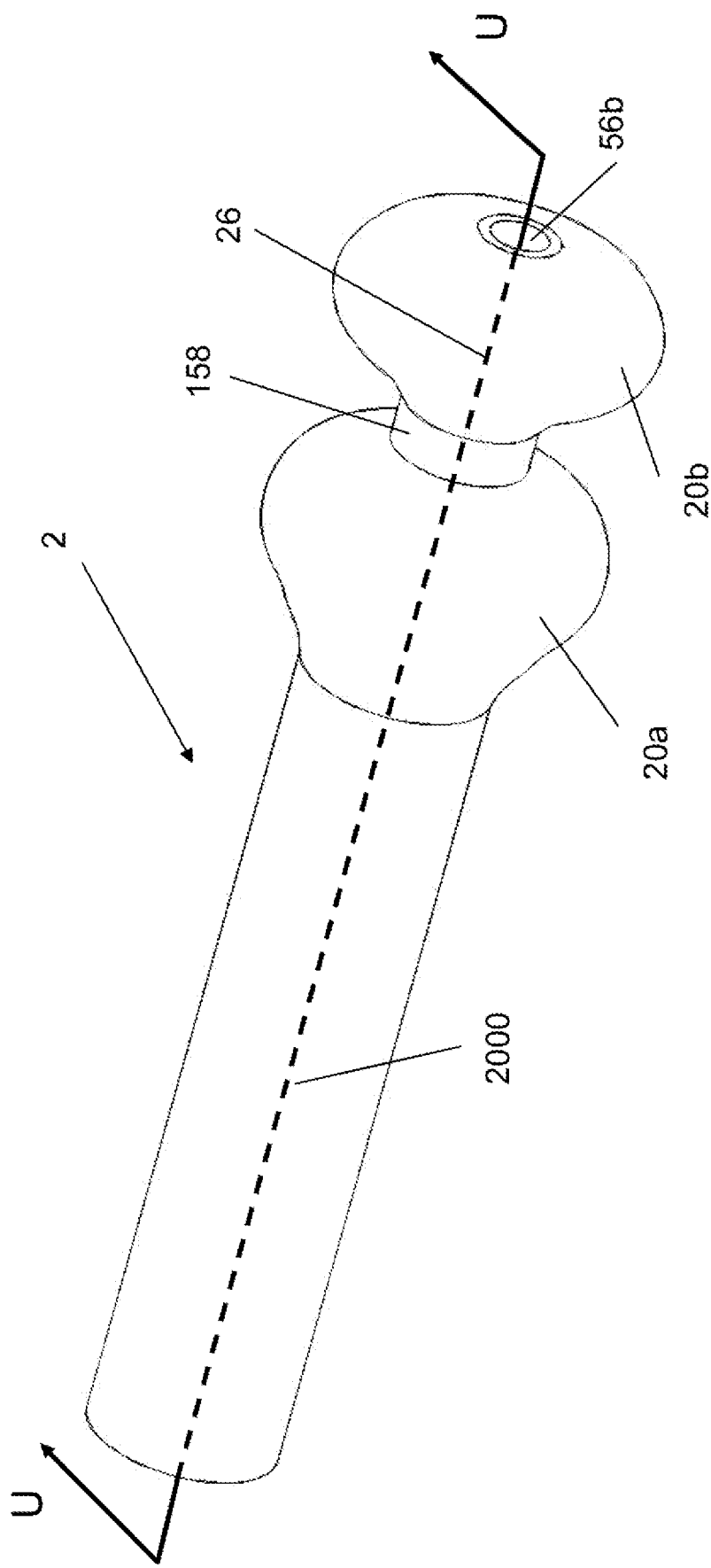
FIG. 35A illustrates a variation of the device.

FIG. 35A illustrates that an inflation device can have a first balloon 20a and a second balloon 20b. The second balloon 20b can be longitudinally distal to the first balloon 20a. The first balloon can be directly attached to the second balloon. The first balloon 20a can be attached to a proximal end of a balloon joint 158. The second balloon 20b can be attached to a distal end of the balloon joint 158.

The first balloon can be in fluid communication with the second balloon. The first balloon can be inflated and/or deflated concurrent with the second balloon. The first balloon can be in fluid isolation from the second balloon. The first balloon can be inflated and/or deflated precedent or subsequent to the second balloon's inflation or deflation.

The distal terminal end of the second balloon 20b can have a balloon second fluid port 56b. The balloon second fluid port 56b can be in fluid communication with the hollow shaft 2000 and/or the first and/or second balloons 20a and/or 20b.

Figure 35B:
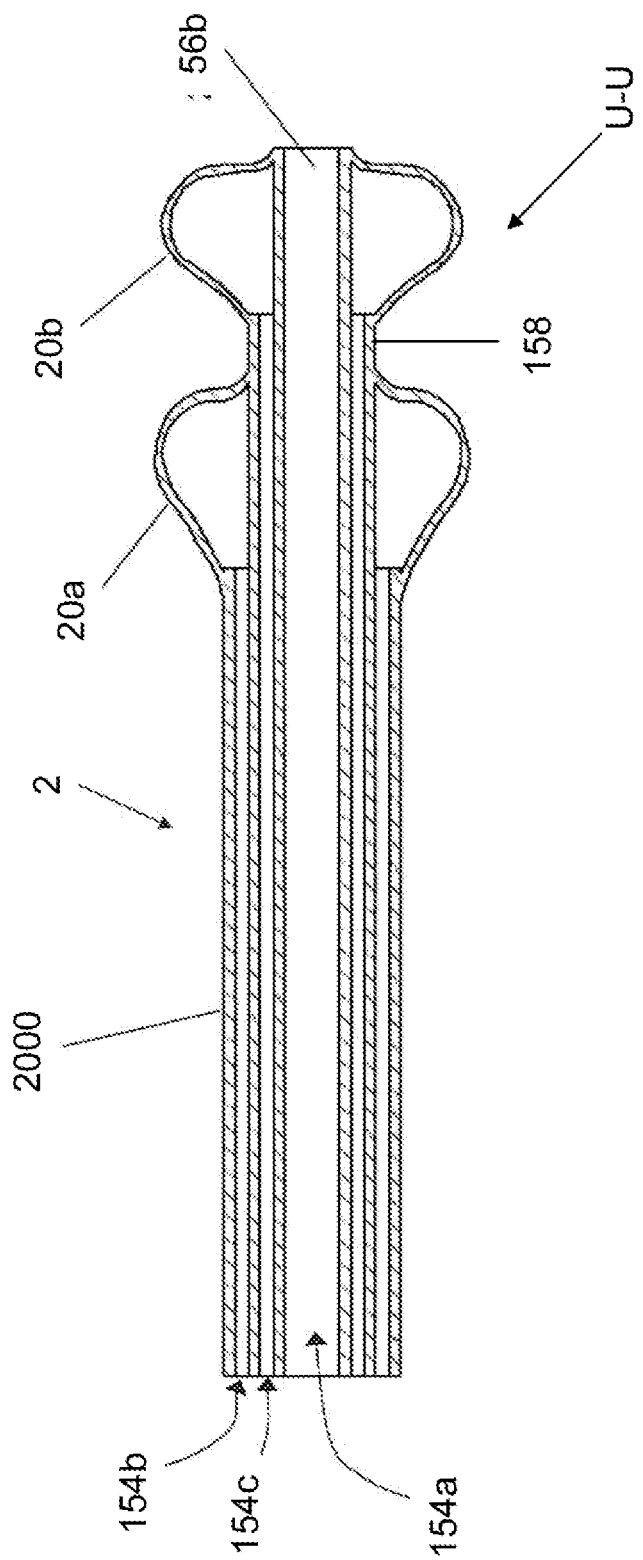
FIG. 35B is a variation of cross-section U-U of FIG. 35A.

FIG. 35B illustrates that the fluid port can be in fluid communication with an inner lumen. The inner lumen and balloon second fluid port can be made of a material that does not bond to or degrade by exposure to common bone cements, such as methyl methacrylate. A middle lumen 154c can be in fluid communication with the interior of the second balloon 20b. The middle lumen 154c can inflate the second balloon 20b.

The outer lumen 154b can be in fluid communication with the interior of the first balloon 20a. The outer lumen 154b, can inflate the first balloon 20a. Various pumps, syringes or pressure sources (not shown), or combinations thereof, can attach and deliver fluid pressure to the inner, middle or outer lumens 154a, 154c, 154b.

The device 2 can be inserted into a structure in the body. The structure can be bone. As described herein, the first and second balloons 20a and 20b can be inflated to create a balloon void in the body structure. One of the balloons 20 can be deflated and left in the body. An adhesive, (for instance, bone cement) can be injected though the inner lumen 154a and emerge from the balloon second fluid port 56b into the balloon void created in the body. The adhesive can fill or partly fill the portion of the balloon void created by the just-deflated balloon. The adhesive can cure while the other balloon remains inflated. The remaining balloon can then be deflated and the inflation system withdrawn. Adhesive can be injected to fill or partially fill the lumen created in the body structure by the inflation system. More than two balloons (e.g., three or four) can be used with the inflation system.

FIGS. 36A and 36B illustrate that the balloon 20 can have a toroidal or annular shape. A fluid conduit 176 can extend from the hollow shaft 2000 to the balloon 20. The fluid conduit 176 can delivery fluid pressure to inflate and deflate the balloon 20. The balloon 20 can have an inner wall 22a and an outer wall 22b. The inner wall 22a can be radially inside the outer wall 22b. The balloon 20 can have an annular lumen 160 passing through the radial center of the balloon 20. The annular lumen 160 can open to an annular lumen distal port 162a and an annular lumen proximal port 162b.

The distal end of the annular lumen 160 can be attached to one or more distal tensioners 164a. The distal tensioners 164a can be elastic or inelastic wires, fibers or threads. The distal tensioners 164a can be fixed at distal tensioner first ends evenly or unevenly angularly distributed around the distal end of the balloon 20. The distal tensioners 164a can attach at distal tensioner second ends to a distal tension anchoring wrap 166a. The distal tension anchoring wrap 166a can be fixed to the hollow shaft 2000.

The proximal end of the annular lumen 160 can be attached to one or more proximal tensioners 164b. The proximal tensioners 164b can be elastic or inelastic wires, fibers or threads. The proximal tensioners 164b can be fixed at proximal tensioner first ends evenly or unevenly angularly distributed around the proximal end of the balloon. The proximal tensioners 164b can attach at proximal tensioner second ends to a proximal tension anchoring wrap 166b. The proximal tension anchoring wrap 166b can be fixed to a tensioning collar 168.

The second step can form a waist. The waist can have additional hoop wrapped fibers. The waist can be substantially non-compliant. The waist can be from about 0 mm to about 12 mm in the balloon longitudinal direction, more narrowly from about 3 mm to about 9 mm. The waist diameter can be from about 2 mm to about 35 mm, for example about 3 mm, about 6 mm, about 20 mm, or about 23 mm.

The tensioning collar 168 can be slidably attached to the hollow shaft 2000. The tensioning collar 168 can translate longitudinally, as shown by arrows in FIG. 36B, along the shaft. The tensioning collar can be pulled and/or pushed by a control line 170 or rod. Before deployment of the inflatable device and after deployment but before removal of the inflatable device, the balloon can be deflated and contracted against the hollow shaft. For example, the control line can be pulled to retract the proximal end of the balloon. For example, the balloon can fold and contract against the hollow shaft. The balloon may be pleated such that, when the tensioning collar is pulled or when a vacuum is applied tot the inflatable device, the balloon contracts into a small, packed form (not shown).

The balloon can have a distal segment 172a and a proximal segment 172b. The distal segment 172a and the proximal segment 172b can be annular or toroidal. The annular or toroidal planes can be perpendicular to the balloon longitudinal axis 26. The distal segment 172a can be longitudinally adjacent to the proximal segment 172b. The distal segment 172a can be directly bonded to the proximal segment 172b or joined to the proximal segment 172b by a segment joint 174. The segment joint 174 can be open and allow fluid communication between the proximal segment 172b and the distal segment 172a (not shown) or can be closed to isolate the fluid volume or the proximal segment 172b from the fluid volume of the distal segment 172a.

The distal segment and/or the proximal segment may be inflated by a tube. The tube may be attached to the hollow shaft.

The outer wall, the inner wall, or both walls, may contain a radiopaque material as described herein.

The outer wall of the distal segment can form the first step. The segment joint can form the second step. The outer wall of the proximal segment can form the third step. The second step can be radially smaller than the first step and the second step. A device, such as a minimally invasive replacement heart valve can be attached to the outside of the balloon.

Figure 37B:
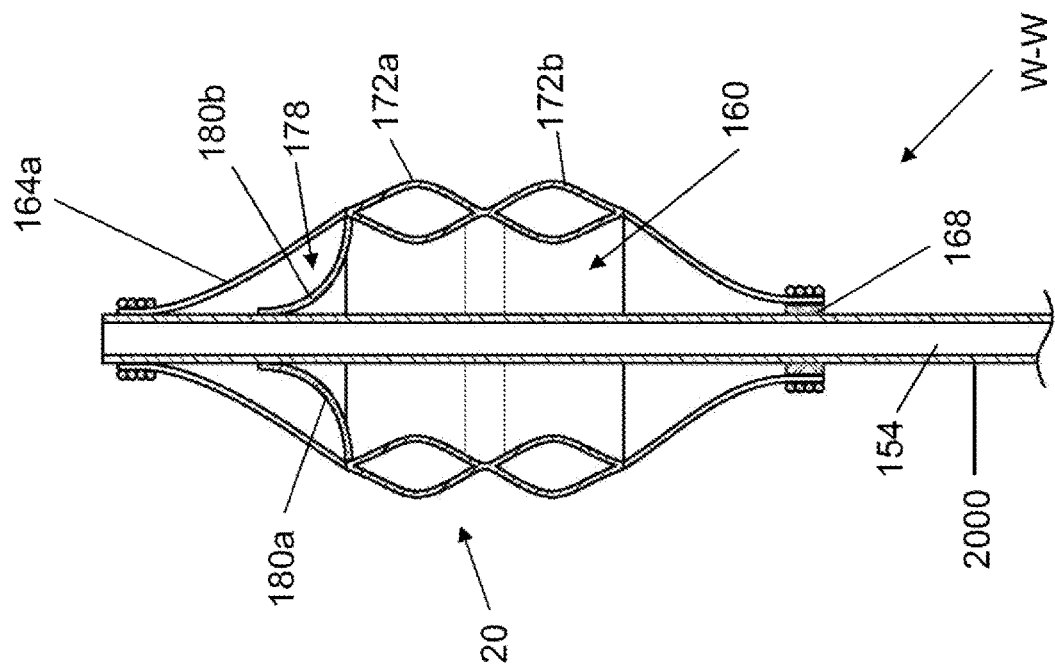
FIG. 37B is a variation of cross-section W-W of FIG. 37A.
Figure 37A:
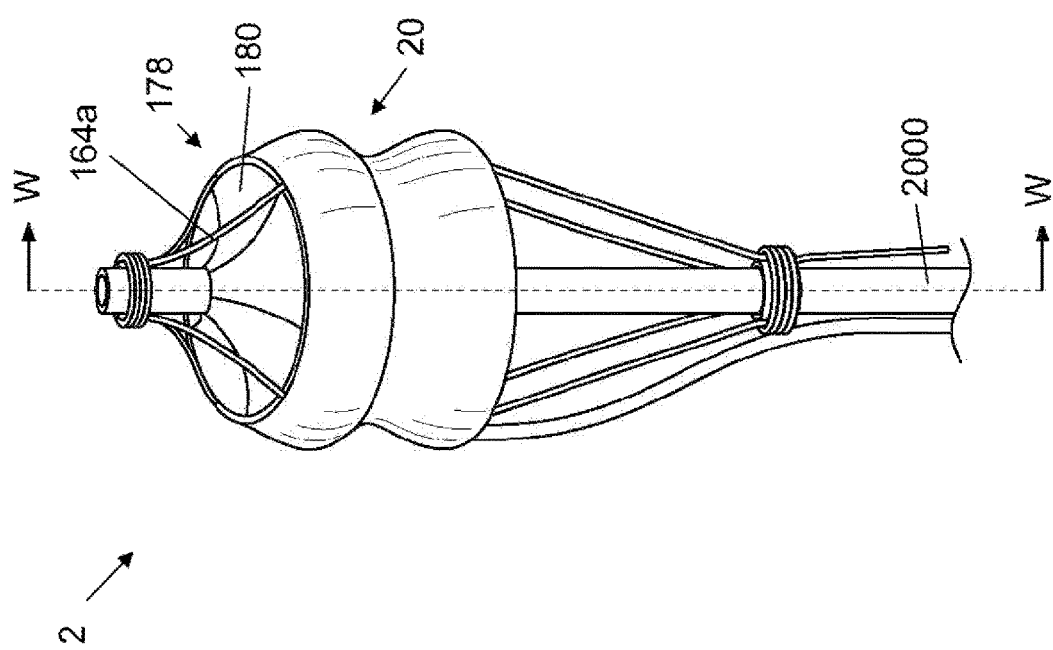
FIG. 37A illustrates a variation of the device.

FIGS. 37A and 37B illustrate that the device (shown in 36A and 36B) can have a valve 178. The valve 178 can have a first leaflet 180a, a second leaflet 180b, a third leaflet (not shown), or more. The leaflets 180 can be thin and flexible. The leaflets 180 can collapse inside the annular lumen when the balloon is in a contracted configuration. The valve can allow flow through the annular lumen 160 in the distal direction and prevent flow through the annular lumen 160 in the proximal direction. The valve 178 can be fixed to the distal end of the distal segment of the balloon. The leaflets 180 can be oriented to allow flow distally through the annular lumen and impede or prevent flow proximally through the annular lumen. The leaflets 180 can be oriented to allow flow proximally through the annular lumen and impede or prevent flow distally through the annular lumen.

Figure 38B:
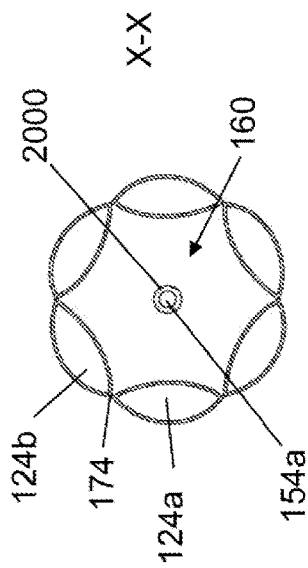
FIGS. 38B, 38C and 38D are variations of cross-section X-X and Y-Y of FIG. 38A.
Figure 38C:
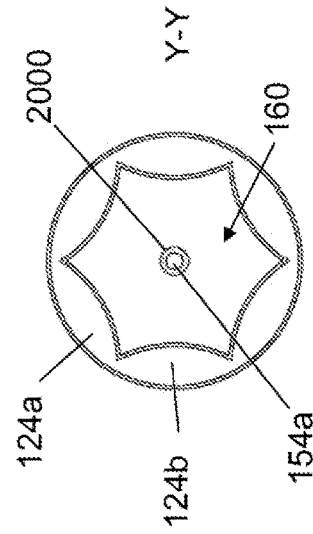
Figure 38D:
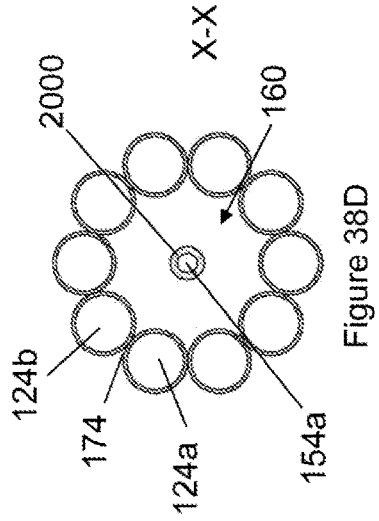
Figure 38A:
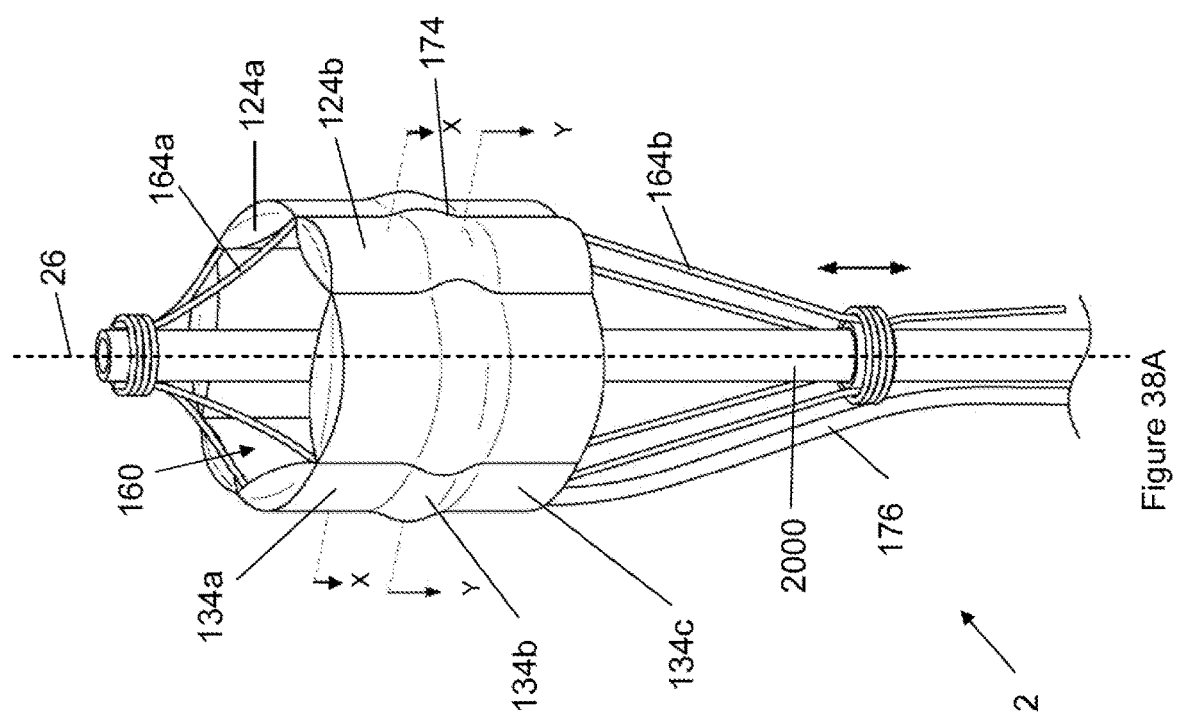
FIG. 38A illustrates a variation of the device.

FIG. 38A illustrates that the balloon can have segments that can be angularly adjacent to each other. For example, the segments and the segment joints can be parallel with the longitudinal axis. The second step can have a larger radius than the first step or the third step. The proximal and distal tensioners can attach to the segments and/or segment joints.

The segments may be inflated by a tube. The tube may be attached to the hollow shaft 2000. The distal and/or proximal tensioners can attach to the balloon at the segment joints and/or at the segments.

The segment walls can have a radiopaque foil and/or a wire, such as a radiopaque marker wire.

FIG. 38B illustrates that the segments can be in fluid isolation from each other at the length along the balloon shown in FIG. M1. The segments can have a flattened circle longitudinal cross-sectional configuration. For example, the segments can be almond or eye-shaped.

FIG. 38C illustrates that the segments can be in fluid communication with each other at a length along the balloon shown in FIG. M1.

FIG. 38D illustrates that the segments can have a circular longitudinal cross-sectional configuration. For example, the segments can be cylindrical.

Figure 39B:
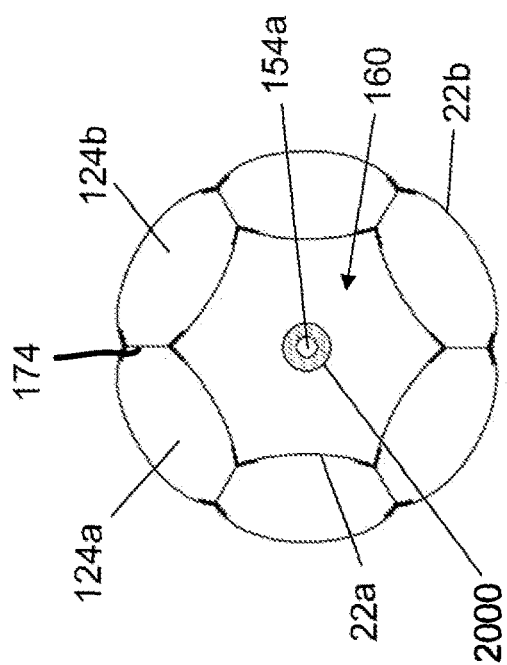
FIGS. 39B, 39C are variations of cross-section Z-Z and AA-AA respectively of FIG. 39A.
Figure 39C:
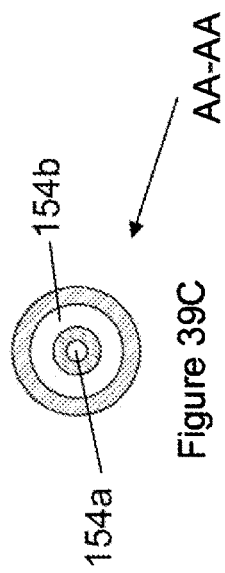
Figure 39A:
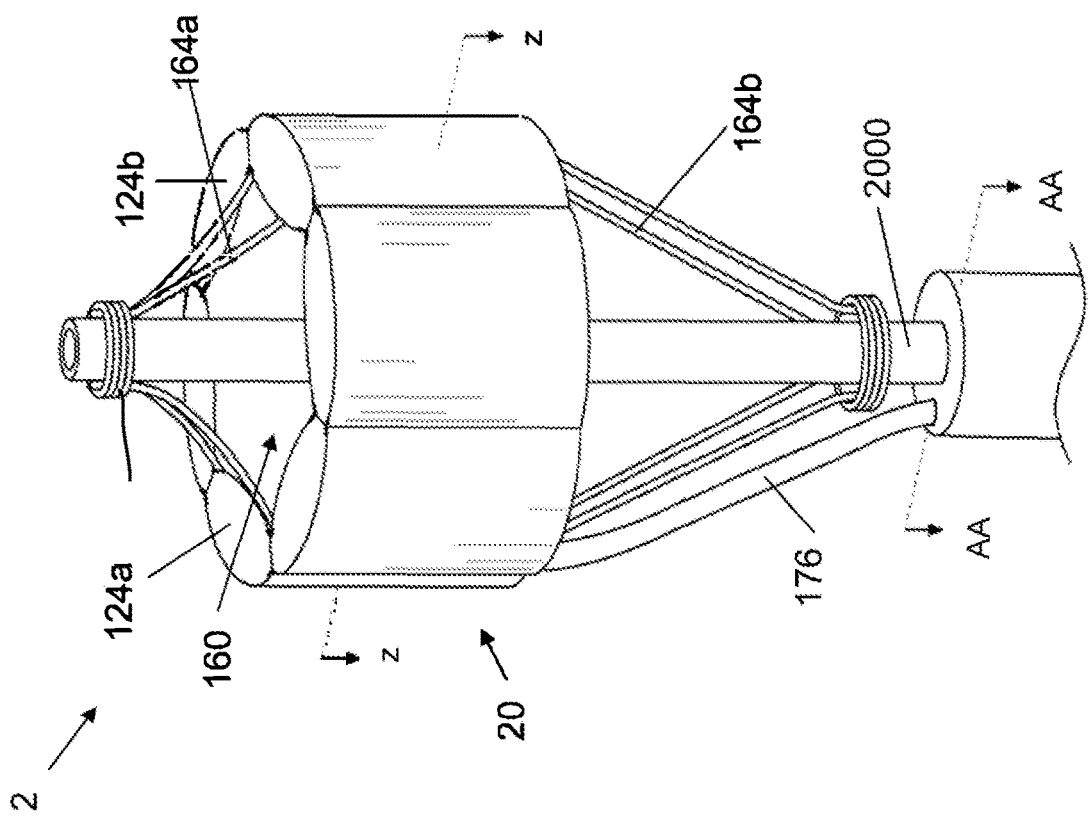
FIG. 39A illustrates a variation of the device.

FIGS. 39A and 39B illustrate that the balloon can have a constant outer diameter when measured along the longitudinal axis nope, it won't quite do that. For example, the balloon can have a single step. The balloon can have an inner wall 22a, an outer wall 22b and segment joints 174. The segment joints 174 can connect the inner wall to the outer wall. The segment joints 174 can minimize the inward radial collapse of the inner wall during inflation.

FIG. 39C illustrates that the hollow shaft can have an inner lumen 154a and an outer lumen 154b. The fluid conduit can be in fluid communication with the outer lumen and the balloon. The outer lumen can deliver pressure through the fluid conduit and to the balloon. The inner lumen can be a through lumen. The outer lumen can extend through the distal proximal tip.

Figure 40:
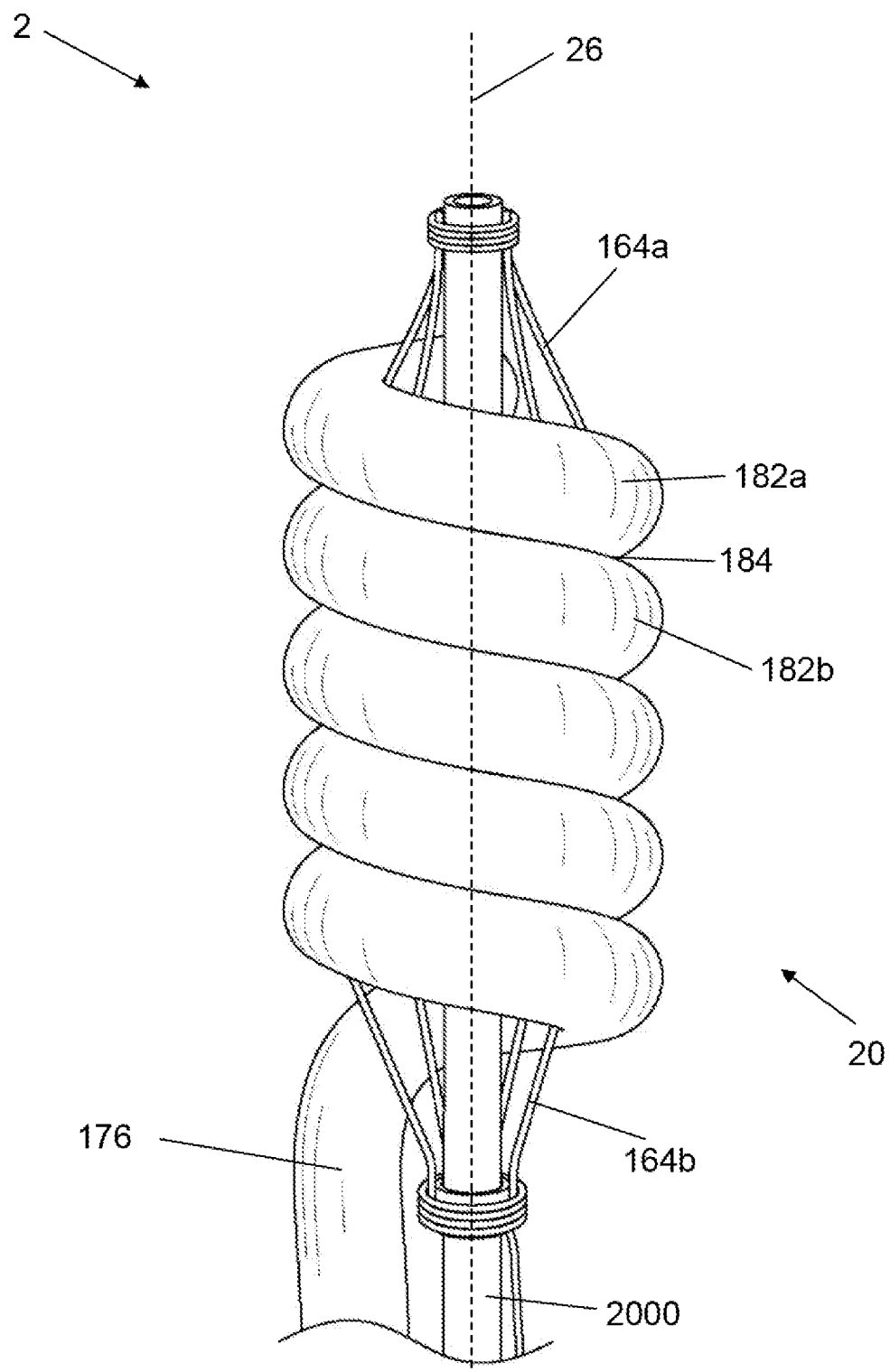
FIG. 40 illustrates a variation of the device.

FIG. 40 illustrates that the balloon can have a spiral or helical configuration. The spiral can have a first winding 182a, a second winding 182b, and more (e.g., five, as shown) windings. The first winding 182a can be joined to the second winding 182b at a winding joint 184. The winding joint 184 can have an adhesive or a weld joint. The winding joint 184 can have a strip of elastic or inelastic material attached to the adjacent windings. The balloon 20 can be formed from a single continuous lumen.

Figure 41A:
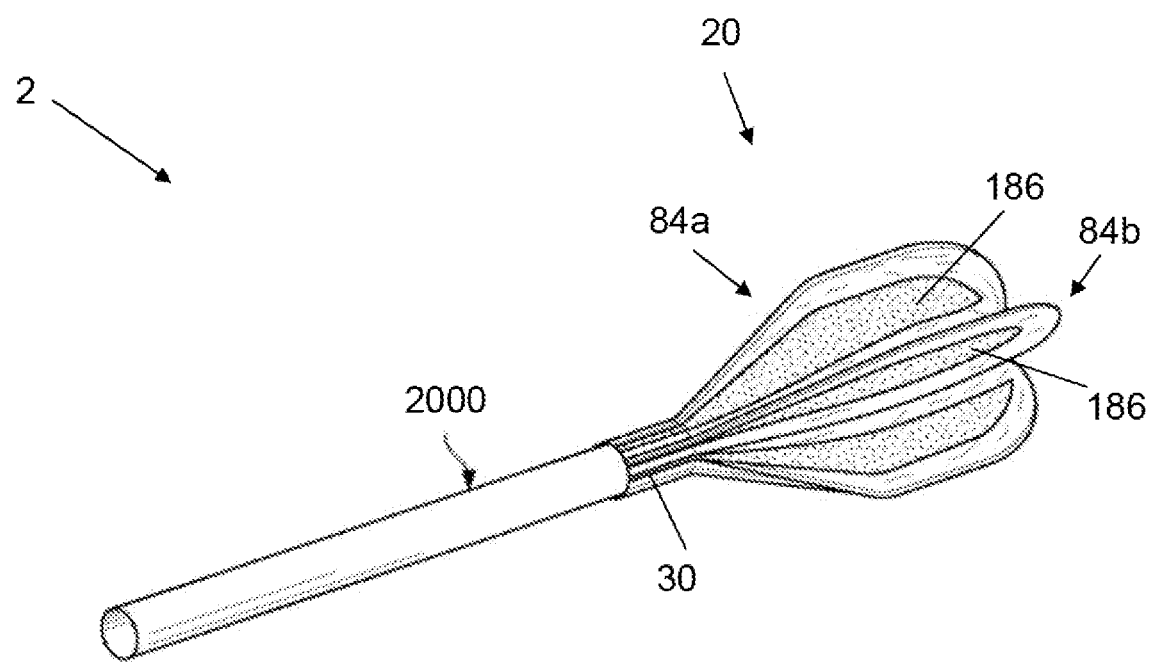
FIGS. 41A and 41B illustrate a variation of the device in deflated and inflated configurations, respectively.

FIG. 41A illustrates that the first flute can have a first vane 186a. The second flute can have a second vane 186b. The vanes 186 can be embedded within or attached to the inside or outside of the balloon wall 22. All, some, one, or none of the flutes can have vanes. The vanes 186 can be reinforcements. For example, the vanes 186 can be a laminate, foil or wafer. The foil or wafer can be a plastic or metal listed herein, such as tantalum. The vane 186 can be strong enough to cut soft or hard tissue adjacent to the pleat. The vanes 186 can be rigid or flexible.

Figure 41B:
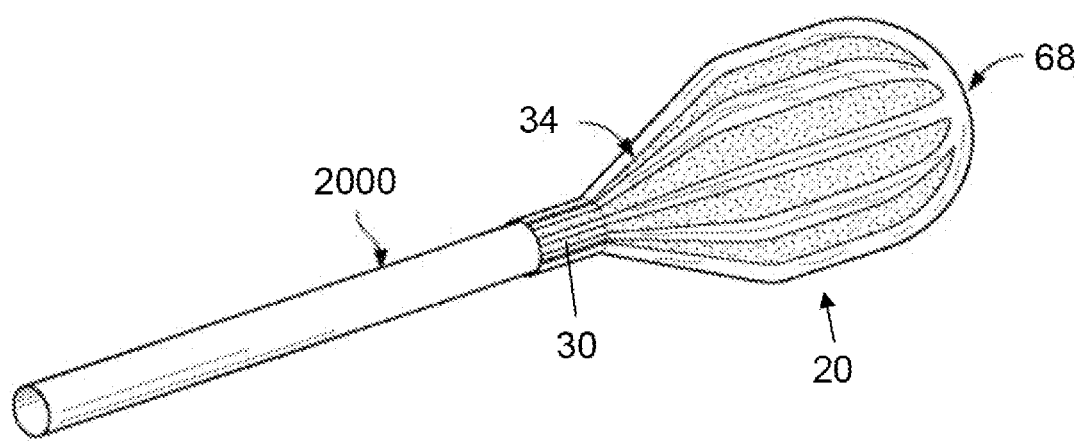

FIG. 41B illustrates that in an inflated or expanded configuration, the vanes 186 can lie flat along the wall.

A single radiopaque layer can encompass substantially the entire area of the balloon (as shown in FIG. 1, but with a radiopaque layer congruent with the balloon 20). The radiopaque layer can be a tantalum or other metal foil selected from a radiopaque metal such as those listed herein. The radiopaque layer can be a single continuous layer, for example as a deposition or foil lining with e.g. a deposition or foil of a metal such as tantalum. FIG. 42A illustrates that the balloon can have vanes can be spaced evenly around the balloon longitudinal axis. The vanes can be radiopaque and/or echogenic. The vanes can be rectangular, triangular, circular, oval, or combinations thereof. The vanes can be oblong having a major axis and a minor axis. The major axis can be parallel with the balloon longitudinal axis.

FIG. 42B illustrates that the balloon can have first vanes spaced evenly around the balloon longitudinal axis. The balloon can have one or more second vanes at the balloon distal terminal end.

FIG. 42C illustrates that the balloon can have a third vane at the proximal taper. The second and/or third vanes can partially or completely circumferentially envelope the balloon around the balloon longitudinal axis.

FIG. 42D illustrates that the balloon can have marker spots 188 evenly or unevenly distributed around the balloon. The marker spots 188 can be radiopaque and/or echogenic. The marker spots 188 can be circular, oval, square, triangular, rectangular, pentagonal, hexagonal, or combinations thereof. The marker spots 188 can be in a layer of the balloon wall or attached to the inner or outer surface of the balloon wall.

42E illustrates that the balloon can have a marker wire 190 in a helical configuration about the balloon longitudinal axis. The marker wire 190 can be radiopaque and/or echogenic. The wires 190 can be electrically conductive. The wires 190 can carry electrical current, for example for RF delivery, resistive heating, or combinations thereof. The marker wire 190 can be in a layer of the balloon wall or attached to the inner or outer surface of the balloon wall 22.

The marker wire 190 can carry a tensile load. For example, the wire can have a 0.001 in. diameter and maintain a tensile load of 0.3 N without yield or failure. The wire can be gold.

The marker wire 190 or another configuration of a panel or wire, such as shown in FIG. 45, can be a resistive heating or RF element. The system can have a power supply for delivering energy, such as electrical current, to the resistive heating element. The system can have a heat control unit for controlling the level of energy delivery to the resistive heating element. The heating element can be separated positive and negative electrodes on the balloon wall outer surface and contact the target site tissue directly, within the balloon wall, or on the radial inside of the inside surface of the balloon, or combinations thereof. The heating element can have a dielectric material. Radiofrequency energy can be delivered across the dielectric material of the heating element to create ohmic heating in the tissue.

The vanes 186, the marker spots 188 and the wires 190 can be on the inside of the balloon wall 22, the outside of the balloon wall 22, or within the balloon wall 22.

Figures 43, 44:
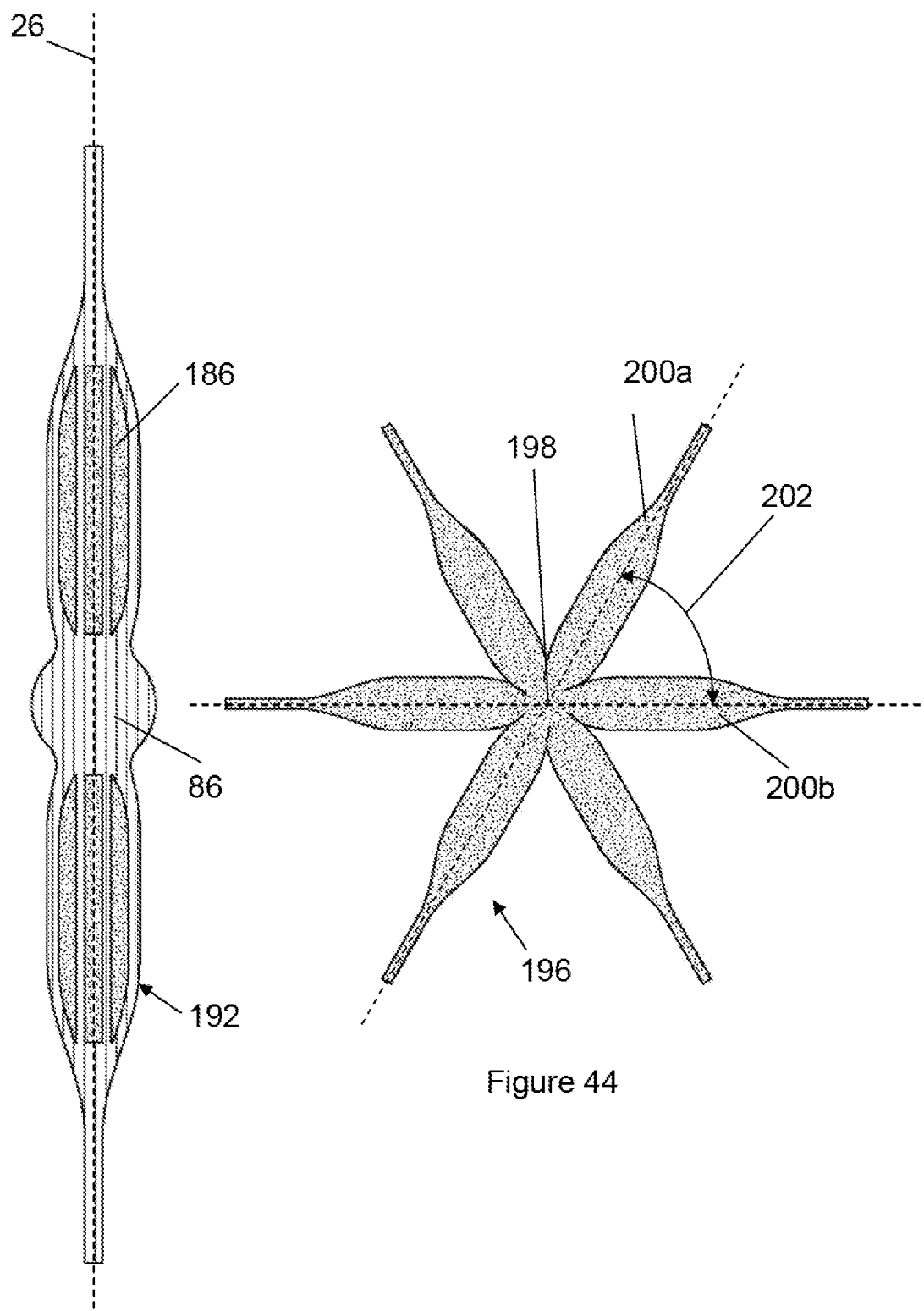
FIG. 43 illustrates a variation of an elongated element or strip.
FIG. 44 illustrates a variation of an element of the device.

FIG. 43 illustrates a panel 196 that can be configured as an elongated member or strip 192 that can be placed in a layer of the balloon wall. The strip 192 can have a strip longitudinal axis 194. The strip 192 can have one or more reinforcement fibers, for example, parallel and/or perpendicular with the strip longitudinal axis 194. The strip can have one or more vanes. For example, the strip can have multiple rows of vanes.

FIG. 44 illustrates a panel can have one, two, three, four, five, six (as shown) or more panel arms 200, such as panel first arm 200*a* and panel second arm 200*b*. The 196 panel can be a rosette. The panel 196 can have a panel center 198. The panel arms 200 can extend from the panel center 198. The panel arms 200 can have arm longitudinal axes. The angle between adjacent arm longitudinal axes can be arm angles 202.

The panel or radiopaque foil pattern can have panel arms that can be folded over a balloon 20 during manufacture such that radiopaque foil panel can be embedded within the balloon wall 22. The radiopaque foil and any other radiopaque or metal element herein can be made from gold, platinum, platinum-iridium alloy, tantalum, palladium, bismuth, barium, tungsten, or combinations thereof. Any of the layers can have particles of gold, platinum, platinum-iridium alloy, tantalum, palladium, bismuth, barium, tungsten or combinations thereof. Any of the layers can have radiopaque dyes.

The foil can be less than about 30 μm thick, for example less than about 20 μm thick, for example about 15 μm, about 12 μm, about 10 μm or about 8 μm thick. Radiopaque foils can be cut or patterned by laser cutting, wire EDM, die cutting or deposition. The foils may be mounted to a removable backing before cutting such that a pattern of foils may be easily applied during the balloon construction process.

The panels and/or vanes can cover the distal half of the balloon. The panels and/or vanes can cover the proximal half of the balloon. The panels and/or vanes can overlap in the longitudinal center of the balloon.

The panel, such as a foil, can be located in the balloon wall 22 in an area that is exposed to increased stresses during inflation. A radiopaque foil can strengthen the balloon wall 22.

The balloon 20 can have pleats or flutes between vanes or panels. The vanes or panels can form the pleats or flutes. A panel or vane, such as a radiopaque foil, can minimize leaks from forming between fibers in the balloon during use.

FIG. 45 illustrates that the balloon can have a resistive heating element 204 in a layer of the balloon wall or on the radial outside or radial inside of the balloon wall. The heating element 204 can have a resistive wire on a panel. The panel can be made from copper or another metal. The heating element 204, such as the resistive wire or panel, can be connected to a heating lead 206. The heating lead 206 can extend proximally along the hollow shaft 2000. The heating lead 206 can be proximally connected to a controller and power source. The balloon 20 can be used to heat, cool (e.g., when the panel is a Peltier junction), emit RF power, or combinations thereof.

The heating element can be substituted for or configured in combination with a UV-emitting element, visible light-emitting element, microwave-emitting element, ultrasonic-emitting element, or combinations thereof. The heating element 204 can be replaced or configured with a strain gauge, a peltier junction or a temperature measuring device, or combinations thereof.

The balloon can be used to treat abnormal mucosa in an esophagus, for example by positioning the heating element near or in contact with the abnormal mucosa and delivering heat. The mucosal layer of the esophageal wall, for example the columnar epithelium, can be injured or ablated and made necrotic with the balloon to normalize mucosa in the esophagus.

Figure 46A:
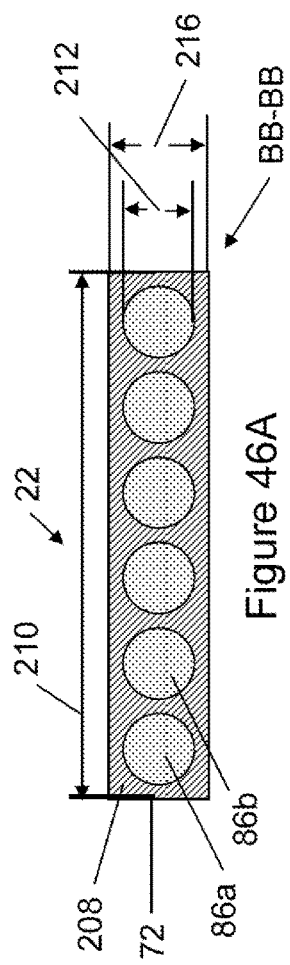
FIGS. 46A through 46O are sectional views through variations of cross section BB-BB of FIG. 1.

FIG. 46A illustrates that the balloon wall 22 at section BB-BB or at other sections taken through a single wall of the balloon can have a layer 72 that can have a fiber tape matrix. The fiber tape matrix can have one or more reinforcement fibers 86 and one or more resins. The resin can be a flexible adhesive 208. The flexible adhesive can remain flexible when cured or melted to form the medical inflatable device 2.

The fiber tape (also referred to as unidirectional fiber reinforced tape, unidirectional tape, and uni-tape) may have one, two or more monofilaments 86 running substantially parallel to each other and embedded in a flexible adhesive 208. Uni-tape may be produced with a removable backing. The removable backing can be made of paper, plastic, film, metal, elastomer, foam, fabric or combinations thereof. The substantially parallel monofilaments may be positioned within the flexible adhesive such that they are touching each other along their length. The substantially parallel monofilaments may be positioned such that there is flexible adhesive separating each fiber along its length.

FIG. 46A illustrates fiber array layer 72 having a layer width 210 in cross-section. The layer width 210 can include a number of fibers 86, for instance first fiber 86*a* and second fiber 86*b*. The layer 72 can have a linear quantity fiber density measured, for example, as the number of fibers 86 per unit of layer width 210. The linear quantity fiber density can be equal to or greater than about 500 fibers per inch, more narrowly equal to or greater than about 1000 fibers per inch, more narrowly equal to or greater than about 2000 fibers per inch, yet more narrowly equal to or greater than about 4000 fibers per inch. For example, the liner quantity fiber density can be from about 1,000 fibers per inch to about 2,000 fibers per inch.

The fibers 86 or monofilaments can be high strength and inelastic. The fibers can have a fiber or monofilament diameter 212, for example, from about 1 μm to about 50 am, for example less than about 25 μm, more narrowly less than about 15 μm. The unidirectional fiber-reinforced tape can have the same or different sizes and materials of fibers within the same unidirectional fiber-reinforced tape.

The fiber tape layer 72 can have a layer thickness 216 from about 1 μm to about 50 u μm, more narrowly from about 8 μm to about 25 μm, yet more narrowly from about 10 μm to about 20 μm.

Figure 46B:
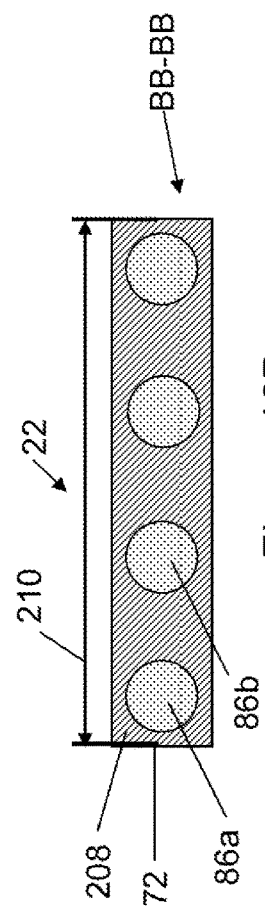

FIG. 46B illustrates that the fiber density can be less than the fiber density shown in FIG. 46A. For example, the fiber density can be about 500 fibers per inch.

Figure 46C:
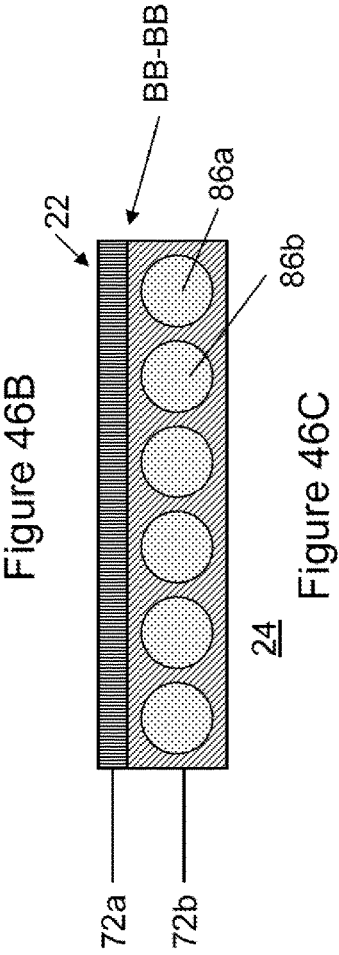
Figure 46D:
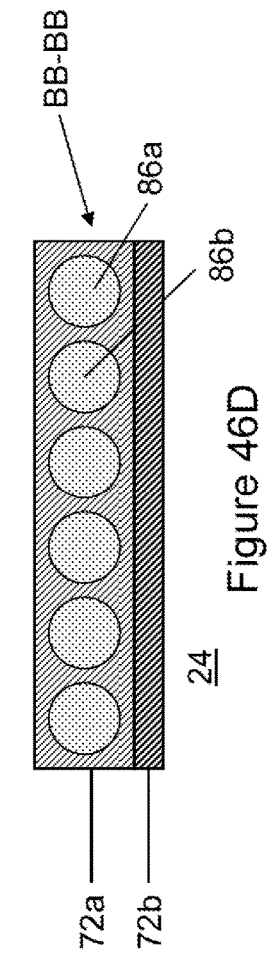

FIG. 46C illustrates that the inner layer 72*b* can have a fiber tape having reinforcement fibers 86 in an adhesive 208. The outer layer 72*a* can have a polymer film. The laminate shown can be a part of or the entire balloon wall 22, FIG. 46D illustrates that the outer layer 72*a* can be a fiber tape. The inner layer 72*b* can be a polymer film.

Figure 46E:
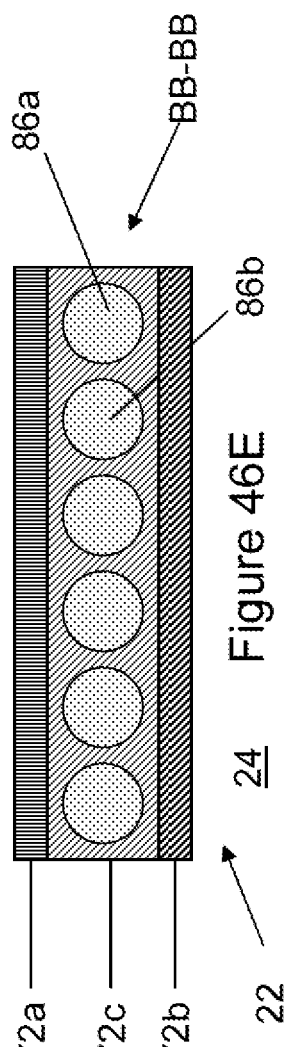

FIG. 46E illustrates that the outer layer 72*a* and the inner layer 72*b* can be polymer films. In any variation, the polymer films can be the same or different polymers, or any combination thereof. The first middle layer 72*c* can be a fiber tape.

Figure 46F:
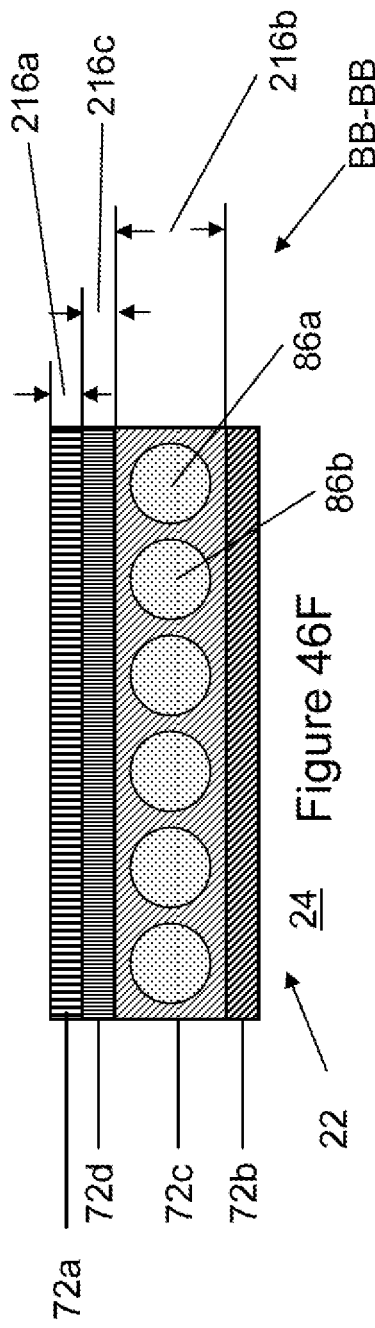

FIG. 46F illustrates that the outer layer 72*a*, inner layer 72*b*, and second middle layer 72*d* can be polymer films. The first middle layer 72*c* can be a fiber tape. Any adjacent layers, such as the third middle layer 72*e* and the outer layer 72*a*, can be joined with adhesive, by melting, solvation, welding or combinations thereof.

Figure 46G:
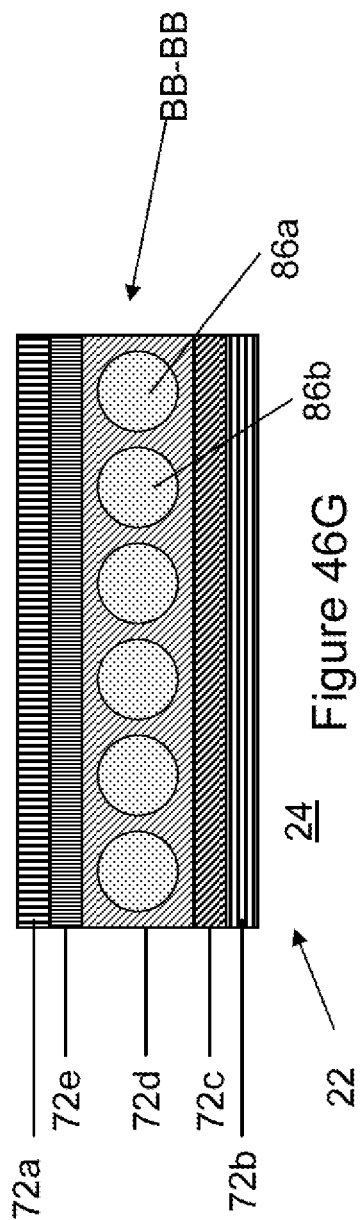

FIG. 46G illustrates the outer layer 72*a*, inner layer 72*b*, first middle layer 72*c* and third middle layer 72*e* can be polymer films. The second middle layer 72*d* can be a fiber tape.

FIG. 46H illustrates that the outer layer 72*a* can be a first fiber tape. The inner layer 72*b* can be adjacent to the outer layer 72*a*. The inner layer 72*b* can be a second fiber tape. The first and second fiber tapes can be uni-tapes. The fiber in first fiber tape can form an angle with the fiber in the second fiber tape. Part or all of the balloon wall 22 can have multiple fiber tape layers in a wall section area 131. The area 131 can include a number of fibers.

Part or all of the balloon wall 22 can have a volumetric quantitative density of fibers measured, for example, as the number of fibers per unit of area. The area quantity fiber density can be equal to or greater than about 100,000 fibers per square inch, more narrowly equal to or greater than about 250,000 fibers per square inch, more narrowly equal to or greater than about 1,000,000 fibers per square inch, yet more narrowly equal to or greater than about 4,000,000 fibers per square inch. The area quantity of fiber can be about 25% of the area of a wall cross section, more narrowly about 50%, more narrowly about 75%

The ratio of the volume of the fiber tape to the volume of the fibers 86 can be about equal to or greater than about 15%, more narrowly equal to or greater than about 30%, more narrowly equal to or greater than about 50%, yet more narrowly equal to or greater than about 75%.

FIG. 46I illustrates that a balloon wall 22 can be made by positioning, as shown by arrows, an inner layer 72*b* having a first laminate 130*a* on the outer layer 72*a* having a second laminate 130*b*. The first laminate 130*a* can be consolidated to the second laminate 130*b*. Consolidation can include heating, pressurizing, solvating, or combinations thereof of the first laminate 130*a* and the second laminate 130*b*.

FIG. 46J illustrates that the outer layer 72*a*, and inner layer 72*b* can be polymer films. The first middle layer 72*c* and the second middle layer 72*d* can be fiber tapes.

Figure 46L:
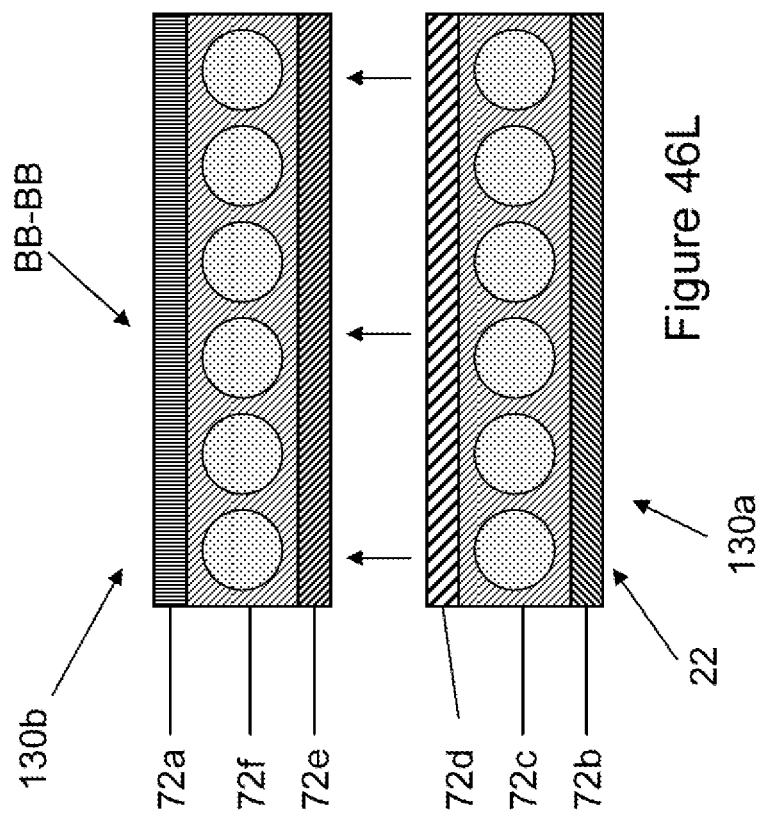
Figure 46K:
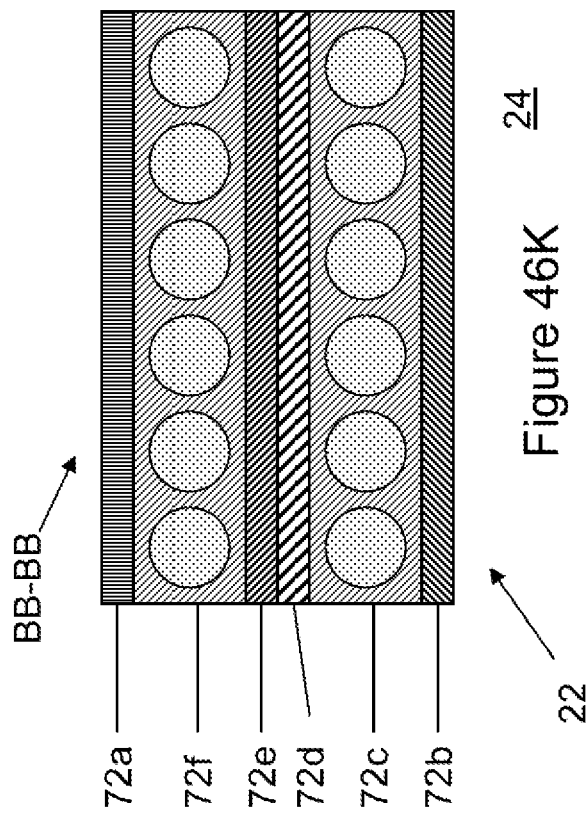

FIG. 46K illustrates that the outer layer 72*a*, inner layer 72*b*, second middle layer 72*d*, and third middle layer 72*e* can be polymer films. The first middle layer 72*c* and the fourth middle layer 72*f* can be fiber tape.

FIG. 46L illustrates that the balloon wall 22 can be made by positioning, as shown by arrows, a first laminate 130*a* on a second laminate 130*b*. The first laminate 130*a* can be consolidated to the second laminate 130*b*. The first laminate 130*a* can have the outer layer fixed to the fourth middle layer, which can be fixed to the third middle layer. The second laminate 130*b* can have the inner layer fixed to the first middle layer, which can be fixed to the second middle layer.

Figure 46N:
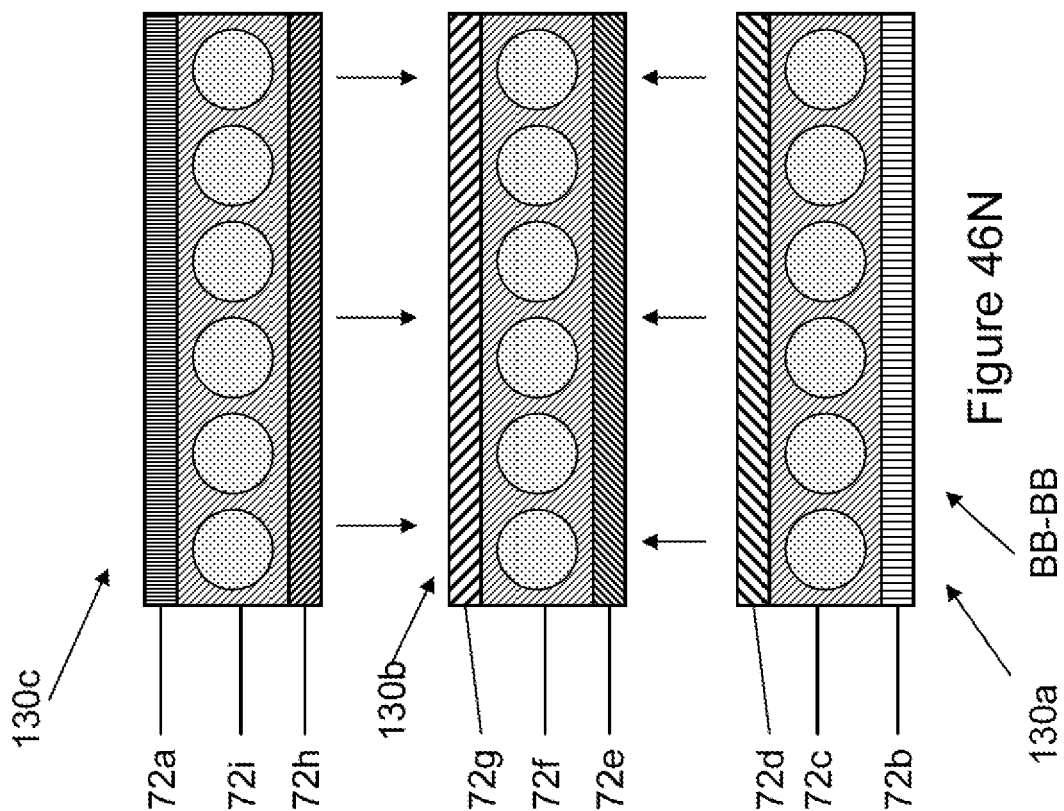
Figure 46M:
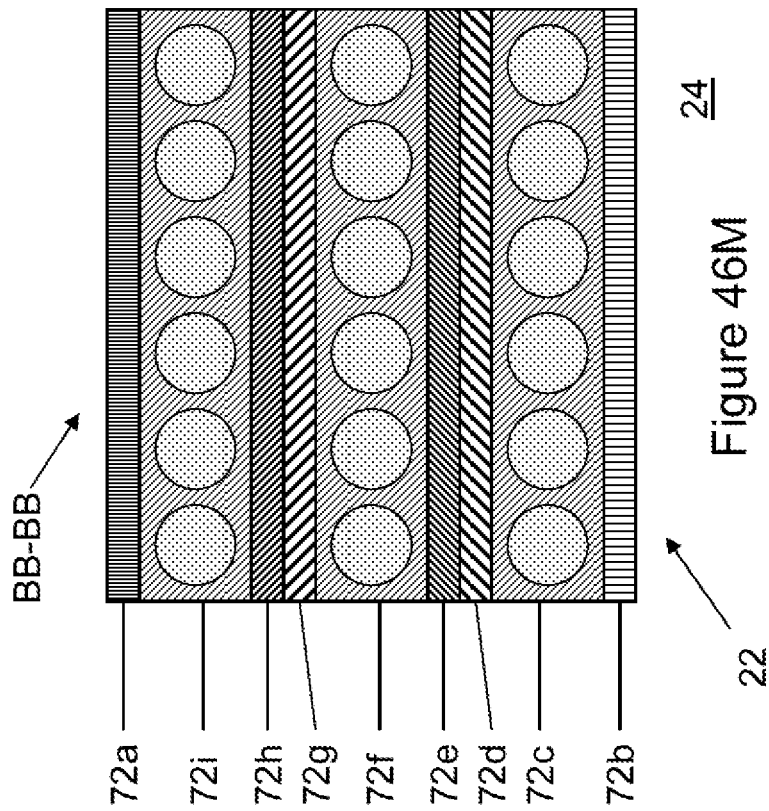

FIG. 46M illustrates that the outer layer 72*a*, inner layer 72*b*, second middle layer 72*d*, third middle layer 72*e*, fifth middle layer 72*g*, and sixth middle layer 72*b* can be polymer films. The first middle layer 72*c*, fourth middle layer 72*f* and seventh middle layer 72*l* can be fiber tapes.

FIG. 46N illustrates that the balloon wall 22 can be made by joining, as shown by arrows, a first laminate 130*a*, a second laminate 130*b*, and a third laminate 130*c*.

FIG. 46O illustrates that the outer layer 72*a* can be an MMA-resistant and MMA-releasing polymer film. The inner layer 72*b* can be a leak proof bladder made from a polymer film. The first middle layer 72*c* can be a fiber tape, for example with the fibers oriented as longitudinal fibers. The second middle layer 72*d* can be a resin or adhesive. The third middle layer 72*e* can be a fiber tape, for example with the fibers oriented as latitudinal or hoop fibers. The fourth middle layer 72*f* can be a resin or adhesive. The fifth middle layer 72*g* can be a radiopaque layer, such as a metal foil. The sixth middle layer 72*h* can be a resin or adhesive.

Any of the polymer or fiber tape layers can be leak proof, water tight, air tight, MMA-resistant, MMA-releasing, or combinations thereof.

Magnetic resonance visualization enhancement materials, such as magnetic contrast agents, can be added to the adhesive, the film or the fiber. The magnetic resonance visualization enhancement materials can enhance the visualization of the balloon during an magnetic resonance imaging (MRI) procedure. For example, the magnetic resonance visualization enhancement material can be gadolium, Omniscan, Optimark, ProHance, Magnevist, Multihance, or combinations thereof.

Any of the layers, for example the outer layer, can be tinted or dyed a visible spectrum color. For example, a pigment, coloring additive, dispersions or other coloring agents, such as an coloring additive from Plasticolors (Ashtabula, Ohio) can be added to the adhesive, laminate or fiber before consolidation. A paint or coating can be added to a layer surface or to the outer surface of the balloon wall.

The color can be selected for branding, market differentiating, as an indication of the type of device, the size of the device, or combinations thereof. For example, devices having a selected diameter, length, pressure rating, clinical indication or efficacy, other common performance metric, or combinations thereof, can be dyed a specific color (e.g., green for a first type of device, red for a second type of device).

The layers can have one or more optical fibers. The fiber optic can be a strain sensor. The strain sensor can monitoring the laminate's mechanical status in real time. The fiber optic can guide light delivery into the body. The fiber optic can visualize a target site (e.g., gather light from the body to produce a visual image).

FIG. 47 illustrates polymer films from which the layers can be made. The thickness of the polymer films can be from about 2 μm to about 50 μm, more narrowly from about 2 μm to about 18 μm, yet more narrowly from about 4 μm to about 12 μm.

FIG. 48 illustrates materials from which the reinforcement fibers can be made.

FIG. 49 illustrates that the adhesive can be an elastomeric thermoset material, an elastomeric thermoplastic material, or a combination thereof. The adhesive can be selected from any of the materials, or combinations thereof, listed in FIG. 49. The matrix can have a resin and a fiber. The resin can be an adhesive.

Method of Manufacture

Figure 50:
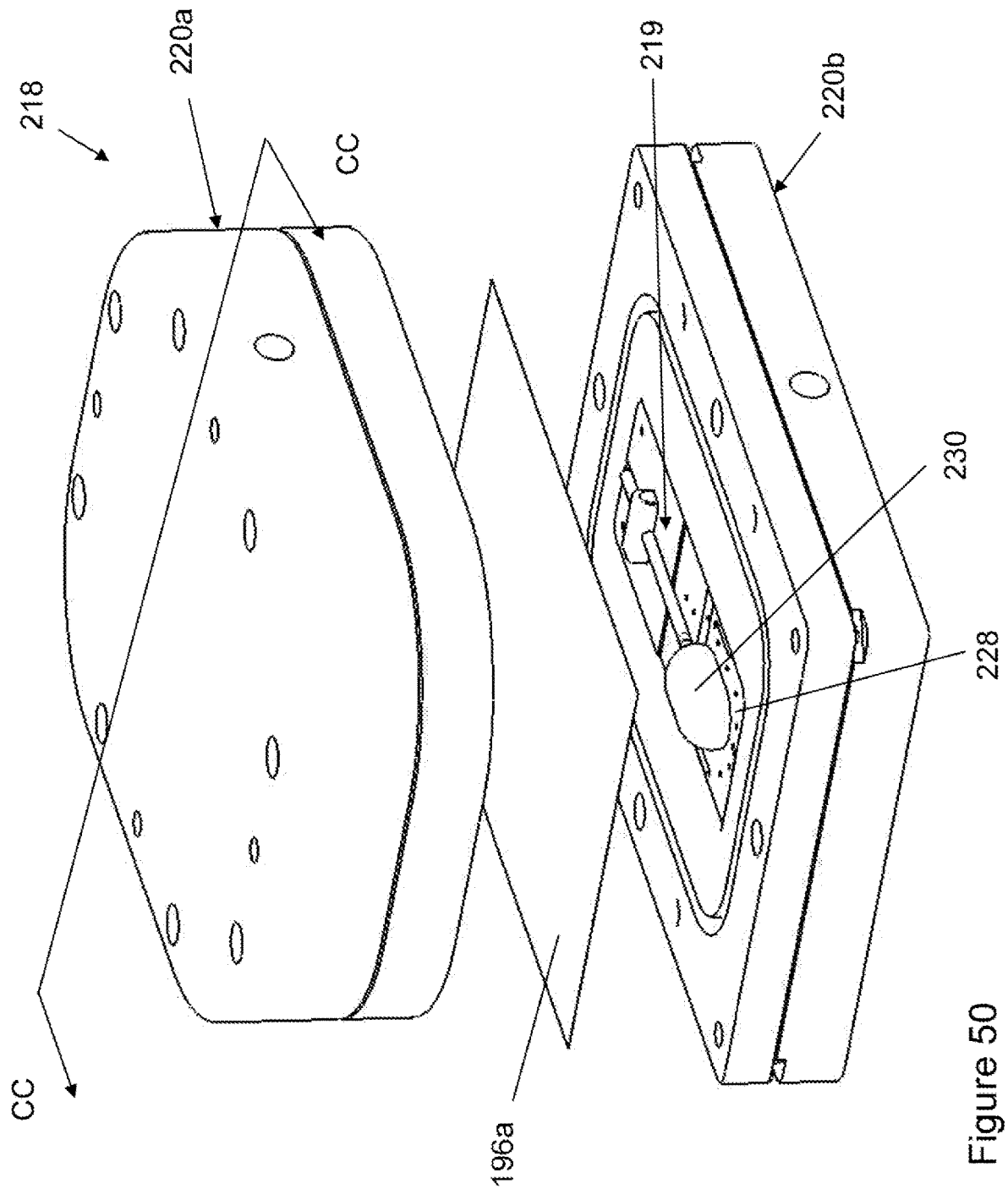
FIG. 50 illustrates a variation of a tool for manufacturing a variation of the inflatable device.
Figure 51:
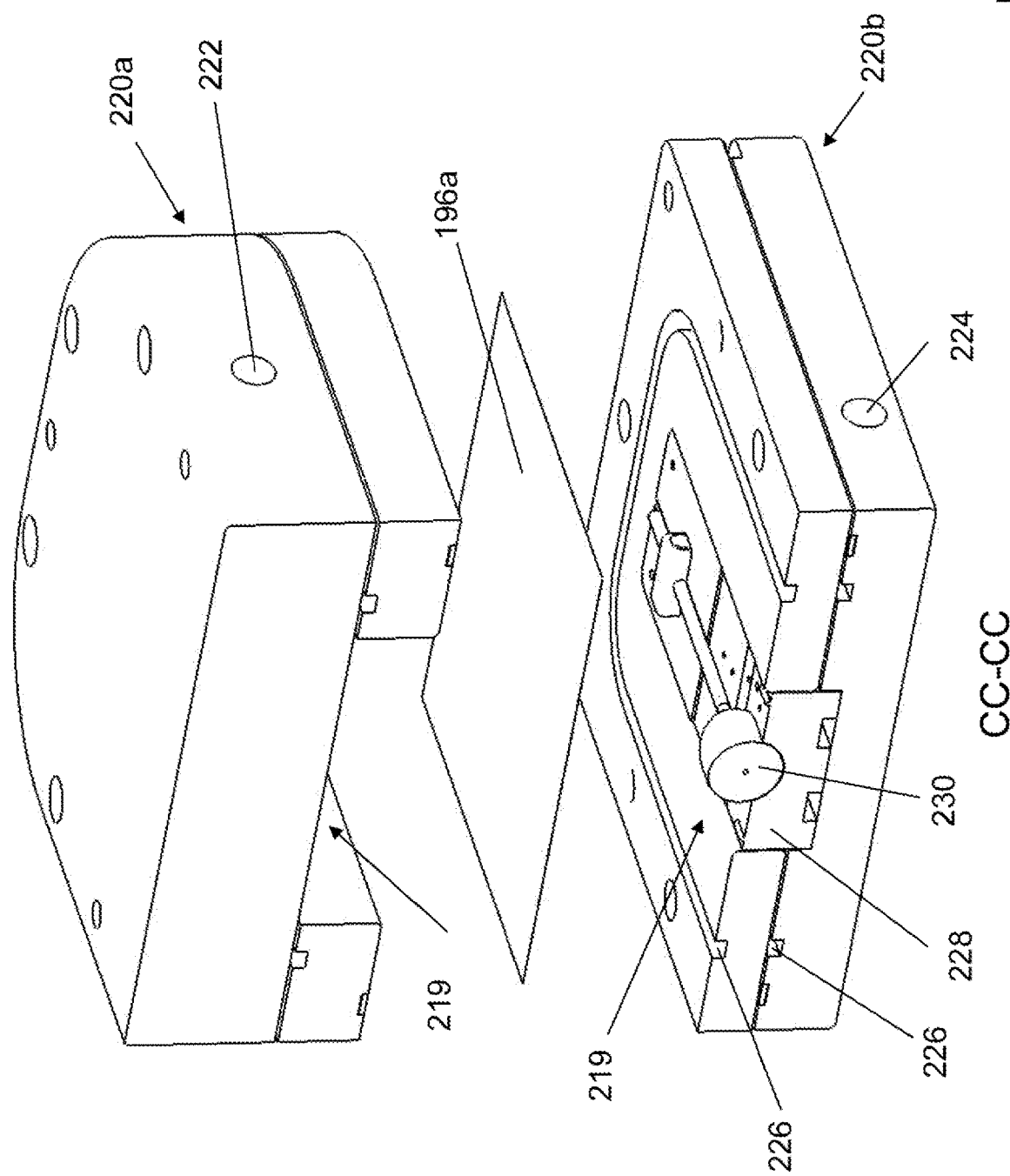
FIG. 51 is a variation of cross-sectional view CC-CC of FIG. 50.

FIGS. 50 and 51 illustrate that the device can be partially or completely manufacturing in a pressure chamber 219. The pressure chamber 219 can be in a pressure chamber case 218. The pressure chamber case 218 can have a case top 220a separatable from a case bottom 220b. The case top 220a can have a case top port 222. The case bottom 220b can have a case bottom port 224. The case top port 222 can be in fluid communication with the top of the pressure chamber 219. The case bottom port 224 can be in fluid communication with the bottom of the pressure chamber 219.

The case top can screw or otherwise tightly join to the case bottom. The pressure chamber case can have one or more o-rings (not shown) in o-ring seats 226.

The pressure chamber can have a mandrel seat 228. The mandrel seat 228 can be configured to receive a mandrel 230. The mandrel seat 228 can have holes or pores. The holes or pores in the mandrel seat 228 can allow pressure from the case bottom port and the bottom of the pressure chamber to reach the top surface of the mandrel seat around the mandrel and/or directly under the mandrel.

The mandrel 230 can have the inner dimensions of the balloon 20.

The mandrel 230 can be a water soluble mandrel. The mandrel may be made from a low melting point wax or metal, a foam, some collapsing structure or an inflatable bladder. The mandrel can be made from a eutectic or non-eutectic bismuth alloy and removed by raising the temperature to the melt point of the metal. The mandrel can be made from aluminum, glass, sugar, salt, corn syrup, hydroxypropylcellulose, ambergum, polyvinyl alcohol (PVA, PVAL or PVOH), hydroxypropyl methyl cellulose, polyglycolic acid, a ceramic powder, wax, ballistic gelatin, polylactic acid, polycaprolactone or combinations thereof.

FIG. 52 illustrates characteristics of bismuth alloys from which the mandrel can be made. The characteristics are characterized by melting temperature (as shown in the third row of FIG. 52) of the bismuth alloy.

The mandrel can be transparent or translucent to light and/or an electron beam. The mandrel can be hollow. The outside surface of the mandrel can be coated in a release agent.

The mandrel may be molded, machined, cast, injection molded or combinations thereof.

The mandrel can be in the mandrel seat and a first panel to be formed into about half of the inner layer of the balloon wall can be placed between the case top and the case bottom. The case top can then be secured to the case bottom.

FIG. 53 illustrates that the outer surface of the mandrel can have some glue or first adhesive. The first adhesive can be located around the perimeter of the first panel's contact area with the mandrel. The first adhesive can be water soluble. The first adhesive can be a sugar syrup.

FIG. 54 illustrates that a positive pressure can be applied to the top of the pressure chamber (e.g., through the case top port) and/or a negative pressure or suction applied to the bottom of the pressure chamber (e.g., through the case bottom port). The layer can get sucked and/or pressed down onto the mandrel. The first panel can be smoothly fitted to the mandrel and adhered to the mandrel at the first adhesive.

Figure 55:
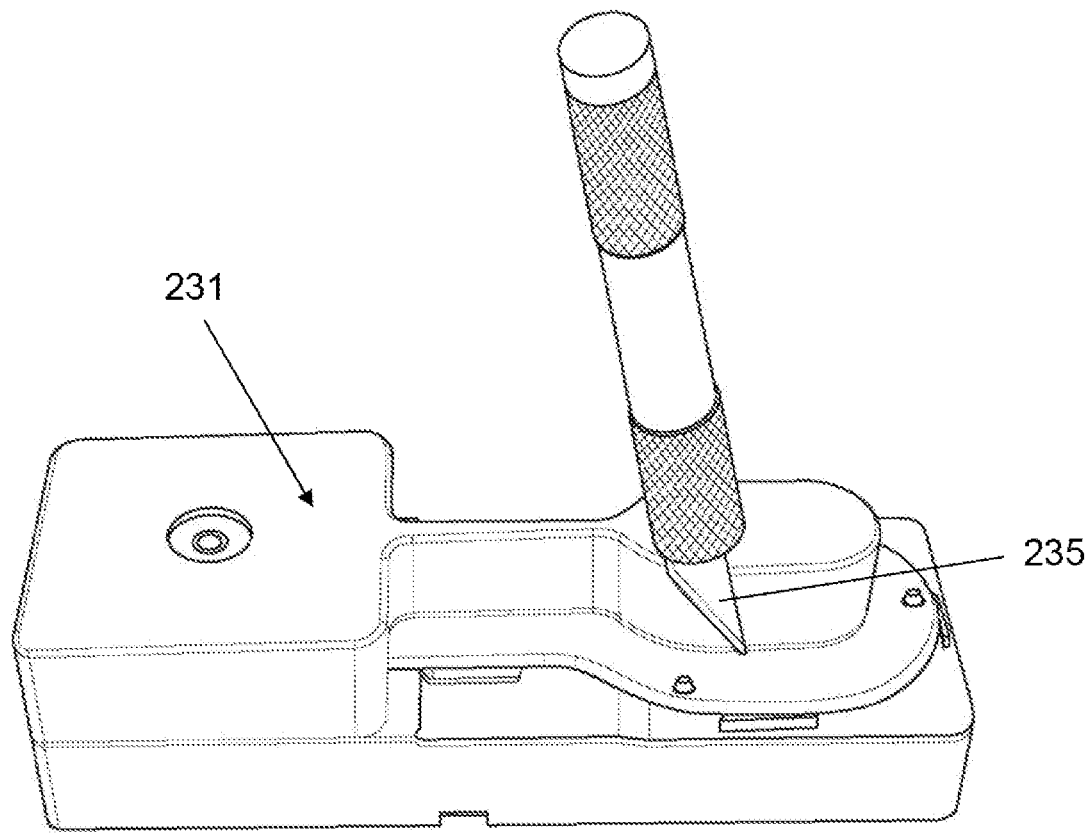

FIG. 55 illustrates that the mandrel and layer can be mounted into a trimming jig 231. Any excess portion of the first panel extending from the mandrel can be trimmed with a blade 235, with a laser, with a water jet cutter or with a die cut tool. The trimming jig 231 can cover the mandrel and the first panel attached to the mandrel. Several layers can be formed over the mandrel and cut. The layers may be trimmed at the same time or one at time.

Figure 56:
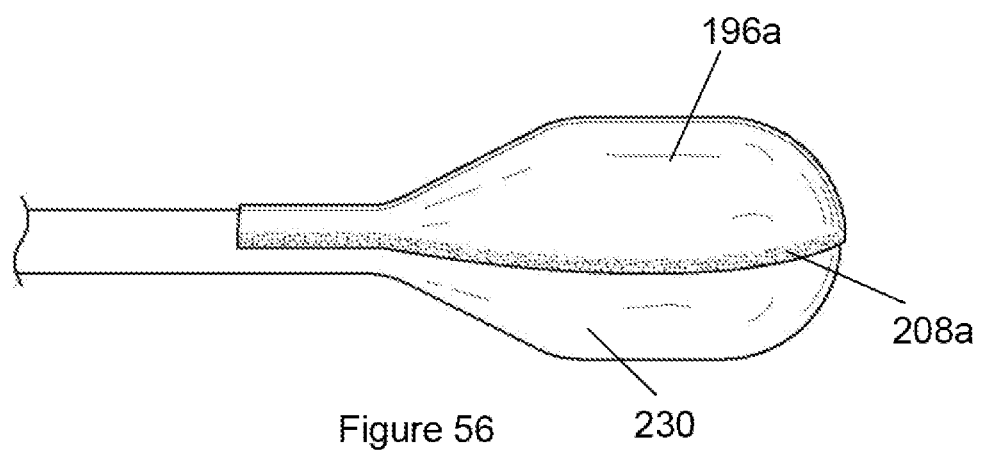

FIG. 56 illustrates that the mandrel can have the excess area or the first panel removed in preparation for attachment to the second panel.

Figure 57:
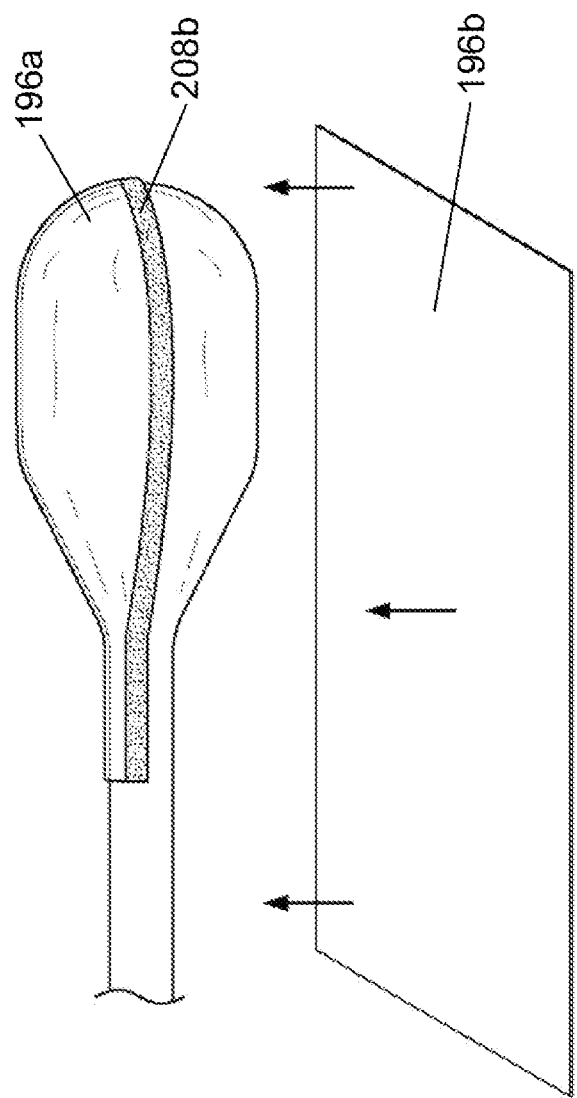

FIG. 57 illustrates that a second adhesive can be applied to the first panel around the perimeter of the second panel's contact area with the first panel. The second adhesive can be an epoxy, urethane, a cyanoacrylate, a UV cure, or combinations thereof. The mandrel can be seated in the mandrel seat with the first panel in the mandrel seat. The second panel can be placed on the mandrel as shown (upside down relative to the FIGS. 50 and 51 for illustrative purposes).

Figure 58:
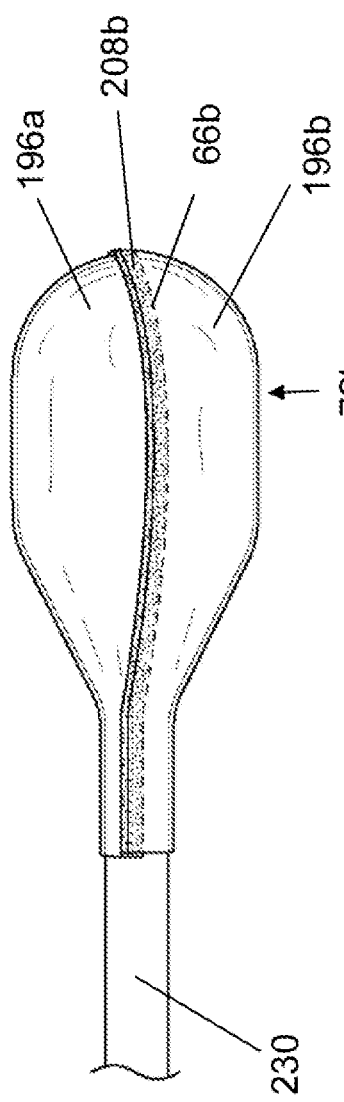

FIG. 58 illustrates that after the case top is secured to the case bottom, the positive and/or negative pressures can be applied to the pressure chamber as described infra. The second panel can be smoothly fitted or pressure formed to or against the mandrel and adhered to the first panel at the second adhesive. The first and second panels can form the inner layer of the balloon wall. Multiple layers can be made by repeating the method described infra. The pressure chamber can be heated, for example, to decrease the viscosity of and decrease the modulus of the panels.

Figure 59:
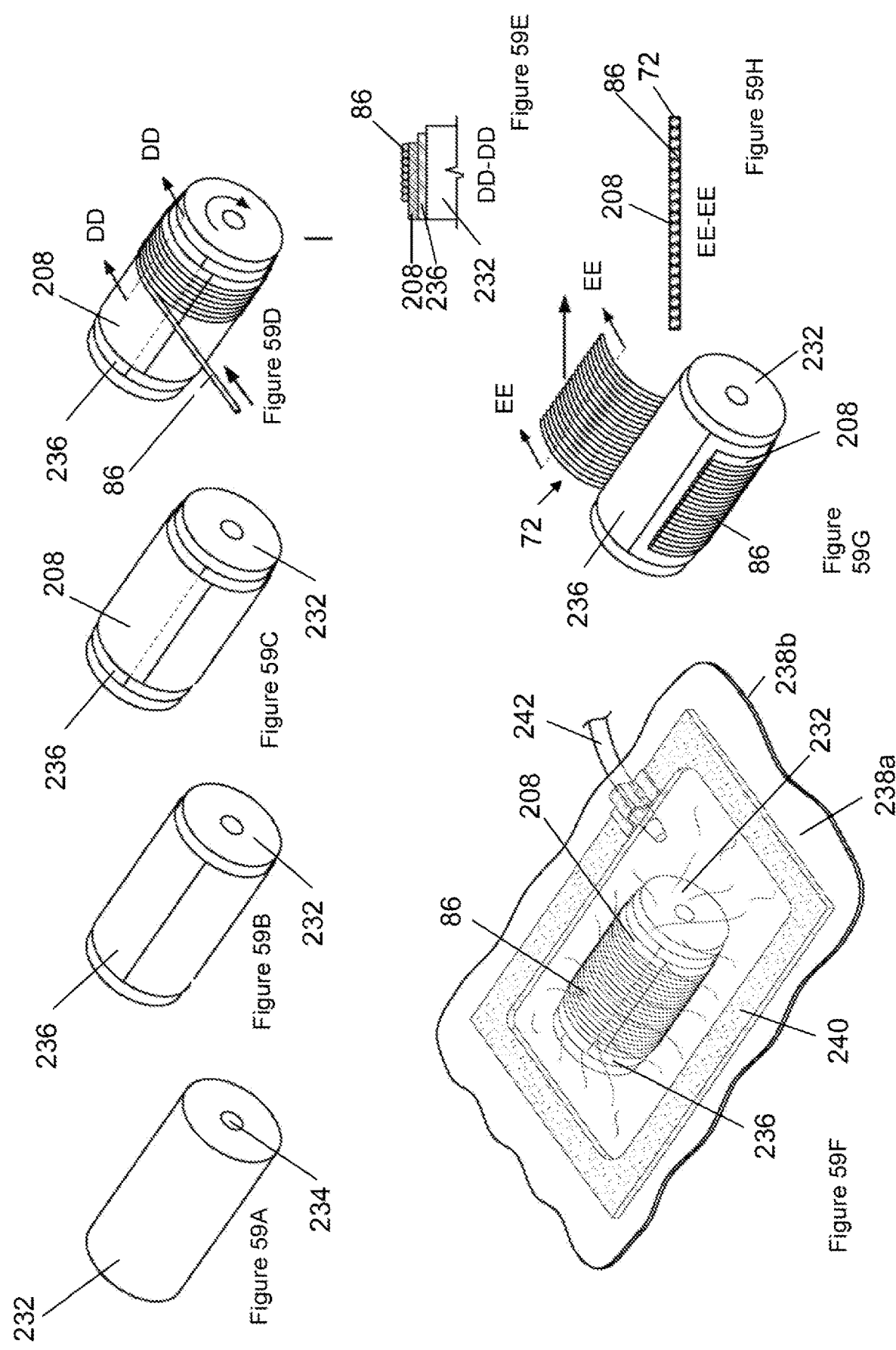
FIGS. 59A through 59H illustrate a method of making fiber tape.

FIG. 59A illustrates that a layer of fiber tape can be made on a roller 232. The roller can be configured to rotate about a roller axle 234. The roller may have a diameter from about 1 mm to about 100 mm. The roller may be made or coated with an anti-stick material such as a fluoropolymer.

FIG. 59B illustrates that a releaser 236, such as a release layer, can be placed around the circumference of the roller 232. The release layer can be a low friction film or coating. The release layer may be a thin/flexible fluoropolymer sheet.

FIG. 59C shows that an adhesive layer can be placed on the releaser or directly onto the roller (e.g., if no releaser is used). The adhesive layer may be a thermoplastic film. The adhesive layer may be a thermoset adhesive. The adhesive layer may be a solvated thermoplastic or thermoset.

FIG. 59D shows the application of fiber to the roller. Fiber may be unwound from a spool (not shown) and rolled onto the top surface of the adhesive. The fiber may contain one or more monofilaments. The fiber may have been previously flattened as detailed in this application. Any coating or sizing on the fiber may have been removed using a solvent. The fiber may be placed with a gap between each successive fiber wrap. The gap may be less than 25 um, preferably less than 5 um.

FIG. 59E shows a reinforcement layer on top of the adhesive on top of the release layer.

FIG. 59F illustrates that the roller can be placed between a vacuum top sheet 238*a* and a vacuum bottom sheet 238*b*, for example in a vacuum bag. A vacuum seal tape 240 can surround the roller between the vacuum bottom and top sheets. The air can be removed from between the vacuum top and bottom sheets and within the vacuum seal tape, for example by suction from a suction tube 242. Inside and/or outside of the vacuum bag, the roller can be heated, for example to melt or cure the adhesive.

FIG. 59G shows the removal of the layer. For instance, a cut may be made substantially perpendicular to the fiber. The layer may be peeled away from the release layer.

FIG. 59H illustrates that the layer of fiber tape can be removed from the roller. For example, the layer can be peeled off the releaser.

The layer can be cut into a pattern. For instance, the layer can be cut with the trimming jig, a laser, a water jet cutter, a die cut tool, or a combination thereof. The layer can be cut to form a strip similar to the one shown in FIG. 121.

Figure 60:
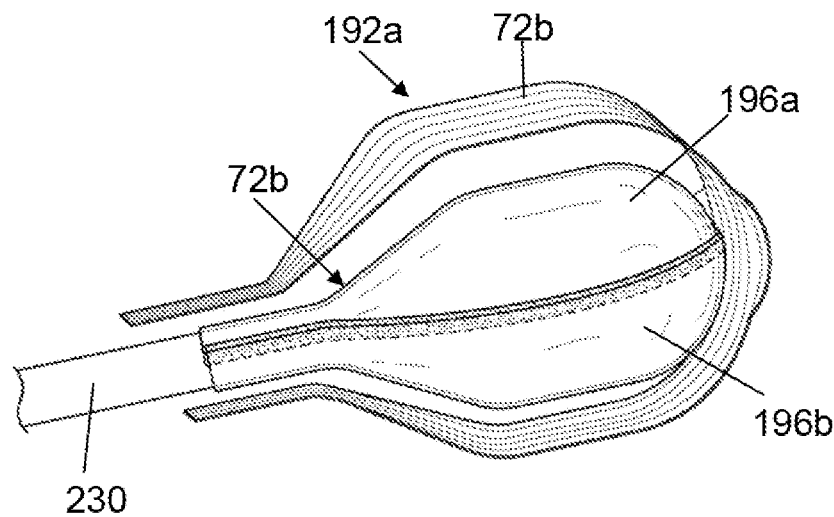
FIGS. 60 through 67 illustrate a variation of a method for manufacturing the device.

FIG. 60 illustrates that a strip can be applied to the inner layer or the mandrel. Each strip can be placed around the distal terminal end of the mandrel. The circular section may be centered on the distal end of the mandrel. The strips may be adhered to the mandrel using an adhesive or by melting the adhesive such that it bonds to the underlying layer.

Figure 61:
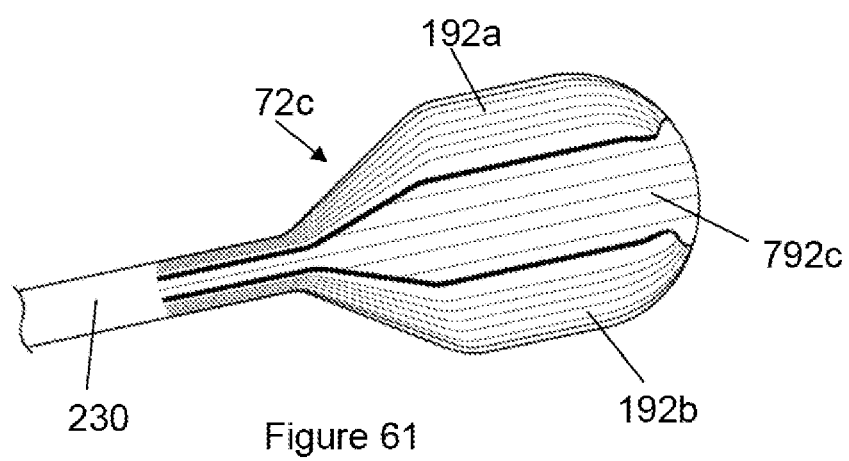

FIG. 61 illustrates that a first, second and third strip can be laid onto the mandrel. For example, the strips can be placed on the inner (or another) layer 72. The strips can cover the outermost (at the time the strips are applied) layer. The ends of the strips can end on the proximal taper or proximal stem.

Figure 62:
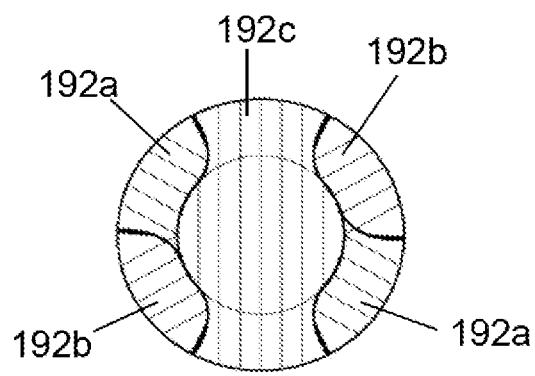
Figure 63:
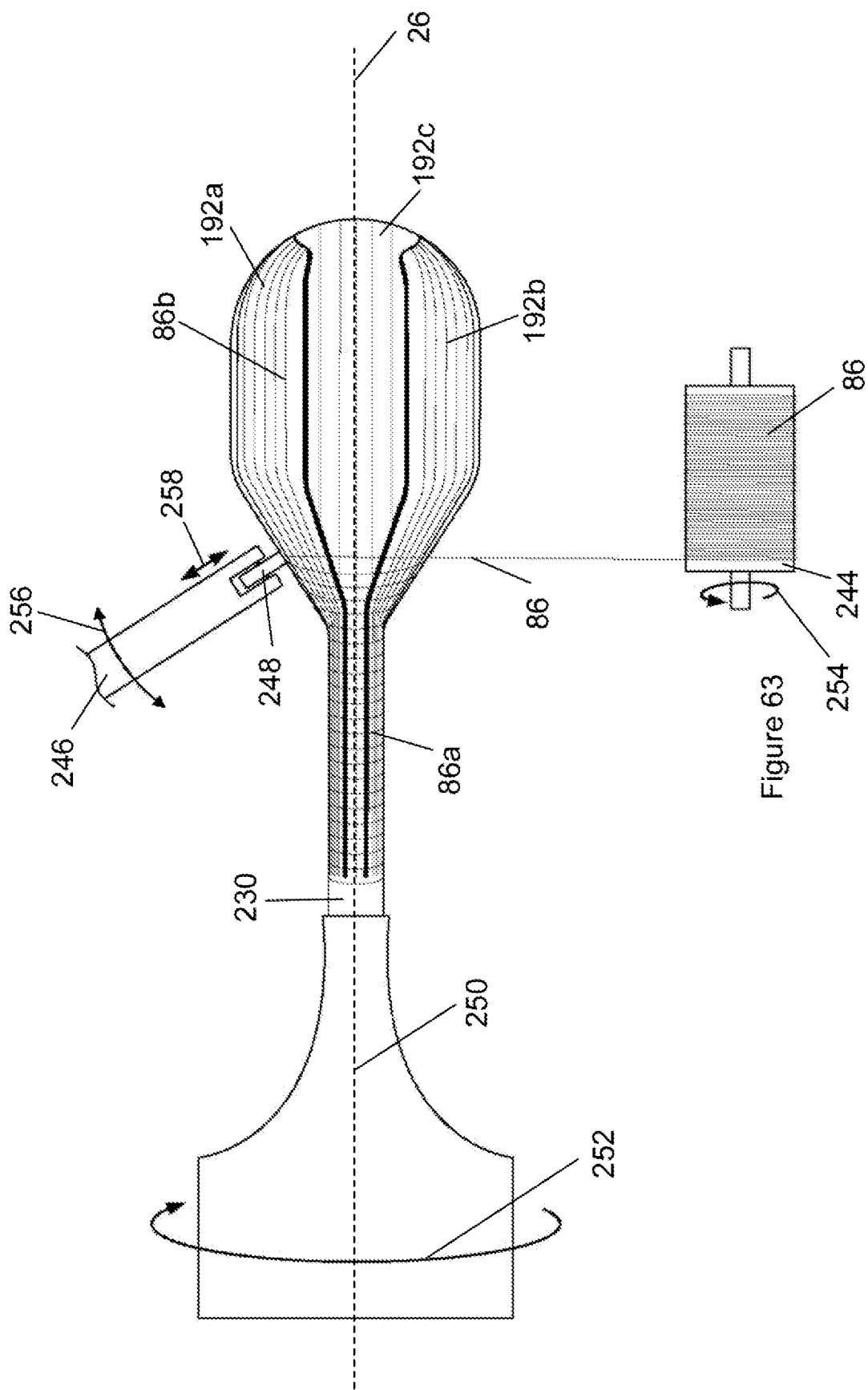

FIG. 62 illustrates that the circular sections of each strip can line up with each other. The circular sections can be aligned with the balloon distal terminal end. There may be fibers located approximately every 60 degrees at the distal tip FIG. 63 illustrates that fiber can be wound over the mandrel. For example, a tool arm 246 can be attached to a rotating tool wheel 248. The mandrel can be rotated, as shown by arrow 252, about the mandrel longitudinal axis 250 or balloon longitudinal axis. The spool 244 can be passively (e.g., freely) or actively rotated, as shown by arrow 254, deploying the fiber. Before winding, the fiber may be infused with an adhesive, a solvent, or both. A fiber distal end can fix to the top layer or directly to the mandrel. The tool arm 246 can rotate and translate, as shown by arrows 256 and 258, to track the tool wheel with the surface of the top layer.

The tool wheel can press the fiber against the top layer. The tool wheel can be heated to soften or melt the material on the surface of the top layer. Another heat source may be used to tack the fiber in place. For example, a separate resistive heater, a laser, or an RF welder may be used. The tool wheel can be made of or coated with a non-stick material. The fiber may be wound with a gap between each successive fiber wind. The gap can be less than about 25 μm, more narrowly less than about 5 μm. The winding process can terminate substantially before reaching the distal tip. The winding process can terminate when the fiber reaches the area where the strips overlap.

The resulting layer deposited in FIG. 63 can have a layer thickness of from about 1 μm to about 50 μm, more preferably, 8 μm to about 25 μm.

Figure 64:
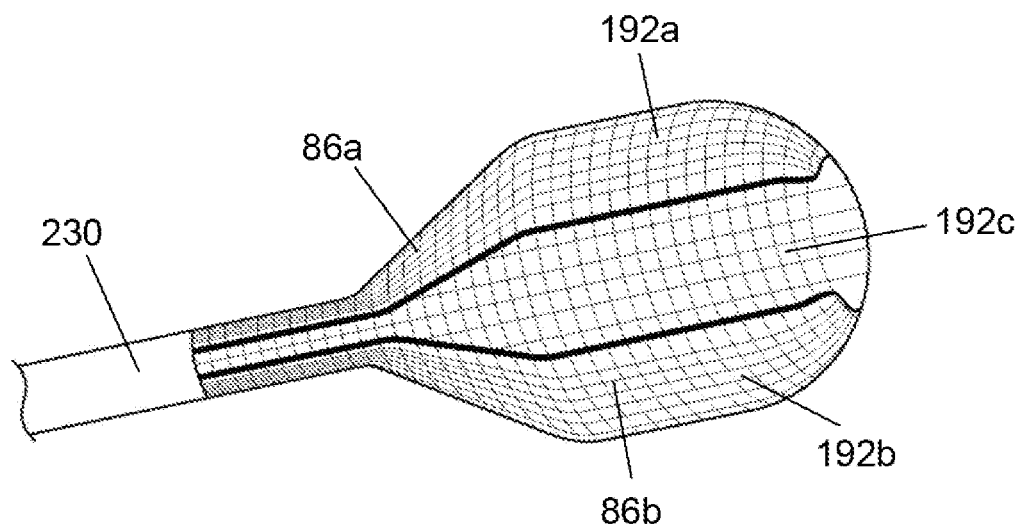

FIG. 64 illustrates that a string, wire or fiber can be helically wrapped around the mandrel, for example on the inner (or another) layer.

Figure 65:
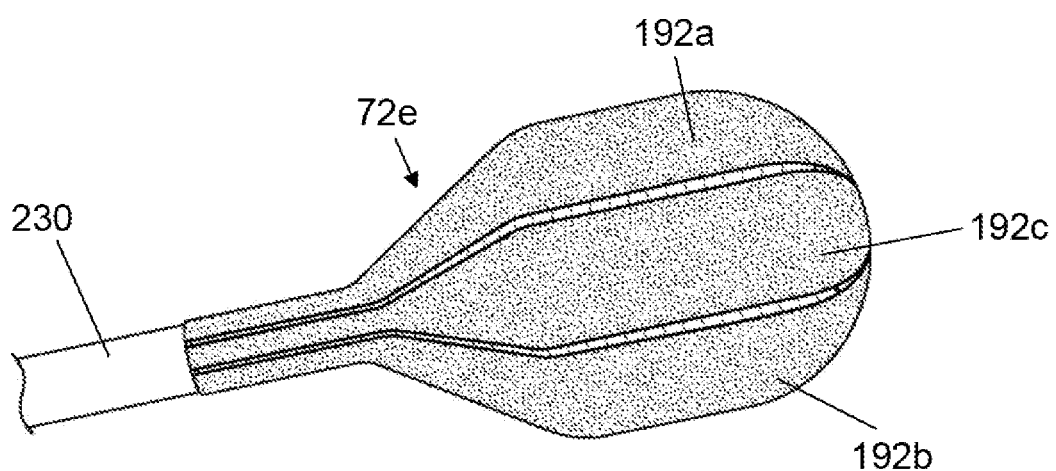

FIG. 65 illustrates that a rosette, vanes, or spots of a single panel can be placed onto the mandrel. The panel can be made from a metal foil. The rosette may be that shown in FIG. 44. The panel may provide radiopacity to the balloon. The panel may strengthen the balloon. The panel may make the balloon significantly more resistant to puncture.

Any methods of adding a layer to the mandrel or previous layer can be repeated to add additional layers, such as an outer layer of an MMA-resistant film.

The mandrel and the layers, including the panels, strips, wires or fibers, rosette, or combinations thereof, can be adhered, heated and/or pressurized, for example, to melt solvate, or otherwise bond the layers, for example by creating molecular bonds and decreasing the viscosity and modulus of the layers.

Figure 66:
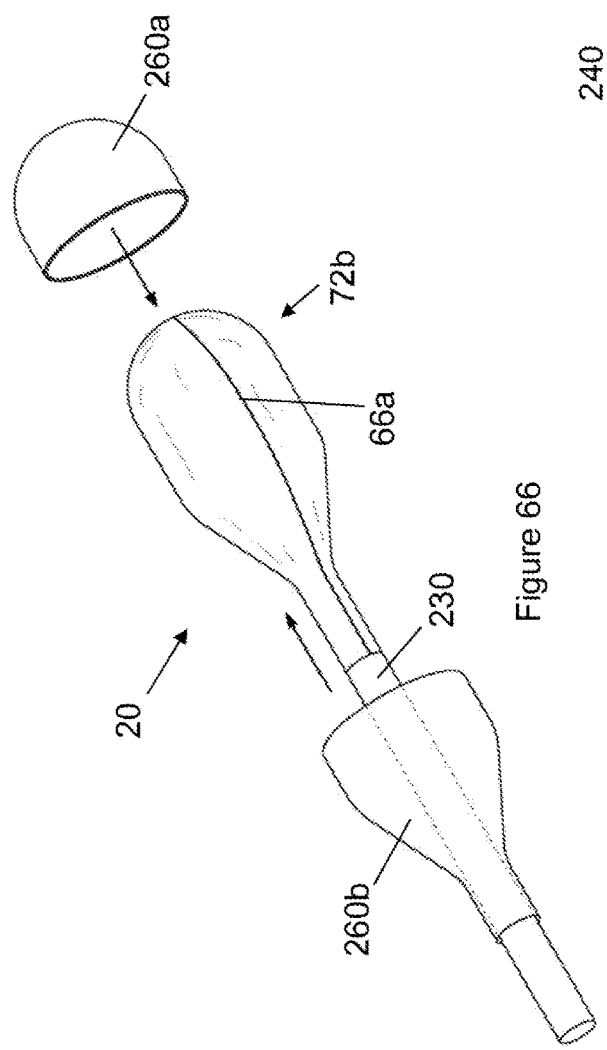

FIG. 66 illustrates that after the layers of the balloon have been assembled on the mandrel, a distal caul 260*a* can be placed over the distal end of the balloon. A proximal caul 260*b* can be slid over the mandrel and the proximal end of the balloon. The proximal caul 260*b* can be sealed to the distal caul 260*a*. The cauls 260 can be made from a fluoropolymer. The cauls 260 can have thermoformed FEP with a 0.005 in. initial thickness.

Figure 67:
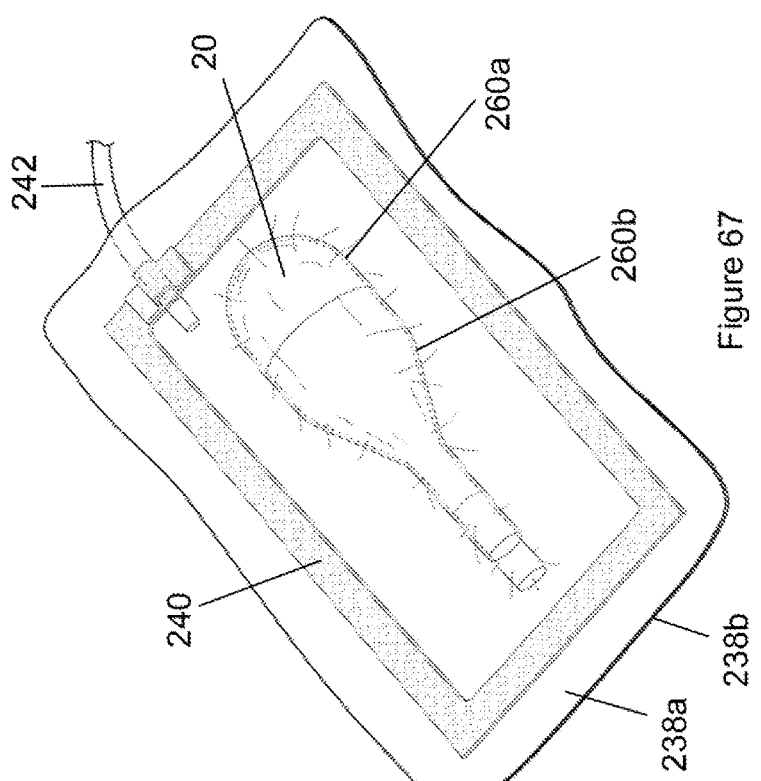

FIG. 67 illustrates that the mandrel, balloon and cauls can be placed into a vacuum bag. The balloon proximal stem and/or the mandrel can be placed inside of a vacuum bag. The interior of the vacuum bag can be heated. The vacuum bag can be inserted inside of an oven or autoclave. The layers of the balloon on the mandrel can be thermally cured or melted, for example under from about 1 ATM to about 30 ATM of pressure.

The bag delivery channel can suction the interior of the vacuum bag. For example the pressure in the vacuum bag can be less than about 0.1 ATM.

Figure 68:
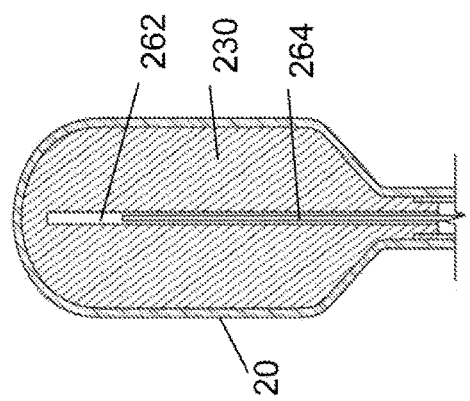
FIG. 68 illustrates a variation of a method for removing the mandrel.

FIG. 68 illustrates that a wash tube 264 can be inserted into a mandrel washout port 262. A dissolving or solvating fluid can be delivered through the wash tube and into the washout port. The mandrel can be removed by delivery of a fluid solvent such as water, alcohol or a ketone. The solvent may be applied during the consolidation process such that the solvent melts or partially softens the mandrel and concurrently pressurizes the bladder. The mandrel can be removed by raising the mandrel to a melting temperature for the mandrel. The mandrel can be removed by deflating the mandrel or by collapsing an internal structure.

The balloon may be expanded under pressure inside of a female mandrel. The mandrel inside diameter may be sized so that a pressurized balloon just contacts the inner wall of the mandrel. Heat may be applied. Heat may cause the wall of the balloon to soften and form against the inside of the female mandrel. This may give the balloon a smoother outer layer and serve to tension the fibers in the balloon.

Figure 69:
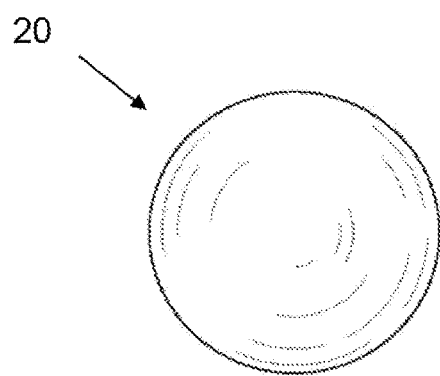
FIG. 69 illustrates a variation of the device in an inflated state before being pleated.

FIG. 69 illustrates that a pleated balloon in an expanded or inflated configuration can be substantially circular in cross-section.

Figure 70:
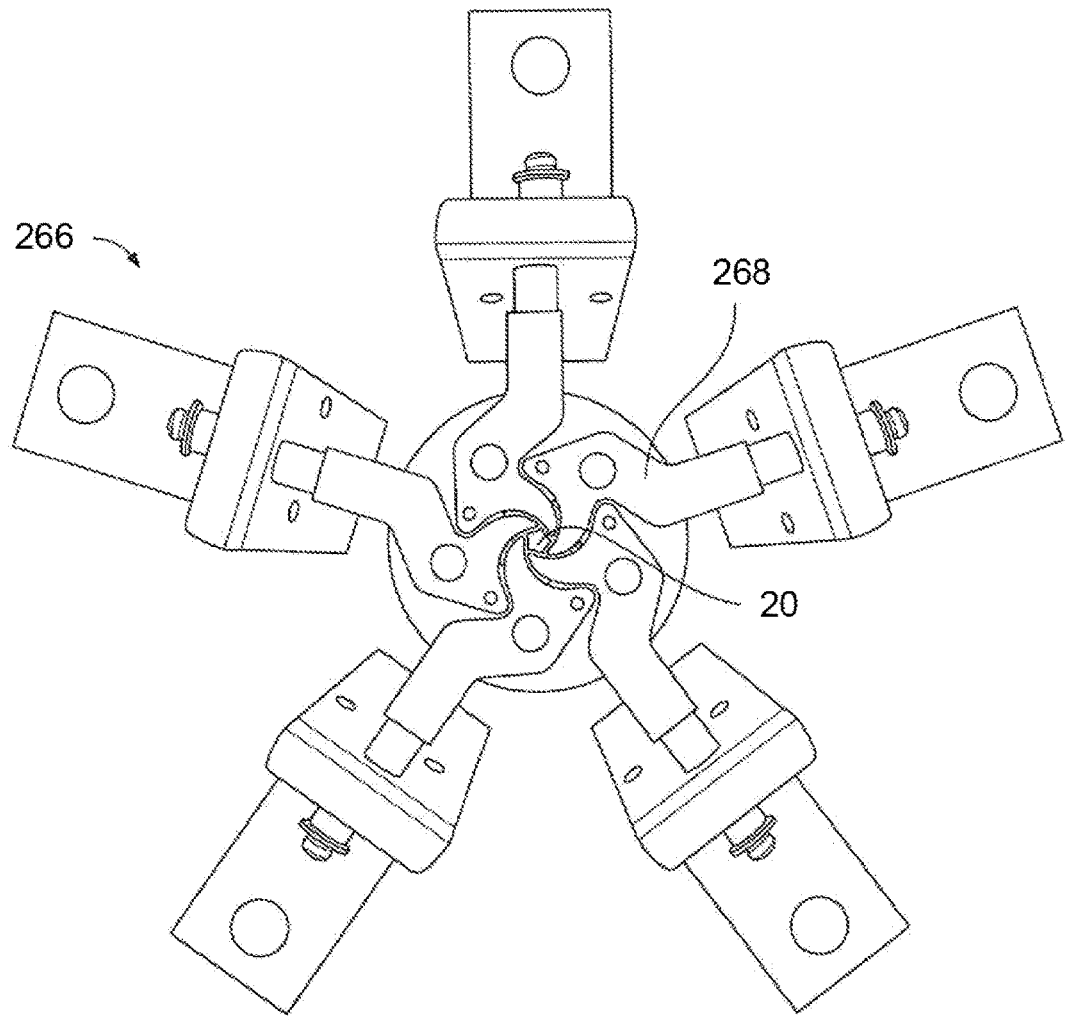
FIG. 70 illustrates a method of adding pleats or folds to a variation of the device.

FIG. 70 illustrates that a balloon can be clamped in a pleating tool 266 with two, three, four, five or more removable pleating blocks 268. Heating the pleating blocks 268 to about 80 Celsius and then pressing them against the balloon for about 1 minute causes the balloon to become pleated or fluted. Commercial pleating machines such as balloon folding machinery from Interface Associates (Laguna Niguel, Calif.) can also be used. A small amount of wax may be used to hold the pleated and folded balloon into its desired shape.

Figure 71:
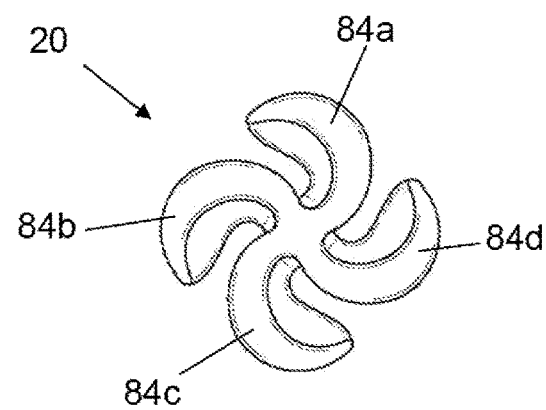
FIG. 71 illustrates a variation of the device in a deflated, pleated state.

FIG. 71 illustrates that a pleated balloon in a deflated or contracted configuration can have one or more pleats.

Uni-Tape Layers can be their Own Layers.

Figure 72:
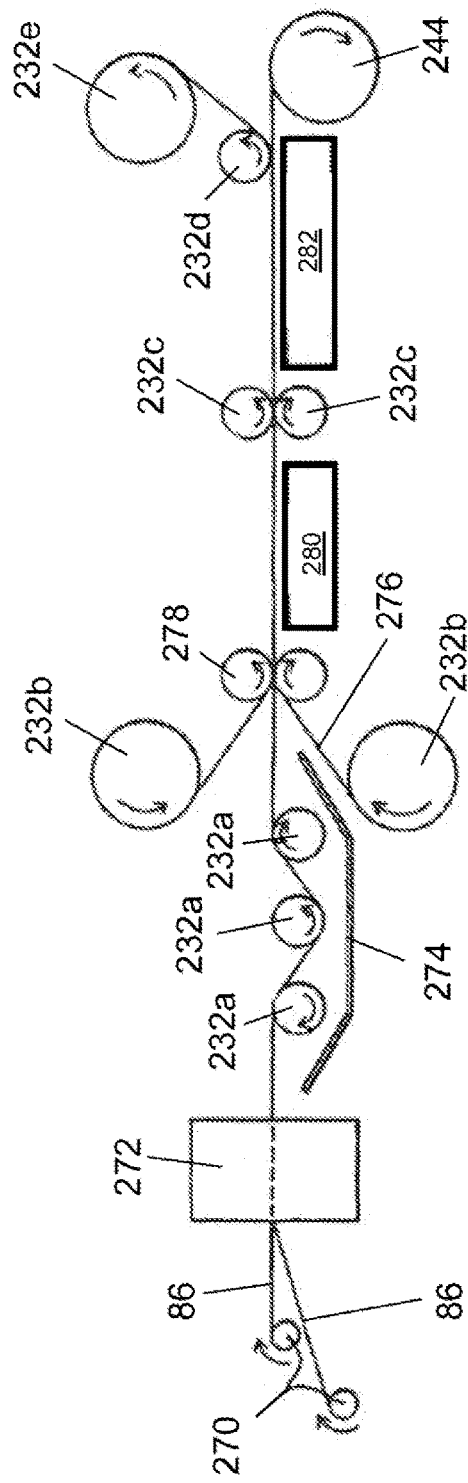
FIG. 72 illustrates a portion of a method that may be used to produce unidirectional fiber tape.
Figure 73:
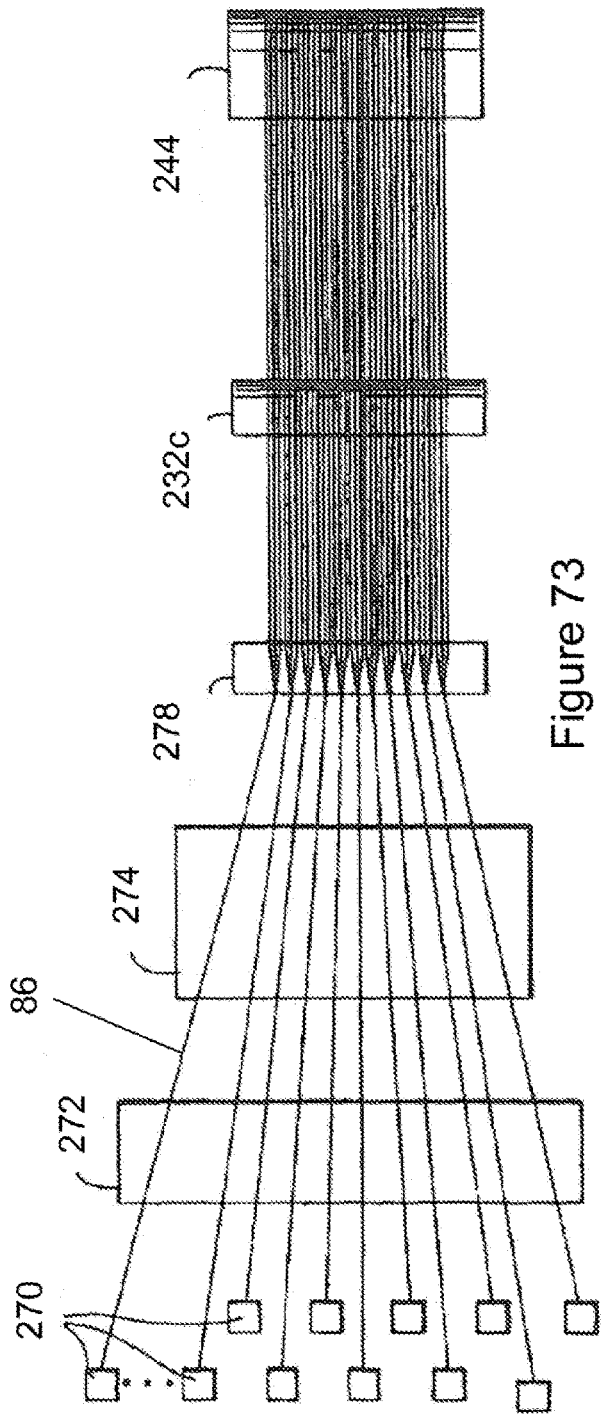
FIG. 73 illustrates a portion of a method that may be used to produce unidirectional fiber tape.

FIG. 72 and FIG. 73 illustrate one method of uni-tape fabrication. Tows or bands 270 provide the extruded monofilaments or fibers 86 which are optionally passed through a treatment bath 272 to improve adhesive bonding features of the exterior of the monofilaments via chemical etching, plasma arc etching or corona discharge etching. The pretreated monofilaments from the tows are pulled through an adhesive bath 274 over and under first rollers 232a where the matrix adhesive coats and surrounds the monofilaments.

The adhesive-coated monofilaments are drawn through a fixed gap rotary die 278. Release material 276 from second rollers 232b can be applied to the top and bottom of the adhesive coated monofilaments, for example, prior to the pulling of the tows 270 through the fixed gap rotary die 278 which controls adhesive content and spreads the filaments. During a pull-trusion process, the individual tows are laterally joined to form a uni-tape which is heated by a heater 280 for viscosity change, after which the tape is compacted via rolls third rollers 232c. The compacted tape can then be passed over a chill plate 282 to the spool 244, with the top sheet of release material being removed at roll fourth roller 232d and reeled up on fifth roller 232e.

The monofilaments can be subject to less than about 0.02 pounds of tension during assembly substantially immediately before the monofilaments set in the adhesive matrix. For example, substantially no tensioning can be applied to the monofilaments during manufacturing immediately before the monofilaments set in the adhesive matrix.

Another kind of fiber tape (hereafter referred to as woven tape) may have a woven, knitted or braided fiber cloth, a flexible adhesive, and an optional removable backing or combinations thereof. The removable backing can be made of paper, plastic, film, metal, elastomer, foam, fabric or combinations thereof.

Woven, knitted and braided cloths are known though modern textile products. Typically, weave patterns feature a warp threads, running in a first direction, and weft threads, running in a second direction. The angle between the first and second directions may be 90 degrees. The angle between the first and second directions may be 75 degrees. The angle between the first and second directions may be 60 degrees. The angle between the first and second directions may be 45 degrees. The angle between the first and second directions may be oriented at any appropriate angle. In the process of weaving, the threads may be interlaced in various ways to form weave patterns depending on the properties desired.

Another kind of fiber tape (hereafter referred to as matted tape) can have matted fiber, a flexible adhesive, and an optional removable backing or combinations thereof. The removable backing can be made of paper, plastic, film, metal, elastomer, foam, fabric or combinations thereof. The matted fiber may be a collection of randomly oriented fibers of different lengths.

Figure 74:
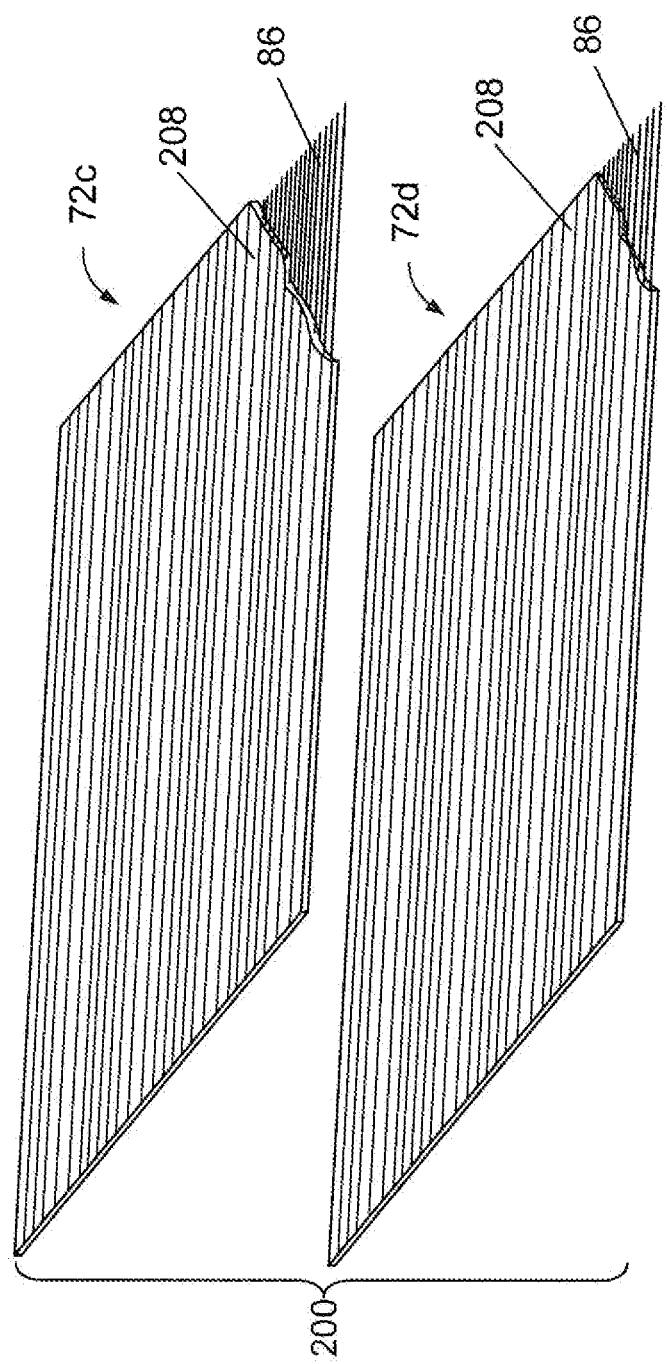
FIGS. 74 through 77 illustrate variations of arrangements of unidirectional fiber tape.

FIG. 74 shows that layers 72c and 72d can have reinforcement fibers 86 oriented in the same direction. This is a 0-0 arrangement, because of the angle that each layer 72d makes with a vector aligned with the fibers of the bottom layer 72c. This arrangement may provide twice the strength in the fiber direction as the uni-directional tape itself.

Figure 75:
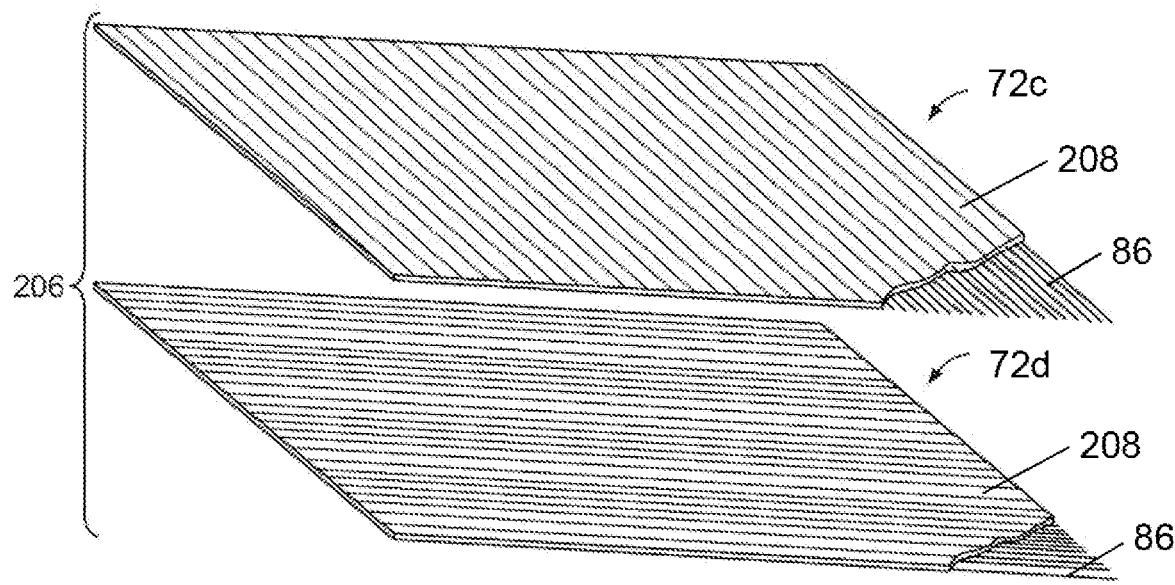

FIG. 75 shows that layers 72c and 72d can have reinforcement fibers 86 oriented perpendicular to each other. This is a 0-90 arrangement, because of the angle that the second layer 72d makes with a vector aligned with the fibers of the bottom layer 72c. This arrangement may provide substantially the same strength in the 0 degree and 90 degree direction as the uni-directional tape itself.

Figure 76:
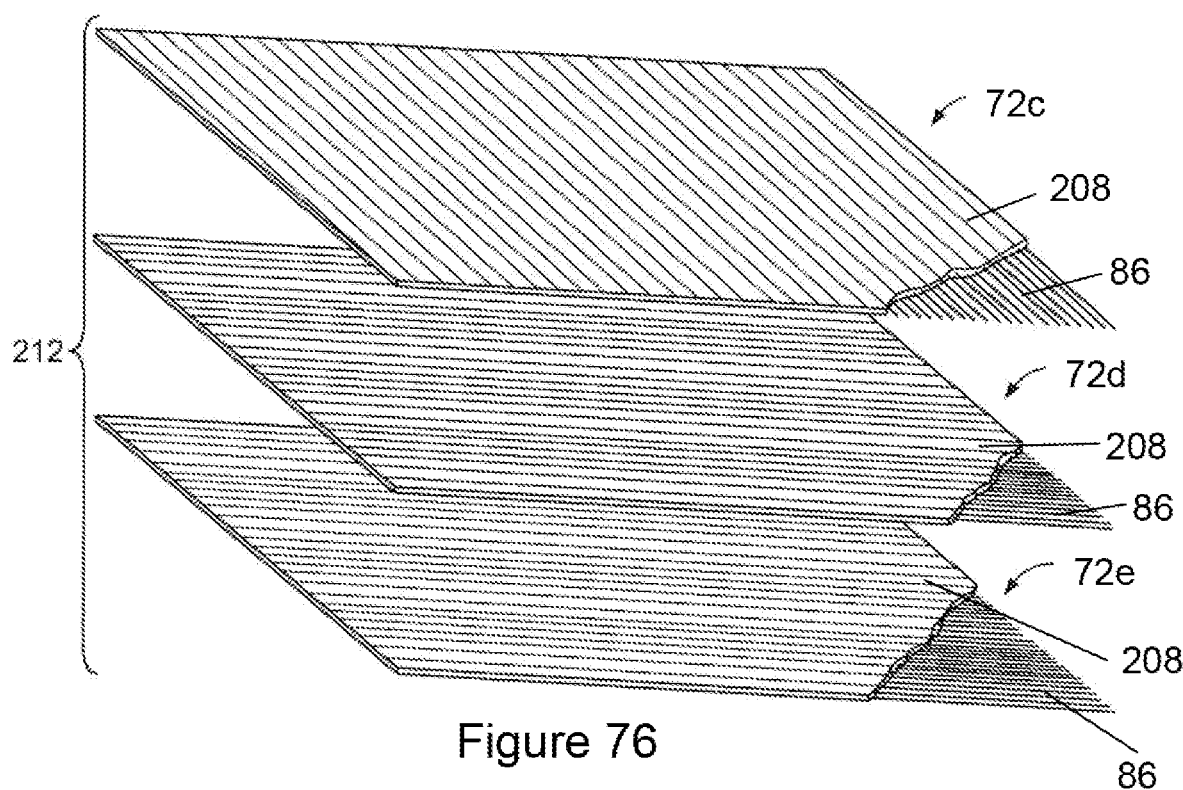

FIG. 76 shows that layers 72c, 72d and 72e can have reinforcement fibers 86 oriented at 0-0-90 to each other. This arrangement may provide approximately twice the strength in the 0 direction than a single layer of uni-tape provides. This arrangement may provide strength in the 90 direction approximately equal to that of a single uni-tape.

Figure 77:
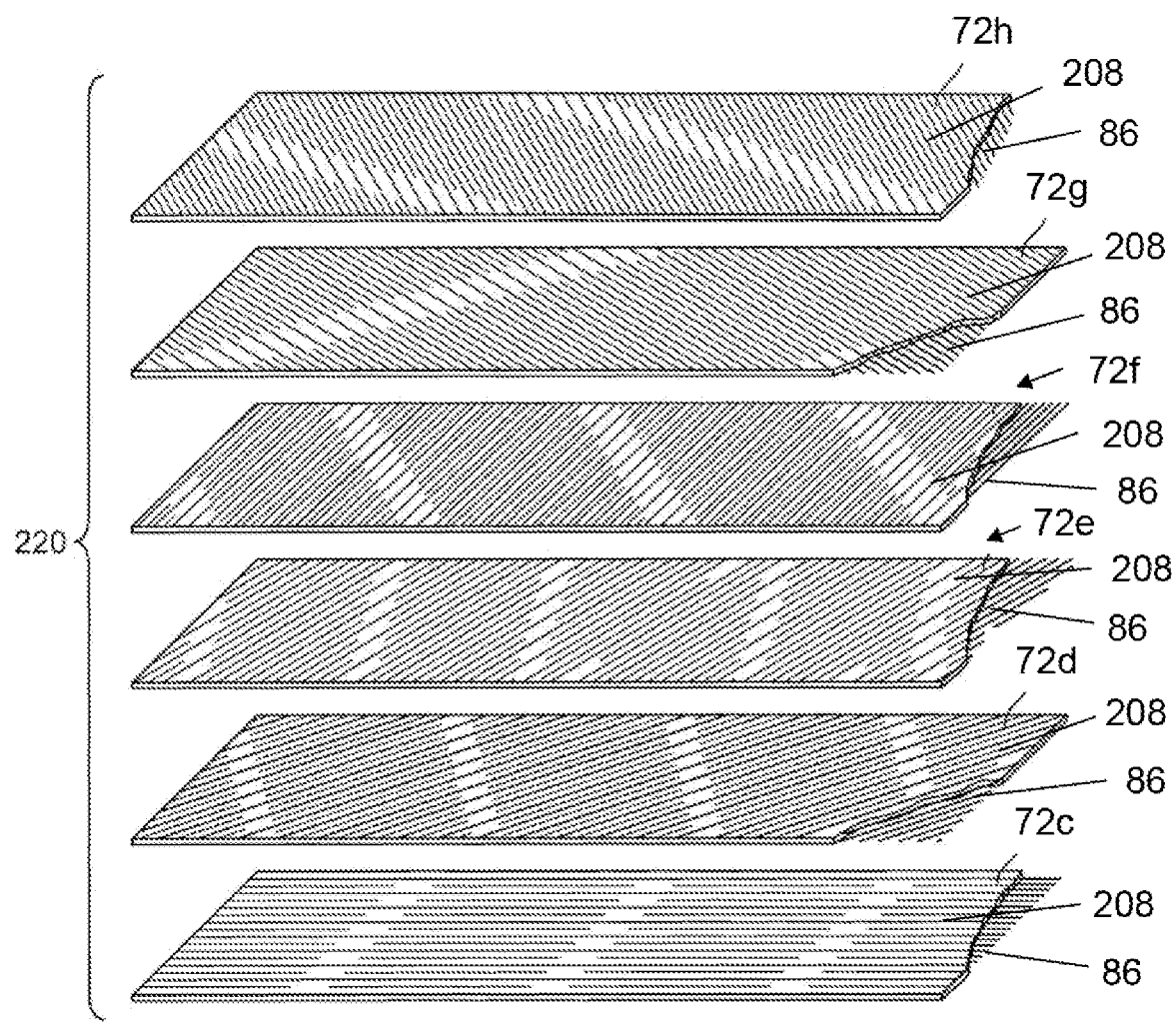

FIG. 77 shows that layers 72c, 72d, 72e, 72f, 72g, and 72h can be oriented at 0, 30, 60, 90, −30, −60 respectively to each other.

A laminate may include one or more fiber tapes. A laminate may include one or more polymer films.

The one or more fiber tapes and, optionally, the one or more polymer films can be consolidated into a laminate. Consolidation may include compaction and curing or melting. Compaction can occur before curing or melting. Compaction may include the application of heat and/or light and/or an electron beam, the application of force (i.e., pressure), and the passage of time. Curing or melting may include the application of heat or light, the application of force (i.e., pressure), and the passage of time.

During the process of consolidation, fibers may shift position within the laminate. During the process of consolidation, the fibers may get closer to each other within the laminate.

The polymer film or polymer films may melt during the consolidation process or the polymer films may not melt. The polymer films can be on one or both outer surfaces of the laminate and different materials can be put on each side. The polymer film can be on only one side of the laminate, or absent altogether.

The polymer film could be formed by applying a polymer in a wet application process, such as spraying, dipping, painting, or combinations thereof.

The polymer film may be coated with a material. The coating may be applied by, for instance, sputter coating. The material that is coated on the polymer film may provide substantial radiopacity.

Figure 78:
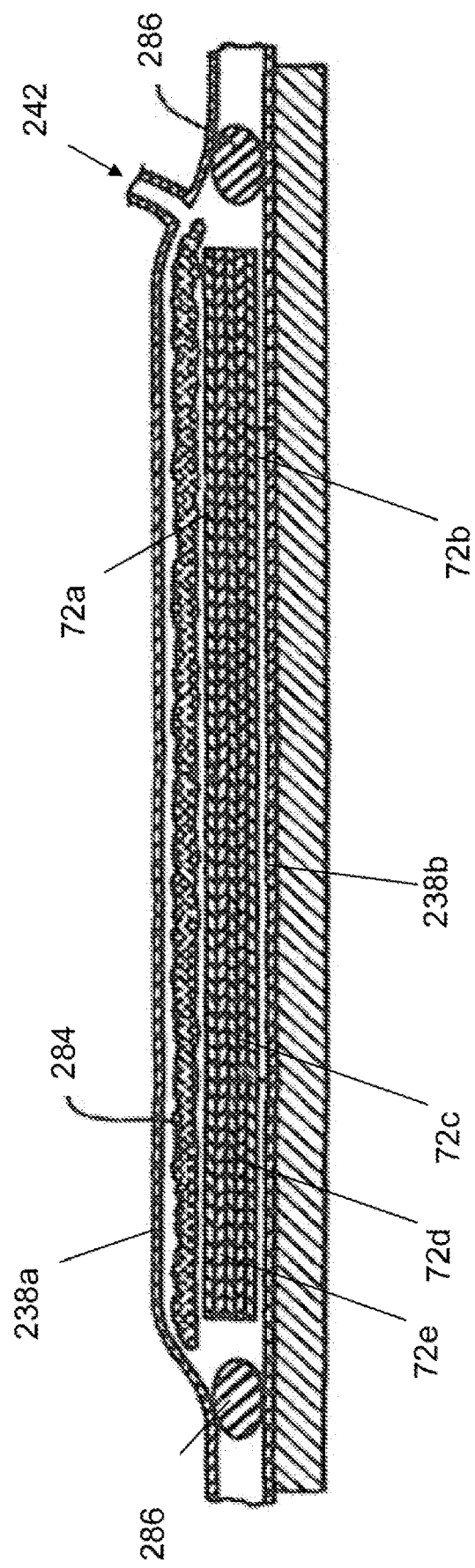
FIG. 78 illustrates a variation of a method for making a laminate.

FIG. 78 shows an example of the fabrication of a laminate by using an auto clave. Various layers of fiber tape material 72c, 72d, and 72e can be between an outer layer 72a of a film and an inner layer 72b of a film. The fiber tape material and the films can be between a top vacuum sheet 238a and a bottom vacuum sheet. The bottom vacuum sheet can be placed on a rigid plate or platen 288. Sealing is provided by seals 286. A breather material 284 may be between the outer layer 72a and the top vacuum sheet 238a, for example for evacuating gas from between the vacuum sheets. The enclosed volume or bag between the top and bottom vacuum sheets can be evacuated at the suction tube 242.

Figure 79:
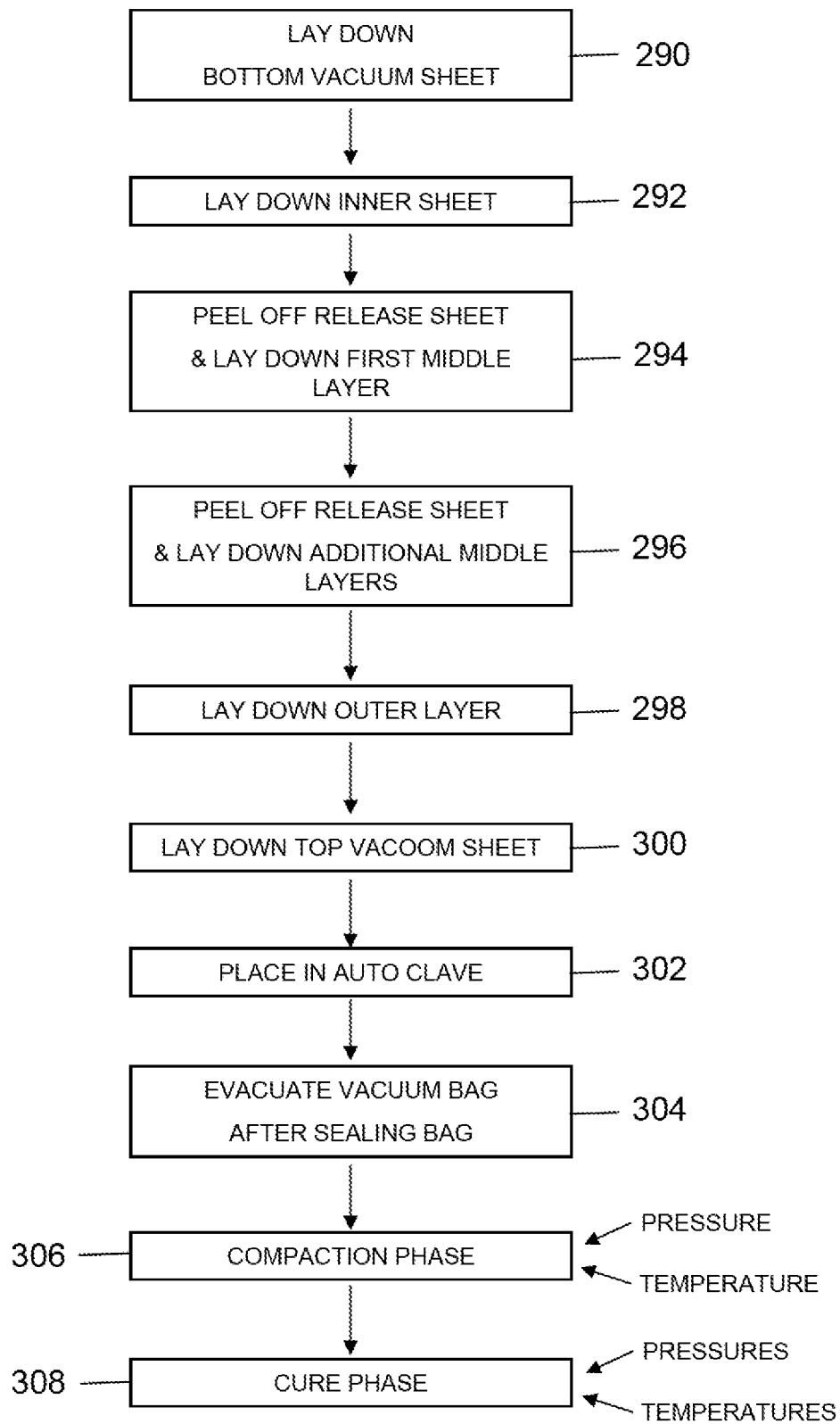
FIG. 79 is a process flow chart of a variation of a process for making a laminate.

During the autoclave process as illustrated in FIG. 79, the process steps are first to lay down the bottom vacuum sheet as illustrated at 290. Secondly, one optionally lays down the inner layer 292 to be laminated or consolidated as illustrated at 292, followed by the peeling off of the removable backing and laying down the first middle layer as illustrated at 294. Thereafter as illustrated at 296, optional additional middle layers can be laid down after removal of their removable backing. Additional fiber tape can be laid down in additional directions as needed. Thereafter, the outer layer can be optionally laid down as illustrated at 298. A breather material 284 may be positioned between the outer layer and the and top vacuum sheet. The top vacuum sheet can be laid down over the breather material 284 as illustrated at 300. The structure can be placed in an autoclave as illustrated at 302. The volume between the bottom and top vacuum sheets can be evacuated after sealing the edges as illustrated at 304.

Thereafter, as part of a consolidation phase, follows a compaction phase as illustrated at 306 at the requisite pressures and temperatures. Thereafter, as part of a consolidation phase, follows a curing or melt phase as illustrated at 308 at associated pressures and temperatures.

Figure 80:
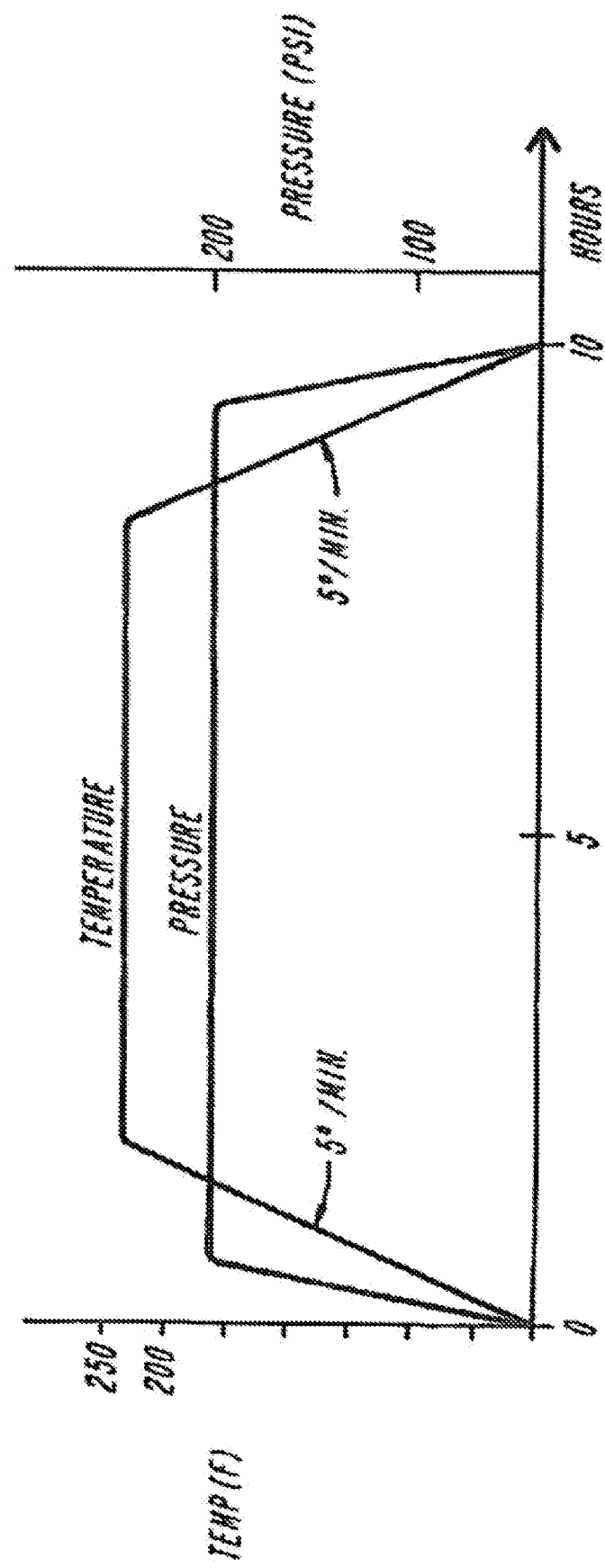
FIG. 80 is a graph illustrating a variation of temperature and pressure verse time graph for a method for compacting or curing or melting that can be used with a fiber tape.

One set of pressures and temperatures useful for a compaction or cure or melt phase is illustrated in FIG. 80 by the temperature time graph and associated temperature pressure graph.

Several laminates, each with different fiber orientations and a different number of layers, may be created. Alternately, a single laminate may be constructed with multiple fiber orientations and layer quantities placed into different regions of the larger laminate. From this single laminate, smaller laminates with specific fiber orientations can then be removed and used to create a medical inflatable.

The choice of a film for the inner or outer surface can provide desirable properties.

If it is desired that the outside of the laminate be low friction and resistant to harm from chemicals, or that the laminate readily release from certain adhesives (such as, for instance, Methyl methacrylate, a principal ingredient in bone cement), a fluoropolymer such as FEP (Fluorinated ethylene propylene) may be selected for the outer layer. One side or both sides of the FEP film may be treated via a plasma method a corona discharge method or via an etchant or by some combination thereof. These treatments may make the fluoropolymer film easily bondable on one or both of its surfaces. The film may also be purchased in a bondable state. A treated surface can form a strong bond with an adhesive, such as the adhesive in the fiber matrix. A surface made bondable may be restored to an unbondable state.

A metal film or foil layer on the outside of the balloon can also be used to resist chemical attack. This metal film or foil layer may give the balloon radiopacity. The outer surface of the balloon may also have a coating that may help the balloon resist chemical attack. The coating may be fluoropolymer based.

The laminate can be made as describe in U.S. Pat. No. 5,333,568 or 5,470,632, both of which are herein incorporated by reference in their entireties.

A layer may be leak tight. The layer may be made by dip molding, for example, urethane or nylon, over a mandrel. The layer may be made by rotational molding.

The layer may be made by coating a substance over the mandrel or the balloon. A coating may be, for instance, parylene. A coating may be a metal, such as gold. A coating may electrodeposited, electroless deposited or via physical vapor deposition or a combination thereof. A coating may have significant radiopacity. A coating may increase the toughness of the balloon, or increase its lubricity. A coating may reduce or eliminate attack or adhesion from chemicals. For instance, a coating may cause the balloon to not be attacked or to adhere to bone cement.

A layer may be formed by conformal coating. A conformal coating may include a fluoropolymer. The coating may be dipped on, sprayed on or applied by electrostatically charging the substrate or by combinations thereof. Coatings may be Cured by baking.

A layer may be formed by blow molding. The blow molding process can include a parison. The parison may be open at both ends, or only open at one end (a "blind" parison).

Figure 81A:
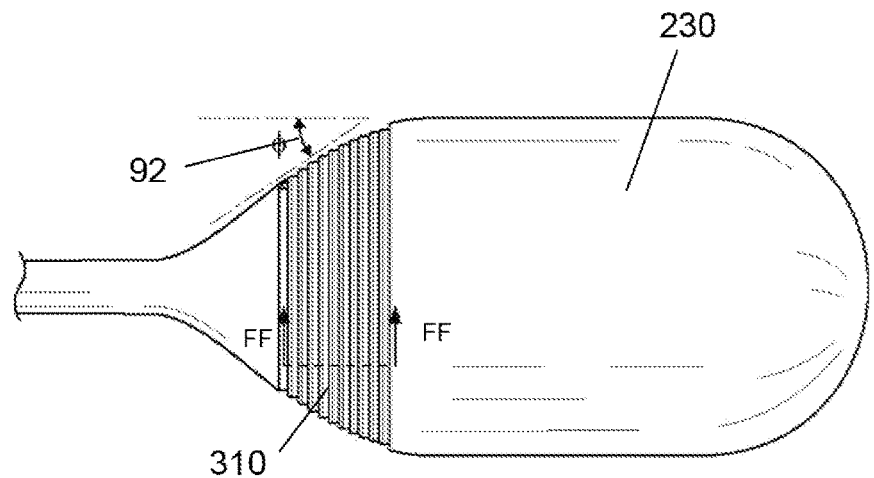
FIG. 81A-81D illustrates a variation of the mandrel.

FIG. 81A illustrates that the mandrel can have a spiral groove. The fiber can be wound in the spiral groove. The spiral groove can be on the proximal stem, proximal taper, constant diameter section, distal taper, any steps, or combinations thereof.

Figure 81B:
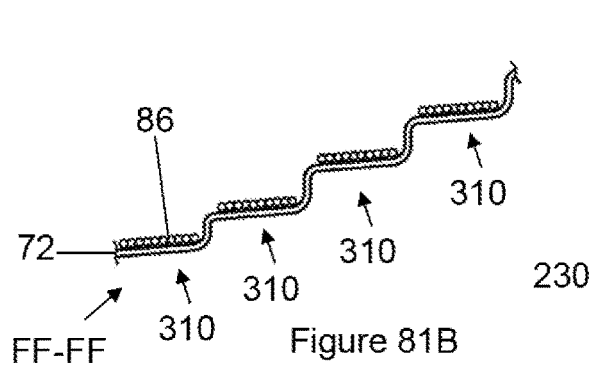

FIG. 81B illustrates that the mandrel groove 310 can be stepped along the length of the mandrel. The fiber can be wound one or more (as shown) times on each step of the groove 310.

Figure 81C:
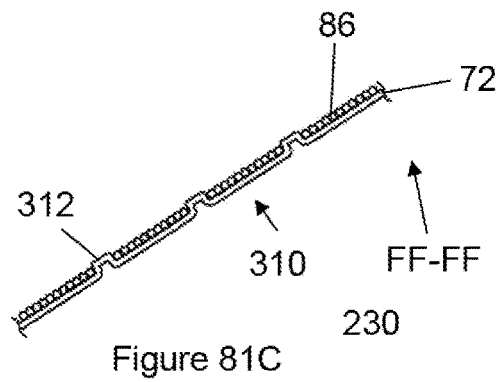

FIG. 81C illustrates that the mandrel groove 310 can be bound by groove edges 312 that can be raised above the level of (i.e., have a larger radius than) the mandrel groove. The groove edge 312 can interference fit against the fiber. The groove edge height can be equal to or greater than the diameter of the fiber.

Figure 81D:
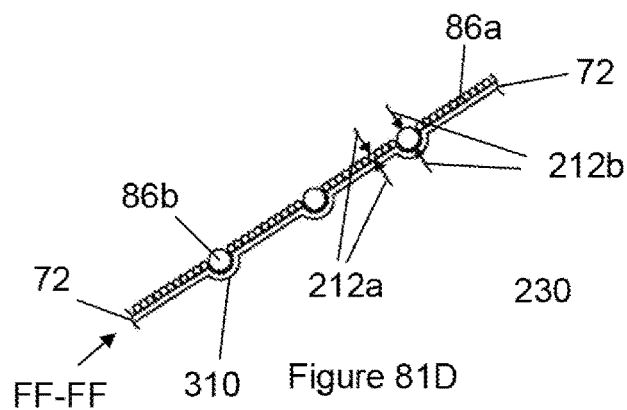

FIG. 81D illustrates that the mandrel groove can be configured to receive a second fiber having a second fiber diameter. The second fiber can be wound into the second mandrel groove. A first fiber having a first fiber diameter can be wound between the windings of the mandrel groove. The second fiber can act as a groove edge to the first fiber, interference fitting the first fiber to trap the first fiber between windings of the second fiber. The fibers can have a diameter of from about 0.0005 in. to about 0.004 in. For example the first fiber can have a first fiber diameter of about 0.00075 in. and the second fiber can have a second fiber diameter of about 0.004 in.

FIG. 82A illustrates that a fiber tool 314 can be used to configure the fiber into a spiral configuration. The fiber tool 314 can have a fiber tool first part 316a removably attached to a fiber tool second part 316b. The fiber tool second part can have a tool axle 322. The fiber tool first part can have a tool hub 320. The tool axle 322 can be rotatably and/or removably received by the tool hub 320.

The fiber tool 314 can form a fiber gap 318 between the fiber tool first part 316a and the fiber tool second part 316b. The fiber gap 318 can have a fiber gap width 324. The fiber gap 318 can be adjusted by, for example, the use of a feeler gauge. The gap width can be from about 15 μm to about 200 μm, more narrowly from about 15 μm to about 100 μm, more narrowly from about 15 μm to about 35 μm. The fiber gap width 324 can be about, or nominally larger than, the diameter of the fiber.

FIG. 82B illustrates that the fiber can be wound into the fiber gap 318. The fiber gap can be straight, for example having a circular configuration. A first release layer and a second release layer may be placed on the inside walls of the fiber gap. An adhesive may be placed in contact with the fiber. The adhesive may be a thermoplastic or a thermoset. The adhesive may be cured or melted. The adhesive may be in place before, during or after the fiber is added to the fiber tool. The adhesive can be a resin. A port (not shown) can be added to the tool such that, under pressure, resin and/or solvent can be infused into the fiber in the gap. The resin and/or solvent can extrude out the perimeter of the gap. The gap can be sealed created a closed volume. The resin and/or solvent can be delivered under pressure into the closed volume of the gap to infuse the fiber.

FIG. 83 illustrates that after the adhesive is cured or melted, the fiber tool first part can be removed from the fiber tool second part. The wound fiber and adhesive, as shown, can then be removed from the fiber tool. The wound fiber can have a substantially flat or conical configuration.

Figure 84:
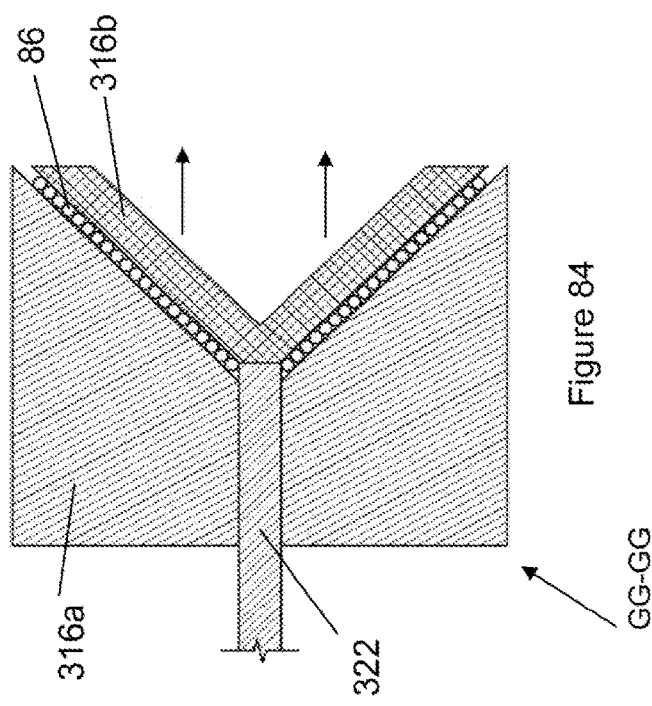
FIG. 84 is a variation of cross-sectional view GG-GG of FIG. 82A.

FIG. 84 illustrates that the fiber gap can be v-shaped in cross-section, for example having a conical configuration.

Figure 85:
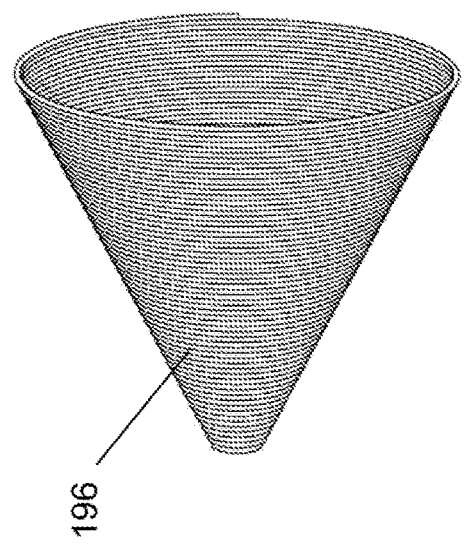
FIG. 85 illustrates a variation of the fiber during a variation of a method for manufacturing the device.

FIG. 85 illustrates the fiber and adhesive panel after coming out the tool pictured in FIG. 84.

Figure 86:
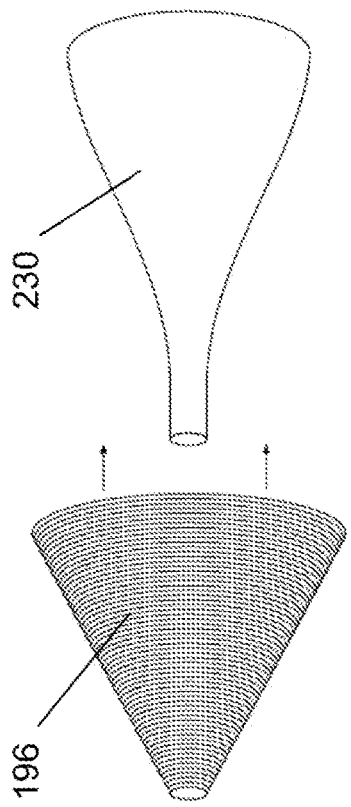
FIG. 86 illustrates a variation of a method for manufacturing the device.

FIG. 86 illustrates that the wound fiber can be pressure-formed on a mandrel.

Figure 87:
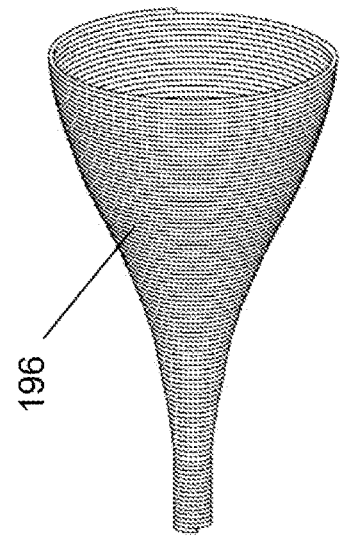
FIG. 87 illustrates a variation of the fiber during a variation of a method for manufacturing the device.

FIG. 87 illustrates that the shape of the fiber can be distorted by the mandrel to have a wall having a concave, convex or s-curve.

Pressure forming may allow the conical panel to be formed into a shape that more readily matches the shape of a portion of the balloon. The resulting conical panel may be placed onto the balloon and cured or melted into place.

Figure 88:
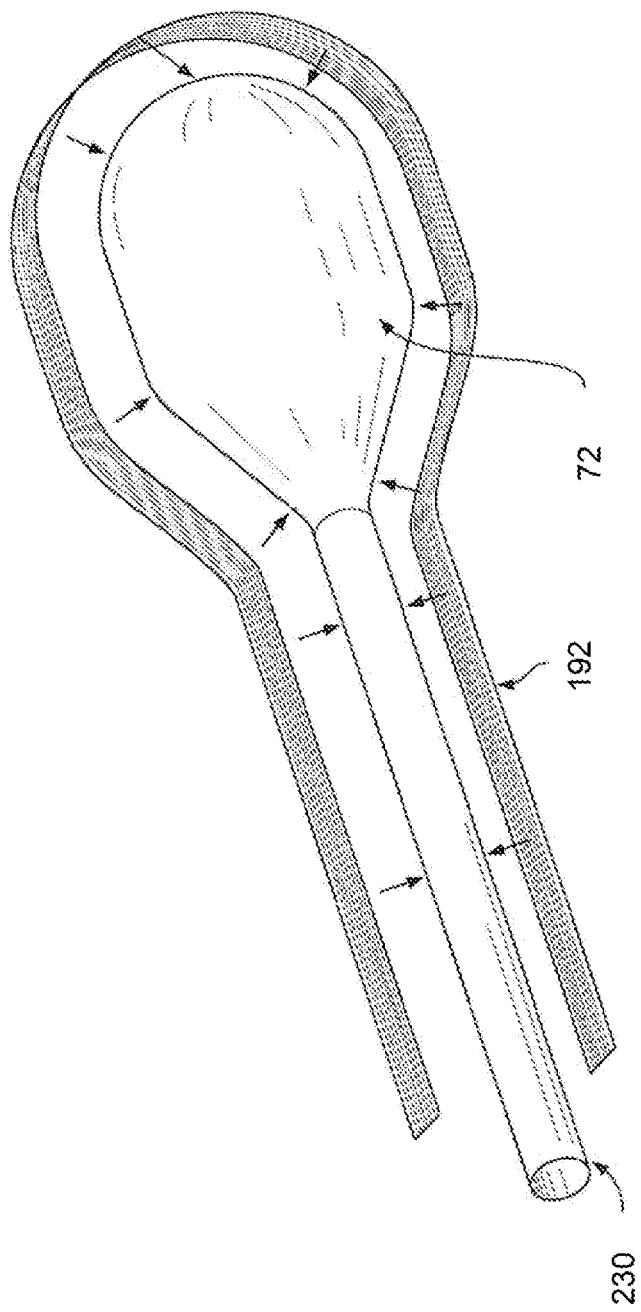
FIG. 88 illustrates a variation of a method for manufacturing the device.

FIG. 88 illustrates an alternate method of applying a fiber tape to a balloon 20. The balloon 20 can have continuous laminates that start at a first end of a mandrel, 230 go to the opposite end of the mandrel 230 and return to the first end of a mandrel 230. The laminate may start substantially at the first end of the mandrel, 230 or near the first end, for example within 4 mm. The balloon 20, the bladder or inner layer, or a mold can be substituted for the mandrel 230 in this variation.

Figure 89:
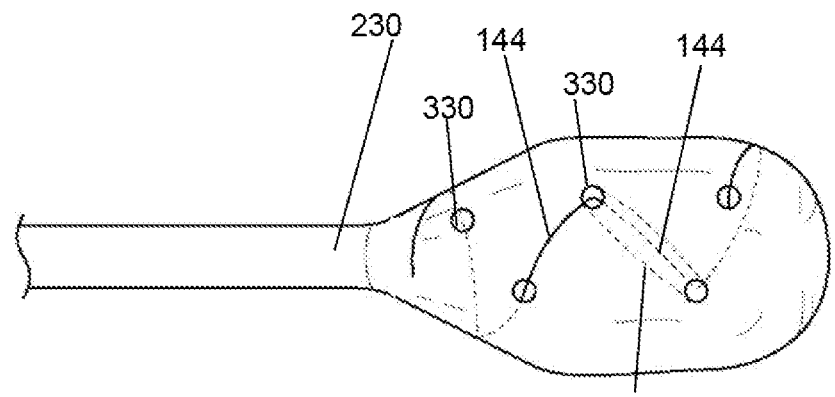
FIGS. 89 through 91D illustrate variations of a method for manufacture of the device.
Figure 90:
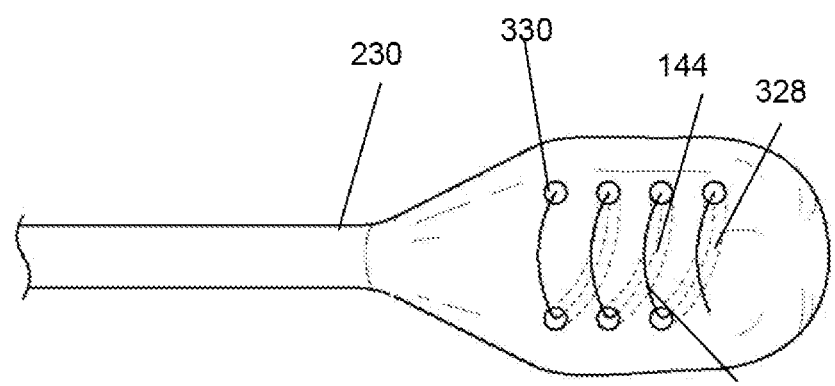

FIG. 89 illustrates that the mandrel can have one or more cross channels 328 through the mandrel. The cross channels 328 can have cross channel ports 330 on the surface of the mandrel. One or more internal restraints can be placed through the mandrel. The restraints may comprise a fiber. A continuous restraint may pass thru one, some or all of the holes in the mandrel FIG. 90 illustrates that the mandrel can have a cross channels that can be parallel with one or more (shown as three) adjacent cross channels. The cross-channels can be curved.

Figure 91A:
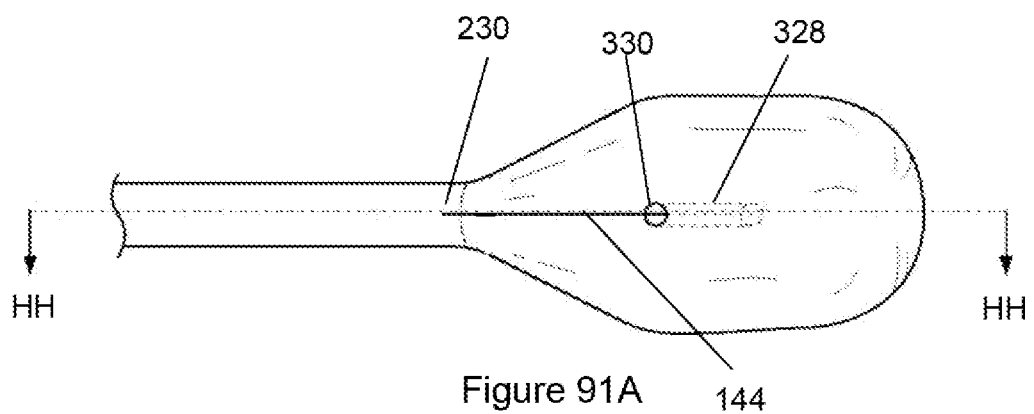

FIG. 91A illustrates that the cross-channel can transect the diametric center of the mandrel. The cross-channel can be straight.

FIG. 91B illustrates that the balloon can have an inner layer and an outer layer. The internal restraint can be fixed to the radial outside of the outer layer.

FIG. 91C illustrates that the internal restraint can be fixed between the inner layer and the outer layer.

FIG. 91D illustrates that the internal restraint can be fixed to the radial inside of the inner layer.

Figure 92:
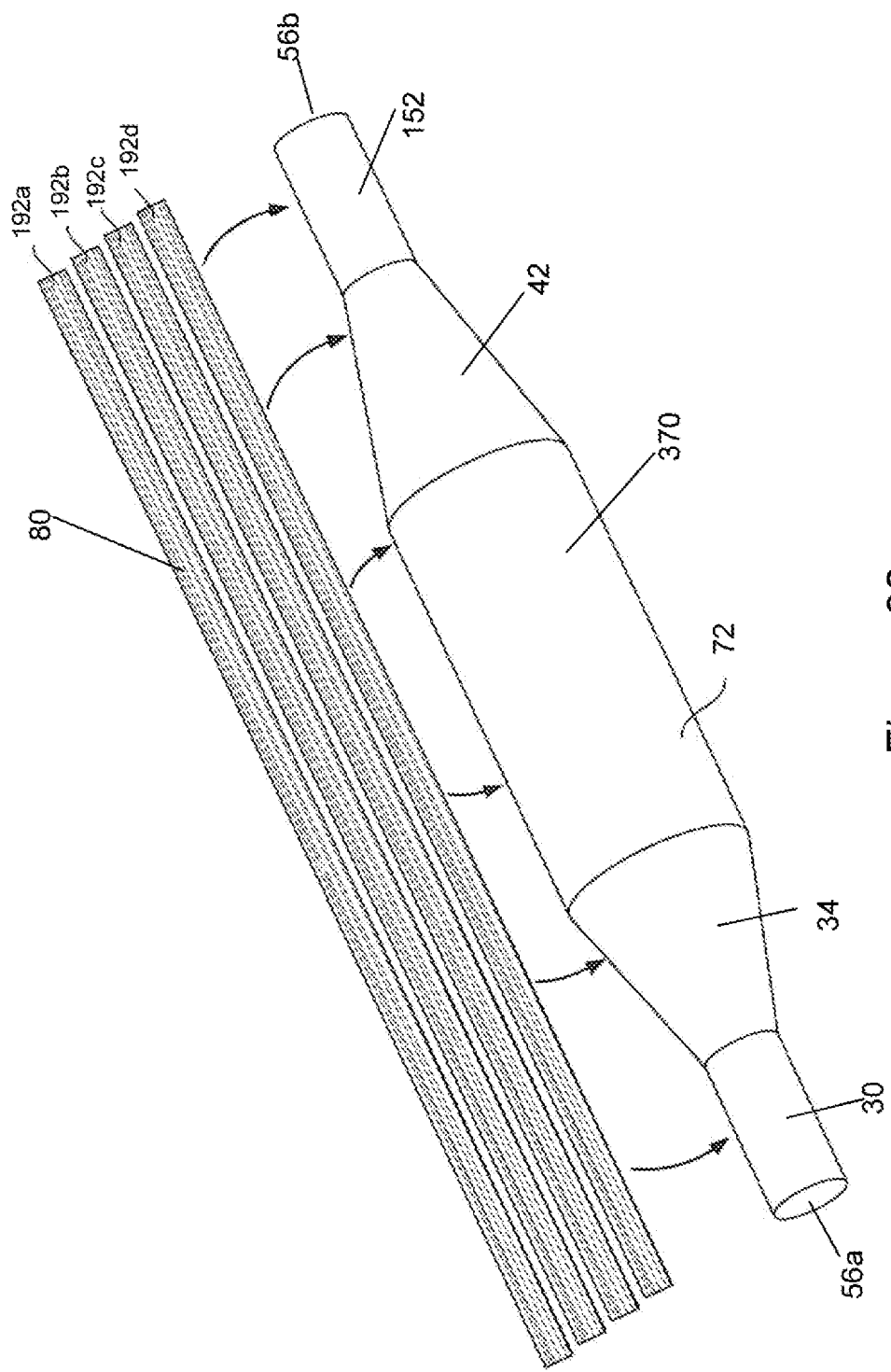
FIGS. 92 through 94 illustrate variations of methods for manufacturing the device.

FIG. 92 illustrates a portion of an alternate process for applying fiber tape to a mandrel. FIG. 92 illustrates that the first, second, third and fourth strips 192a, 192b, 192c, and 192d may have one or more layers of uni-tape oriented along the long axis of the laminate (this fiber orientation is shown in the figure). The strips 192 can be rectangular. The strips 192 can have adhesive. Each strip may be oriented parallel to the mandrel longitudinal axis or balloon longitudinal axis. Enough strips can be used such that the strips encircle the mandrel's largest diameter. The strips may overlap each other. The mandrel can have one or more layers on the mandrel before the strips are applied.

Figure 93:
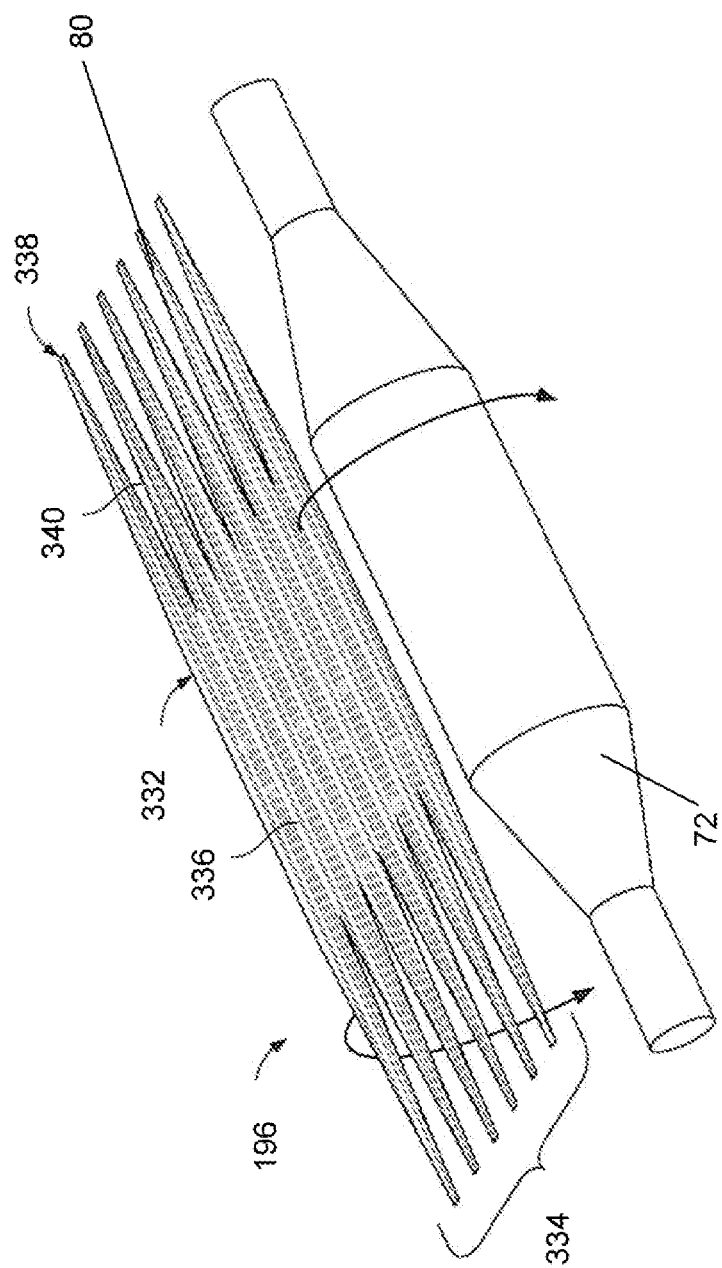

FIG. 93 illustrates that a panel may be applied to a mandrel with none, one or more layers on the mandrel. The panel can have one or more layers of uni-tape oriented along the long edge panel longitudinal edge 332. The panel can have a panel width 334. The panel can have a panel rectangular section 336 and one or more panel serrations 338. The angle between the serrations 338 can be a panel serration angle 340. The panel serration angle 340 can be about 30°, about 20°, about 10°, or about 00. The panel longitudinal edge can be oriented parallel to the mandrel longitudinal axis or the balloon longitudinal axis. Parts of the panel may overlap other parts of the panel.

Figure 94:
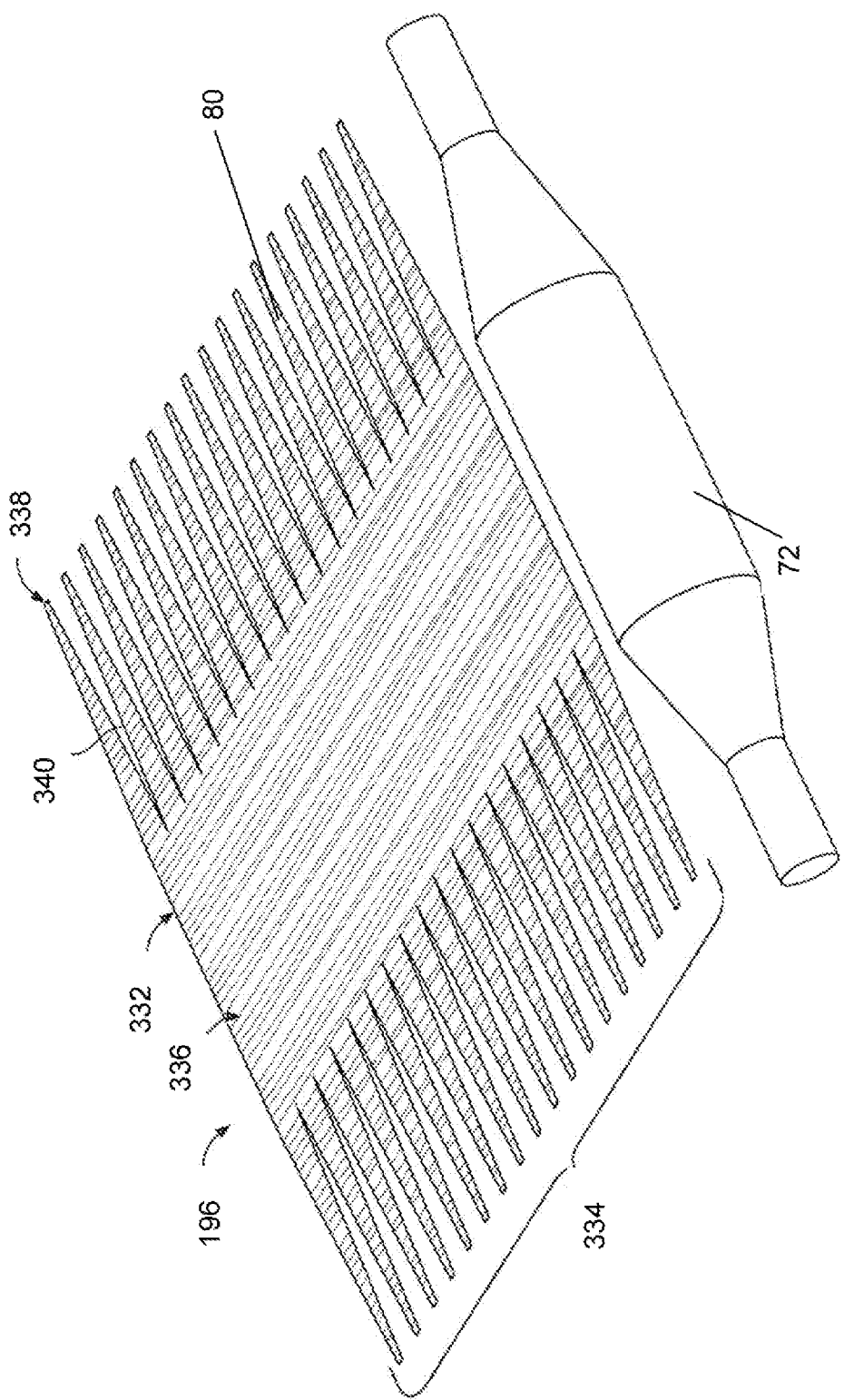

FIG. 94 illustrates that the panel can be applied to a mandrel with none, one or more layers on the mandrel. The panel can have one or more layers of uni-tape oriented perpendicular to the panel longitudinal edge 332. The panel can have multiple layers of uni-tape oriented at different angles in the panel (not shown). The uni-tape may make angles (not shown) of about 30°, about 45°, or about 60° with panel longitudinal edge 332.

The panel width can be more than about three times the circumference of the balloon, layer or mandrel. The panel can be wrapped around the balloon, layer or mandrel about three times. The panel width can be more than about five times the circumference of the balloon, layer or mandrel. The width can be more than about ten times the circumference of the balloon, layer or mandrel.

FIG. 95 illustrates that a first panel 196a can have eight serrations and a panel latitudinal edge 333. The first panel 196a can be a laminate of resin and fiber, as described herein. A first line 346a can be marked on the surface of the first panel 196a and may be parallel to the latitudinal edge 333 and located about 3 mm from the latitudinal edge 333. The first panel 196a can have a panel bottom edge 344 and the panel longitudinal edge 332. The panel bottom edge 344 can have a length of about 58 mm (2.3 in.). The panel longitudinal edge 332 can have a length of about 50 mm in length. The distance from the serration tip 342 to the first line 346a can be about 16 mm. The distance from the panel bottom edge 344 to the first line 346a can be about 47 mm. The second line 346b can be marked on the surface of the panel. The second line 346b can be perpendicular to first line 346a. The second line 346b can intersect a serration tip 342. The second area 348b of the panel below the first line 346a can have four unidirectional reinforcement fiber tapes laid sequentially in the 0 degree direction. The second area 348b can have two uni-tapes laid sequentially in the 90 degree direction. The first area 348a of the panel above the first line 346a can have two uni-tapes oriented sequentially in the 0 degree direction and two uni-tapes oriented sequentially in the 90 degree direction.

FIG. 96 illustrates that a second panel 196b can be circular. The second panel 196b can be about 28 mm in diameter and can have about four slits or cuts 350. Each cut 350 can be about 7 mm long. Four tabs 352 can be formed by the cuts 350. The second panel can have one each of the uni-tapes oriented sequentially at each of 0°, 30°, 60°, 90°, −30°, and −60° angles.

FIG. 97 illustrates that a third panel 196c can be shaped like a parallelogram with first side edge 356a parallel to second side edge 356b and third side edge 356c parallel to fourth side edge 356d. The first side edge 356a can form an acute angle with third side edge 356c of about 70°. The first side edge 356a can be about 13 mm long. The third panel 196c can have one uni-tape oriented in about the 0° direction and one uni-tape oriented in about the 90° direction.

FIG. 98 illustrates that a fourth panel 196d can be rectangular. The fourth panel 196d can have first and second long edges 358a and 358c and first and second short edges 358b and 358d. The long edges 358a and 358c can be about 58 mm. The short edges 358b and 358d can be about 3 mm long. The fourth panel can have about three uni-tapes oriented sequentially in about the 0° direction and about one uni-tape oriented about in the 90° direction.

Figure 99:
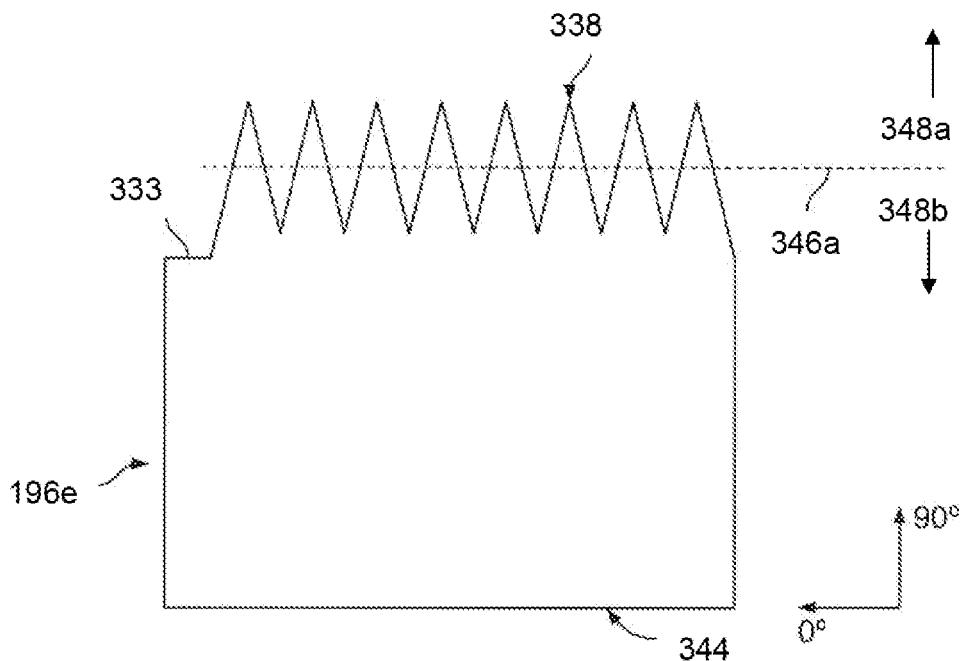

FIG. 99 illustrates that the fifth panel 196e can have panel serrations 338 and a panel latitudinal edge 333. The first line 346a can be marked on the surface of the fifth panel 196e and may be parallel to the latitudinal edge 333 and located about 8 mm from latitudinal edge 333. The fifth panel can have a bottom edge 344 about 57 mm in length. The distance from the tip of the serrations to the dotted line can be about 7 mm. The distance from the bottom edge to the dotted line can be about 43 mm. The second area 348b of the panel below the first line 346a may have four uni-taps oriented sequentially in the 0° direction and two uni-tapes oriented sequentially in the 90° direction. The first area 348a of the panel above the first line can have two uni-tapes oriented sequentially in the 0° direction and two uni-tapes oriented sequentially in the 90° direction.

Figure 100:
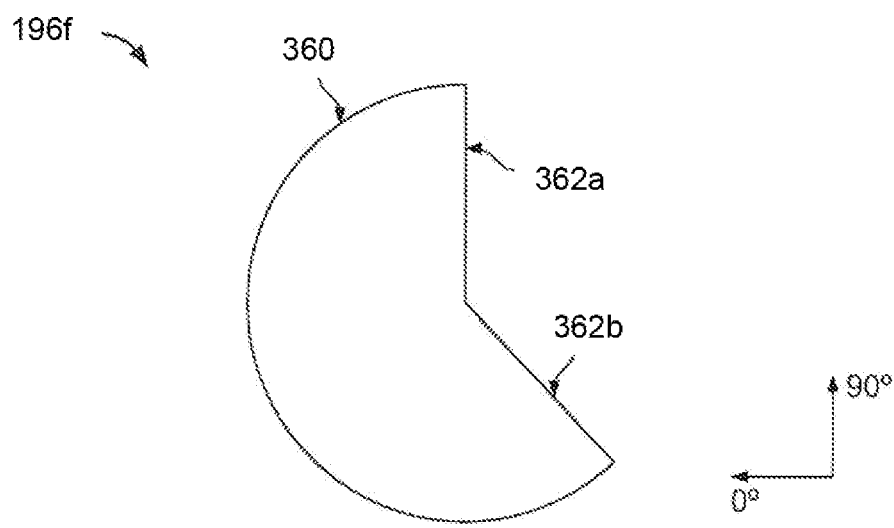

FIG. 100 illustrates that the sixth panel 196f can have a circular edge 360 with a radius of curvature of about 20 mm. The sixth panel 196f can have panel first and second radial edges 362a and 362b that connect to the panel circular edge 360 and connect to the center of the radius of curvature of the panel circular edge 360. The sixth panel can have one each of the uni-tapes oriented sequentially at each of 0, 30°, 60°, 90°, −30°, and −60° with respect to each other.

Figure 101:
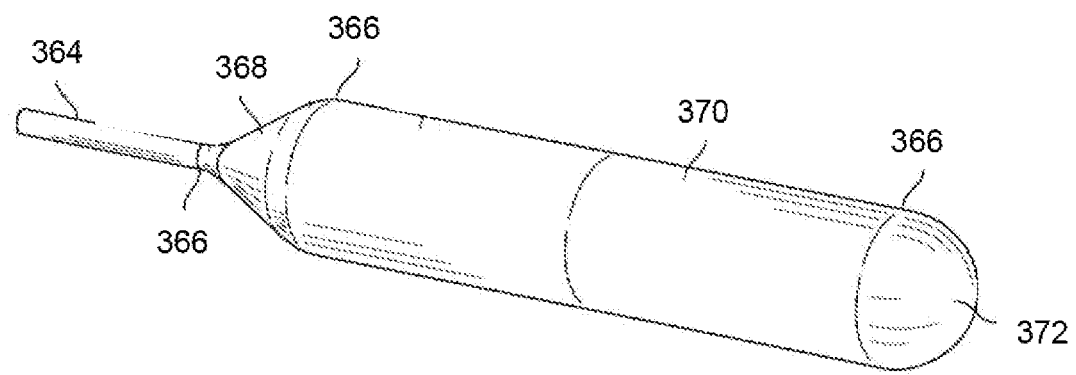
FIGS. 101 through 107 illustrate a method for manufacturing the device.

FIG. 101 illustrates that the mandrel 230 can have a mandrel constant diameter section 370 of about 17.07 mm in diameter and about 76 mm in length. The mandrel 230 can have a mandrel transition 366 where the first constant diameter section meets the distal taper approaching the mandrel terminal distal end 372. The mandrel 230 can have a mandrel stem 364 and mandrel proximal taper 368. The mandrel 230 can have mandrel transition 366 where the proximal taper 368 meets the mandrel constant diameter section 370. The mandrel 230 can have a mandrel transition 366 where the radius stem 416 meets transition radius. The mandrel can have transitions 366 between lengths.

Figure 102:
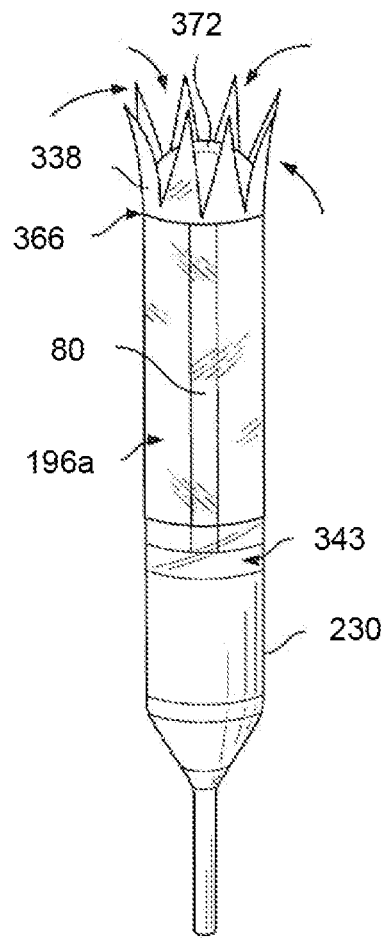

FIG. 102 illustrates that the first panel 196a can be wrapped around the distal end of the mandrel 230. The first line 346a can be aligned with mandrel transition 366 at the distal end of the mandrel 366. Adhesive can be placed in the region of overlap seam 66 to secure the panel on the mandrel. The adhesive can hold the panel closed around the mandrel. Standard cellophane tape 374 (also element 343) can secure the panel to the mandrel. Adhesive may next be applied to completely cover the outer surface of the serrations. Every other serration can be first folded over the mandrel distal taper. The remaining serrations can then be folded onto the mandrel distal taper.

Figure 103:
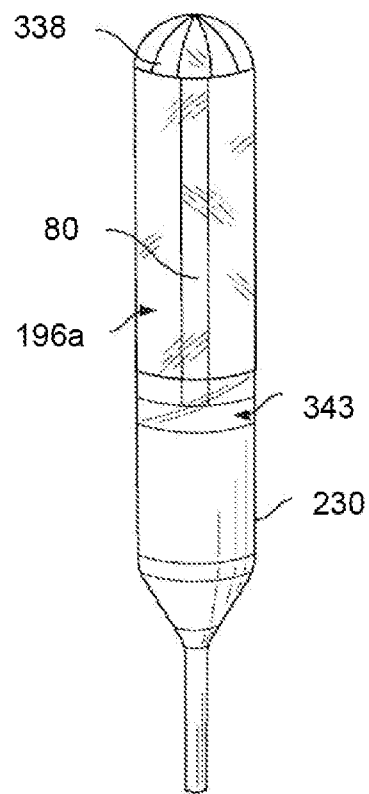

FIG. 103 illustrates the mandrel 230 with the first panel 196 applied to the mandrel 230 as described infra and in FIG. 73.

Figure 104:
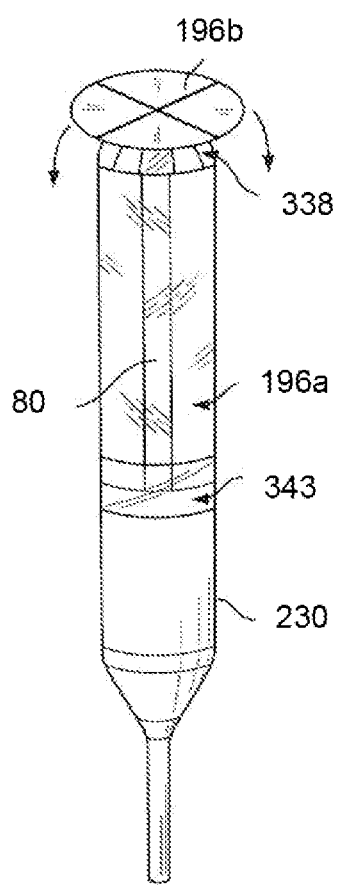

FIG. 104 illustrates that the second panel 196b can be centered on top of the distal taper. Any cut 350 in the panel can be aligned with the second line 346b on the first panel 356a. The four tabs 352 of the second panel can be folded over the serrations 338.

Figure 105:
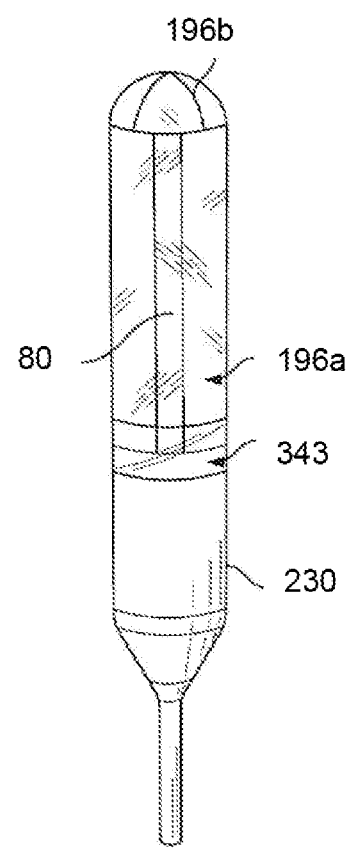

FIG. 105 illustrates the mandrel with the first and second panels 196a and 356b applied to the mandrel as described herein.

Figure 106:
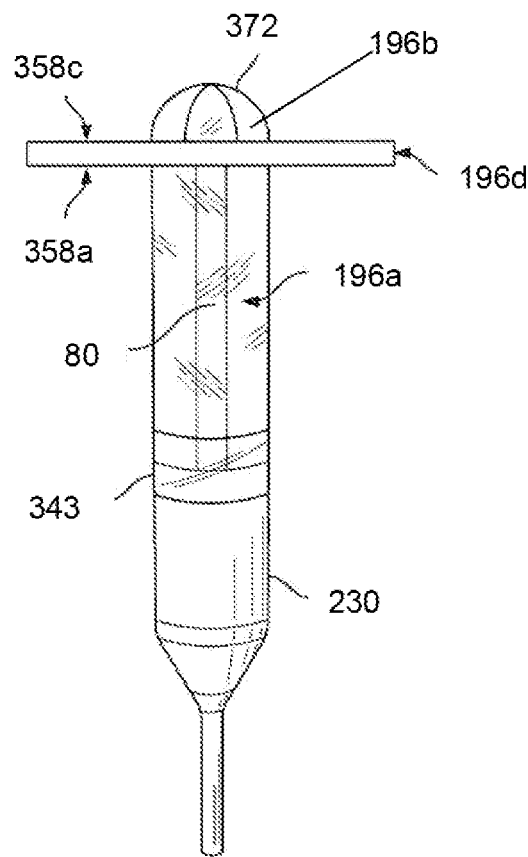

FIG. 106 illustrates that the fourth panel 196d can have adhesive applied to one surface. Second long edge 358c of the fourth panel 196d can be aligned with the first line 346a on the first panel 196a. The first long edge 358a can be positioned proximal to the first line 346a. The fourth panel 196d can be wrapped around the mandrel, with the adhesive on the fourth panel facing toward the mandrel. The balloon second section 384b can be removed from the mandrel.

Figure 107:
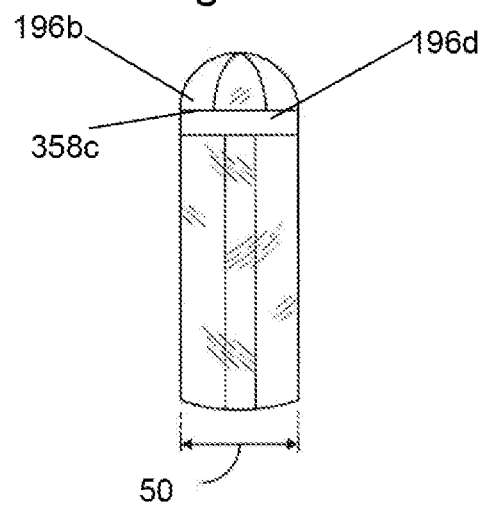

FIG. 107 illustrates that the balloon second section 384b. The distal balloon fragment can have balloon outer diameter 50.

Figure 108A:
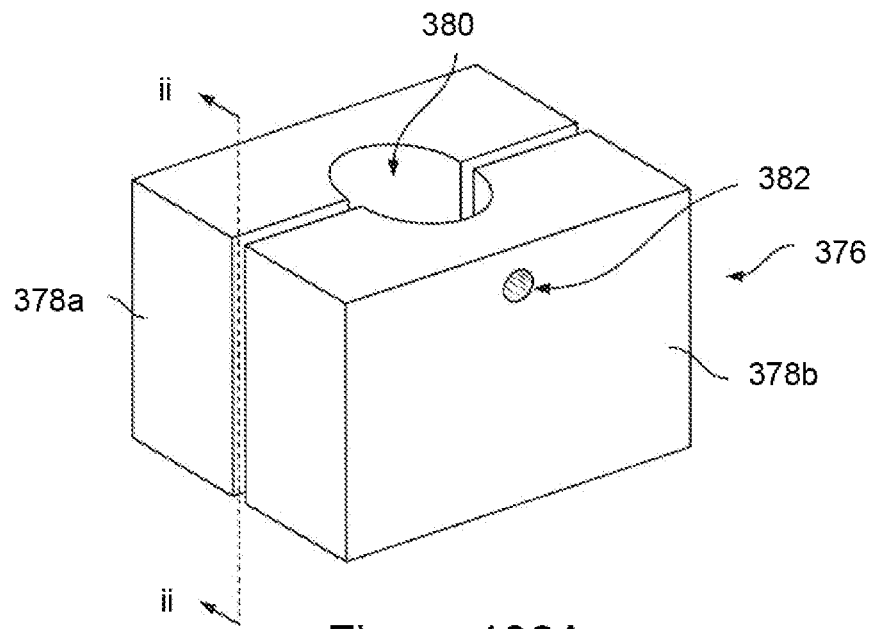
FIG. 108A illustrates a variation of a tool for manufacturing a variation of the inflatable device.

FIG. 108A illustrates that the female mold 376 can be made of a first mold half 378a and a second mold half 378b. When the two mold halves 378a and 378b are brought together, they can form a center mold lumen 380 where the second balloon section 384b may be placed in the mold 376. A mold port 382 in mold second half 378b is in fluid communication with the mold lumen 380. The mold port 382 can be used to connect a vacuum pump when curing a balloon fragment. The balloon fragment 384 can be placed in the mold lumen 380.

Figure 108B:
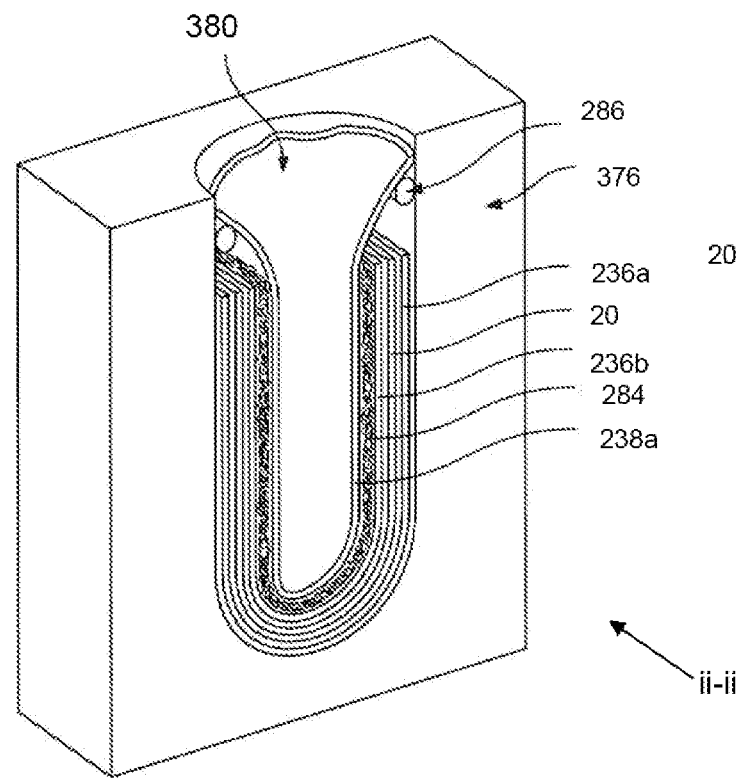
FIG. 108B is a variation of cross-sectional view II of FIG. 108A

FIG. 108B illustrates that an optional first releaser 236a can be applied to the inside of the female mold 376. The first releaser 236a can be a grease, a non-stick film or a non-stick tape or sheet. A second releaser 236b can be placed on top of the balloon fragment 384. This second mold releaser or release agent can be a grease or a non-stick film. A breather material 284 can next be placed for purposes of equalizing the pressure during a curing cycle. A vacuum bag or top vacuum sheet and a seal can be installed. The mold port can forms a fluid connection from outside the mold to the space between the vacuum bag or top vacuum sheet and the inner wall of the female mold. This fluid connection can remain unobstructed by the first mold releaser or release agent, balloon fragment 384, second mold release agent, and breather material 284, when a vacuum pressure is applied to the mold port. The distal balloon fragment 384 may be consolidated.

Figure 109:
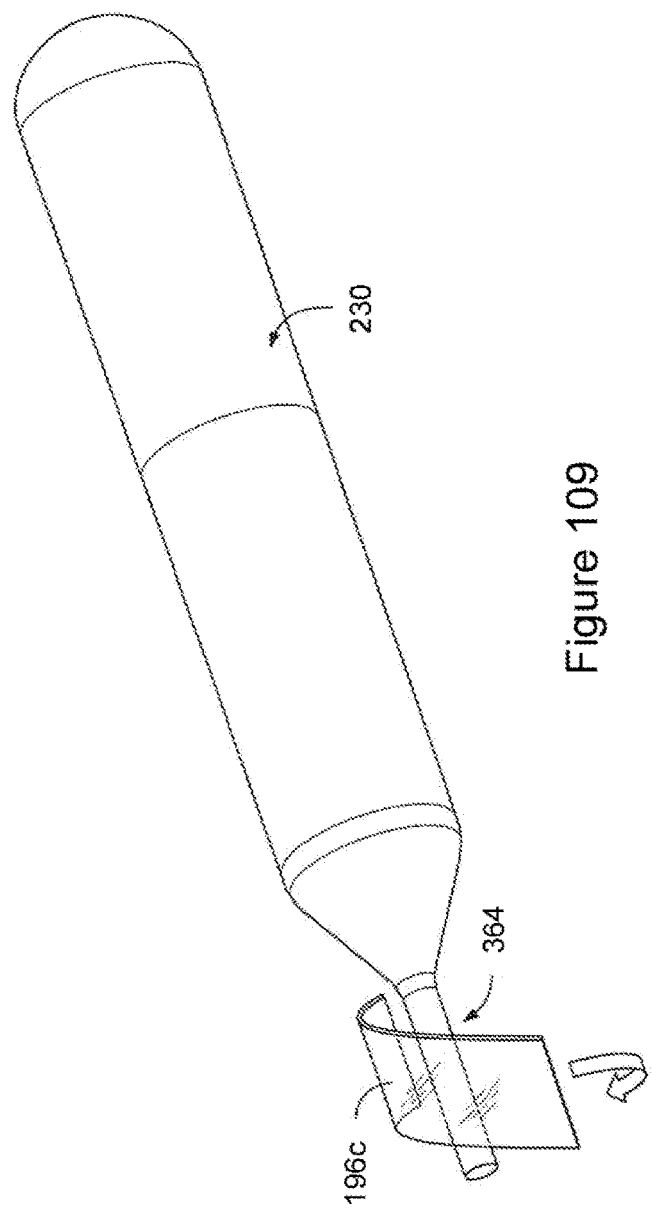
FIGS. 109 through 115 illustrate a variation of a method for manufacturing the device.

FIG. 109 illustrates that the third panel 196c can be coated on one side with adhesive. The third panel 196c may be wrapped around the mandrel stem with the adhesive side facing away from the mandrel stem. The third panel 196c can be wrapped such that the fourth side edge 356d is approximately coincident with the mandrel transition from the mandrel stem to the mandrel proximal taper.

Figure 110:
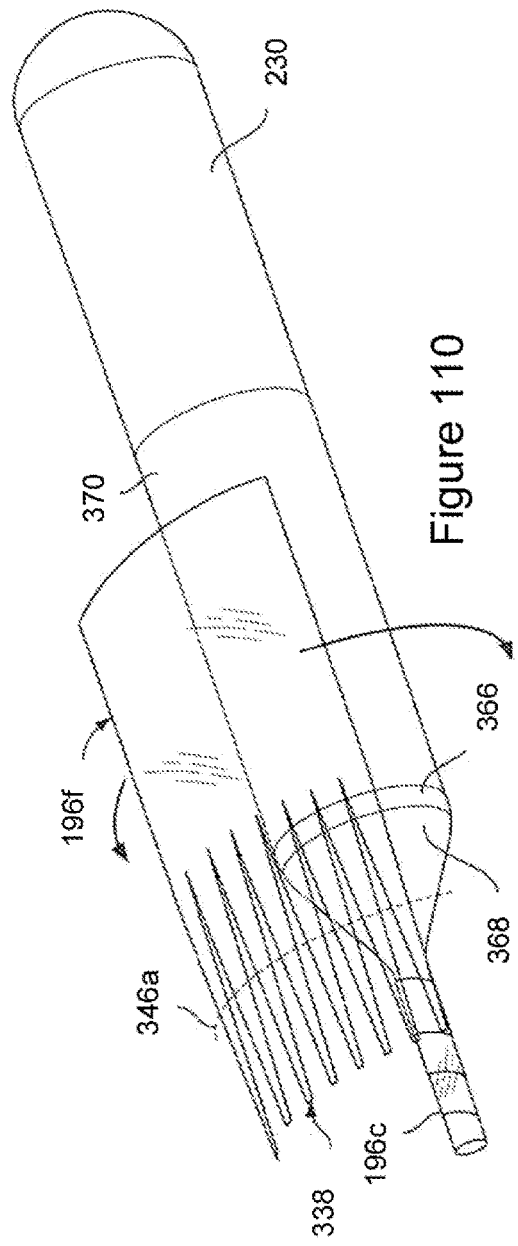

FIG. 110 illustrates that the fifth panel 196e can be wrapped around the proximal end of the mandrel. The serrations can point in the proximal direction. The first line 346a may be aligned about 7 mm proximal to the transition between the mandrel proximal taper and the mandrel constant diameter section. The first line 346a can be aligned parallel to the mandrel transition. Adhesive can be applied on the panel where the panel overlaps with itself. Adhesive can be applied to completely cover the surface of the serrations that face out from the mandrel. Every other serration may first folded over the proximal taper. Then the remaining serrations may be folded onto the cone.

Figure 111:
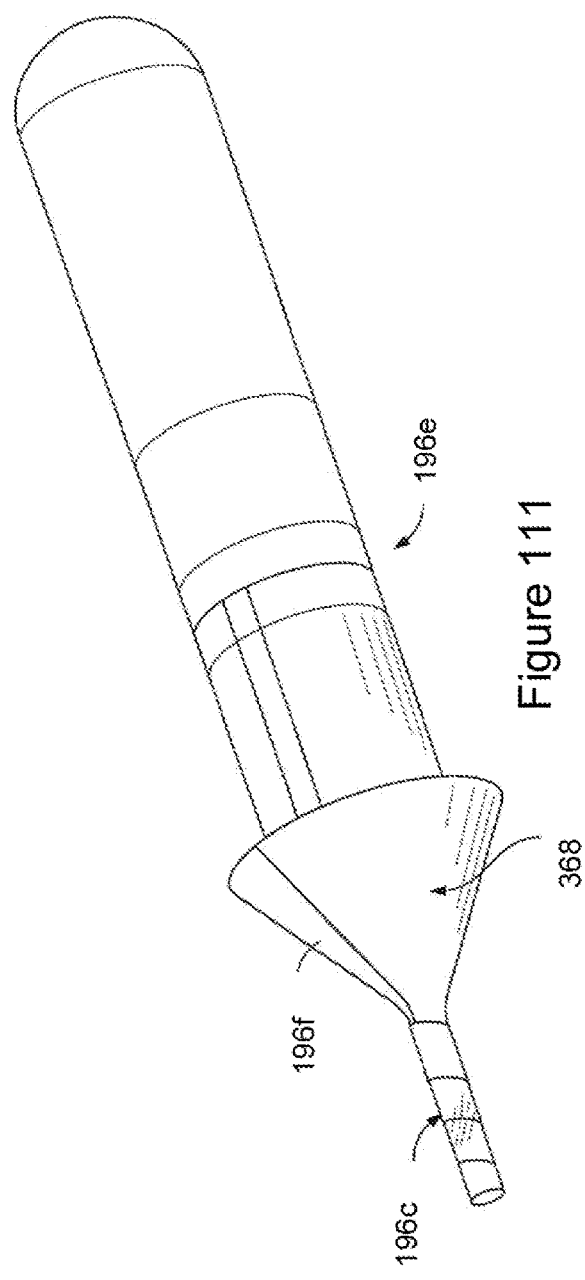

FIG. 111 illustrates that the sixth panel 196f may be wrapped over the proximal taper, the sixth panel, when wrapped around the proximal taper can cover more than about 2 mm of the mandrel stem and more than about 2 mm of the mandrel constant diameter section.

Figure 112:
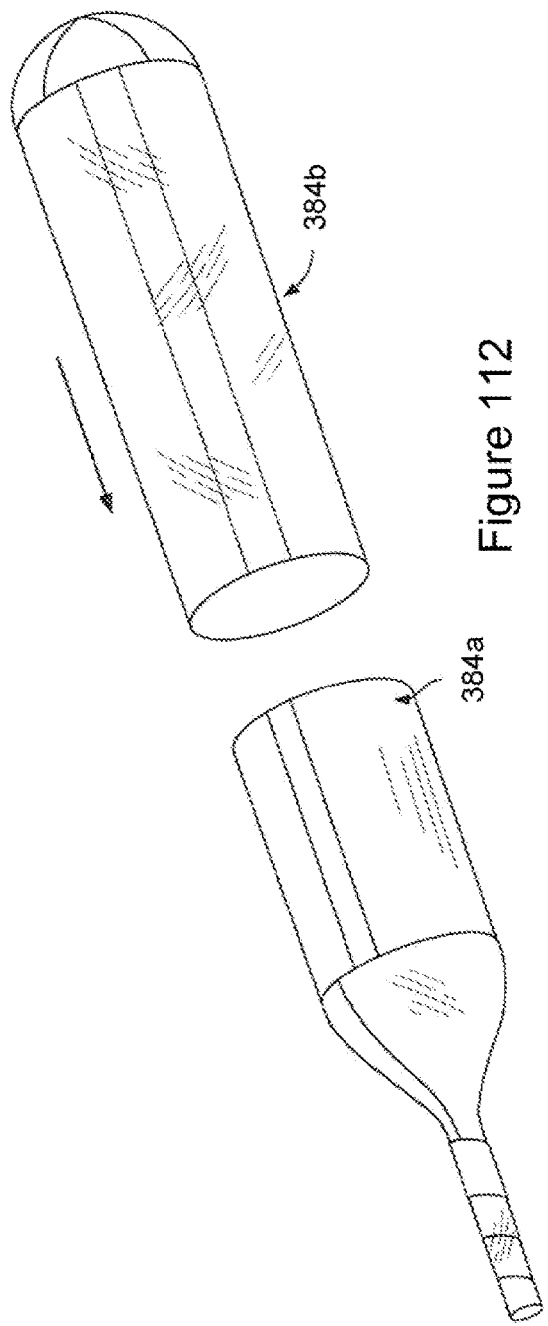

FIG. 112 illustrates that the balloon first and second sections 384a and 384b can be slid together such that they overlap by about 6 mm. An adhesive can be placed in the overlap region or seam. The first and second balloons sections and adhesive may be placed in a female mold. A compliant balloon or bladder may be inserted inside the balloon fragments. The balloon may be consolidated to form a fiber reinforced balloon, 10 and 20, capable of sustaining pressure.

Figure 113:
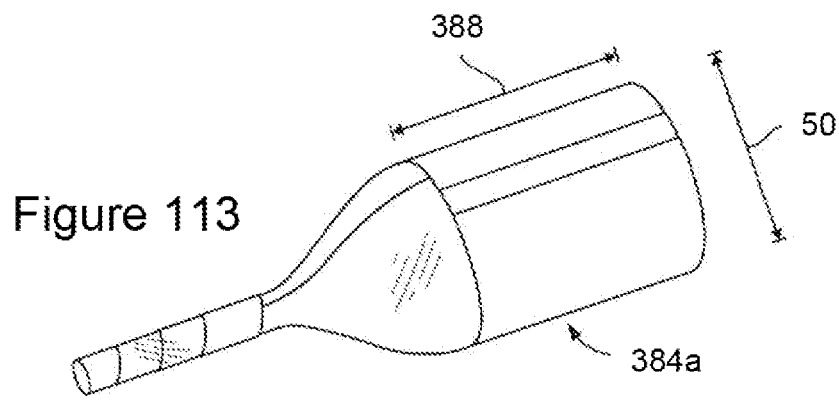

FIG. 113 illustrates that a second balloon fragment 284b that can have the third, fifth and sixth panels 196c, 196e, and 196f combined. The proximal balloon fragment may be placed under vacuum in a female mold and consolidated.

The longitudinal length 388 of the constant diameter section of second balloon section 384b can be trimmed to about 9 mm long.

Figure 114:
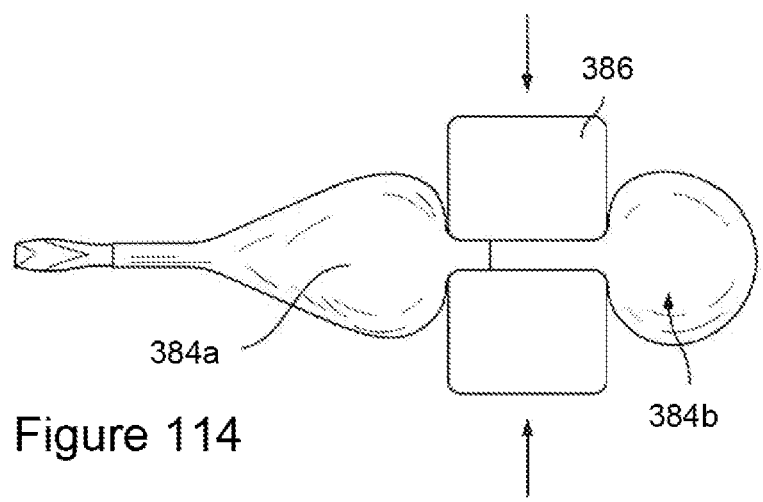

FIG. 114 illustrates that a solid release film (not shown) such as Teflon may be inserted into the interior of the balloon. The first and second balloon sections 384a and 384b can be clamped together by clamps 386. The balloon sections 384 can be consolidated to form a fiber reinforced balloon 20 capable of sustaining pressure.

Additional laminates can be added to areas of a balloon that might require extra strength for certain procedures or uses. A balloon may have different amounts of fiber, adhesive or polymer film in different portions of the balloon wall. A balloon may have different number of fiber layers in different portions of the balloon wall.

Figure 115:
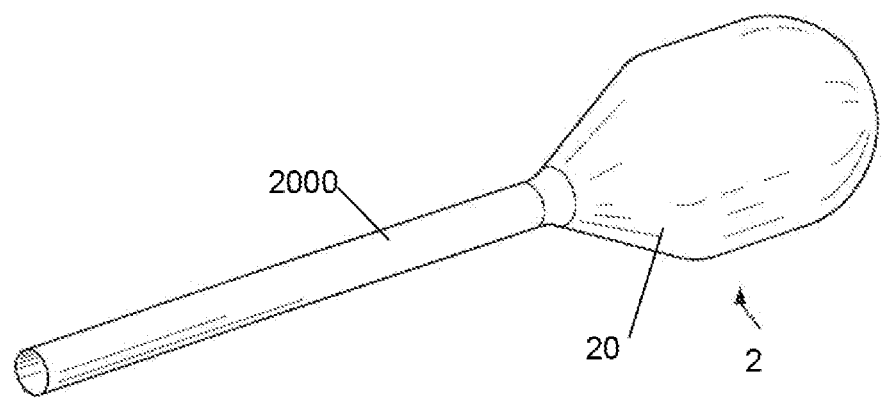

FIG. 115 illustrates a variation of the assembled device.

Figure 116:
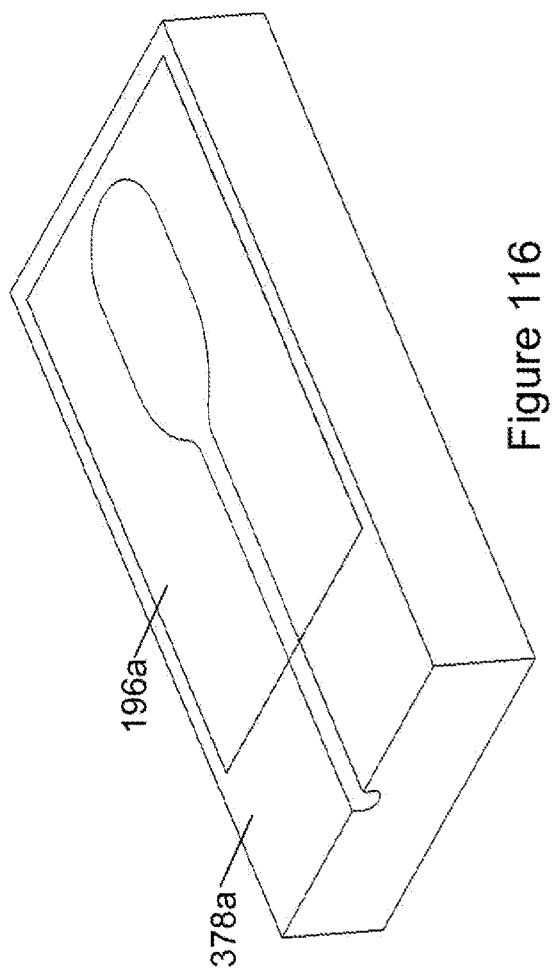
FIGS. 116 through 119 illustrate a method for manufacturing the device.

FIG. 116 illustrates that a first panel of polymer can rest on top of the female mold half. (The first panel can be a see-through polymer for illustrative purposes, for example the contours of the mold may be seen.) The first panel can be a polymer, such as a nylon, PET, polycarbonate, urethane or any other polymer that can be readily formed. The first panel be about 0.002 inches thick, more narrowly about 0.001 inches thick, yet more narrowly about 0.0005 inches thick.

Figure 117:
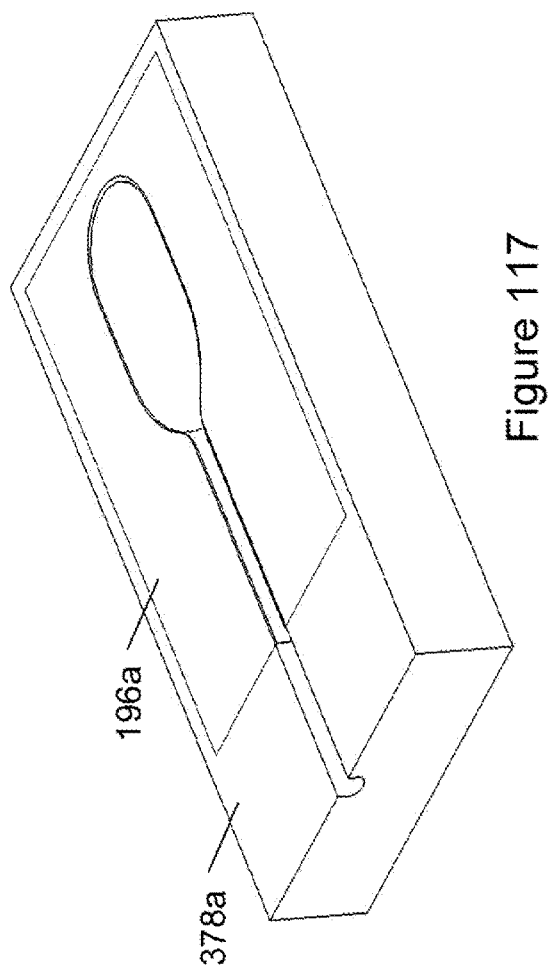

FIG. 117 illustrates that the first panel can be formed to the contours of mold.

Figure 118:
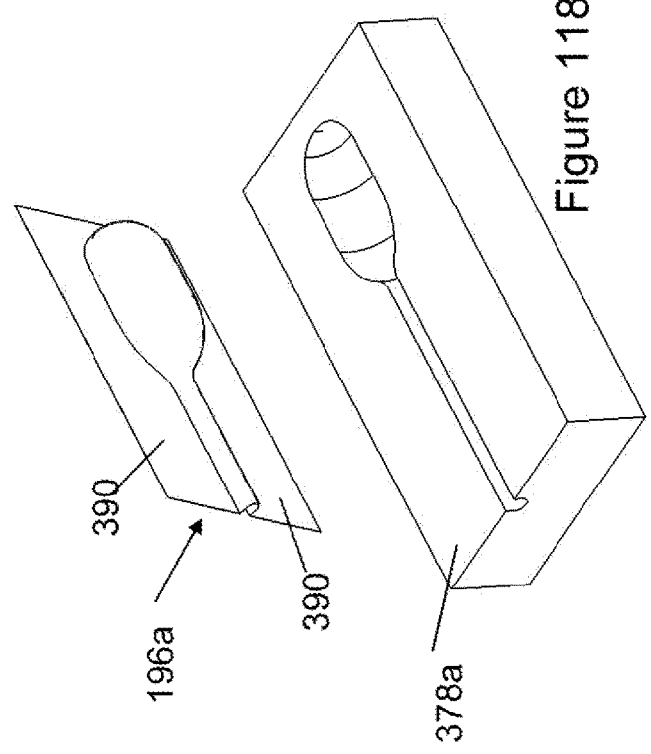

FIG. 118 illustrates that the first panel can be lifted free of the mold. The first panel can have a panel flat 390 that did not enter the form of the female mold during forming. The panel can be trimmed, for example in a trimming jig.

Figure 119:
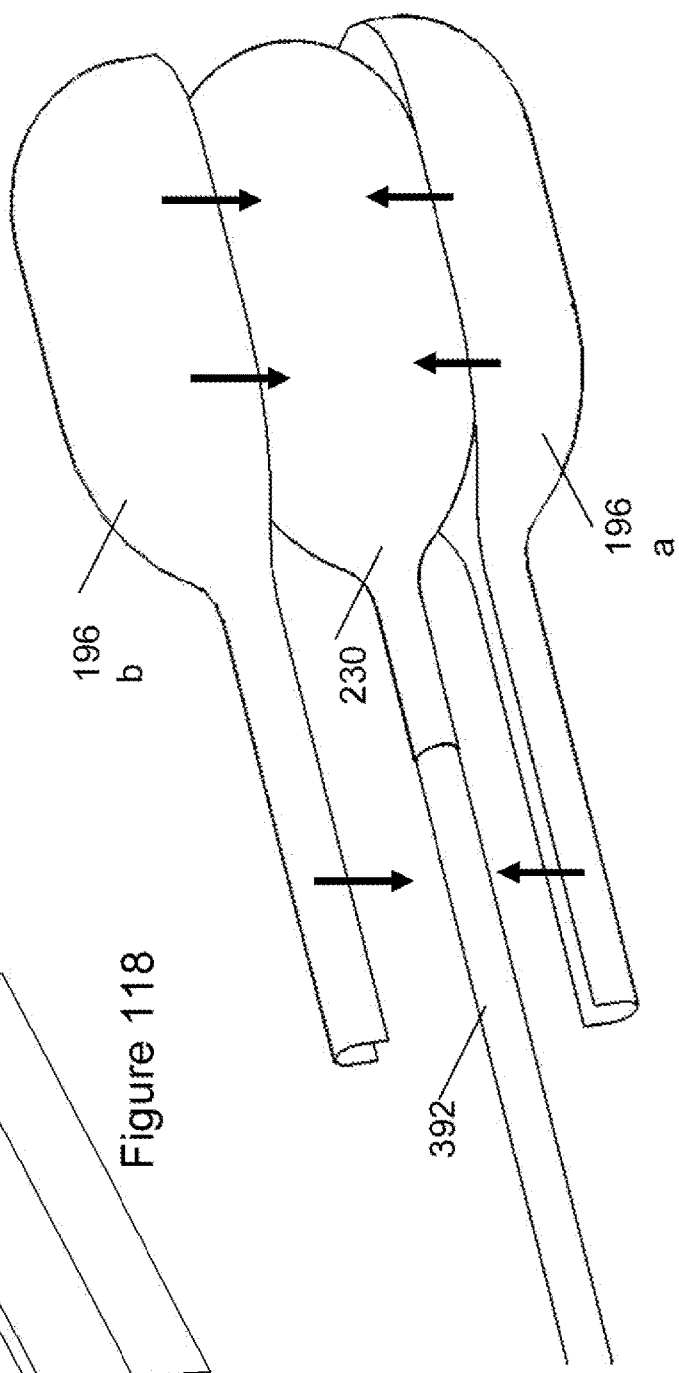

FIG. 119 illustrates that first and second panels can have their flats 390 trimmed. The two panels can be closed tightly around a mandrel and a mandrel shaft 392. The panels can then be bonded to each other at the point where they overlap. The bond may connect all or some of the material that overlaps. The bond may be leak tight to the passage or air and water. Bonding may take place by addition of an adhesive, by the application of heat, by the application of ultrasonic energy, by use of a laser, by the application of radio frequency energy, by the application of pressure or by combinations thereof. A material may be added to the joint that enhances the effectiveness of these bonding techniques.

FIG. 120 illustrates that inner layer may be constructed over a mandrel which is not removable. The inner layer can be constructed inside a female mold (not shown) that matches the intended outer shape of the inner layer. Both a mandrel and a female mold may be used together to create a narrow thickness for the inner layer to be formed in. The inner layer may be thermoformed, or injection molded or constructed via some other method listed supra. The inner layer can be slit 394, removed from the non-removable mandrel and placed over a removable mandrel (as described above). The slit 394 can then be patched with a thin strip of polymer attached to inner layer.

An inner layer may be formed by a standard blow molding process such as extrusion blow molding, injection blow molding, or stretch blow molding. The inner layer may be checked for leaks before being used.

FIG. 121 illustrates that a strip 192 can be an elongated element of polymer film, metal foil or fiber tape cut into a shape that may be useful in creating a fiber reinforced balloon. The shape of the strip 192 may be cut by hand, with a high pressure water jet or with a laser. Extending longitudinally from a first end of the strip 192 to a second end of the strip 192, the strip 192 can have a first narrow section 396a, a first taper, a first wide section 398a, a first central narrowing, a circular section 402, a second central narrowing, a second wide section 398b, a second taper, and a second narrow section 396b. The strip can have one or more reinforcement fibers. The reinforcement fibers can be substantially aligned with the strip longitudinal axis. For example, the strip 192 can have uni-tape. The strip 192 can have one or more layers. The reinforcement fibers can extend the entire length of the strip 192. A polymer film (not shown) can on one side or both sides of the strip 192. The strip 192 can be flexible before and after consolidation.

FIG. 122 illustrates that fibers in strip 192 can be uni-directional and can be substantially aligned with the strip longitudinal axis. The strip can be substantially rectangular. A polymer film (not shown) can be placed on one side or both sides of the strip 192. The strip 192 can be flexible before and after consolidation.

FIG. 123 illustrates that a first, second and third strip 192a, 192b, and 192c can be aligned at equal strip angles 404 to each other to form a rosette. The strip angle 404 can be the angle from the first strip longitudinal axis to the adjacent strip longitudinal axis. The circular section 402 for each strip 192 can be substantially concentric to the circular sections for the other strips 192.

FIG. 124 illustrates that the strips 192 can have no reinforcement fibers.

Figure 125:
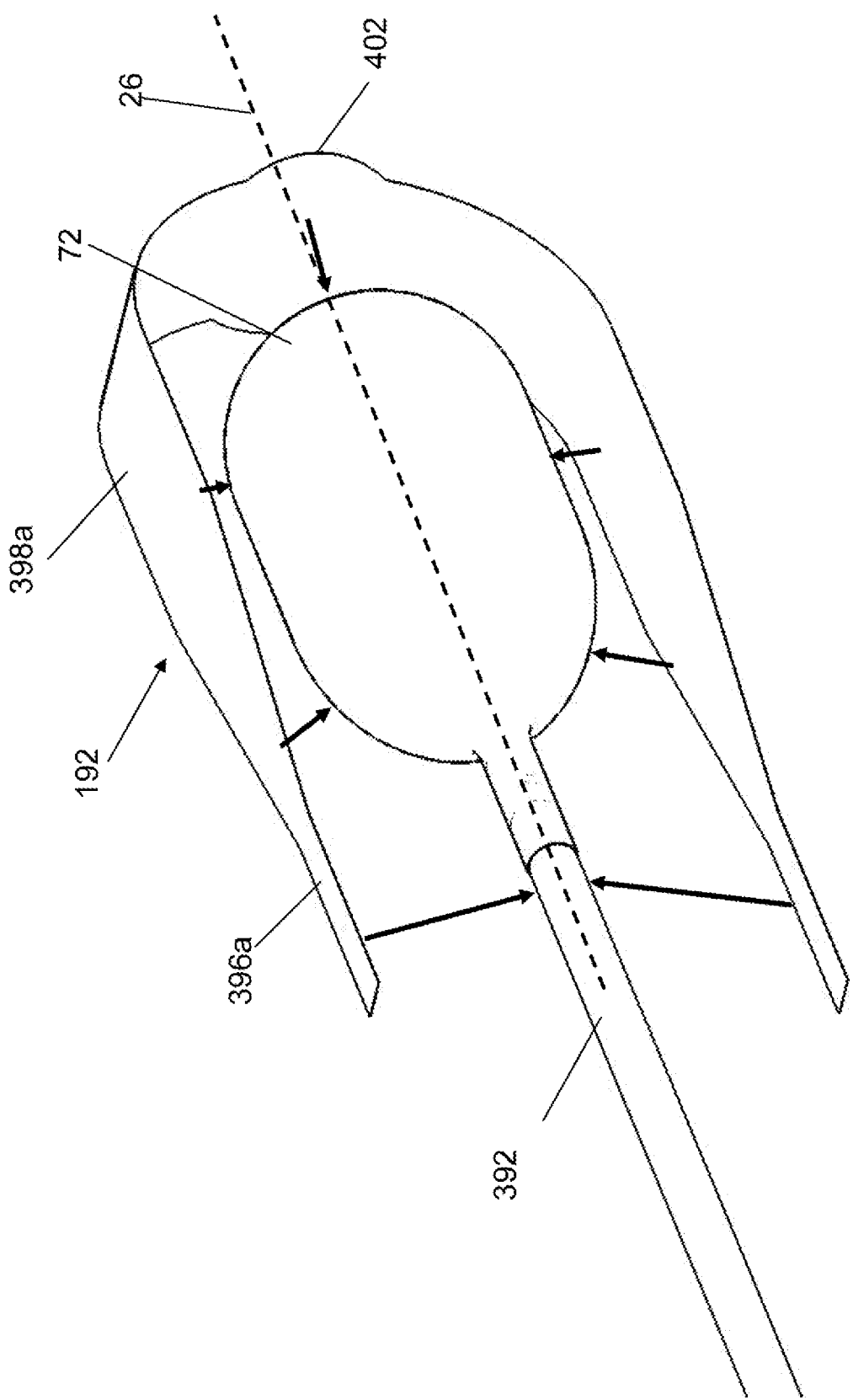
FIGS. 125 through 127 illustrate variations of methods for manufacturing the device.

FIG. 125 illustrates that strip can be applied to the inner layer (e.g., bladder). The inner layer can have a hard mandrel inside of the inner layer. The mandrel can support the surface of the inner layer. The circular section 402 of the strip can be concentrically aligned with the terminal distal end of the inner layer and adhered in place. The remainder of strip can be laid over the contours of inner layer or bladder such that narrow sections of fiber tape partially cover stem on bladder.

Several pieces of fiber tape may be applied to bladder. Each piece may be concentrically aligned with the tip of the distal end of the bladder and adhered in place. However, alignment may be such that the fiber tape cover sections of bladder and shaft that have not yet been covered with fiber tape or have not yet been covered with fiber tape with fibers in substantially similar orientations. Two to eight pieces of fiber tape may be applied in this manner. Application may continue until all of bladder 72b is covered in fiber tape with fibers substantially oriented along the long axis of the mandrel and stem.

Figure 126:
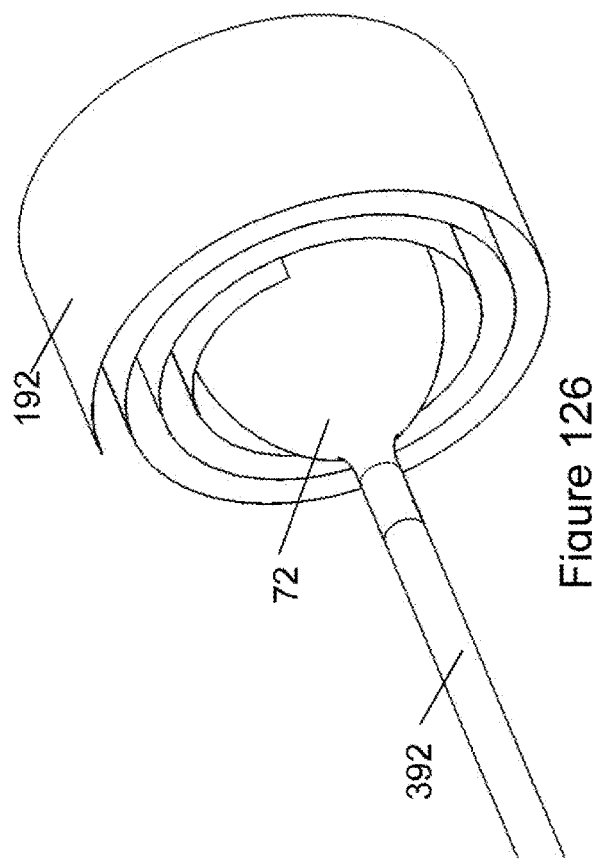

FIG. 126 illustrates that fiber tape may be applied to a flexible bladder or inner layer. The bladder can be supported by the presence of mandrel inside of it. Fiber tape may be wrapped from two to eight times around the largest diameter of the bladder. FIG. 210 shows fiber tape wrapping more than three and less than four times around bladder. At the end of this wrapping procedure, fiber tape may be tightly wrapped around the largest diameter of mandrel.

Figure 127:
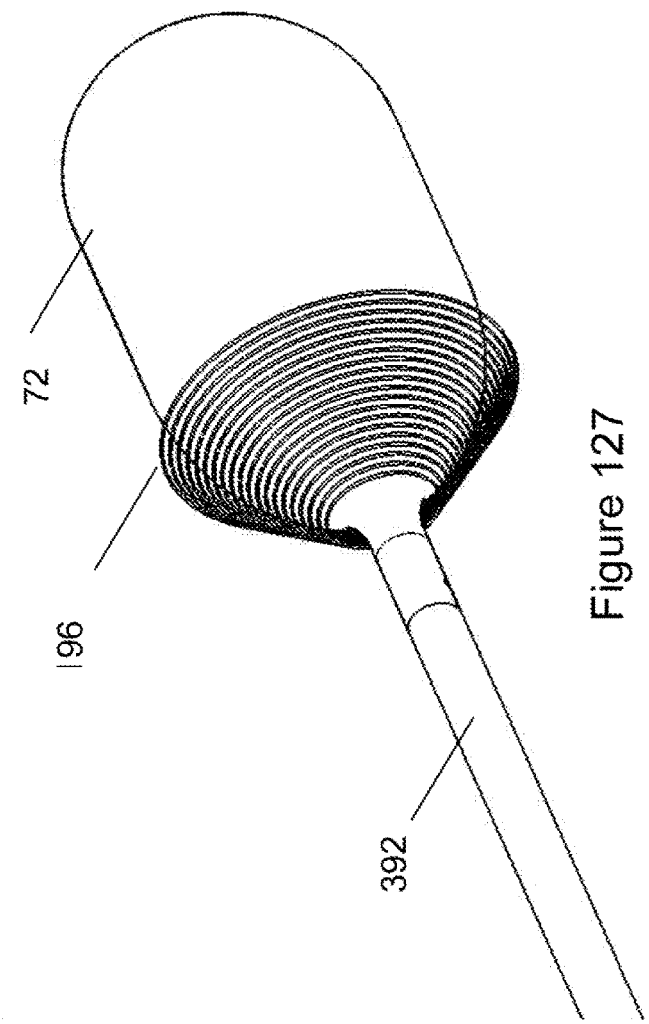

FIG. 127 illustrates that fiber may be wound around flexible bladder or inner layer. Bladder may be supported by the presence of mandrel inside of it. Fiber 86 may be uni-directional fibers with or without adhesive. Fiber may be a continuous piece of fiber. Fiber 86 may be wrapped over a portion or all of bladder. Adhesive may be applied to bladder 72 before application of the fiber, during application of the fiber or after application of the fiber or some combination thereof.

Successive layers of fiber may be used to build a completed balloon. Three pieces of fiber tape may be applied to bladder 72. This may be followed by the application of fiber tape substantially over the main diameter. This may be followed by application of fiber 86 on a portion or all of the proximal taper and stem of the bladder. This may be followed by application of fiber 86 on a portion or all of the distal tip of the bladder. Lastly, a layer of PEN film may be applied. Layers of fiber tape or fiber may be omitted from this sequence. Layers of fiber tape and fiber can be applied in any order. Polymer film may be applied between layers, over the bladder or over the final layer of fiber or fiber tape.

Figure 128A:
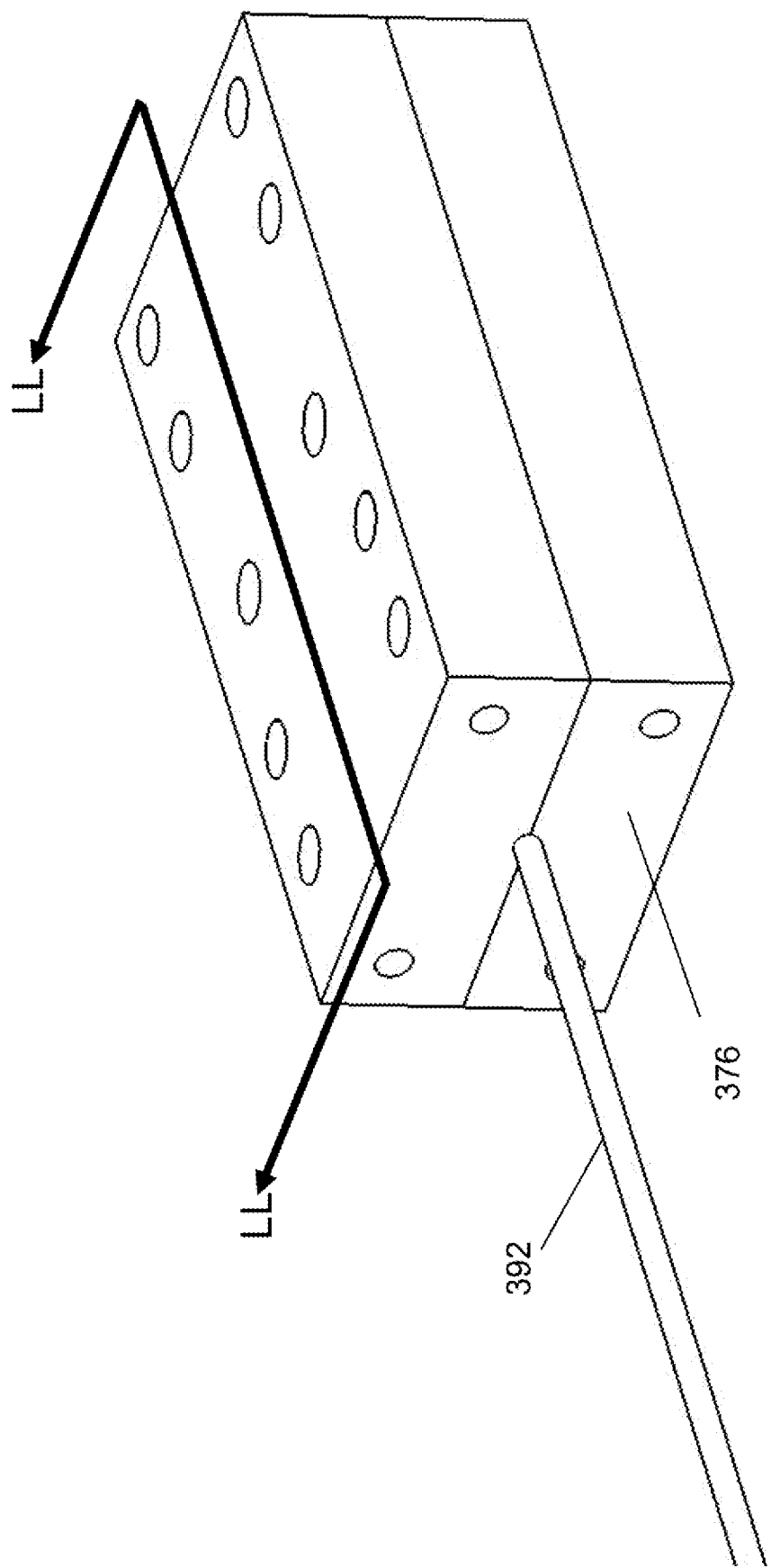
FIG. 128A illustrates a variation of a manufacturing tool.
Figure 128B:
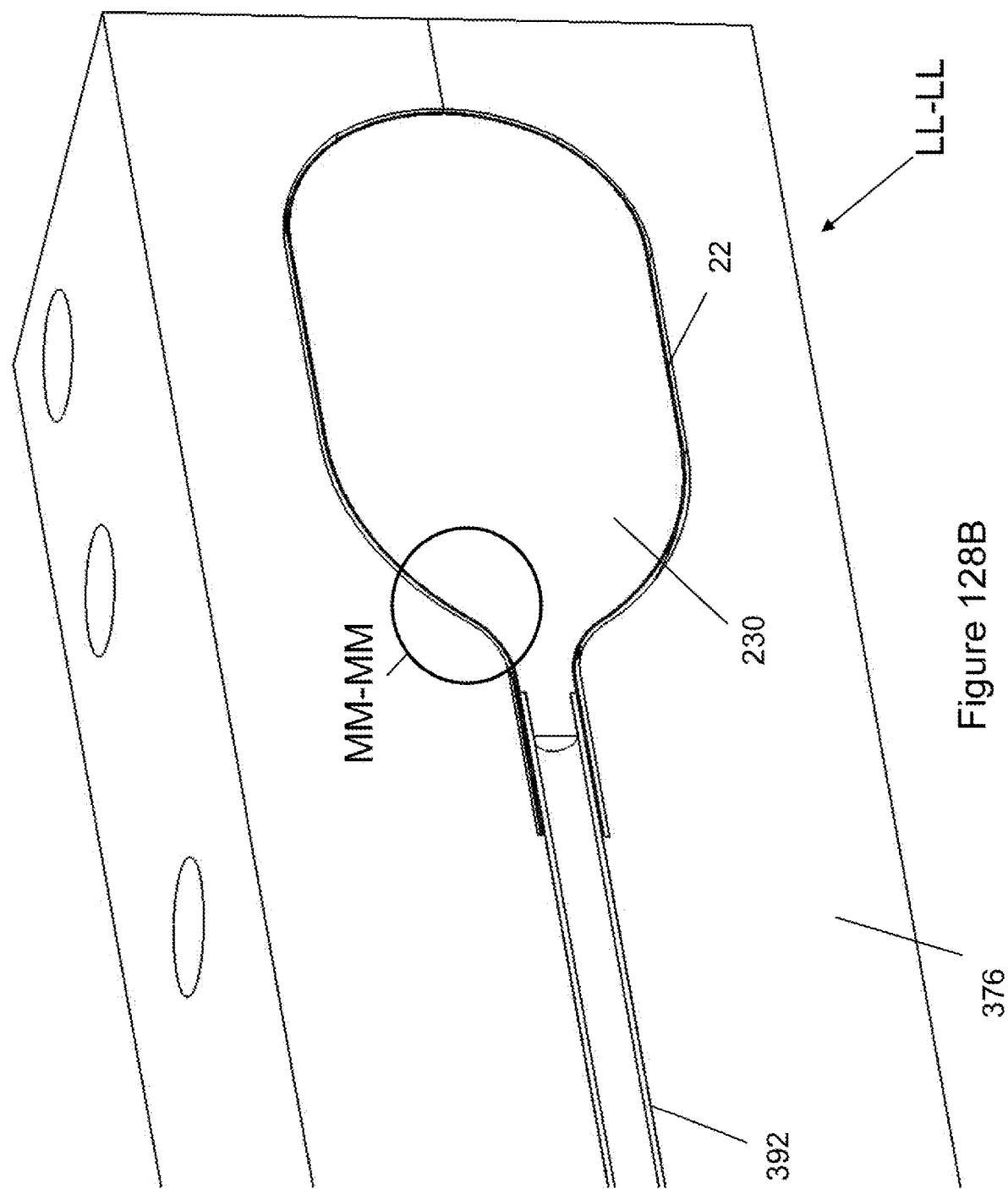
FIG. 128B is a variation of cross-sectional view LL-LL of FIG. 128A.

FIGS. 128A and 128B illustrate that the unconsolidated balloon may be placed in a female mold 376. The unconsolidated balloon can include the shaft 2000, mandrel 230, bladder 72 and the various layers of fiber, fiber tape and film. The female mold 376 may contain a pocket for the unconsolidated balloon that is slightly larger than the unconsolidated balloon.

Figure 128C:
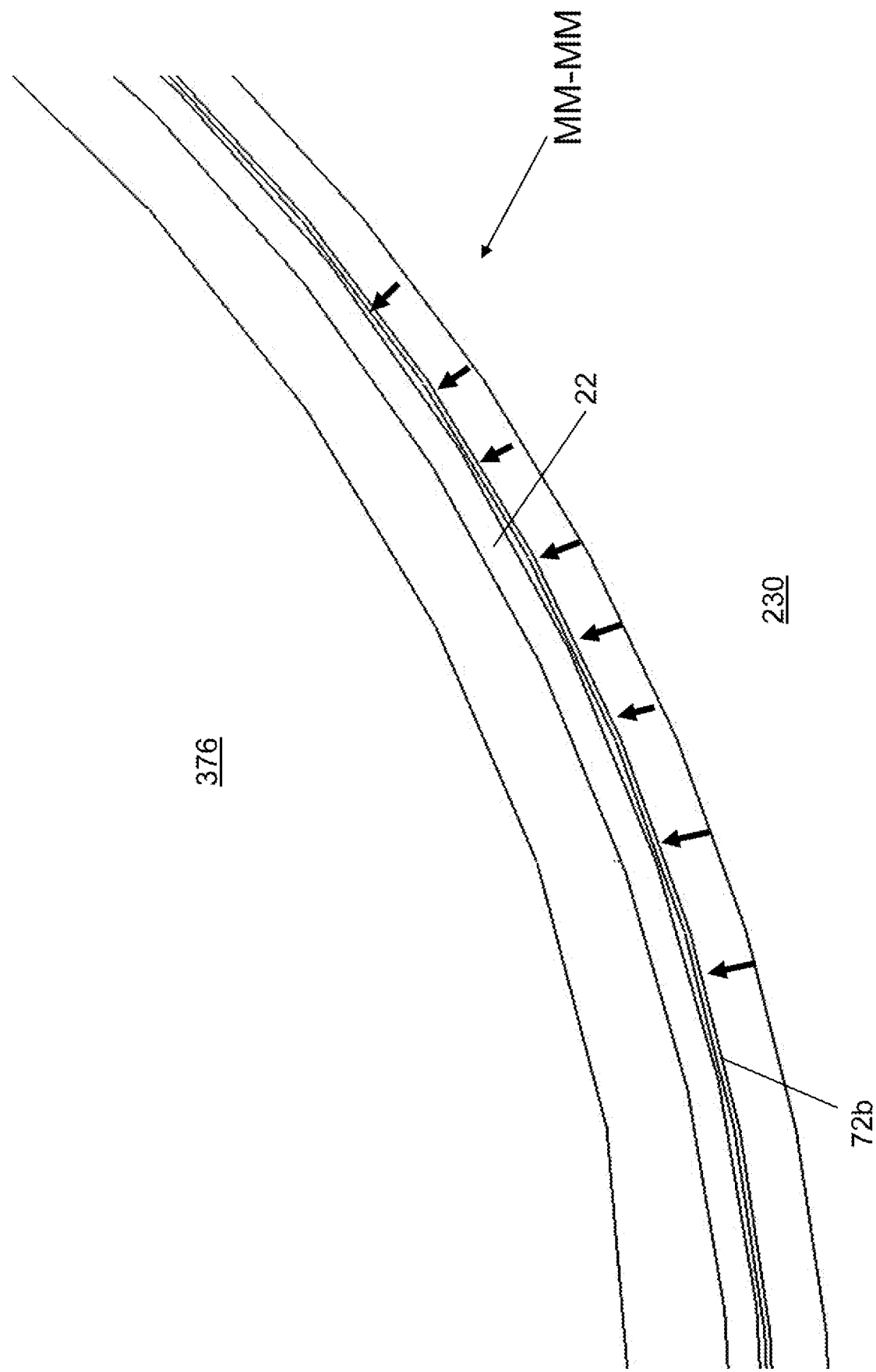
FIG. 128C is a close-up view MM-MM of FIG. 128B.

FIG. 128C illustrates that the lower portion of FIG. 104 is a portion of mandrel 230 and the upper portion of FIG. 104 is a portion of female mold 376. The various layers of fiber, fiber tape and film can be spaced from the surface of the mold 376. This distance may be from about 0.005 in. to about 0.050 in. When the bladder 72 is inflated, the layers 72 can detach from the mandrel 230 and press firmly against the walls of the female mold 376.

FIG. 128C shows the layers after detaching from mandrel 230 but before being pressed against female mold 376. This inflation and expansion may serve to straighten and/or tension the fibers. Heat or light or an electron beam or a combination thereof may be used with the inflation of bladder 72*b* and the passage of time to consolidate a fiber reinforced balloon. Light or an electron beam may be applied, as part of a consolidation, by inserting a source within a hollow lumen in a mandrel. The mandrel can then be removed as described infra.

Method of Use

Figures 129, 130:
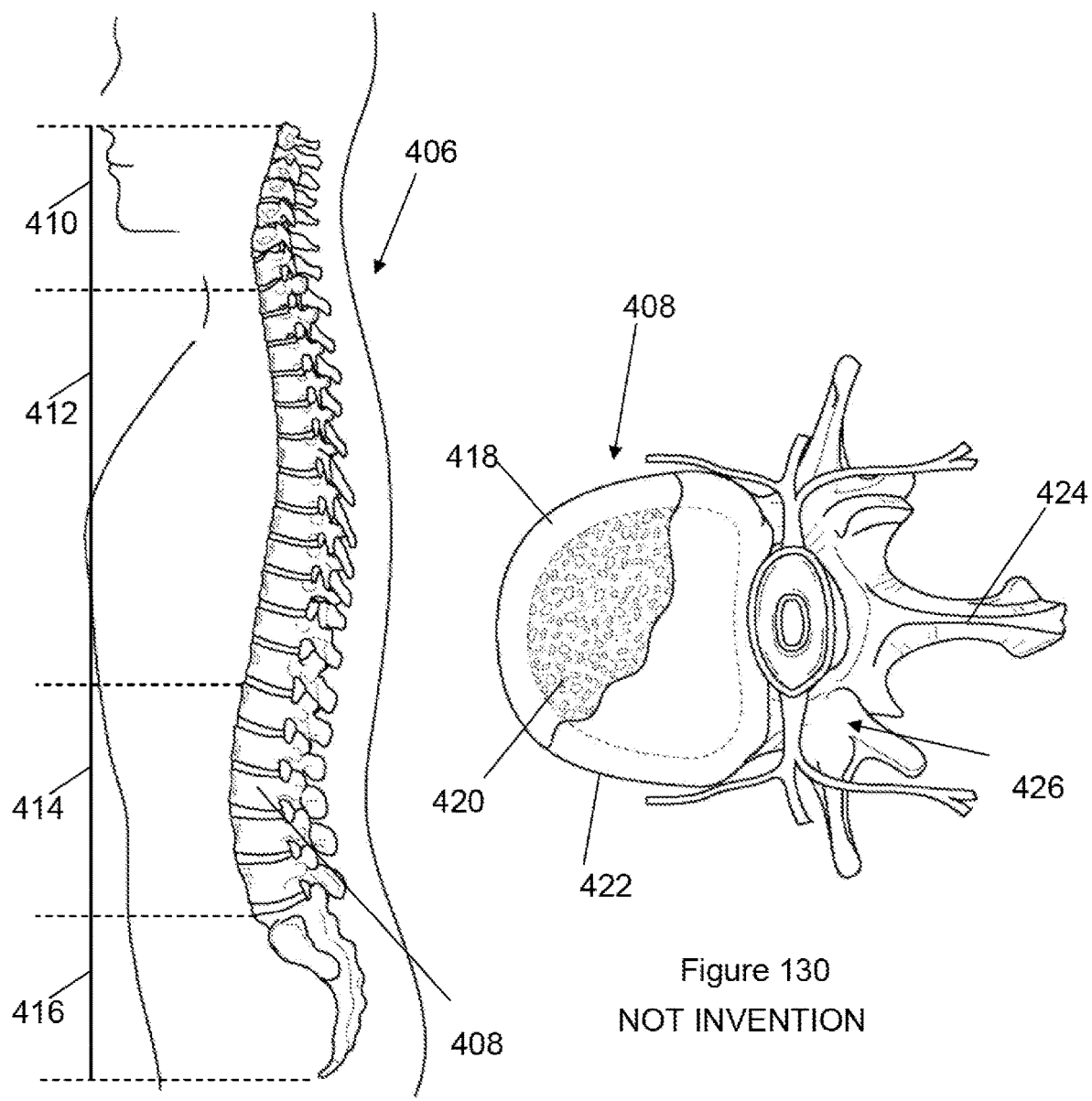
FIG. 129 is a partial see-through view of a sagittal view of a spine in a patient.
FIG. 130 is a partial see-through coronal view of a vertebra.

The device 2, for example including the balloon 20, can be used for Kyphoplasty, angioplasty including CTO dilation, stent delivery, sinuplasty, valvuloplasty, drug or other fluid delivery through the balloon, radiopaque marking, incising the inside of a vessel (e.g., to open or expand a vessel), brachytherapy, intentionally obstruct a vessel, or combinations thereof. The device 2 can be used to deliver one or more stents and/valves and/or emboli filters to the coronary blood vessels (e.g., arteries or veins), carotid artery, peripheral blood vessels, the GI tract, the biliary ducts, the urinary tract, the gynecologic tract, and combinations thereof. The device 2 can be used to prepare a cardiac annulus and/or the leaflets of a natural heart valve for open or percutaneous (minimally invasive) valve replacement. The device 2 can expand and deploy a percutaneously delivered heart valve FIG. 129 illustrates a sagittal view of a patient and the spine 406. The spine 406 can have vertebrae 408 and cervical, thoracic, lumbar and sacral regions 410, 412, 414, and 416. The device 2 can be used in or between vertebrae 408 in any region of the spine 406.

FIG. 130 illustrates a vertebrae 408 that can have cortical bone 418 and cancellous bone 420. The vertebrae 408 can have a vertebral body 422 a vertebral process 424 and pedicles 426.

FIG. 131 illustrates a vertebra that a delivery tube 428, such as a cannula, can be inserted against or into the pedicle. The delivery tube 428 may have a inside diameter of less than about 6 mm, more narrowly from about 2 mm to about 4.5 mm. A bone drill can be passed through the delivery tube 428 to drill to create a drill void 430 in the cancellous bone. The bone drill can then be removed leaving the drill void 430 in the cancellous bone.

Figure 132:
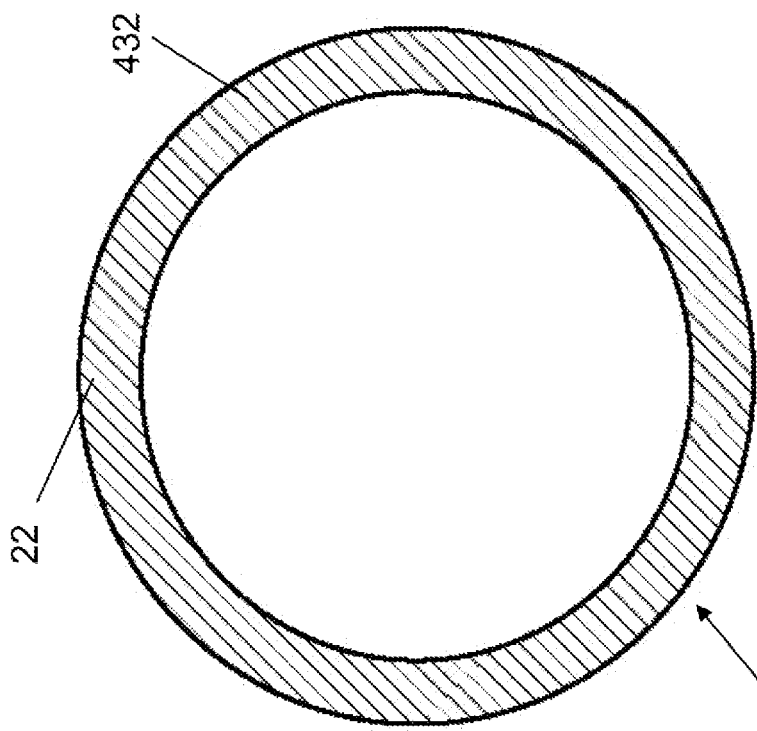
FIG. 132 illustrates a cross-section of a variation of the balloon wall.

FIG. 132 illustrates a cross section of a balloon 20. The balloon 20 can be in a substantially inflated condition. The cross section area is shown. The balloon wall can have a balloon wall area 432.

Figure 133:
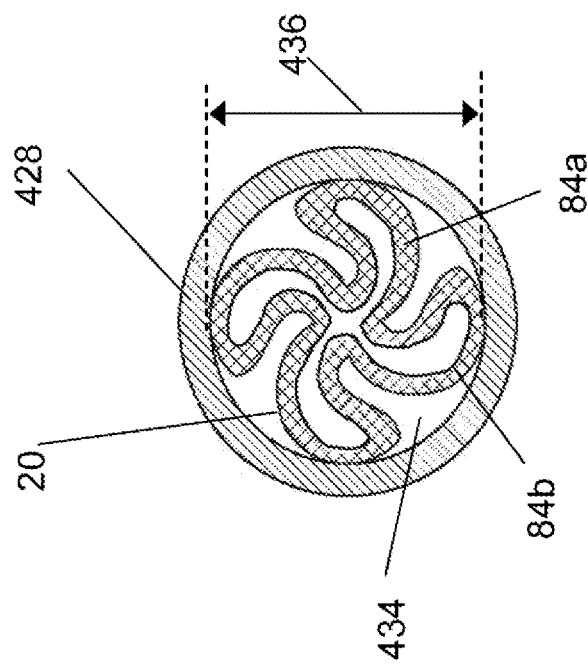
FIG. 133 illustrates a cross-section of a variation of the balloon contracted inside of the delivery tube.

FIG. 133 illustrates a cross section of balloon 20 in a substantially deflated and folded configuration. The balloon 20 is shown in a delivery tube or cannula with a delivery tube inside diameter 436 and a delivery tube area 434. The balloon 20 may be able to slide in the cannula.

The compression ratio of the balloon can be from about 3:1 to about 6:1, more narrowly from about 4:1 to about 5:1. The compression ratio can be the ratio between the outside diameter of the substantially inflated balloon (e.g., as shown in FIG. 132) and the inside diameter of the delivery tube (e.g., the cannula as shown in FIG. 133).

The balloon can have a packing density equal to or greater than about 40%, more narrowly greater than or equal to about 55%, yet more narrowly equal to or greater than about 70%. The packing density can be the percentage ratio between the cross sectional area of the walls of the balloon and the cross sectional area of the inside of the cannula.

The packing density and compression ratios for the balloon can remain substantially constant and the wall strength of the balloon can remain substantially constant with repeated packing and unpackings, and/or compressings and uncompressings.

The balloon can be folded into the cannula and expanded about eight times while not significantly degrading the strength of the balloon wall.

FIG. 134 illustrates that the balloon can be inserted, as shown by arrow, through the delivery tube and into the drill void in the cancellous bone.

FIG. 135 illustrates that fluid pressure can be delivered, as shown by arrow 438, through the hollow shaft 2000 to the balloon 20. The balloon 20 can inflate and expand, as shown by arrows 440. The expanding balloon can compress the cancellous bone surrounding the drill void, creating a larger balloon void 442. The balloon 20 can be deflated and contracted. The balloon can be removed from the vertebral body and the delivery tube.

Figure 136:
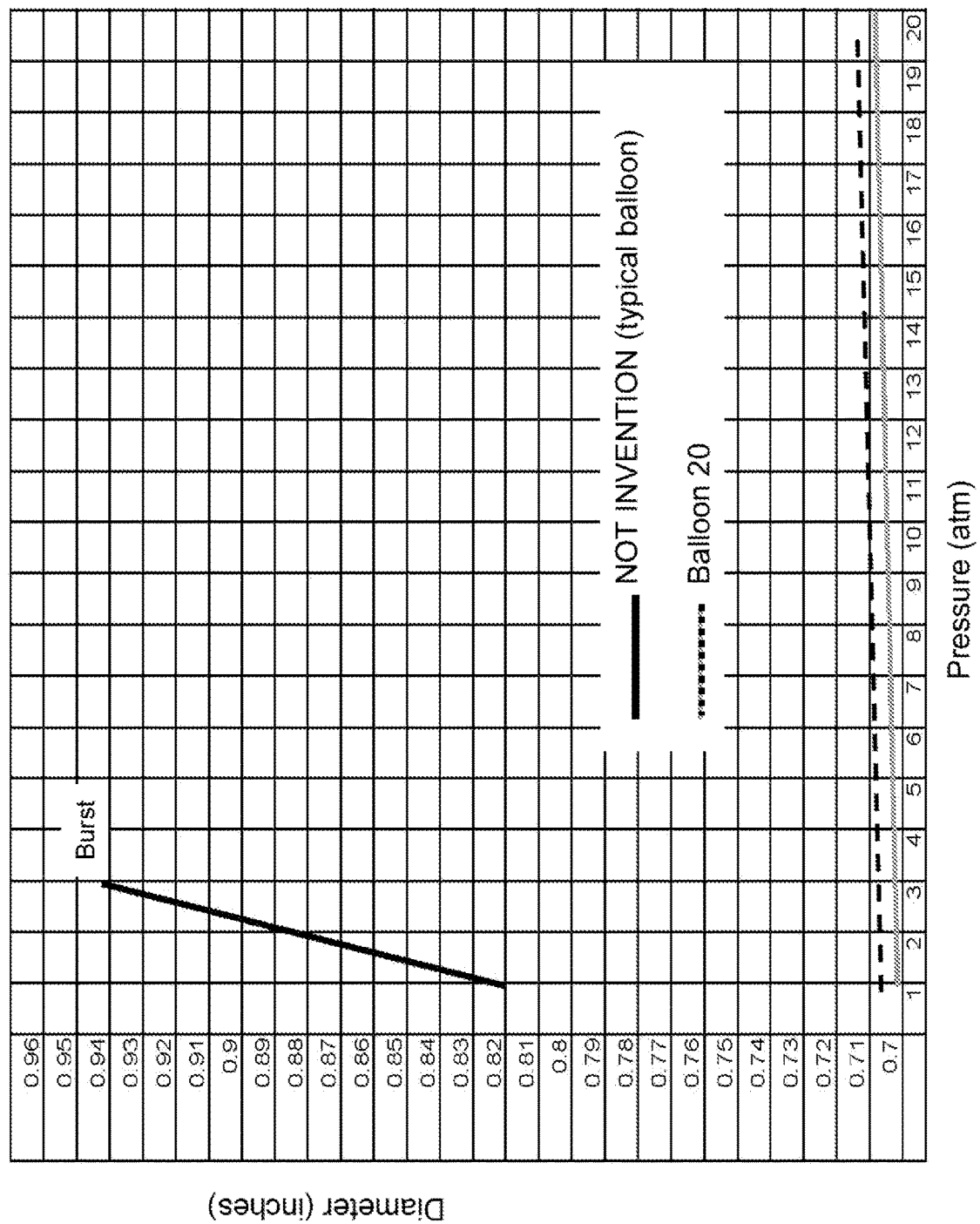
FIG. 136 is a graph of compliance of the variation of the balloon compared with a typical compliant balloon.

FIG. 136 illustrates that the diametric elasticity of existing medical inflatable devices can be approximately 0.06 in./ATM and a typical burst pressure is about 3 ATM. The medical inflatable device 2 can have an exemplary diametric elasticity of 0.0004 in./ATM and a burst pressure above 20 ATM (290 psi). For example, the burst pressure can be from about 290 psi to about 1500 psi. More narrowly, the burst pressure can be from about 500 psi to about 1000 psi. For example, the burst pressure can be about 500 psi, about 750 psi, about 1000 psi, about 1500 psi, or higher than 1500 psi. For example, the burst pressure can be greater than 4 ATM with a diameter of greater than 20 mm, with a diametric compliance of less than about 15%, or less than about 10% or less than 5%.

FIG. 137 illustrates that a hollow balloon void 442 can be formed within the cancellous bone of the vertebral body. The balloon void 442 can remain in place when the balloon 20 is withdrawn from the vertebral body.

FIG. 138 illustrates that a cement conduit 444 can be inserted, as shown by arrow 446, through the delivery tube and into the balloon void. A filler, such as a bone cement 445, can be inserted, as shown by arrow 448, into the balloon void 442.

FIG. 139 illustrates that additional bone cement 445 can be delivered through the cement conduit 444 to the balloon void 442.

FIG. 140 illustrates that the balloon void can be substantially filled with the bone cement. The bone cement can cure. The cement conduit can be removed. The delivery tube can be removed.

Figure 141A:
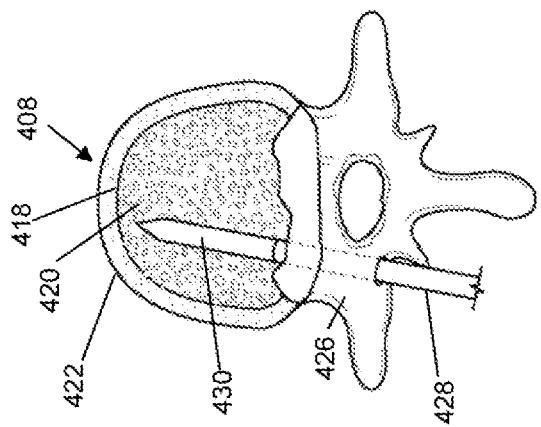
FIGS. 141A through 141$i$ are coronal cross-sectional views of a variation of a method of using a variation of the device in a vertebra.
Figure 141B:
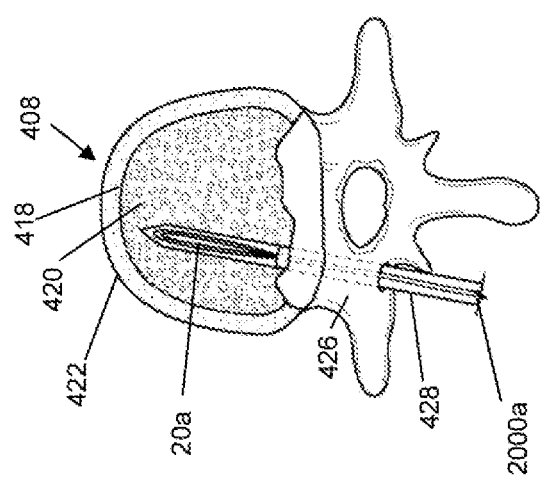
Figure 141C:
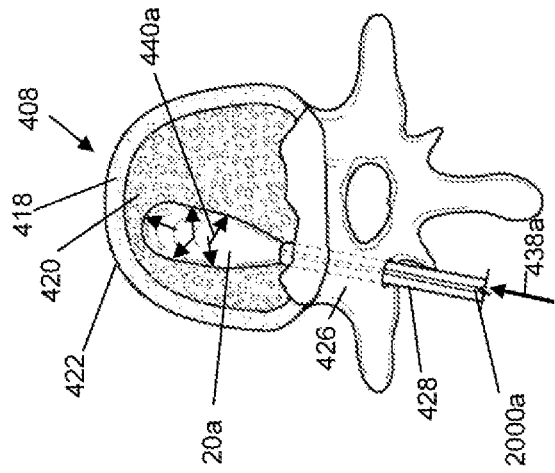

FIGS. 141A through 141C illustrate a method of creating an initial balloon void with a first balloon similar to the methods shown herein. The first balloon 20*a* can create an initial balloon void 442*a* in the cancellous bone.

Figure 141D:
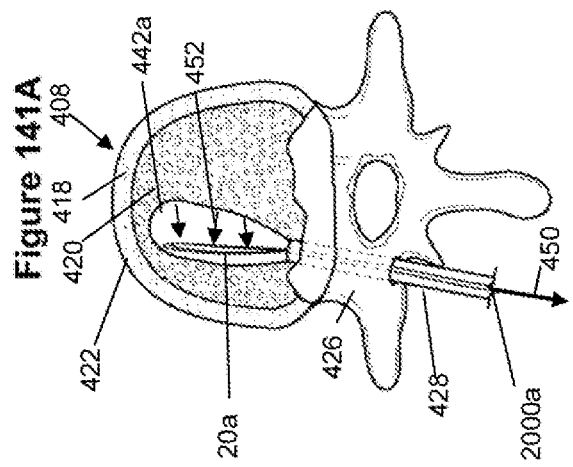

FIG. 141D illustrates that the pressure can be removed, as shown by arrow 450, and/or suction can be applied through the first hollow shaft. The first balloon 20a can deflate and contract, as shown by arrows 452. The first balloon 20a can be left in the initial balloon void. The first hollow shaft can be pushed to the side of the delivery tube.

Figure 141E:
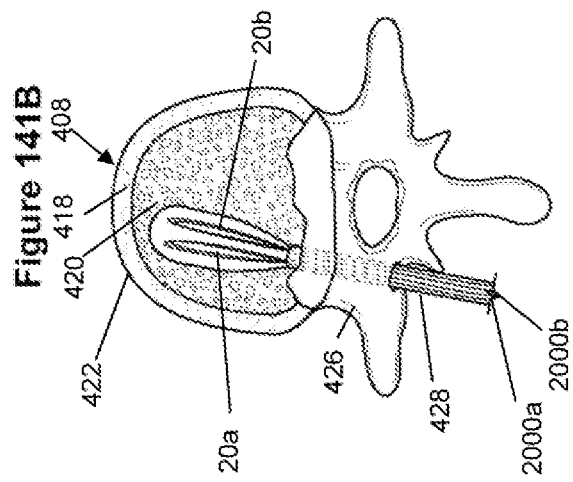

FIG. 141E illustrates that a second balloon attached to a second hollow tube can be inserted, as shown by arrow, through the delivery tube 428 and into the initial balloon void 442a. The second balloon can be placed adjacent to the first balloon.

Figure 141F:
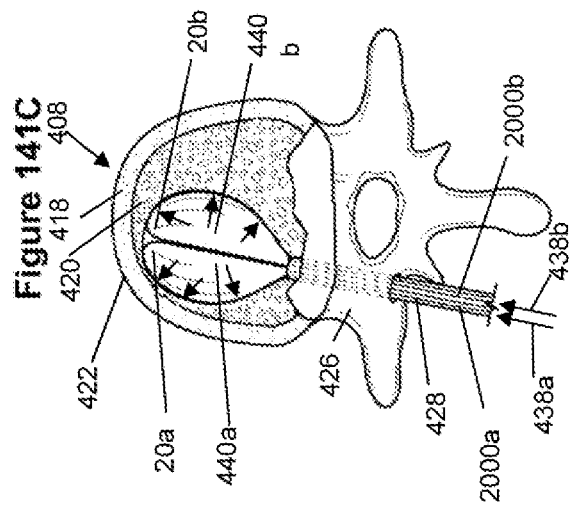

FIG. 141F illustrates that a first pressure can be delivered, as shown by arrow 438a, through the first hollow shaft and into the first balloon. The first balloon can undergo a first balloon final expansion, as shown by arrows 440a. Before, concurrent with, or subsequent to the first balloon final expansion, a second pressure can be delivered, as shown by arrow 438b, through the second hollow shaft and into the second balloon 20b. The second balloon can undergo a second balloon expansion, as shown by arrows 440b. The first balloon final expansion and the second balloon expansion can create a final balloon void 442b in the cancellous bone.

Figure 141I:
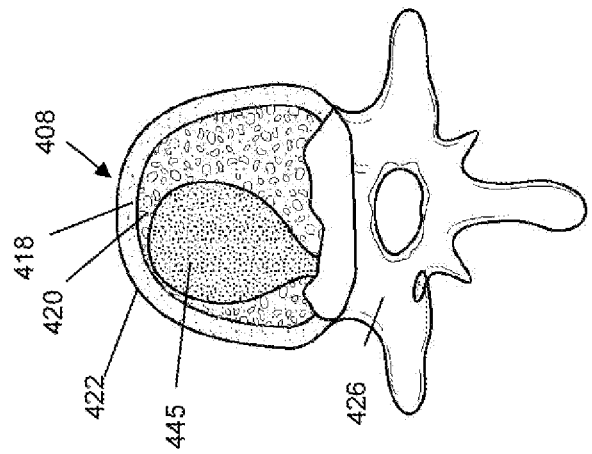
Figure 141H:
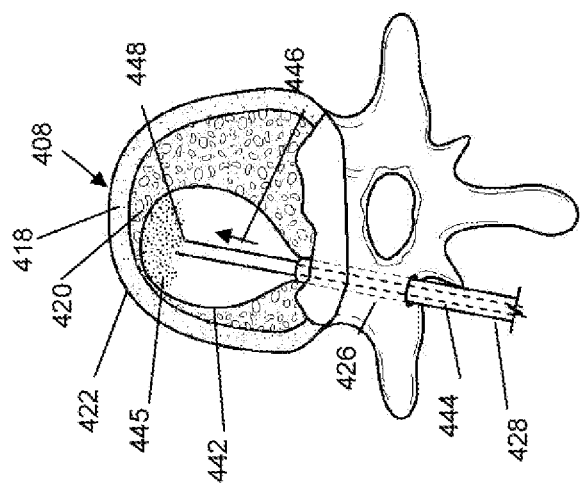
Figure 141G:
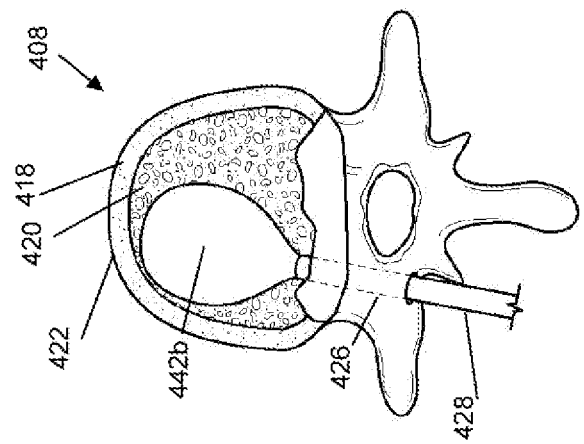

FIG. 141G illustrates that the first and second balloons can be deflated, contracted and removed from the final balloon void 442b. The final balloon void can remain in place with the balloons removed. The final balloon void can be larger than the initial balloon void.

FIG. 141H illustrates that a cement conduit can be inserted, as shown by arrow, through the delivery tube and into the balloon void. A filler, such as a bone cement, can be inserted into the final balloon void.

FIG. 141i illustrates that the final balloon void can be substantially filled with the bone cement. The bone cement can cure. The cement conduit can be removed. The delivery tube can be removed.

Figure 142A:
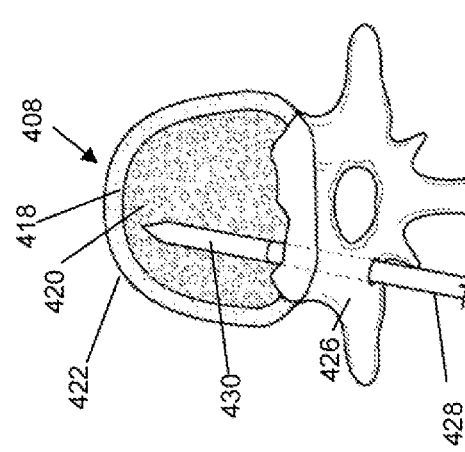
FIGS. 142A through 142F are coronal cross-sectional views of a variation of a method of using a variation of the device in a vertebra.
Figure 142B:
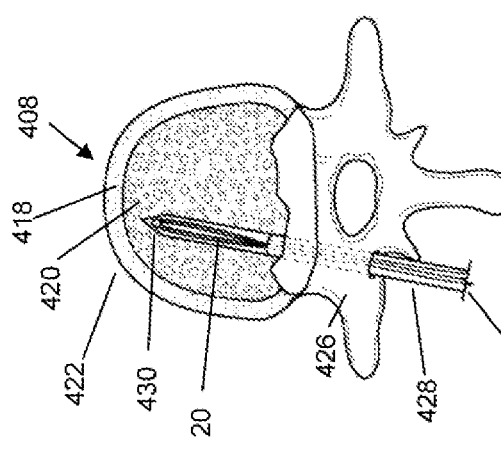
Figure 142C:
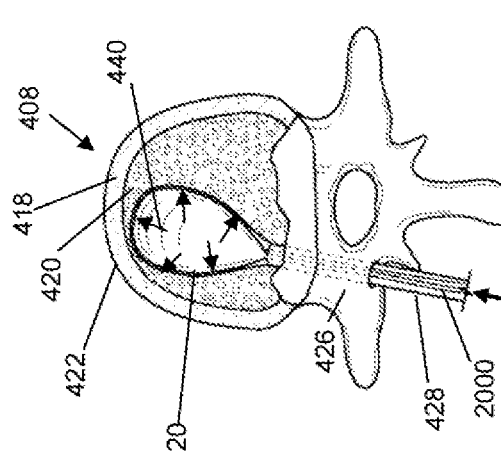

FIGS. 142A through 142C illustrate a method of created a balloon void with a balloon similar to the methods shown herein. The hollow shaft can be attached to a cement conduit.

Figure 142D:
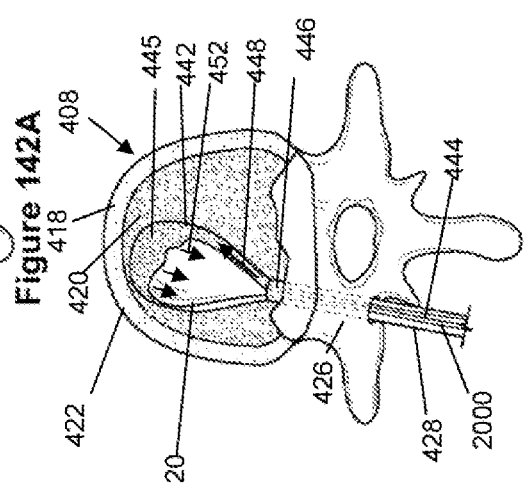

FIG. 142D illustrates that the bone cement can be delivered through the cement conduit and into the balloon void. The balloon can be deflated and contracted, as shown by arrows, and/or the balloon can be pushed out of the way by pressurized bone cement delivered into the balloon void. The bone cement can contact the balloon with or without significantly decaying, eroding or bonding to the balloon wall.

Figure 142E:
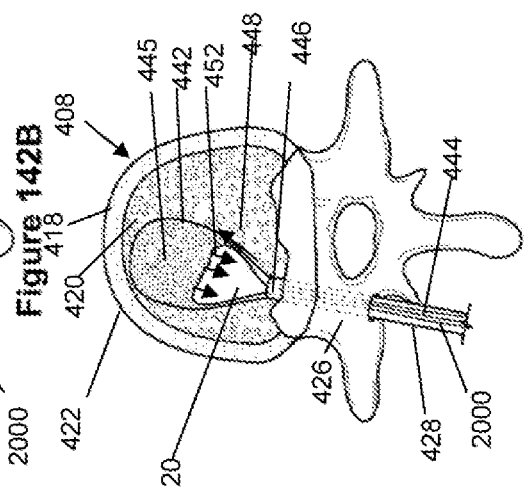

FIG. 142E illustrates that additional bone cement can be delivered to the balloon void as the balloon contracts. The bone cement can partially or completely cure with our without being in contact with the balloon. The balloon wall can peel away or otherwise be separated from cured or uncured bone cement.

Figure 142F:
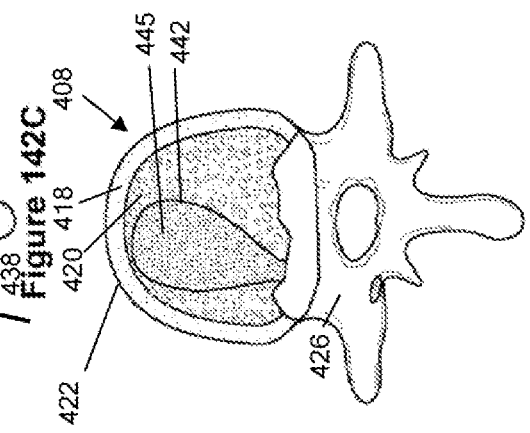

FIG. 142F illustrates that the final balloon void can be substantially filled with the bone cement. The bone cement can cure. The hollow shaft and cement conduit can be removed. The delivery tube can be removed.

FIGS. 131 through 142F illustrate that the one or more balloons can be inserted into the vertebral body unilaterally, through a pedicle on one lateral side of the vertebra.

FIGS. 143A through 143i illustrate a method for deploying the balloons bilaterally, for example including one balloon inserted through each of opposing pedicles 426a and 426b.

FIG. 143A illustrates that a first delivery guide 428a can be through the left pedicle 426a. A first drill void 430a can be formed on the left side of the vertebral body. A second delivery guide 428b can be through the right pedicle 426b. A second drill void 430b can be formed on the left side of the vertebral body.

FIG. 143B illustrates that a first balloon 20a can be inserted into the left side of the vertebral body through the first delivery tube 428a. A second balloon 20b can be inserted into the right side of the vertebral body through the second delivery tube 428b.

FIG. 143C illustrates that the first balloon 20a can be inserted through the first delivery tube 428a. The second balloon 20b can be inserted through the second delivery tube 428b. The first and second balloons can be inflated and expanded. The first and second balloons can form a first void segment 454a and a second void segment 454b, respectively, of the balloon void 442. The void segments 454 may overlap, as shown. The void segments 454 may be separate.

FIG. 143D illustrates that the second balloon can be deflated, contracted and removed from the balloon void.

FIG. 143E illustrates that a second cement conduit can be inserted through the second delivery tube and into the second void segment. Bone cement can be delivered through the second cement conduit and into the second void segment.

FIG. 143F illustrates that the bone cement can fill the second void segment and/or contact the first balloon. The second cement conduit can be removed from the balloon void. The bone cement delivered to the second void segment can cure. The first balloon may not erode, decay or bond to the cement.

Figure 143I:
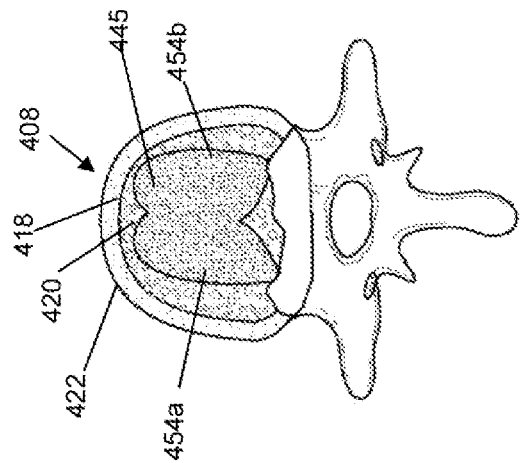
Figure 143H:
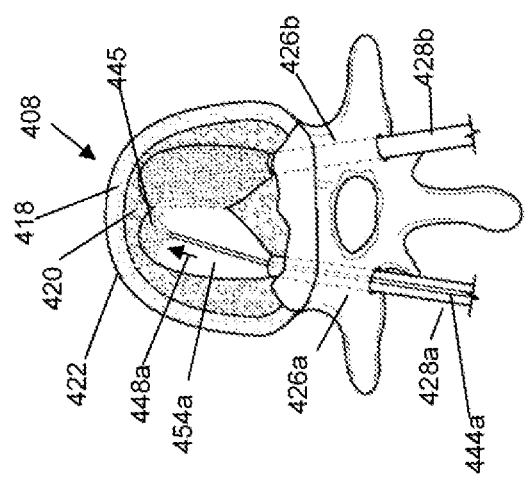
Figure 143G:
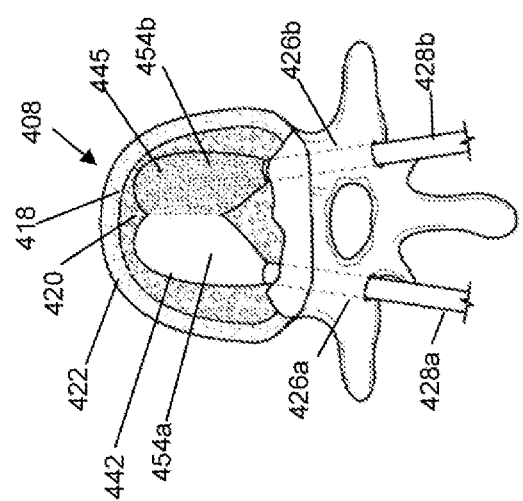

FIG. 143G illustrates that the first balloon can be deflated, contracted and withdrawn from the first void segment. The first void segment can be empty. The second void segment can be substantially filled with bone cement.

FIG. 143H illustrates that a first cement conduit can be inserted through the first delivery tube and into the first void segment. Bone cement can be delivered through the first cement conduit and into the first void segment.

FIG. 143i illustrates that the first and second delivery tubes can be removed from the patient. The balloon void can be substantially filled with bone cement.

Figure 144:
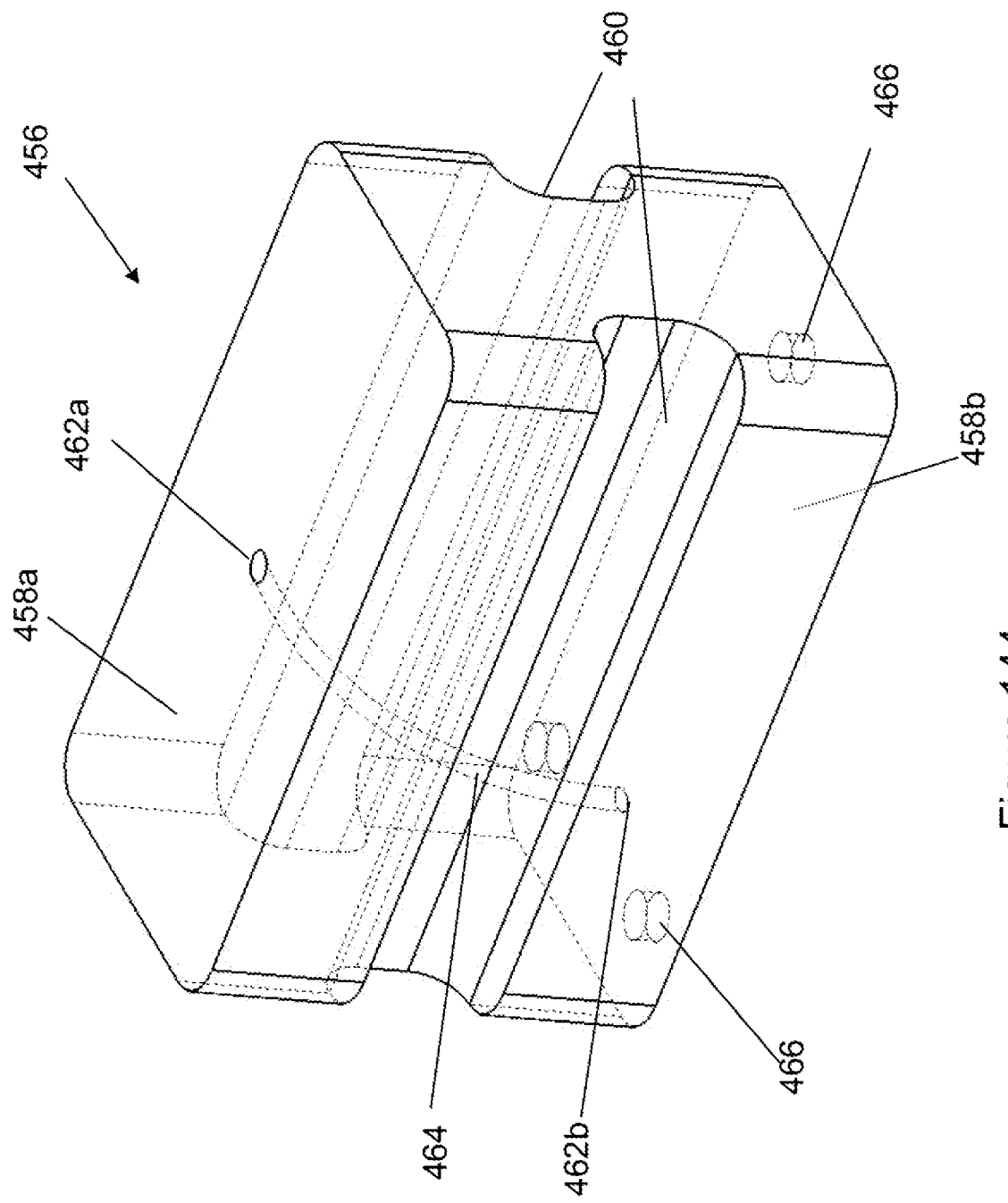
FIG. 144 illustrates a variation of the delivery guide block.

FIG. 144 illustrates that a guide block 456 may have a surface block top surface 458a and a block bottom surface 458b. The block can have finger depressions 460 where a user's fingers may grip the block. The block 456 can have a curved block channel 464 passing though the block 456. The block channel 464 can terminate at a block top hole 462a and a block bottom hole 462b. The block 456 can have one, two, or three radiopaque markers 466 evenly or unevenly distributed about the block 456. The radiopaque markers 466 can have a fixed dimensional relationship to block bottom hole 462b.

The block can be partially or total radiolucent. The block top surface can be placed against a patient's back before a kyphoplasty procedure. The radiopaque markers can locate the block with respect to the patient anatomy. The block bottom hole can be located on the patient's back during use.

Figure 145:
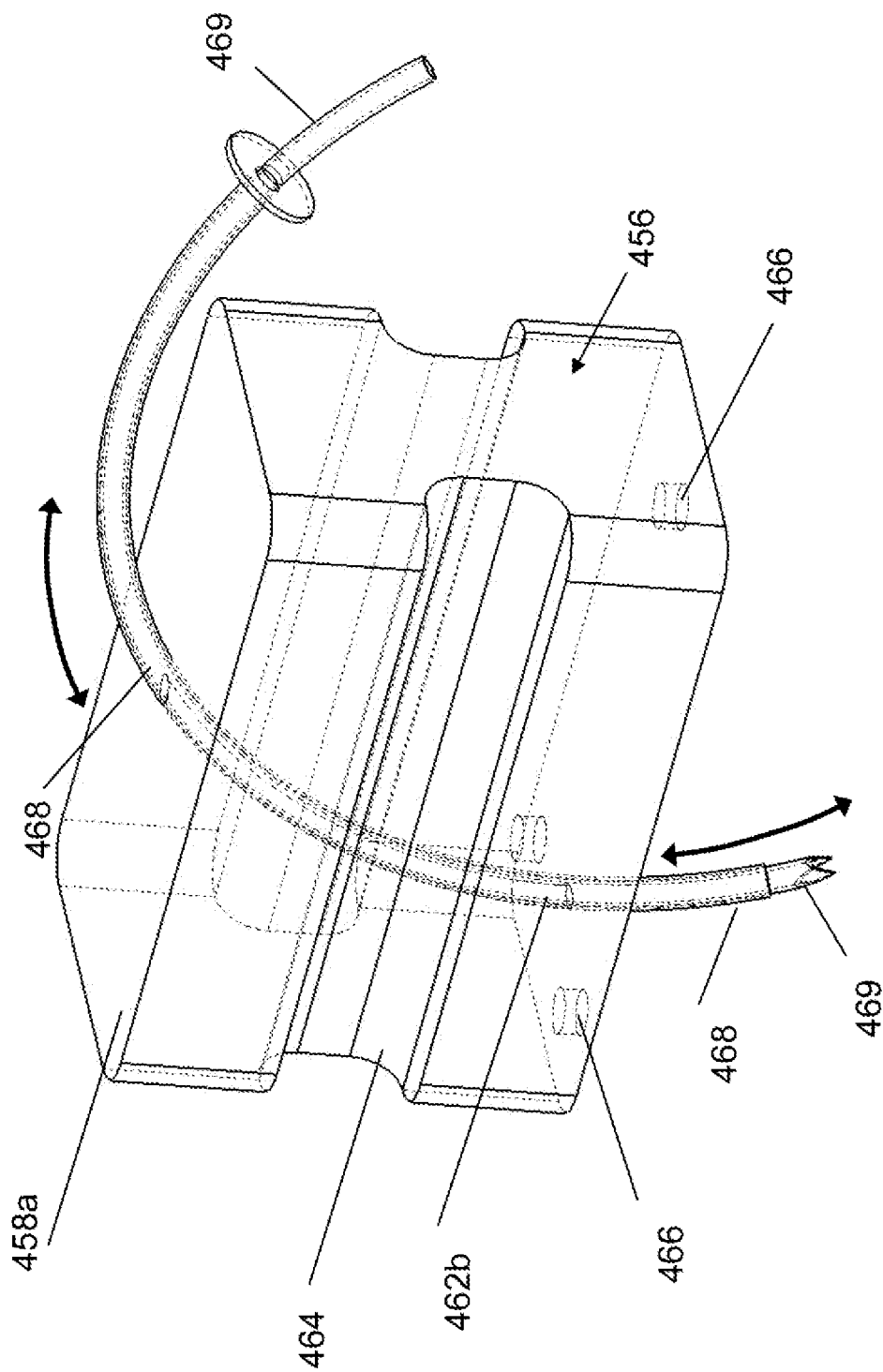
FIGS. 145 and 146 illustrate a variation of a method for using the delivery guide block.

FIG. 145 illustrates that an entry tool, such as a trocar 469 and a delivery tube, such as a cannula 468, may have curvatures that substantially match the curvature of the block channel. The cannula 468 can slide freely in the block channel. The cannula can be lubricated on the outside diameter. The block top hole may be lubricated on the inside diameter. By holding block in place on the patient's anatomy, a medical practitioner may be able to advance the trocar and the cannula into a vertebral body along a curved arc.

Figure 146:
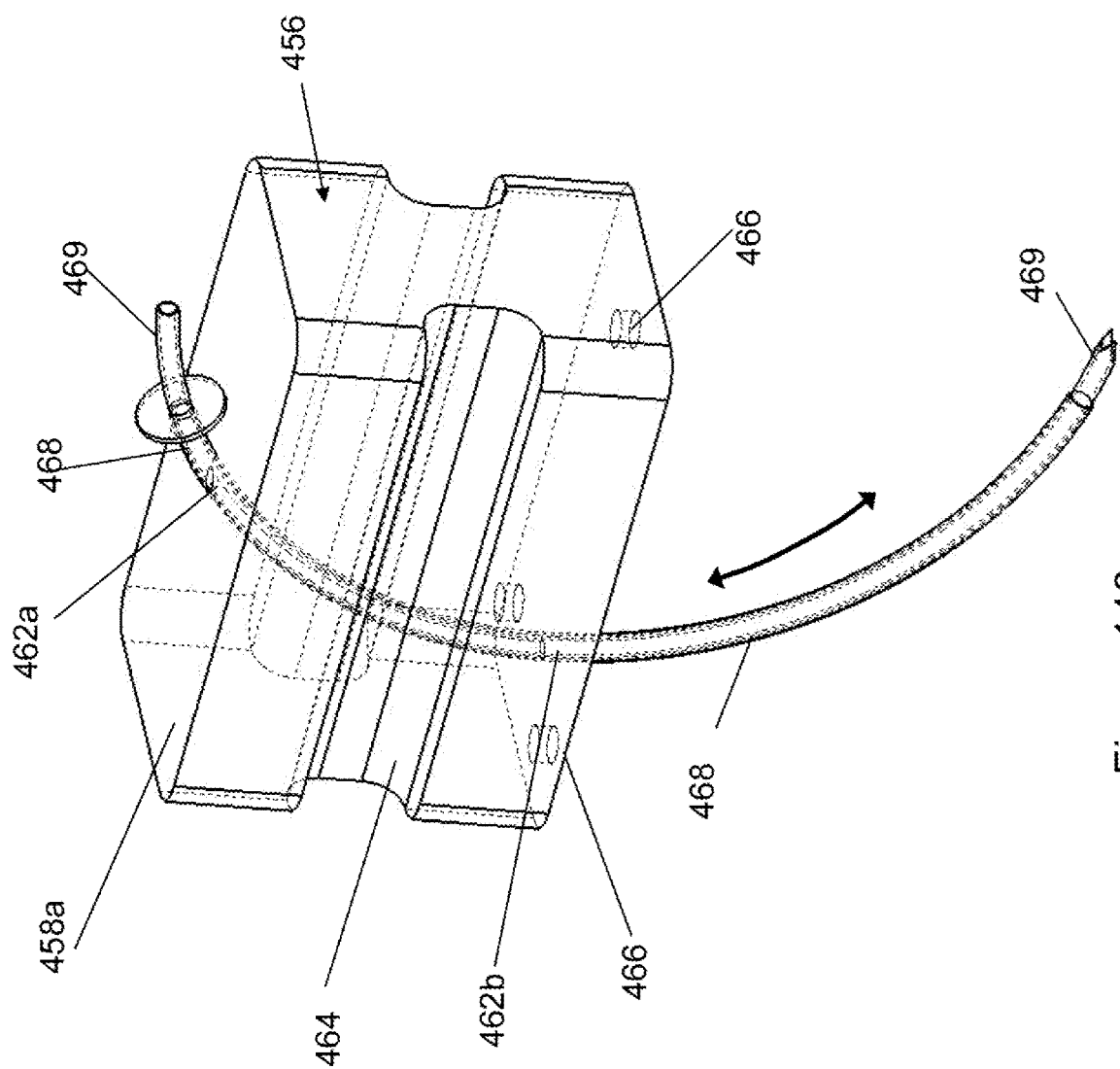

FIG. 146 illustrates that the cannula and trocar may advance further though the block. The trocar can be a torsion shaft with a drill bit on the distal end. Turning the torsion shaft can cause the drill to bore into bone while being guided in a curved path by the cannula.

The cannula can be a flexible tube or series of links. The cannula, for example as a tube, or series of links, may be steerable, for example similar to a catheter or an endoscope.

Figure 147:
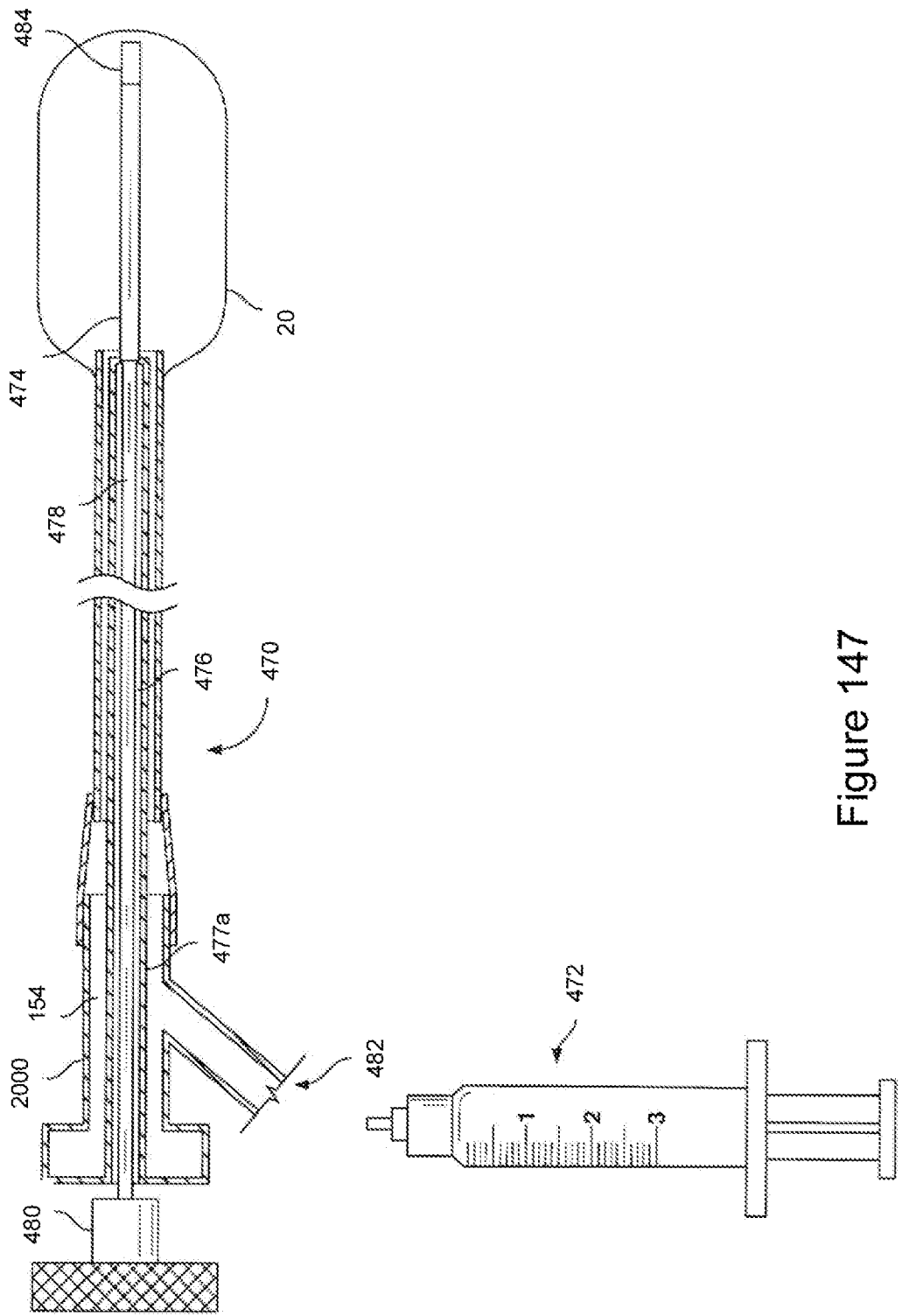
FIGS. 147 through 149 illustrate variations of a deployment tool with the device.

FIG. 147 illustrates that the inflation system 470 can be attachable to a syringe 472 or other source of flow and pressure. The inflation system 470 can include part or all of the hollow shaft 2000, an inner shaft 477a, a stiffening shaft 476, a hollow shaft lumen 154, a stiffening shaft lumen 478, an inflation port 482 and a stiffening rod control 480. The distal end of the stiffening shaft 476 can have a stiffening rod tip 484.

The syringe 472 can be detachable or non-detachable from the remainder of the inflation system 470. The balloon 20 may be inflated by pushing inflation fluid, such as water or dye, from the syringe 472, into the inflation port 482, through the hollow shaft lumen 154 and into the balloon 20. The removable stiffening shaft 476 may be left in place to stiffen the inflation system 470 while positioning the balloon 20 in the body. Once the balloon 20 is in place, the removable shaft stiffener 476 can be removed to allow the hollow shaft 2000 additional freedom of motion outside the body.

The stiffening shaft 476 can be integral with or removably attached to the stiffening rod 474. The stiffening rod tip 484 can have atraumatic geometry, or a soft plastic or elastomeric tip that will minimize puncture or damage the distal end of the balloon. The stiffener 476 can be withdrawn manually automatically.

Figure 148:
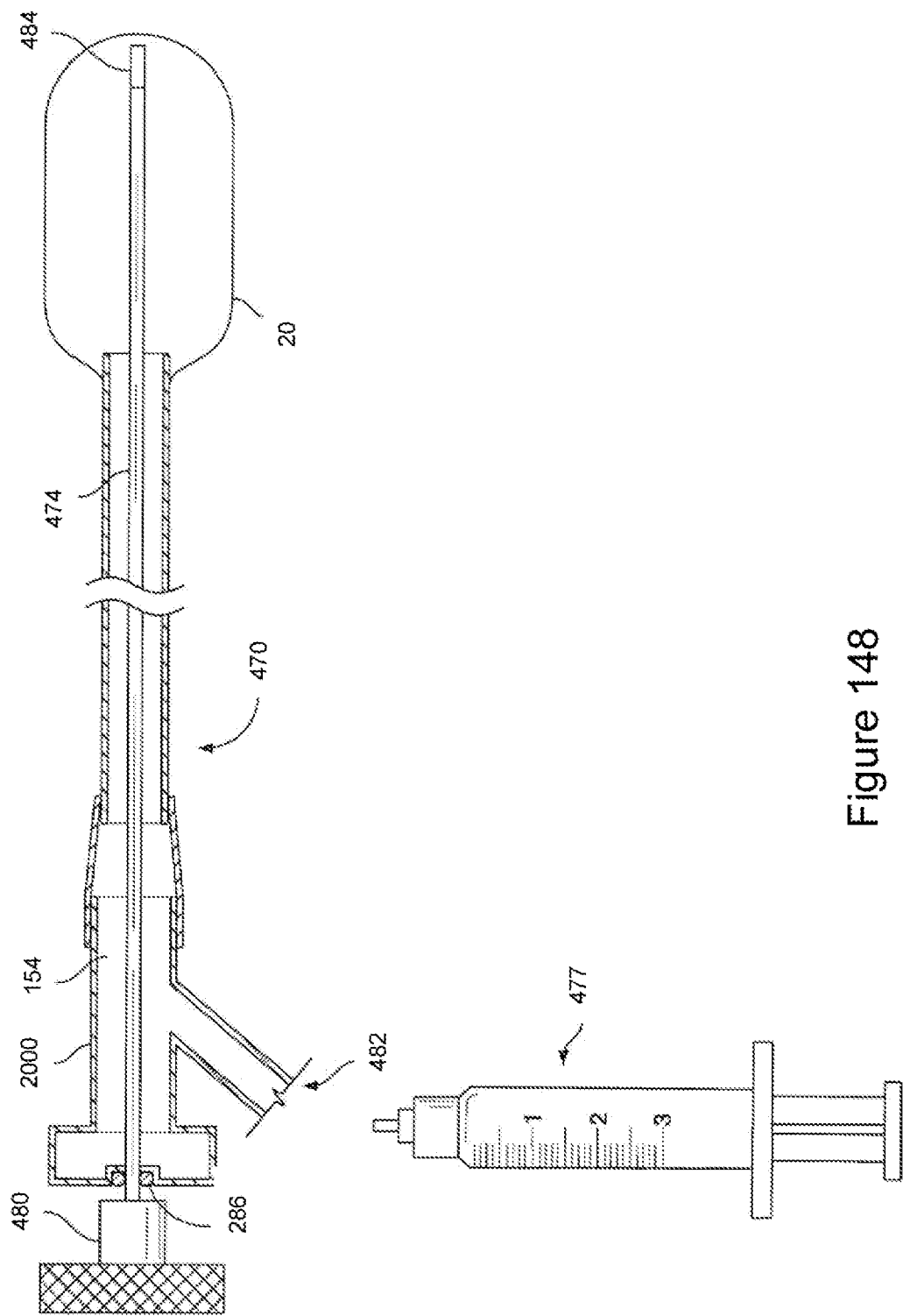

FIG. 148 illustrates that the inflation system 470 can have a balloon 20 that can be inflated by pushing inflation fluid, such as water, saline, a gel or dye, from the syringe 472, into the inflation port 482, though the hollow shaft lumen 154 and into the balloon 20.

The stiffening rod 474 can be removed from the inflation system or left in place to stiffen the inflation system 470 while positioning the balloon 20 in the body. The inflation system can have a stiffening rod control 480, for example a knob or handle on the proximal end of the inflation system to control the position of the stiffening rod. A seal adjacent to the stiffening rod control can prevent pressure from escaping from the hollow shaft lumen. When the balloon 20 is at the target site, the stiffening rod 474 can be removed from the inflation system or left in place.

Figure 149:
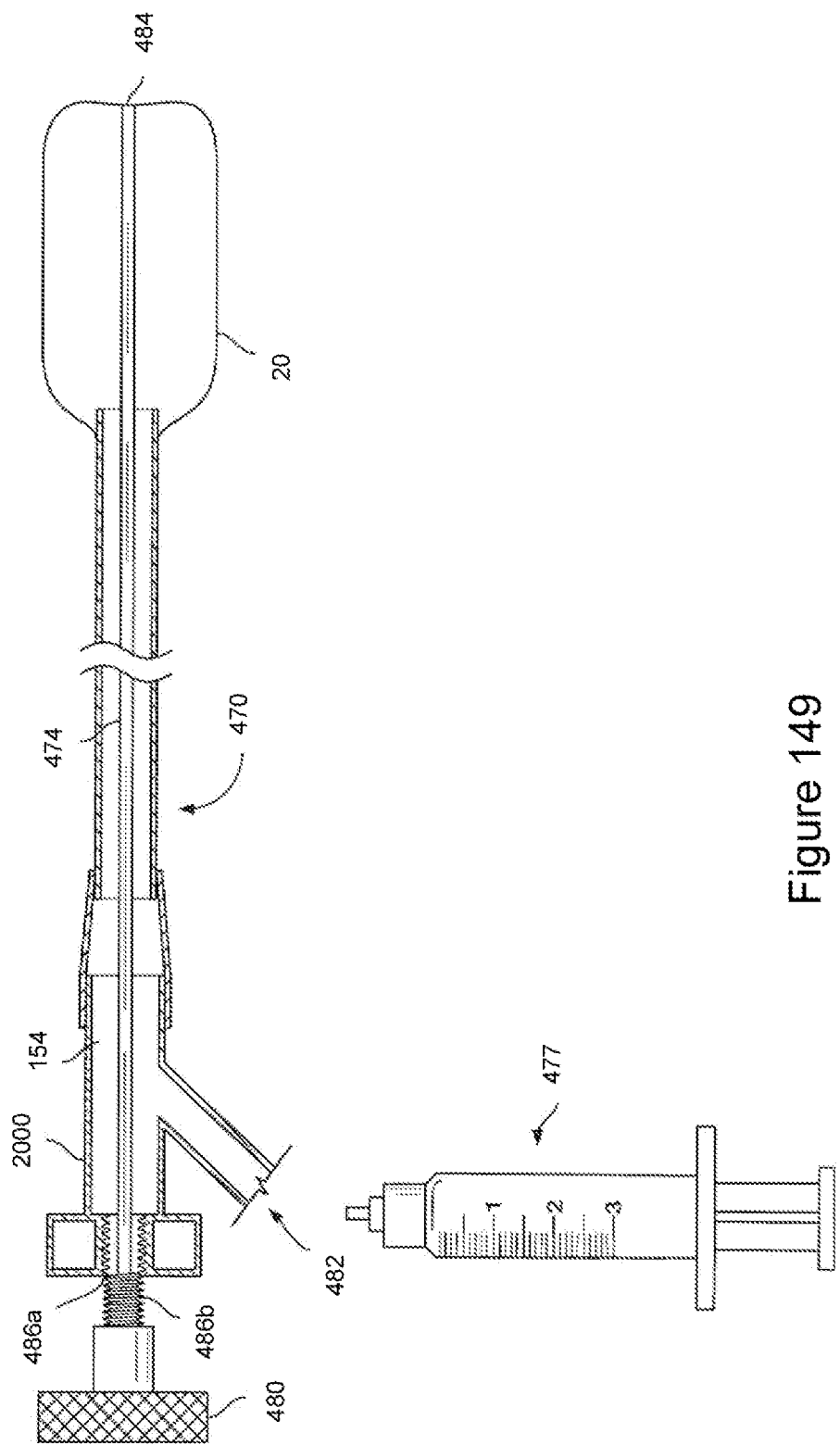

FIG. 149 illustrates that the stiffening rod control 480 can have inner threads 486b. A connector at the proximal end of the hollow shaft 2000 can have outer threads 486a. The stiffening rod control 480 can rotatably interface with the hollow shaft 2000 at the inner and outer threads 486b and 486a.

The stiffening rod 474 can be attached to the inside of the distal end of the balloon 20. The stiffening rod can have a coupling (not shown) internal to the rod that can prevent the rod from applying torque to the balloon 20. The stiffening rod can be made from flexible high strength filaments (not shown). The balloon 20 may be inflated by pushing inflation fluid, such as water or dye, from the syringe 472, into an inflation port, though the hollow shaft lumen or inflation lumen and into the balloon. Turning the stiffening rod control knob may cause the balloon to longitudinally expand or contract. The balloon can evert when the stiffening rod is withdrawn proximally. The balloon's distal end may resemble the distal end 44 shown in FIG. 10d.

Figure 150A:
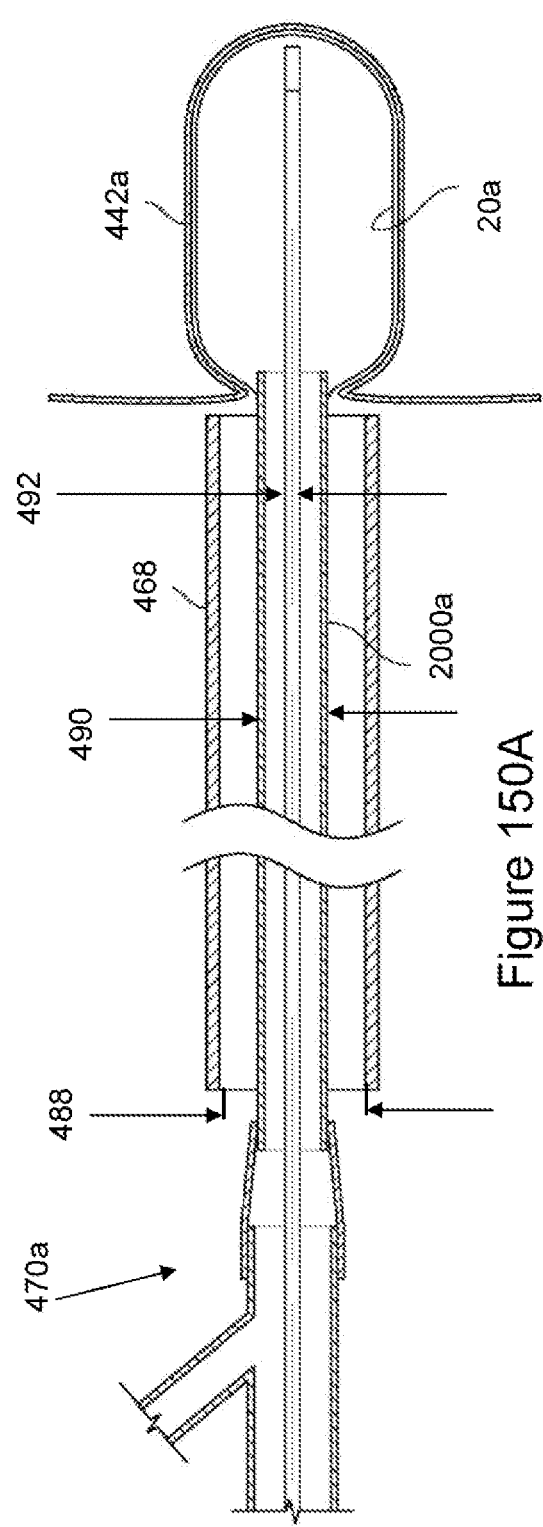
FIG. 150A through 150C illustrate a variation of a method for using the device and the deployment tool.

FIG. 150A illustrates that the first balloon 20a can be inserted into the body through a working channel or delivery tube such as the cannula 468. The first balloon 20a in a deflated configuration can be smaller in diameter than the cannula inner diameter 488. The hollow shaft 2000 can have a hollow shaft outer diameter 490. The hollow shaft outer diameter 490 can be smaller than the cannula inner diameter 488. For example, the cannula inner diameter can be about 3.66 mm (0.144 in.). The hollow shaft outer diameter can be about 2 mm (0.09 in.), more narrowly about 1.5 mm (0.060 in.), yet more narrowly about 0.8 mm (0.03 in.). The stiffening rod can have a stiffener rod diameter. The stiffener rod can have a stiffening rod diameter 492. The stiffener rod diameter can be about 1 mm (0.05 in.), or about 0.8 mm (0.03 in.), or about 0.5 mm (0.02 in.).

The first balloon 20a can be inflated in the body, for example creating a first balloon void, lumen or pocket in the body. The first balloon 20a can be inflated in bone. The first balloon 20a can be inflated in a vertebra of the spine. The first balloon 20a can then be deflated and pushed to the side of the cannula 468.

Figure 150B:
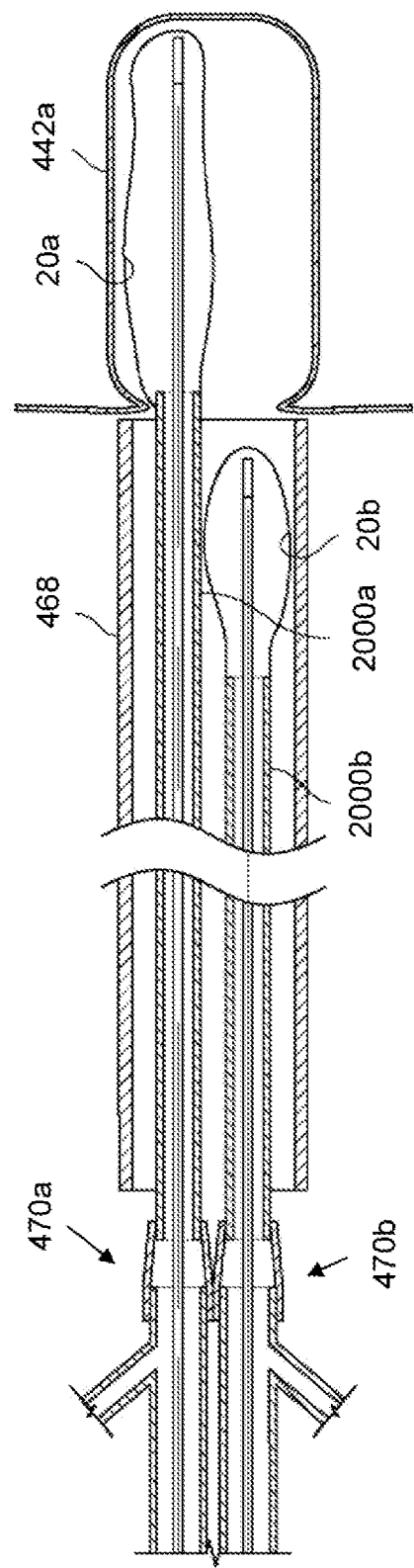

FIG. 150B illustrates that a second balloon 20b can be inserted through the hollow shaft 2000 while the first balloon 20a is positioned through the hollow shaft 2000. The first balloon 20a and the second balloon 20b can be inserted concurrently through the hollow shaft 2000. The first balloon 20a can be deflated before the second balloon 20b is inflated.

Figure 150C:
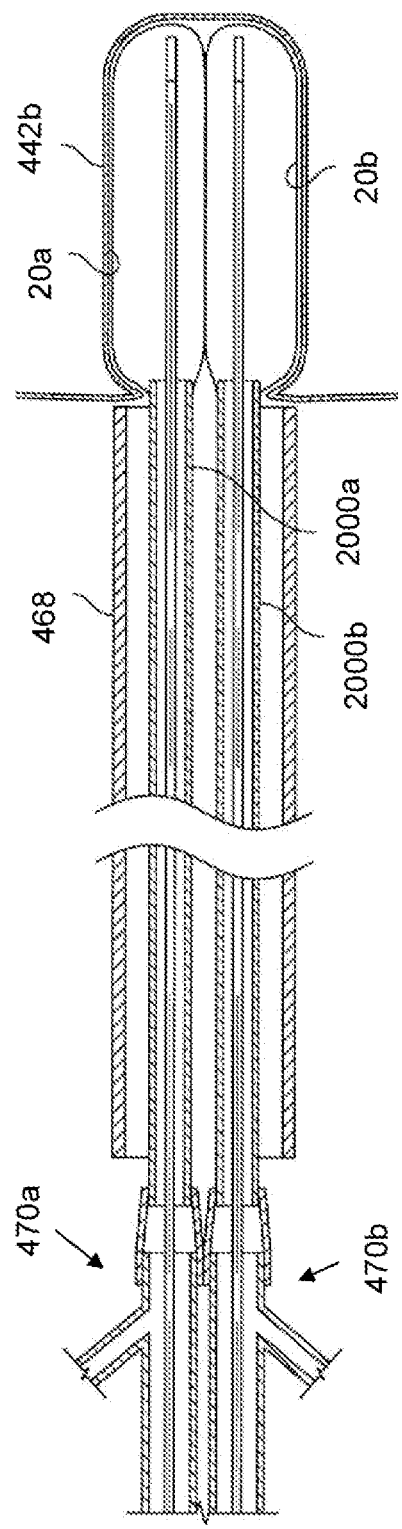

FIG. 150C illustrates that the first balloon 20a and the second balloon 20b can be inserted into the initial void 442a created by a drill and/or the first balloon 20a. The first balloon 20a and the second balloon 20b can be inflated in the initial void 42a. The balloons 20 can create a final balloon void 442b, for example the final balloon void 442b can be larger than the initial balloon void 442a. Additional balloons can be inserted into the void 442 and inflated to further enlarge the balloon void 442.

Figure 151A:
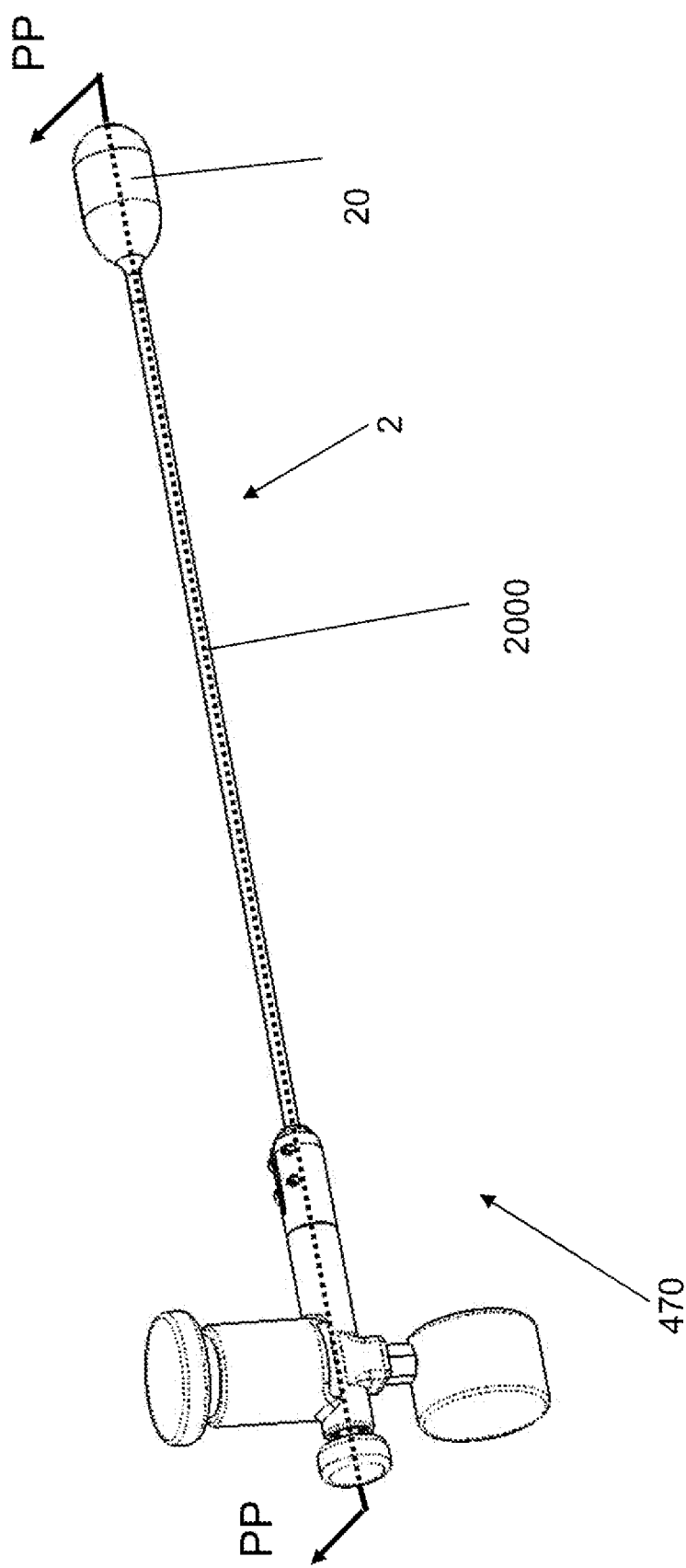
FIG. 151A illustrates a variation of the deployment tool.

FIG. 151A illustrates that an inflation system 470 and the device 2 can create space in the body. The balloon 20 can be substantially compliant or substantially non-compliant. The hollow shaft 2000 can be attached to or integrated with the inflation system 470.

The inflation system 470 can be portable and can be held in and operated by the user's hand. The inflation system 470 can provide a method for inflating the balloon 20. The inflation system 470 can advance and retract the stiffening rod to stiffen the balloon 20 during insertion of the balloon 20 into the body. The hollow shaft 2000 can have an inflation lumen between the inflation system and the balloon 20.

Figure 151B:
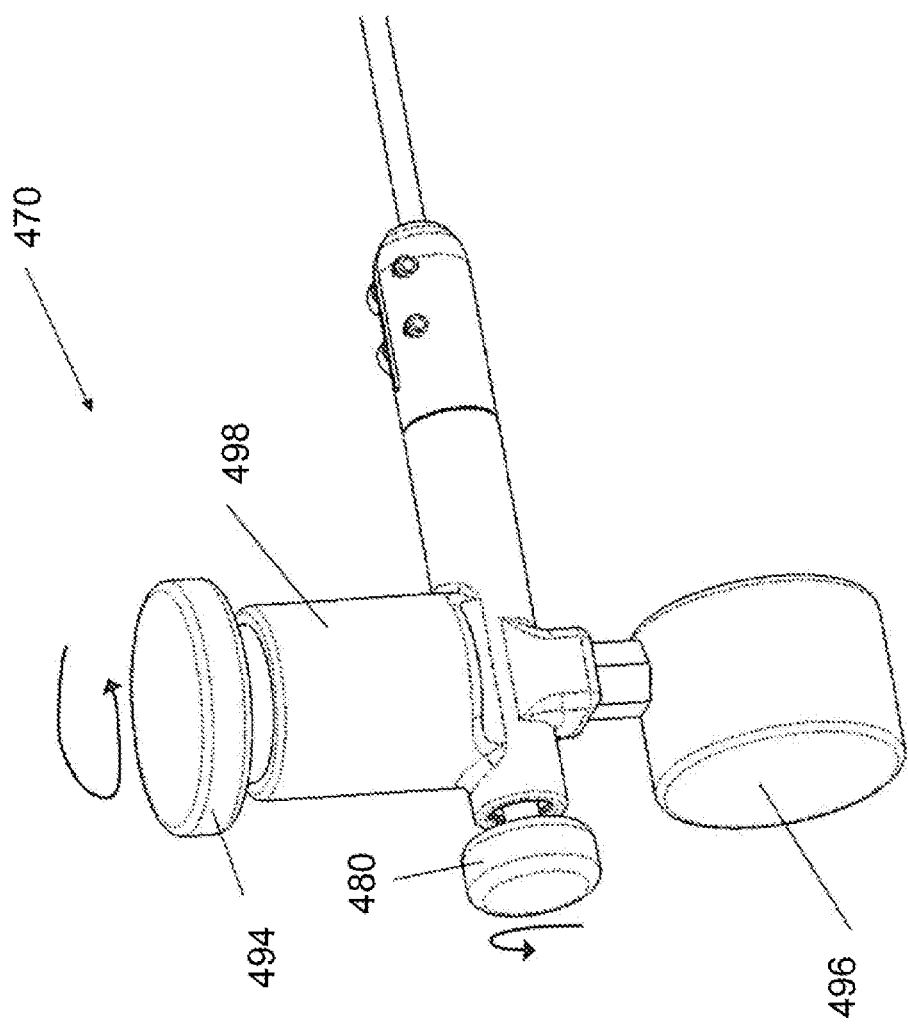
FIG. 151B illustrates the proximal end of the variation of the deployment tool during use.

FIG. 151B illustrates that the inflation system 470 can have a pressure delivery body 498, and a pressure control 494 (also element 590) attached to the pressure delivery body 498. The pressure control 494 can regulate the inflation of the balloon 20. The inflation system 470 can have a stiffening rod control 480. The stiffening rod control 480 can manipulate a stiffening rod 474 in the hollow shaft 2000. For example, the stiffening rod 474 can be advanced through or retracted from the hollow shaft 2000. The stiffening rod control 480 and/or the pressure control 494 can have buttons, knobs, or combinations thereof. The stiffening rod control 480 can be used to regulate the inflation of the balloon 20. A pressure gauge 496 attached to the lumen can show the pressure in balloon 20.

Figure 151C:
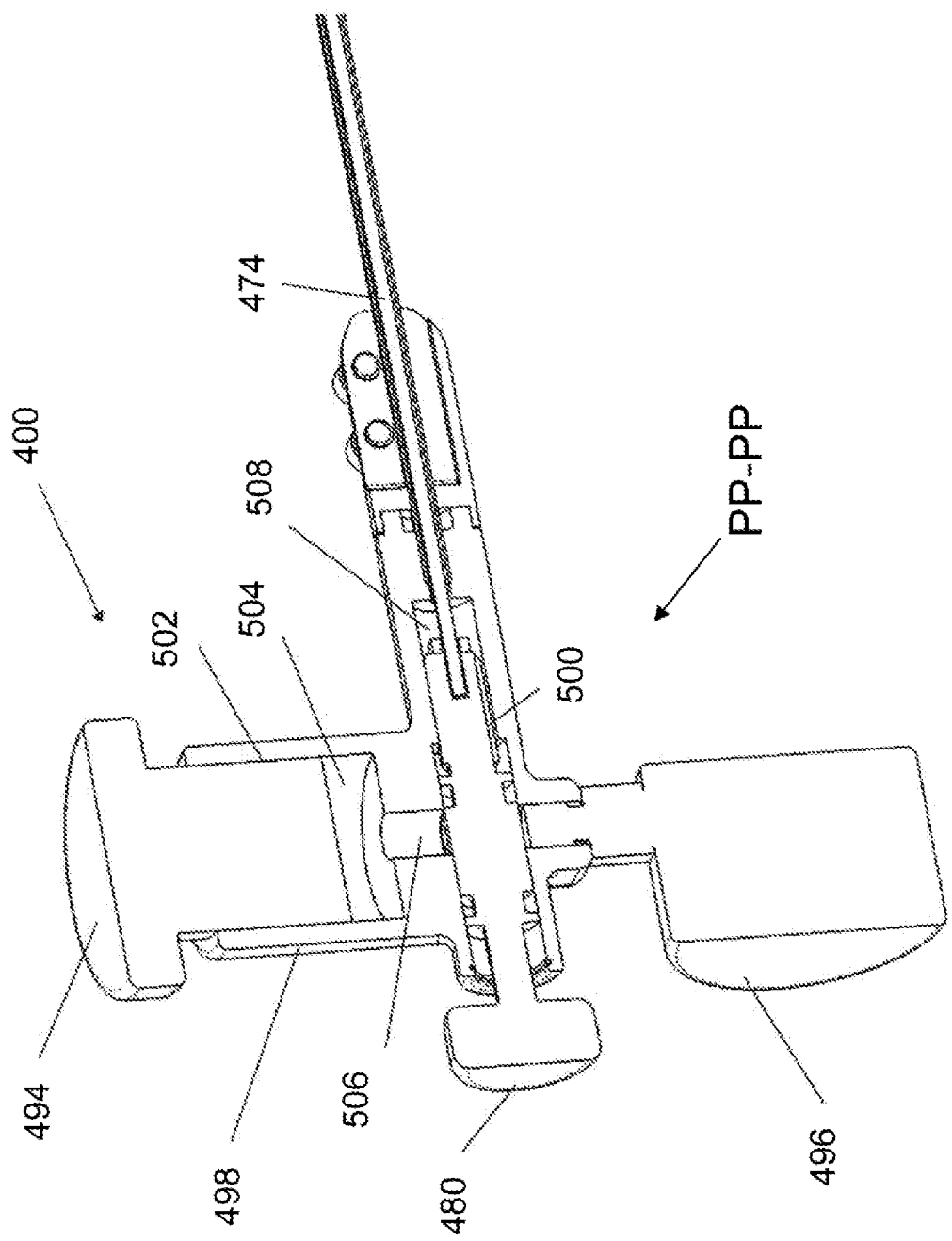
FIG. 151C is a variation of cross-sectional view PP-PP of FIG. 151A shown in a closed configuration.

FIG. 151C illustrates that a pressure control interface 502 can interface the pressure delivery body 498 with the pressure control 494. The pressure control interface 502 can be mating threads. The pressure control interface 502 can have male threads on the pressure control 494 that can mate to female threads on the pressure delivery body 498. Manipulating, such as turning, the pressure control interface 502, can increase or decrease the pre-load volume. When the pressure control 494 closes on the pre-load volume 504, the fluid in the pre-load volume 504 can exit through the pressure delivery body port 506 (also element 592). The fluid in the pre-load volume 504 can have a water or a radiopaque dye.

The stiffening rod control 480 can have a stiffening rod control interface 500 can mate the stiffening rod control 480 with the pressure delivery body 498. The stiffening rod control interface 500 can have mating threads. Turning the stiffening rod control 480 can extend and retract the stiffening rod 474.

The pressure control interface 502 can have male threads on the pressure control 494 that can mate to female threads on the pressure delivery body 498. The pressure control 494 and/or the stiffening rod control 480 can have one or more pressure tight seals to prevent leakage through the control.

FIG. 151C illustrates that the stiffening rod can block the pressure delivery body port 506 when the stiffening rod is in a longitudinally advanced position.

Figure 151D:
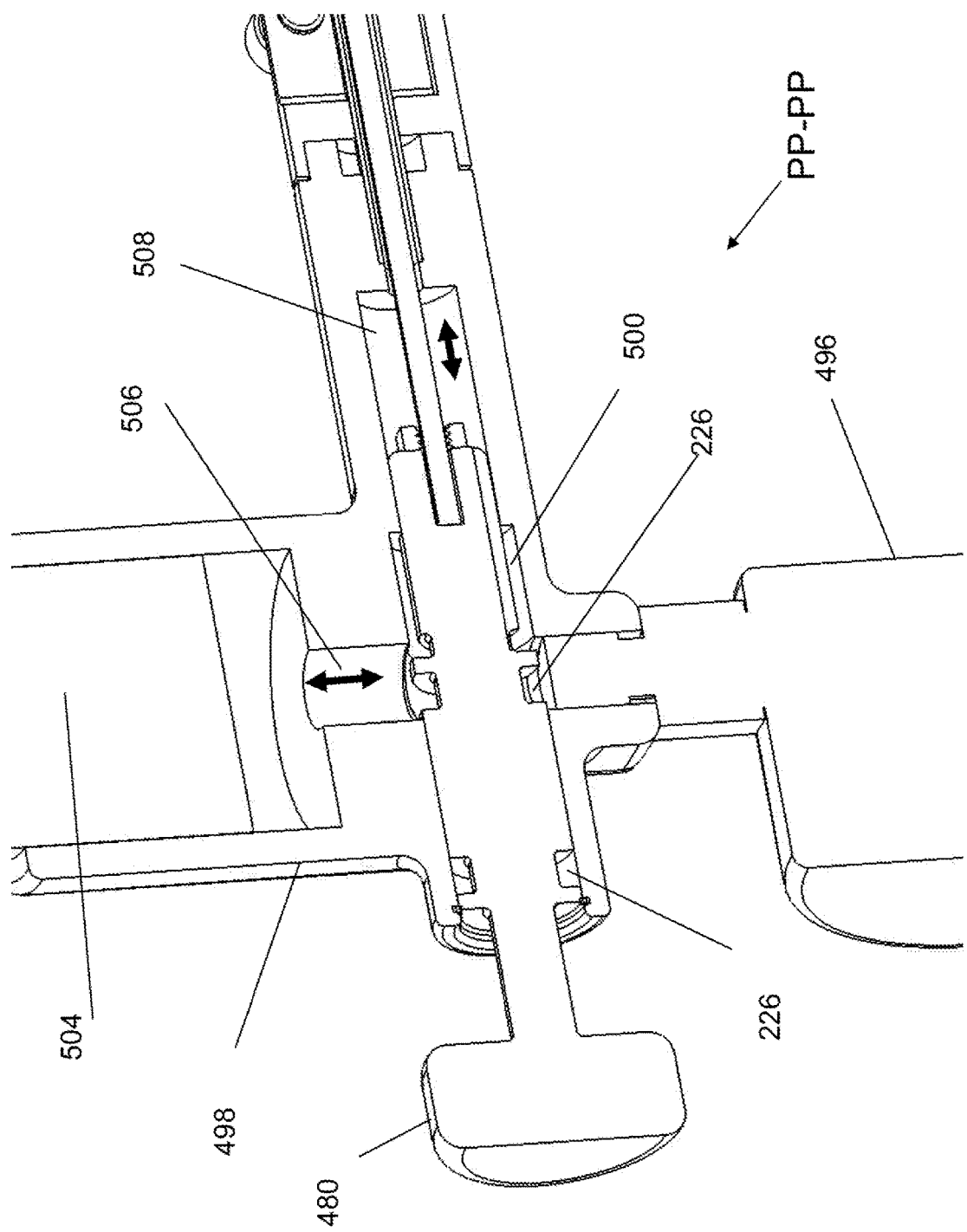
FIG. 151D is a variation of cross-sectional view PP-PP of FIG. 151A shown in an opened configuration.

The o-ring seats 226 can seat o-rings that can seal against the pressure delivery body 498. The seals 286 in o-ring seats 226 can form a pressurized volume between themselves that connects to the pressure delivery body port 506 and the input of pressure gauge 496 (as shown in FIGS. 151C and 151D). The seals 286 in the o-ring seats 226 can form a pressurized volume that does not always connect to the inflation lumen 154. The inflation lumen 154 can connect to the internal volume of balloon 20.

FIG. 151C illustrates that retracting the stiffening rod control 414 (e.g., unscrewing the stiffening rod control 414) can cause the pressurized volume between seals 286 in o-ring seats 226 to no longer be in fluid communication with the inflation lumen, and/or the pressure delivery body port and/or the input of the pressure gauge 496. The stiffening rod control 480 (by, for example, rotating it) may cause the pressure delivery body port 506 and the input of pressure gauge 496 to be connected to the inflation lumen 154 that leads to balloon 20. Manipulating the pressure control 494 can cause fluid to flow though the pressure delivery body port 506, through the inflation lumen 154 and into the balloon 20, inflating the balloon 20.

The distal end of the device 2, for example the balloon 20, can be inserted into the body though a cannula. The stiffening rod control can be manipulated to withdraw the stiffening member. The pressure control can be manipulated to move fluid from the pre-load volume 504 to the balloon volume.

Fluid entering the balloon 20 can cause the balloon 20 to inflate and create a balloon void in the body.

The pressure control 494 can be withdrawn from the pressure delivery body 498. Fluid pressure can then move from the inside of balloon 20 back into pre-load volume 504. The device 2 and inflation system 470 can then be withdrawn from the body.

The fluid that is transferred from pre-load volume 504 to the balloon volume can be sealed in the device before use, for example during manufacturing. The inflation system can have a fixed pre-load volume 504 before use, such that a user does not need to add fluid to the pre-load volume 504 during use. The inflation system can be sealed or otherwise designed to prevent fluid, other than fluid added to the pre-load volume 504 during manufacturing, from entering the pre-load volume 504. The fluid in the pre-load volume 504 can be water, air, saline, radiopaque dye, a gel, or combinations thereof.

The volume of the pre-load volume 504 that can be delivered to the balloon volume can be set to inflate the balloon 20 to a pre-determined inflation size. The pre-load volume can be, sealed when the inflating system is manufactured or fluid can be added or removed from the pre-load volume after manufacture of the inflation system and before use.

For example, the pre-load volume 504 or maximum volume deliverable to the balloon 20 (e.g., pre-load volume minus the volume of the pre-load lumen 508 and the volume of the hollow shaft) can be inflate the balloon 20 to a configuration where the one or more balloon walls 22 are strained less than 5%, for example less than 3%, also for example less than 1%.

The stiffening rod 474 can obstruct fluid from entering the balloon 20 from the pre-load volume 504 when the stiffening rod 474 is in a closed configuration. The stiffening rod 474 can not obstruct fluid from entering the balloon 20 from the pre-load volume 504 when the stiffening rod 474 is in an opened configuration. For example, the stiffening rod can be withdrawn from the remainder of the inflation system in the second configuration. The stiffening rod can be configured not to puncture the balloon 20 in the closed or opened configuration.

FIG. 151D illustrates that the stiffening rod 474 can be in the opened configuration. The pre-load volume can be in fluid communication with the balloon. The stiffening rod can not obstruct the pressure delivery body port.

Figure 152A:
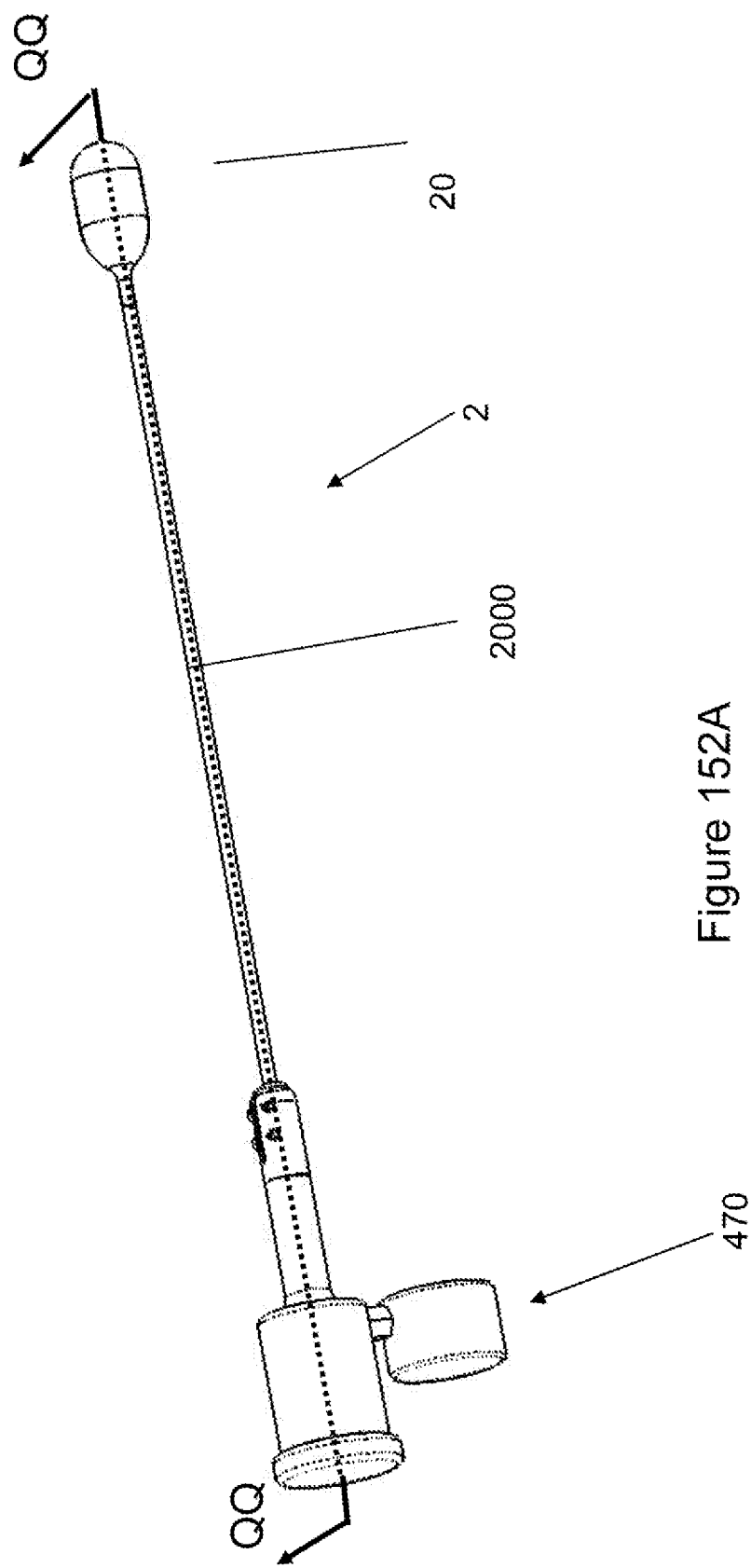
FIG. 152A illustrates a variation of the deployment tool.
Figure 152B:
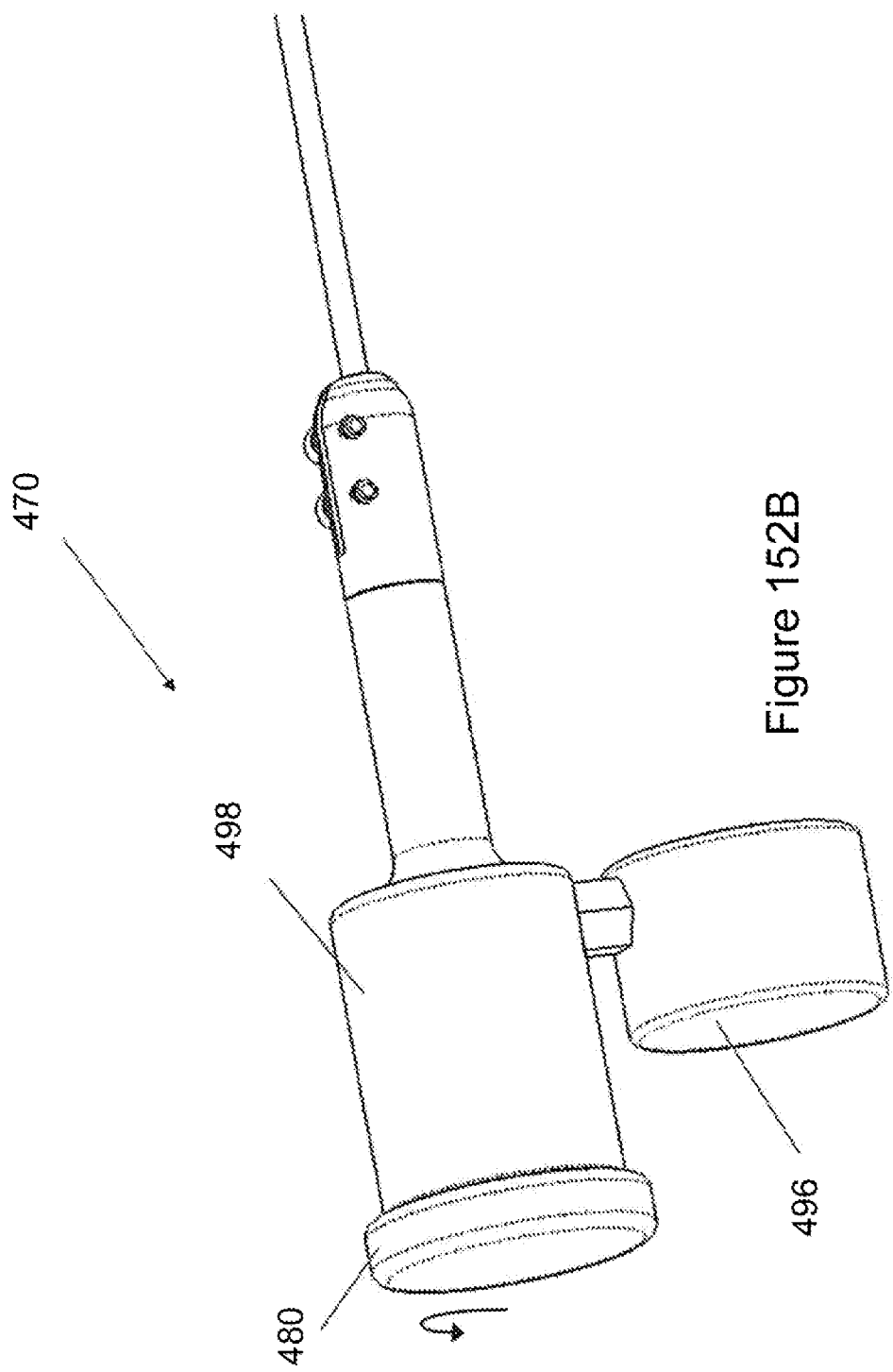
FIG. 152B illustrates the proximal end of the variation of the deployment tool during use.
Figure 152C:
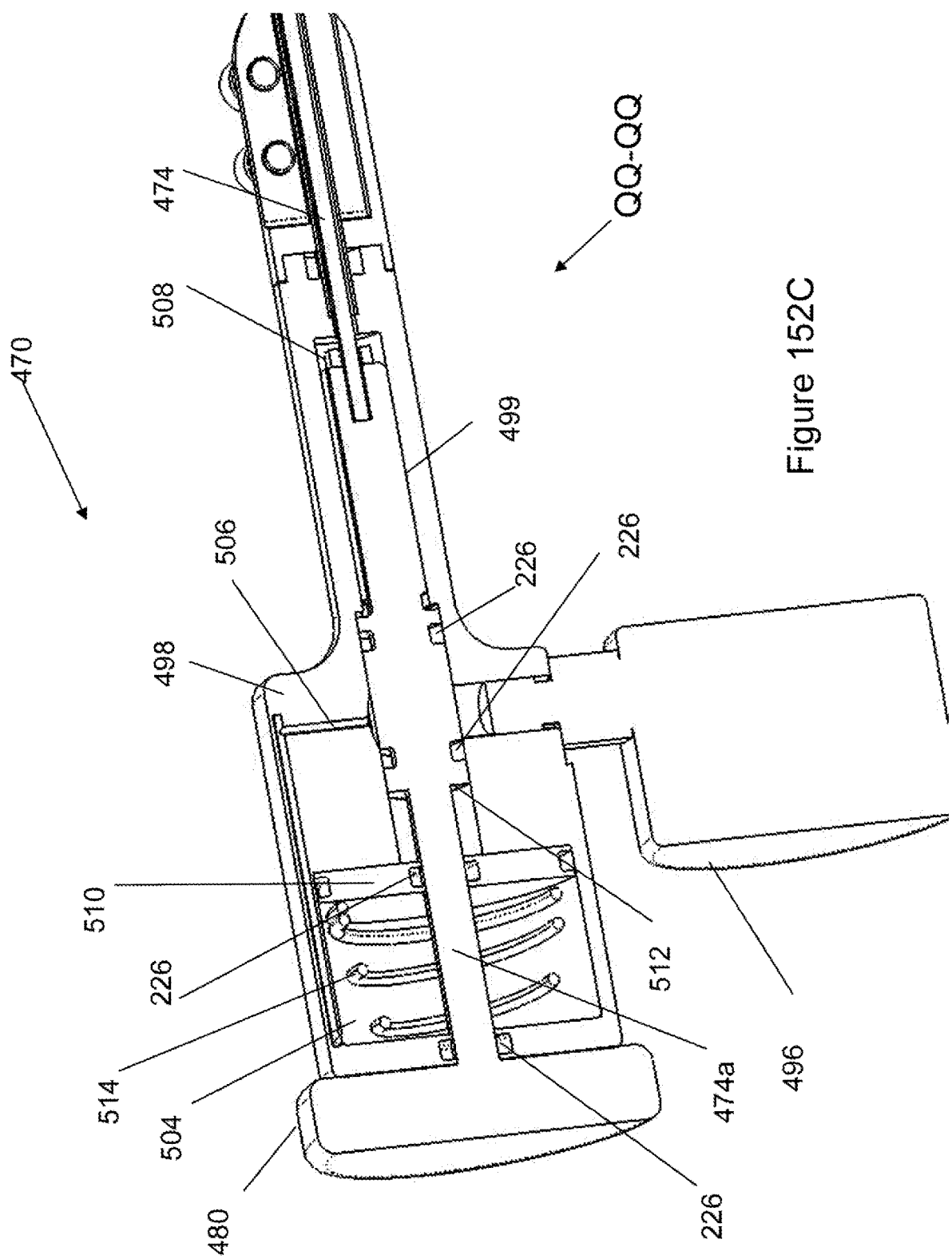
FIG. 152C is a variation of cross-sectional view QQ-QQ of FIG. 152A shown in a closed configuration.

FIGS. 152A through 152C illustrate that the stiffening rod control 480 can control fluid delivery to the balloon 20. The stiffening rod control 480 can manipulate the stiffening rod. The stiffening rod control can retract proximally or extend distally the stiffening rod. The stiffening rod can extend longitudinally along the hollow shaft 2000. The pressure gauge 496 can communicate the pressure in balloon 20 to the user. The balloon 20 can be substantially compliant or substantially non-compliant. The hollow shaft 2000 can have an inflation lumen extending between the inflation system and the balloon 20.

FIG. 152C illustrates that the stiffening rod can have a stiffening rod interface 499 that can mate to the inside of the pressure delivery body, for example at screw threads (not shown). The stiffening rod control can have a pressure tight seal with the pre-load volume, such as at the o-ring seats. The stiffening rod control can be connected to or integral with the stiffening rod. Turning the stiffening rod control can extend and retract the stiffening rod. A pressure disk 510 can have one or more o-ring seats to form a pressure tight sliding seal with the pre-load volume and the stiffening rod. The pressure disk 510 can freely slide proximally and distally on the stiffening rod. A spring 514 can apply a force on the pressure disk 510 to push the pressure disk 510 distally. O-ring seats (with o-rings, not shown) along a stiffening rod step 512 can form a sealed and pressurized pre-load volume when the stiffening rod control is retracted.

Figure 152D:
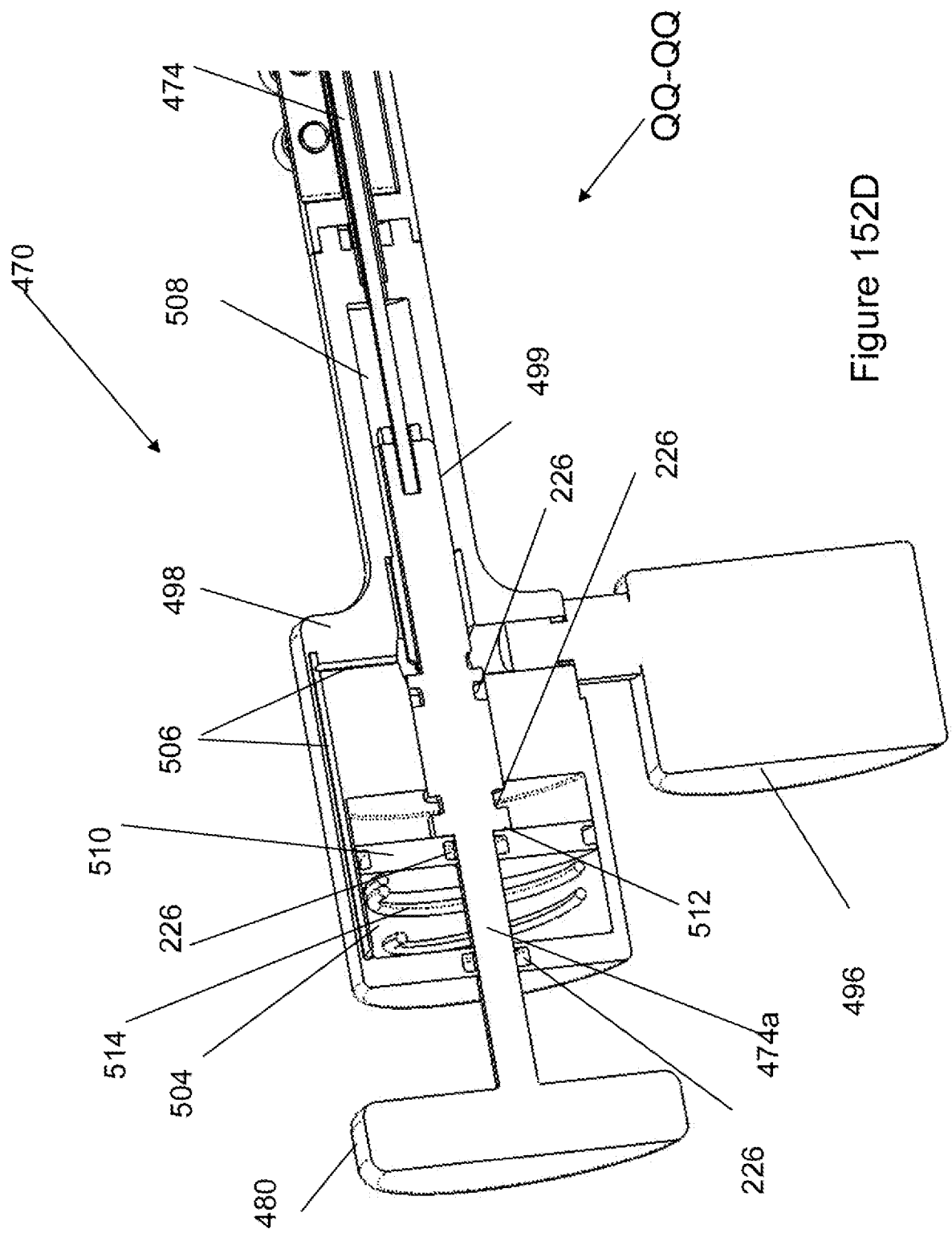
FIG. 152D is a variation of cross-sectional view QQ-QQ of FIG. 152A shown in an opened configuration.

The pressure delivery body port 506 can be obstructed by the stiffening rod step 512 when the stiffening rod is in a closed configuration, for example, distally extended within the inflation system. The pre-load volume and the pressure gauge can be in fluid isolation, for example by one or more o-rings in o-ring seats, from the balloon volume. The pre-load volume can be filled with air, water, saline, radiopaque dye, a gel, or combinations thereof FIG. 152D illustrates that when the stiffening rod control 480 is retracted (for example, rotating the control 480), the stiffening rod can retract proximally within the inflation system into an opened configuration. The stiffening rod step can move proximally. The pressure delivery body port 506 can be in fluid communication with the balloon 20 and the pressure gauge. Proximally moving the stiffening rod control 480 can proximally move the pressure disk within the pre-load volume. The pressure disk can force fluid out of the pre-load volume, through the pressure delivery body port and into the balloon 20. The pre-load volume can decrease in volume. The balloon can inflate.

When the balloon 20 is positioned at a target site to be treated, the stiffening rod control 480 can be rotated and/or retracted to proximally move the stiffening rod with respect to the pressure delivery body. The stiffening rod control and/or the pressure control can regulate the inflation of the balloon 20, for example, by the fluid in the pre-load volume. The inflation and expansion of the balloon can create a void volume within in the body. The stiffening rod control and/or the pressure control can draw fluid from the balloon to the pre-load volume, deflating the balloon. The balloon can then be withdrawn from the target site.

The inflation system can be sealed to prevent fluid from the pre-load volume, or otherwise, from being delivered balloon volume until the stiffening rod has been proximally retracted (or distally extended, depending on the design).

Figure 153:
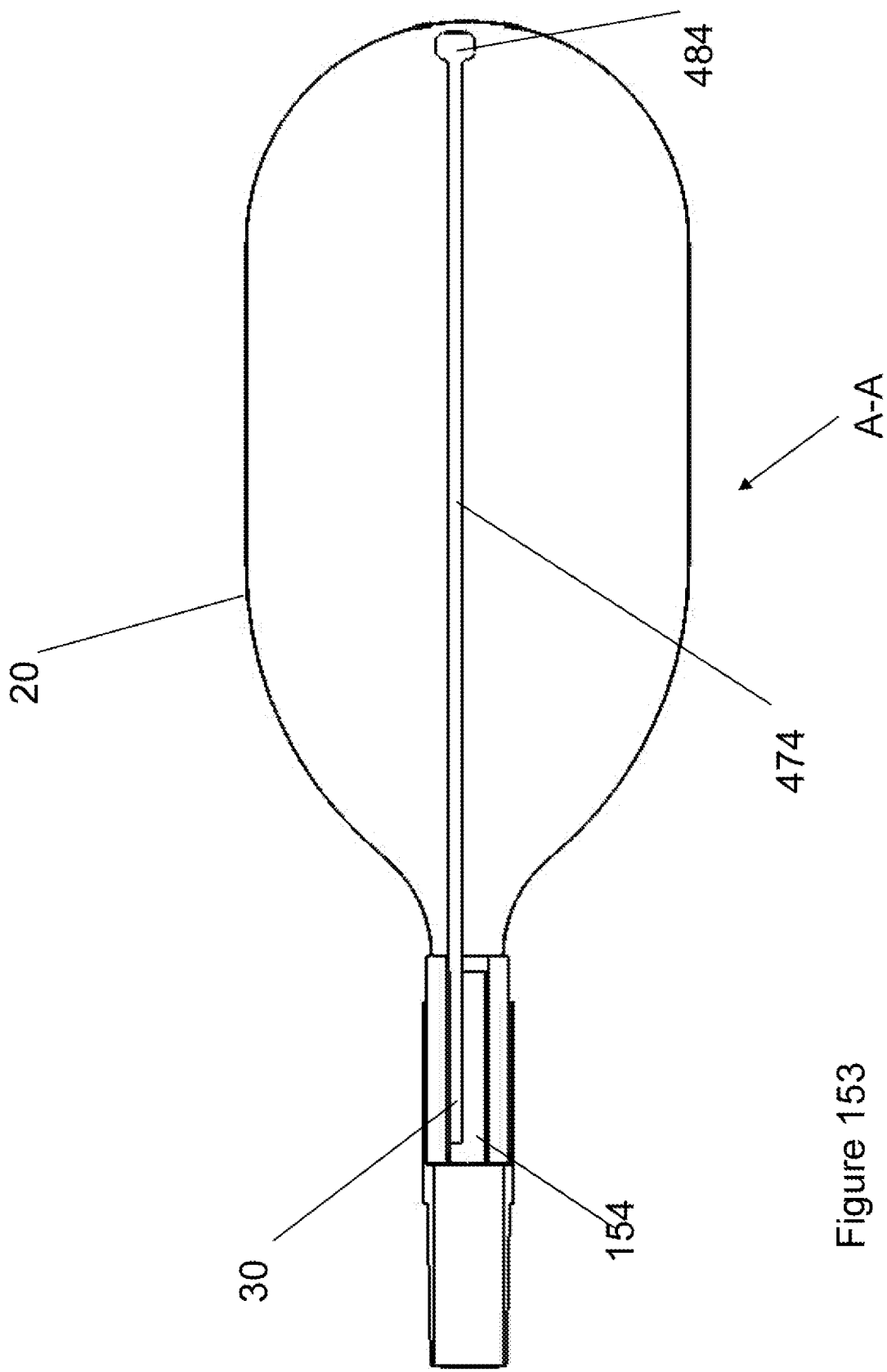
FIG. 153 is a variation of cross-sectional view A-A of FIG. 1

FIG. 153 illustrates that the stiffening rod 474 can have an atraumatic or blunt stiffening rod tip 484 and be anchored at the proximal end or base of the balloon 20. Inflation fluid can enter and exit the balloon 20 through the lumen 154. The length of the stiffening rod 474 is chosen such that when the balloon 20 is fully inflated, the blunt stiffening tip 484 will extend into the balloon volume, but not touch the inside of the balloon wall.

Figure 154A:
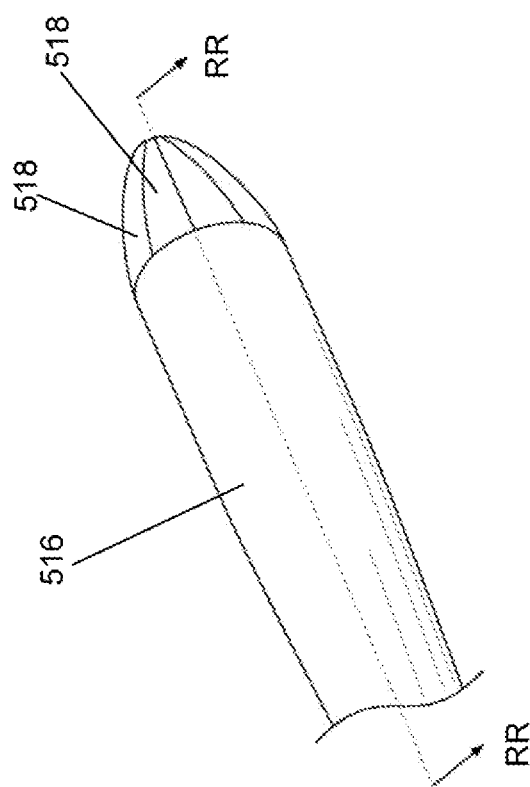
FIG. 154A illustrates a variation of the device with a component for inserting the device into the body.
Figure 154B:
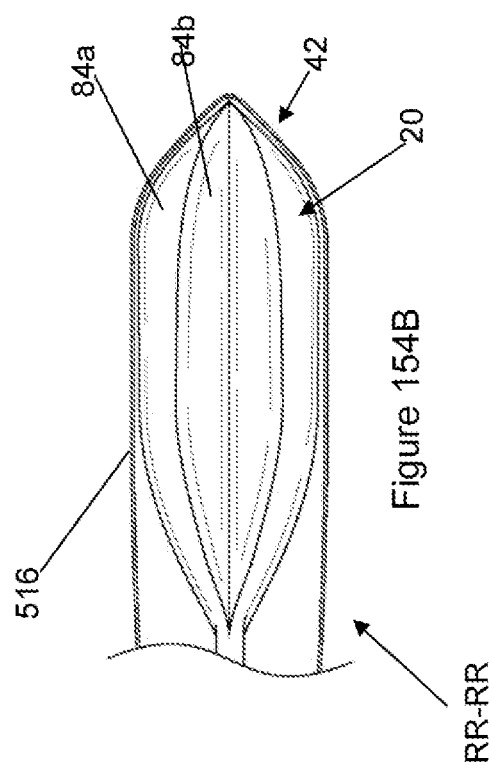
FIG. 154B is a variation of cross-sectional view RR-RR of FIG. 154A.

FIGS. 154A and 154B illustrate that a deployment sheath 516 can be placed circumferentially around a pleated balloon 20 in a contracted configuration. The sheath 516 can contain the balloon and prevent radial expansion of the balloon. The sheath can be retracted with respect to the balloon when the balloon is deployed through a cannula or into a target site. The sheath can have an open distal end. The distal end can have leaflets 518. The balloon can be pushed through the leaflets 518 during deployment.

Figure 155A:
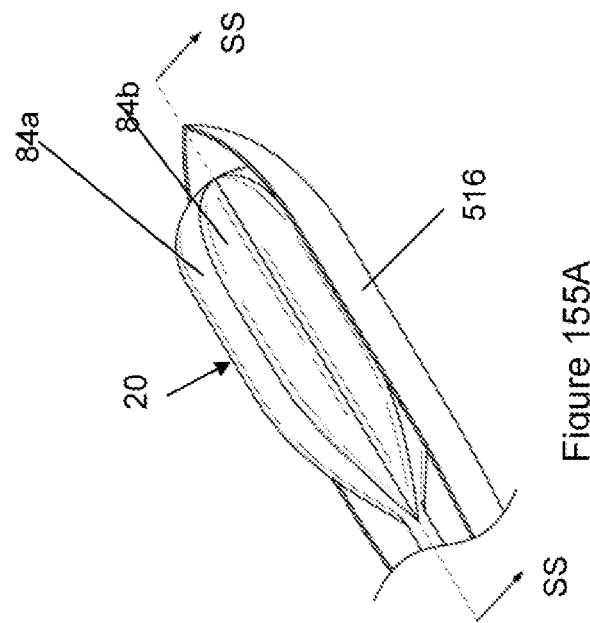
FIG. 155A illustrates a variation of the device with a component for inserting the device into the body.
Figure 155B:
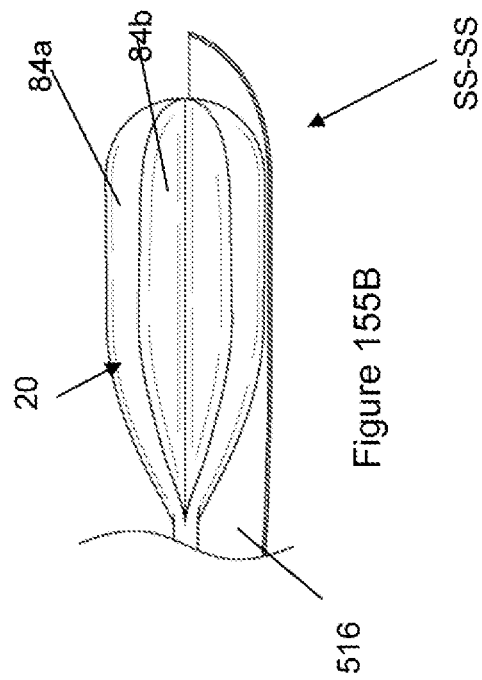
FIG. 155B is a variation of cross-sectional view SS-SS of FIG. 155B

FIGS. 155A and 155B illustrates that the sheath can be placed around half of the balloon. The sheath can be placed around 180° of the balloon, as measured from the longitudinal axis. The balloon can exit from the distal end or lateral side of the sheath.

FIG. 156 illustrates that the inflation system 470 can connect to the hollow shaft or tube 2000. The hollow tube 2000 can be soft and flexible. The hollow tube 2000 can be permanently connected to the inflation system 470. The inflation system can have a delivery syringe and/or pump. The hollow tube 2000 may have a fitting (not shown) that may allow it be disconnected from the inflation system.

The hollow tube 2000 can connect to a fitting. The fitting can connect to the balloon 20. The balloon 20 is shown in a compacted condition such that it can moved though a tube and inserted in the body. The balloon volume can be in fluid communication with the inflation system, for example the pump.

The interior volumes of the tube the pump the balloon and the fitting may be filled with saline solution, radiopaque dye, a gel, air, distilled water, or combinations thereof during manufacture. The volume of fluid in the device 2 and the inflation system can be such that when the inflation system 470 has delivered a maximum output (i.e., all the fluid that can be delivered by the inflation system 470 has been delivered) of fluid to the balloon, the balloon can be substantially inflated to a maximum rated inflation size for the balloon. The inflation system can be sealed, for example to prevent addition or removal of fluid from the system except when used with the balloon 20.

The inflation system can be configured to receive or evacuate excess fluid other than to the balloon. For example the inflation system can have a connector or valve for receiving or evacuating fluid.

The inflation system 470 and/or device 2 can be sealed under vacuum during manufacture. The balloon can be sealed under vacuum during manufacture. A membrane or soft plug can separate the inflation system from the hollow shaft and/or balloon before use. Raising the pressure in the inflation system can cause the membrane or plug to open and allow fluid into the balloon 20.

Figure 157:
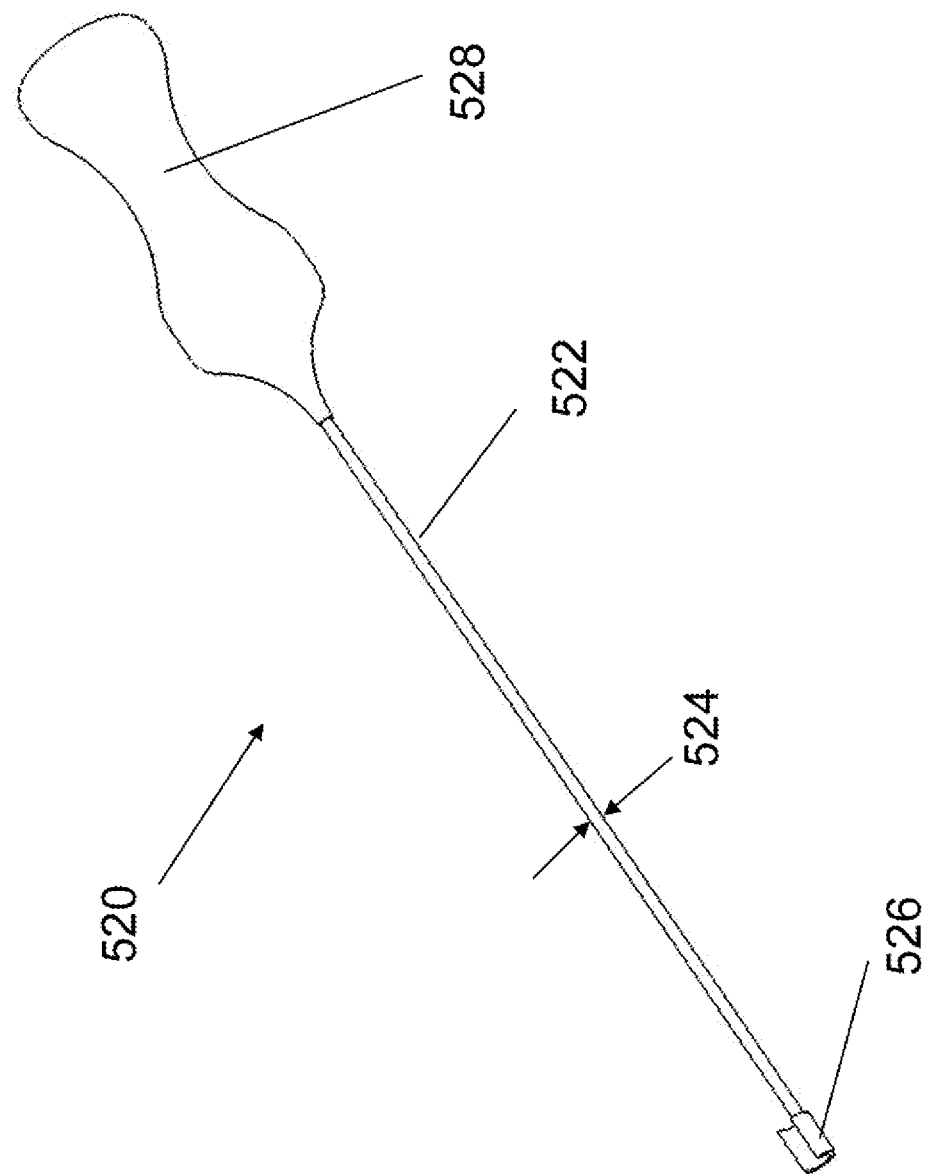
FIG. 157 illustrates a variation of the deployment rod.

FIG. 157 illustrates that delivery rod or manipulation tool 520 can have a manipulation tool handle 528. The manipulation tool 520 can have a manipulation tool shaft 522. The manipulation tool 520 can have an interface fitting or clasp 526. The manipulation tool shaft 522 can have a manipulation tool shaft diameter 524. The manipulation tool shaft 522 can be solid or hollow. The manipulation tool shaft can be rigid or semi-rigid.

Figure 158:
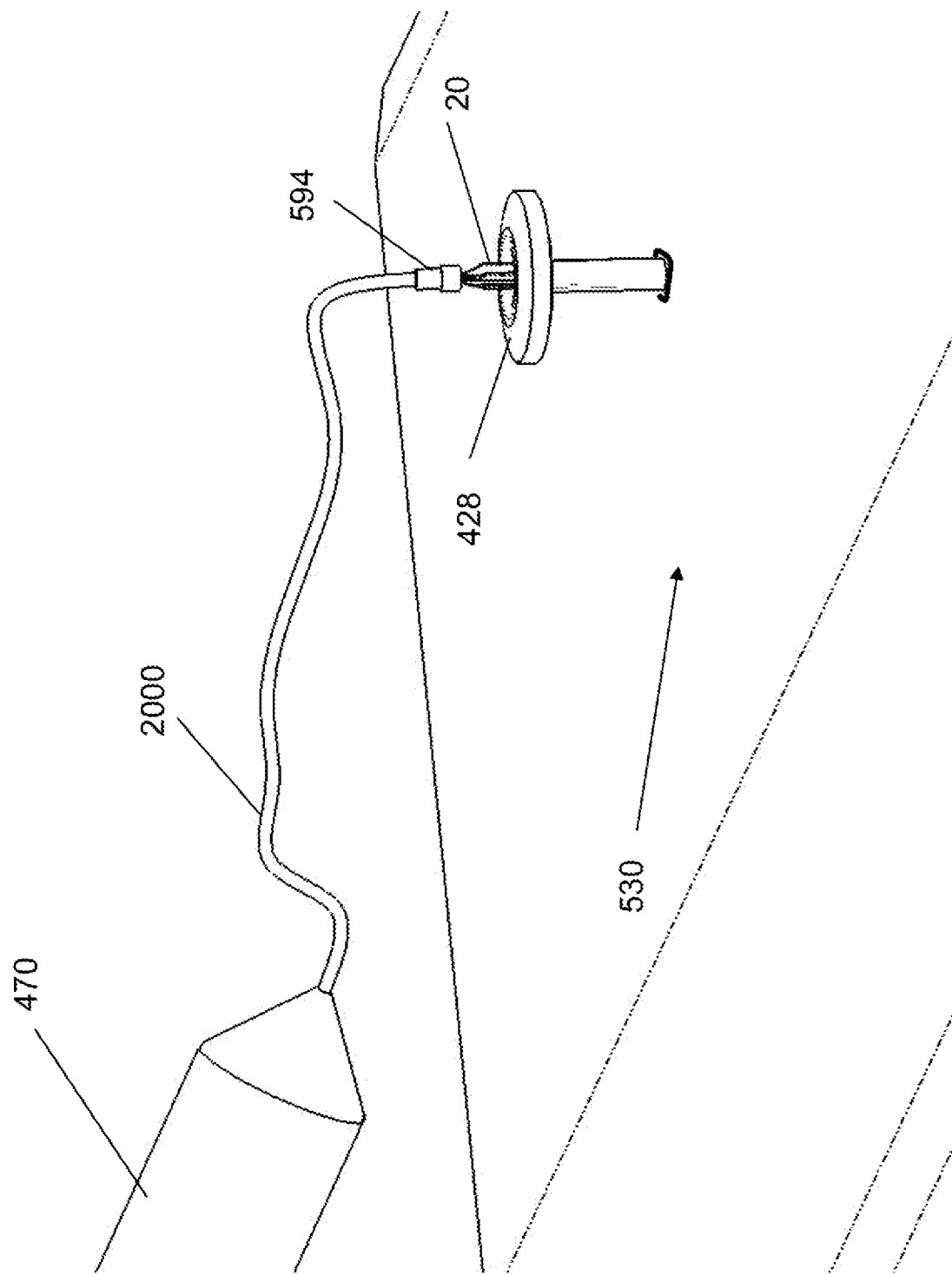
FIGS. 158 and 159 illustrate a variation of a method for using the device.

FIG. 158 illustrates that the cannula 468 has been inserted to a target site within a body 530. The cannula 468 can have an inner lumen that can act as a delivery passage to the target site. The balloon 20 can be inserted into cannula 468 by hand. The balloon 20 can fit tightly or snugly inside of the cannula 468. A force parallel to the longitudinal axis of the cannula can be applied to advance the balloon 20 through the cannula. The hollow tube 2000 can be too flexible to reasonably deliver enough force to advance the balloon 2000 though the cannula.

Figure 159:
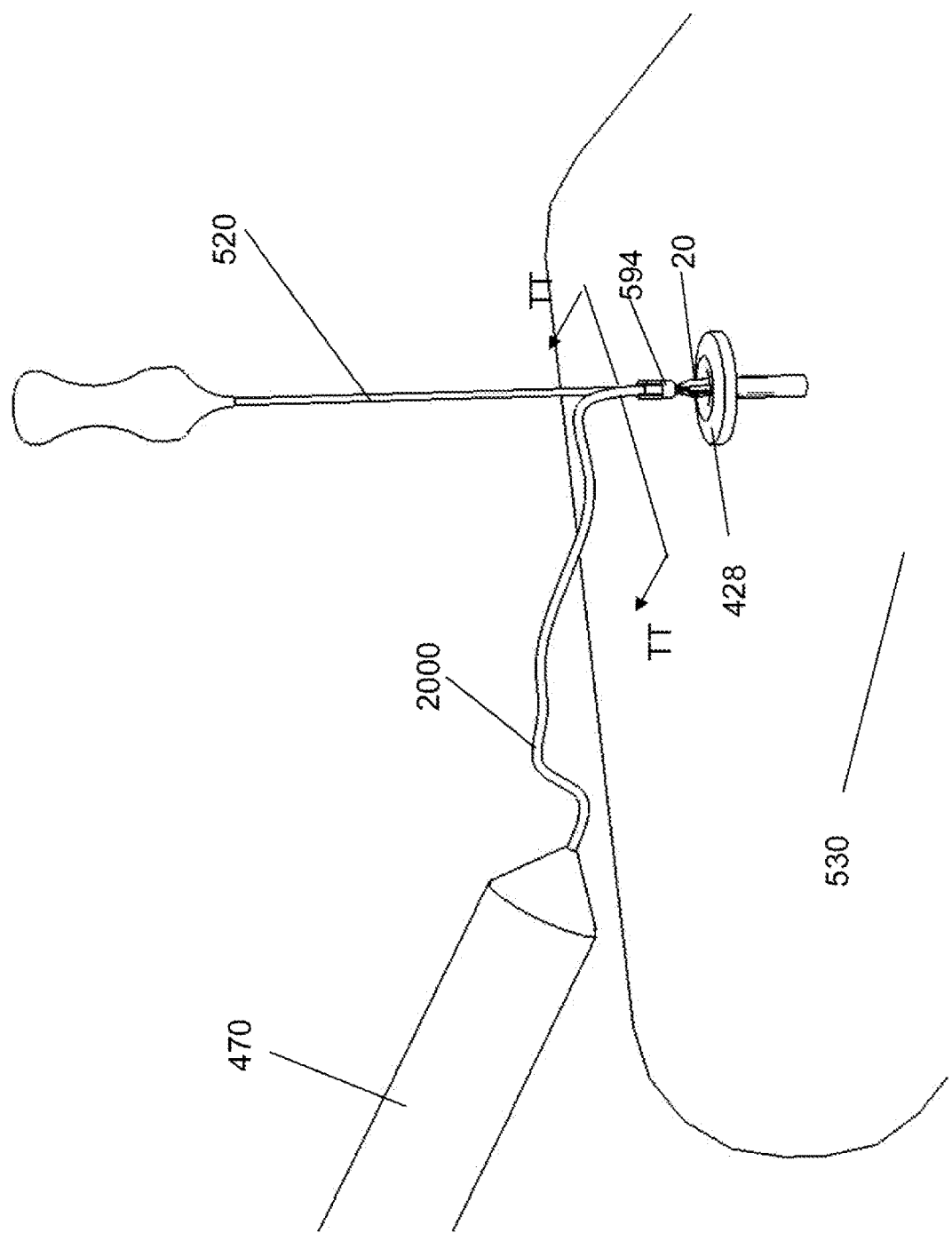

FIG. 159 illustrates that the clasp 526 on the manipulation tool 520 can interface with the fitting 594 so that the manipulation tool 520 can apply forces for maneuvering the balloon 20 outside and inside of the cannula 428. The manipulation tool 520 can translate the balloon 20 longitudinally distal and/or proximal within the cannula. The manipulation tool 522 can rotate the balloon within the cannula.

Figure 160:
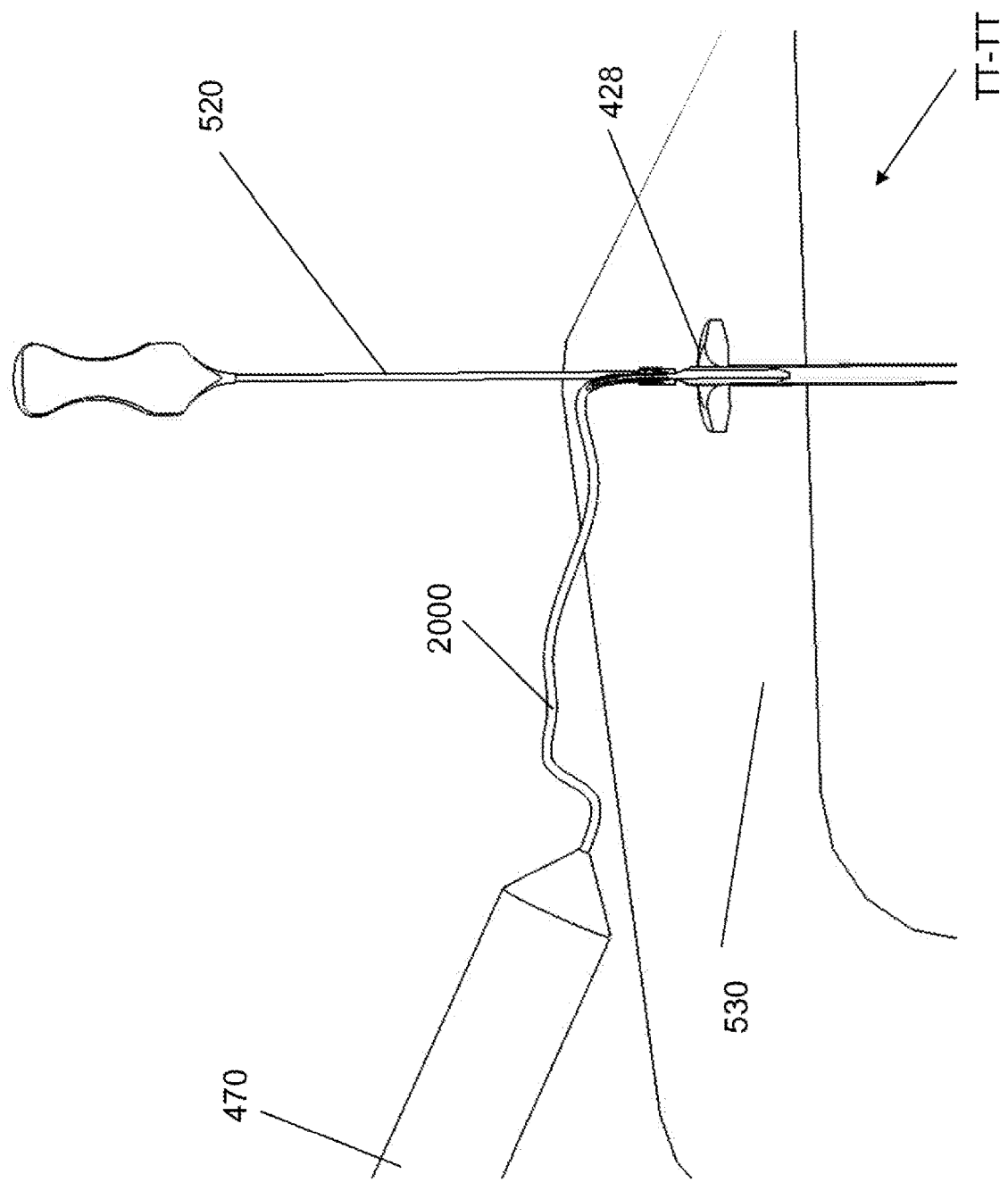
FIG. 160 is a variation of cross-sectional view TT-TT of FIG. 159.
Figure 161:
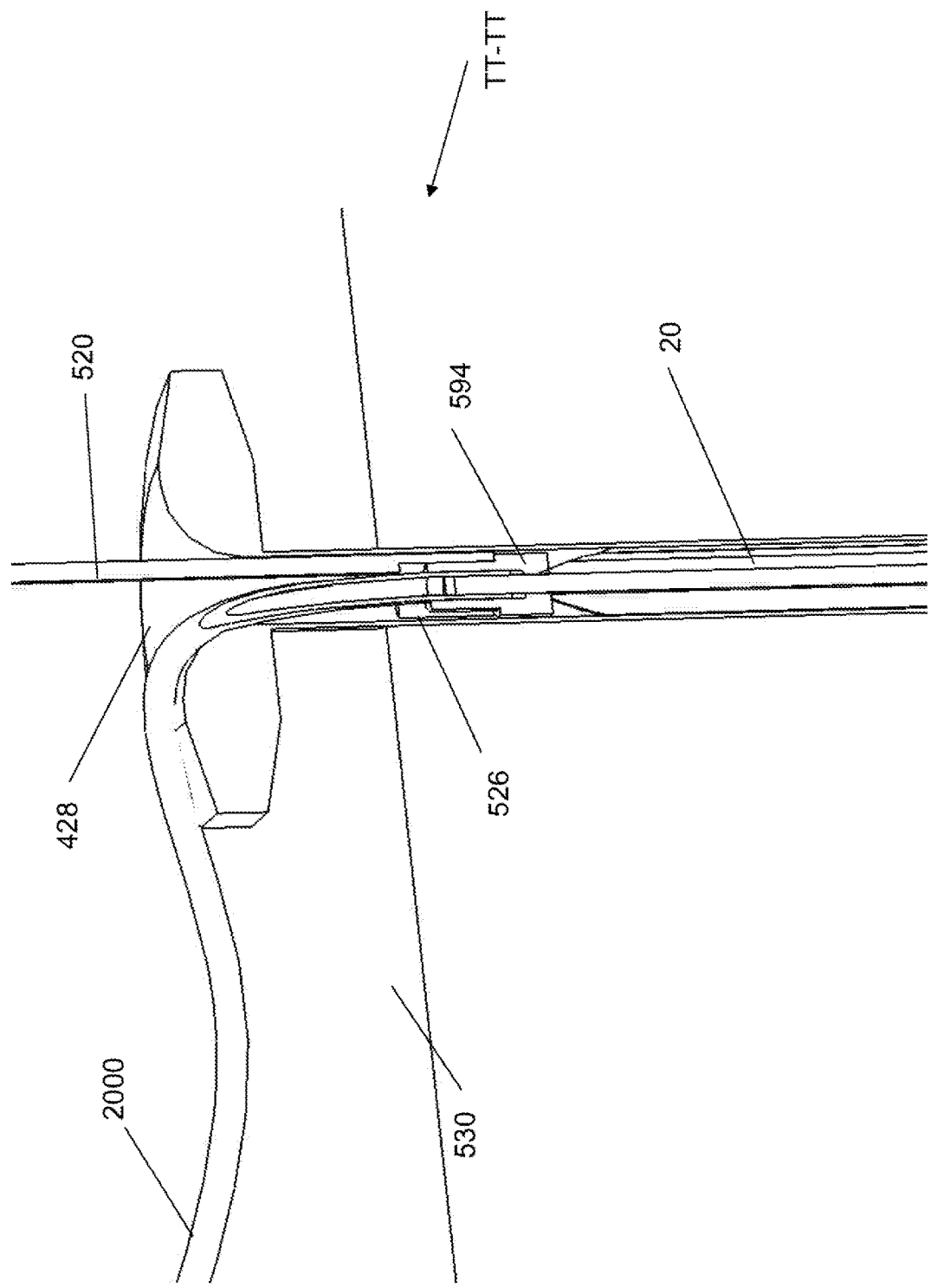
FIG. 161 is a variation of close-up of FIG. 160

FIGS. 160 and 161 illustrate that the manipulation tool 520 can advance the balloon 20 partially into the cannula.

Figure 162:
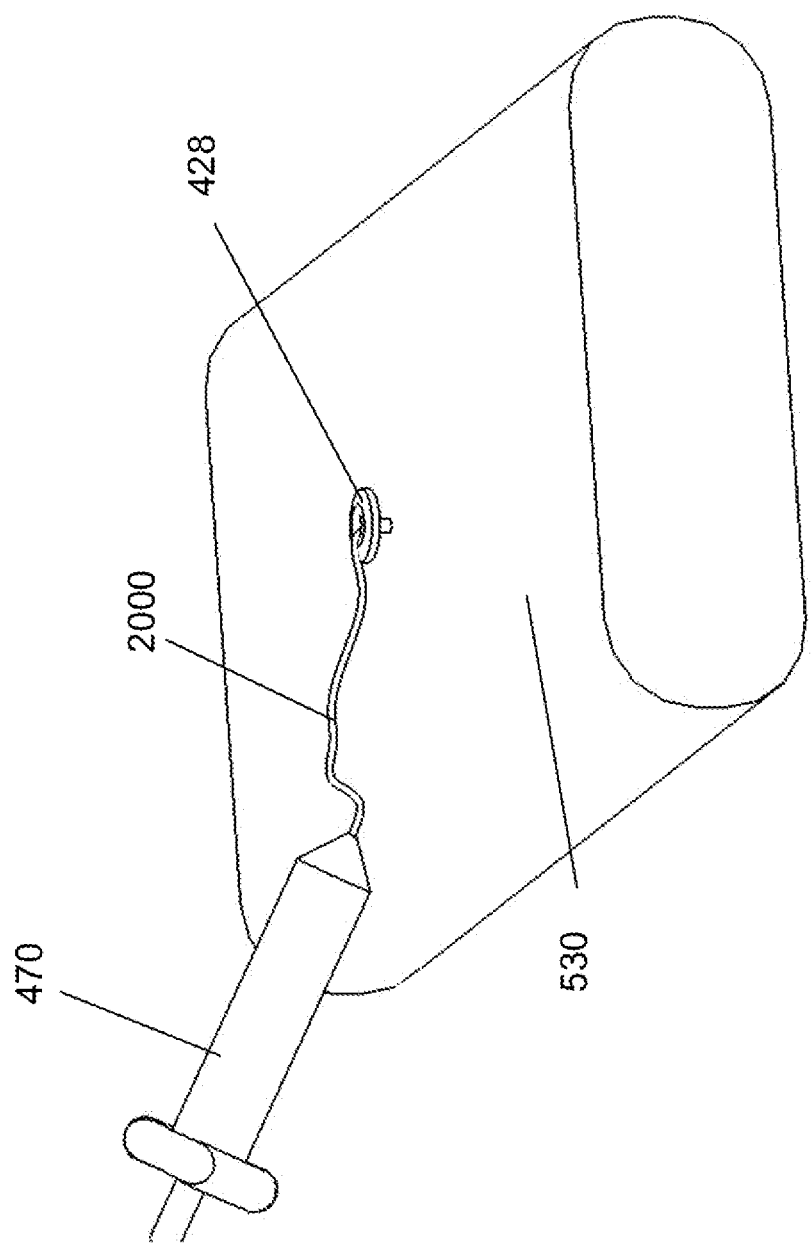
FIG. 162 illustrates a variation of a method for using the device.

FIG. 162 illustrates that the balloon 20 can be delivered to a target site in the body. The manipulation tool 520, for example at the clasp 526, can be removed from the fitting 594. The hollow tube 2000 can be highly flexible. Wherein the hollow tube 2000 exits the cannula 468 the hollow tube can bend and lay substantially flat (as shown) on the top surface of the cannula 468. The tube 2000 can not substantially obstruct the space directly above cannula 448. The hollow tube 2000 can be rigid or floppy and buckle easily. When cantilevered out 2 cm, the hollow tube 2000 can deflect about 1 cm at less than about 0.015 N-m of torque, more narrowly at less than about 0.005 N-m of torque.

FIG. 163A illustrates that the fitting 594 can have a distal shaft interface. The distal shaft interface can have a hexagonal transverse cross-section. FIG. 163B illustrates that the driving rod or manipulation tool 520 can have a clasp 526 at the distal end of the manipulation tool shaft 522. The interface fitting 594 can be configured to transmit force and torque through and removably attach to the clasp 526. The clasp can have a hexagonal transverse cross-section or four sides of a hexagon. The clasp can have an open lateral side for the distal shaft fitting 594 to be inserted and removed.

FIG. 164A illustrates that the fitting 594 can have a square or rectangular cross-section. FIG. 164B illustrates that the clasp 526 can have a square or rectangular transverse cross-section or three sides of a square.

FIG. 165A illustrates that the fitting 594 can have a one or more or pins or pegs extending laterally. The fitting 594 can have a circular or oval cross-section. FIG. 165B illustrates that the clasp 526 can have one, two or more peg receivers. The distal shaft interface can have a circular, oval, partial circle, or partial oval transverse cross-section.

FIGS. 166A and 166B illustrate that the fitting 594 can have a circular-shape with a projecting rectangular feature. The clasp 526 can have a female geometry that interfaces with rectangular feature of the fitting 594. The clasp 526 can be semi-cylindrical.

FIG. 167 illustrates that fitting 594 can be a circular fitting with a stop or longitudinal interference fitting element. The clasp 526 can have a cylindrical or hemi-cylindrical shape, for example that can encompass more than angularly half of the fitting 594.

FIG. 168 illustrates that interface 594 can be a male shear geometry. The clasp 526 can be a scissor-type device having two pivoting grasping jaws.

FIG. 169 illustrates that interface 594 can have a male shear geometry. The clasp 526 can have a tweezer configuration having two resiliently bending jaws.

The clasp 526 may be able to pull, push or turn the fitting 594 through the cannula or at the target site.

FIG. 170 illustrates that the manipulation tool 520 can have jaw arms 534a and 534b. The jaw arms can be parallel to each other and form a continuous U-shaped distal configuration of the manipulation tool. The interface 594 can have a male shear geometry that can mate with the geometry of the jaw arms 534 and/or the u-shaped configuration. The first jaw arms 534a can be rotationally attached to the second jaw arms 534b at a second pivot 532b. The manipulation tool first and second shafts 522a and 522b can be solid or hollow rigid rods or flexible cables. The manipulation tool first shaft 522a can be rotationally attached to the first jaw arm 534a at a first pivot 532a. Pulling the manipulation tool first shaft 522a with respect to the manipulation tool second shaft 522b can cause the outward rotation, as shown by arrow, of the first jaw arm 534a. This rotation can manipulate the position and orientation of the balloon 20, and/or release the fitting 594 from the manipulation tool 520.

FIG. 171A illustrates that the manipulation tool shaft 522 can have a tapered profile. FIG. 171B illustrates that the manipulation tool shaft 522 can have a circular profile. FIG. 171C illustrates that the manipulation tool shaft 522 can have an elliptical profile. FIG. 171D illustrates that the manipulation tool shaft 522 can have a rectangular profile. The corners of the rectangle may be rounded (not shown). FIG. 171E illustrates that the manipulation tool shaft 522 can have a hemispherical profile. FIG. 171F illustrates that the manipulation tool shaft 522 can have a hemispherical profile wherein the normally flat half of the surface can be convex. FIG. 171G illustrates that the manipulation tool shaft 522 can have a hemispherical profile wherein the normally flat half of the surface can be concave. FIGS. 171H and 171i illustrate that the manipulation tool shaft 522 can be a portion of tube, for example 120° or 240° of the tube. The manipulation tool shaft 522 can be open on a lateral side. The manipulation tool shaft 522 can have stops, notches or threads to keep the manipulation tool from being inserted into the cannula past a certain length or allow the insertion into the cannula to happen at a controlled rate.

FIGS. 172A and 172B illustrate that the manipulation tool 520 can have a manipulation tool first shaft 522a radially inside a manipulation tool second shaft 522b. The manipulation tool first shaft can have preformed tangs 534a and 534b at the distal end of the manipulation tool first shaft. The distal end of the manipulation tool second shaft 522b can have a notch 538 that can radially constrain the tangs 534. The tangs 534a and 534b can be formed to spring radially outward when not constrained. When the manipulation tool second shaft is slid down toward the fitting 594, the manipulation tool can press the tangs radially inward around the fitting, attaching the manipulation tool to the fitting. The fitting can be detached from the manipulation tool by sliding the manipulation tool second shaft away from the fitting. The manipulation tool can have a lateral shaft port 536 through which the hollow tube 2000 (not shown) can extend through and exit the manipulation tool.

FIGS. 173A and 173B show that the manipulation tool 522 can straight or curved. The curved manipulation tool shaft, shown in FIG. 173B, can be made of a super elastic material, such as Nitinol. The manipulation tool shaft can be straightened for insertion through the cannula, and curve after exiting the cannula 468.

Figure 174A:
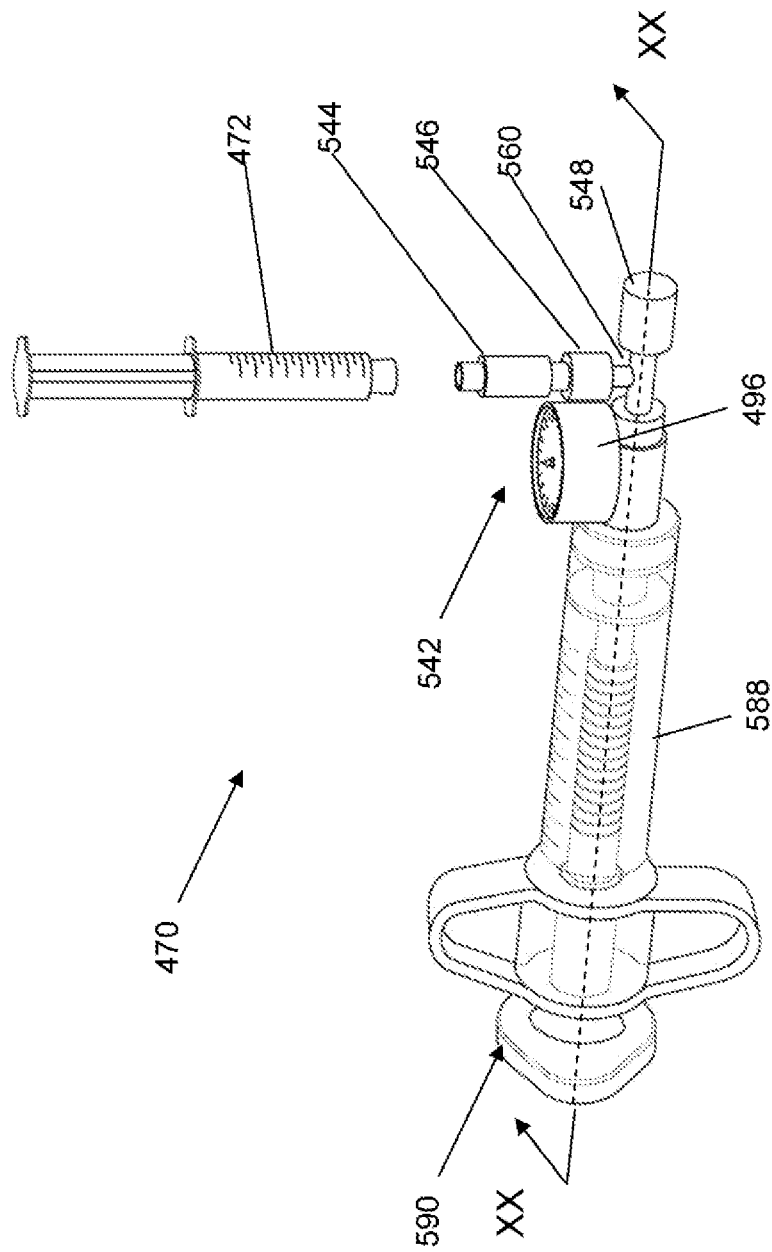
FIG. 174A is a variation of a tool for inflating the inflatable device.
Figure 174B:
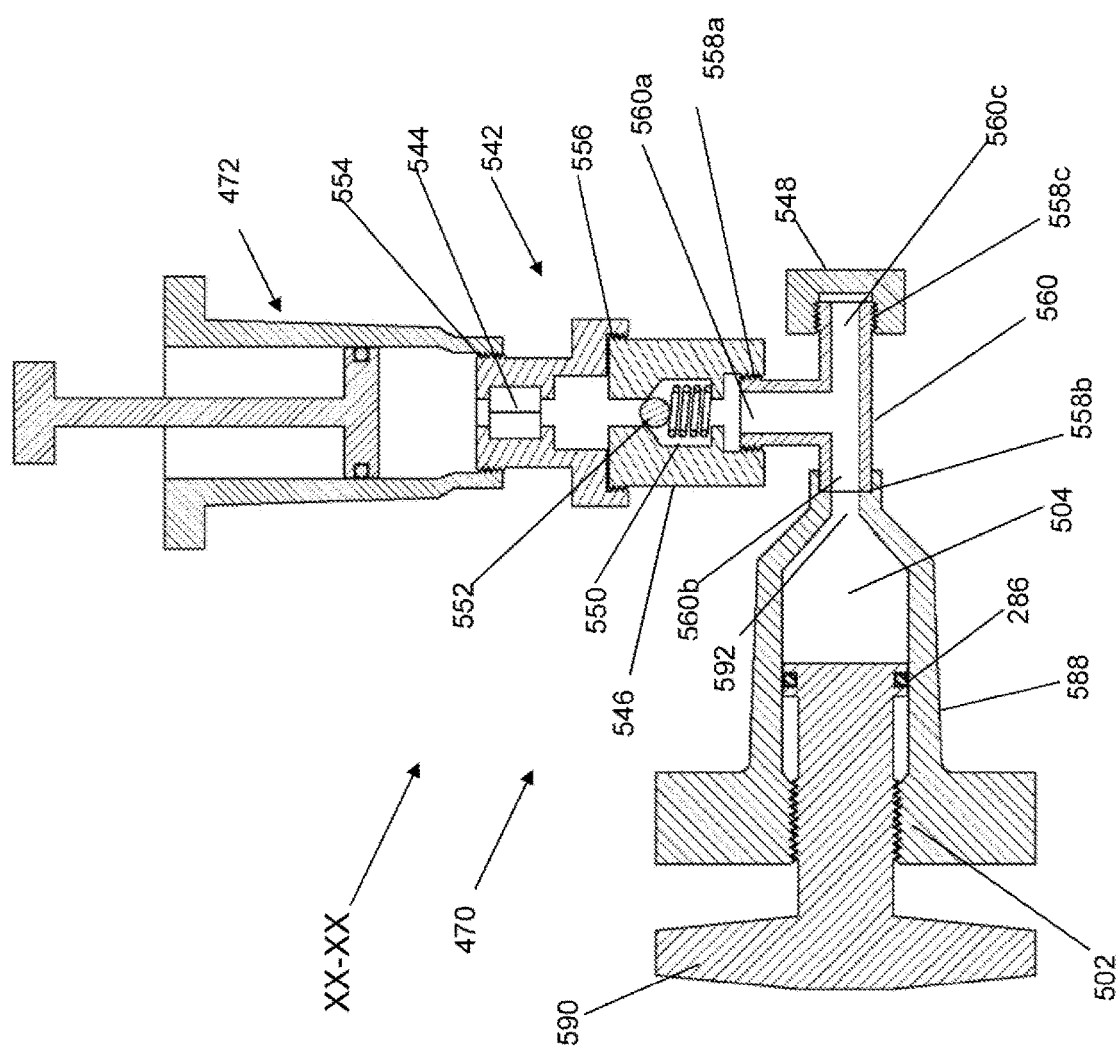
FIG. 174B is a variation of a sectional view of FIG. 174A.

FIGS. 174A and 174B illustrate that the inflation system 470 can have a valve system 542, a filled syringe 472, a t-connector 540, a cap 548 and a delivery pump or delivery syringe 588. The valve system 542 can be attached to a first port 560a of the t-connector 540. The delivery syringe 588 can be connected to a second port 560b of the t-connector 540. The cap 548 can be attached to the third port 550c of the t-connector.

The check valve can have a check spring 550 and a valve ball 552. The swabbable valve can be attached to the filled syringe at a syringe interface 554. The swabbable valve can be attached to the check valve at an intervalve interface 556. The check valve can be attached to the t-connector at a first connector interface 558a. The delivery syringe can be attached to the t-connector at a second connector interface 558b. The cap can be attached to the t-connector at a third connector interface 558c. Any or all of the interfaces in the inflation system can be fixed or detachable connections, such as threaded connectors, luer connectors, glue, snap connectors, welds, or combinations thereof.

The valve system 542 can have a swabbable valve 544 connected to a check valve 546. The check valve 546 can be configured to allow flow into the t-connector 540 and prevent flow out of the t-connector 540 through the valve system 542.

A pre-filled syringe 472 of fluid can be attached to the valve system. The fluid can be a saline solution, a radiopaque solution, water, a gel, an epoxy or curable polymer, or combinations thereof. The fluid can be pushed through the swabbable valve 544 and the check valve 546 and into the delivery syringe 588. The delivery syringe plunger can be pulled as the pro-filled syringe plunger is pushed.

After the fluid is delivered to the delivery syringe 588, the cap 548 can be removed and a fluid conduit, such as the hollow shaft 2000, can be attached to the t-connector third port 558c in place of the cap 548. The fluid conduit 2000 can be positioned to have an output port at a target site, such as into the balloon 20 in a vertebral body. The delivery syringe plunger can be deployed, forcing fluid through the fluid conduit and to the target site. The balloon 20 can inflate, creating a void within cancellous bone at the target site. The check valve and swabbable valve can minimize or prevent flow to the pre-filled syringe during deployment of fluid from the delivery syringe to the fluid conduit. A manual valve does not need to be adjusted to direct the fluid to the fluid conduit.

Figure 175:
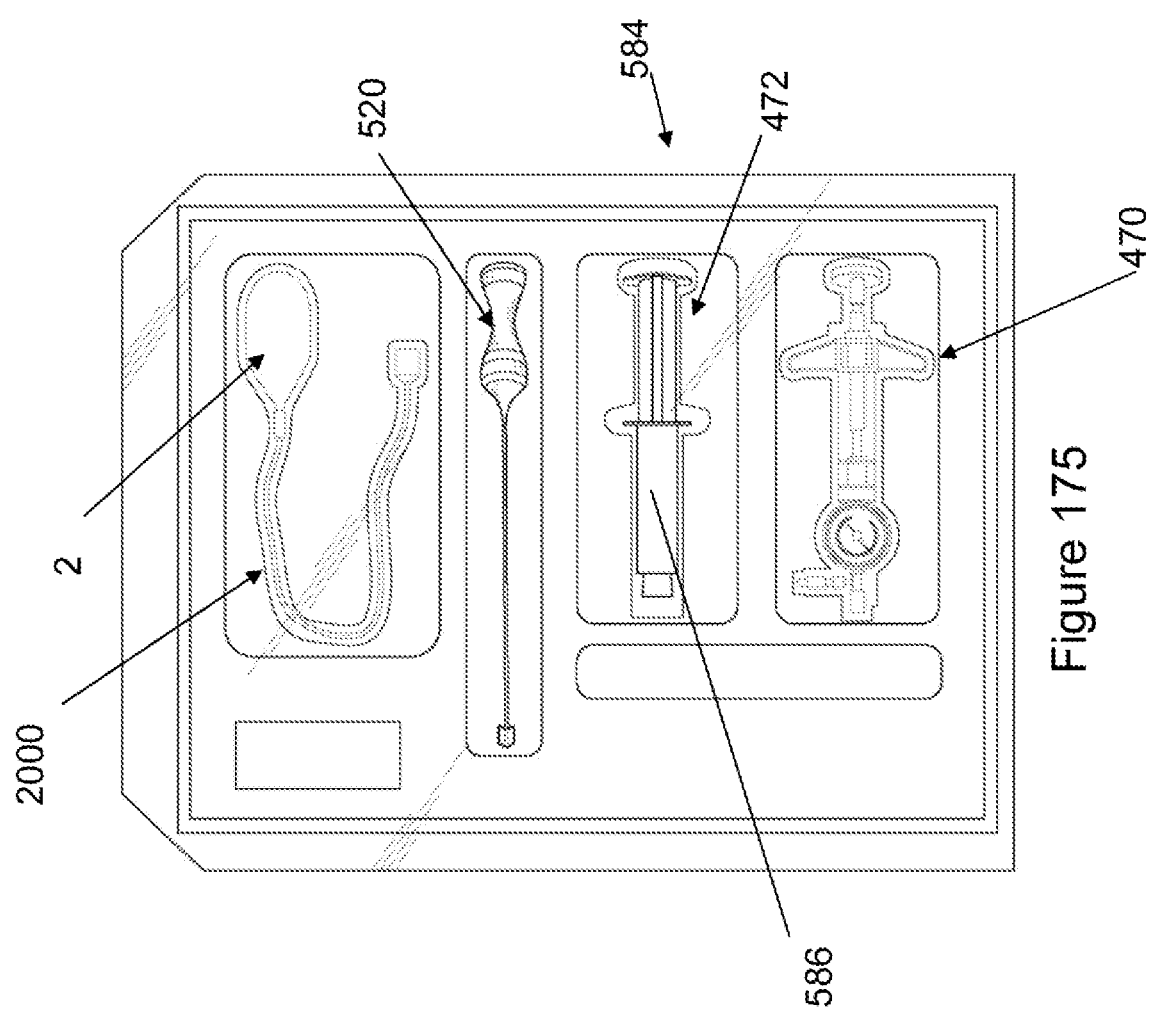
FIGS. 175 through 177 illustrate variations of a kit including the device.

FIG. 175 illustrates that a kit can be packaged to contain a balloon 20, driving rod or manipulation tool, fluid filled syringe 472, delivery or inflation syringe 588, or combinations thereof. The pre-filled syringe can be filled with the inflation fluid 586. The kit can be in a sterile package. The balloon can have a flexible conduit, such as the hollow tube 2000, attached to the first fluid port of the balloon 20.

Figure 176:
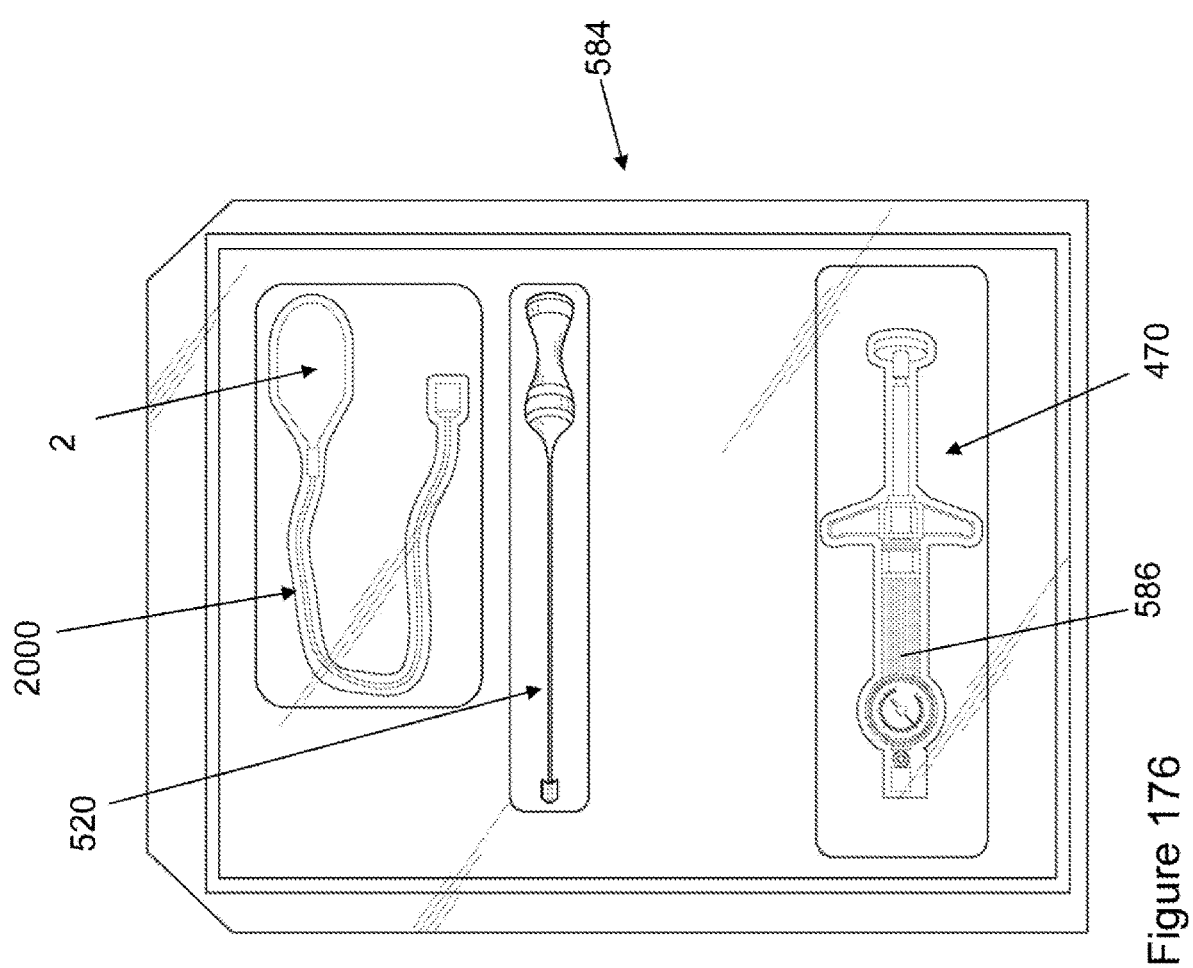

FIG. 176 illustrates that the kit can have the balloon, driving rod, and the inflation syringe. The inflation syringe can be filled with a fluid such as saline solution, a radiopaque solution, water or combinations thereof. The kit can be in a sterile package.

Figure 177:
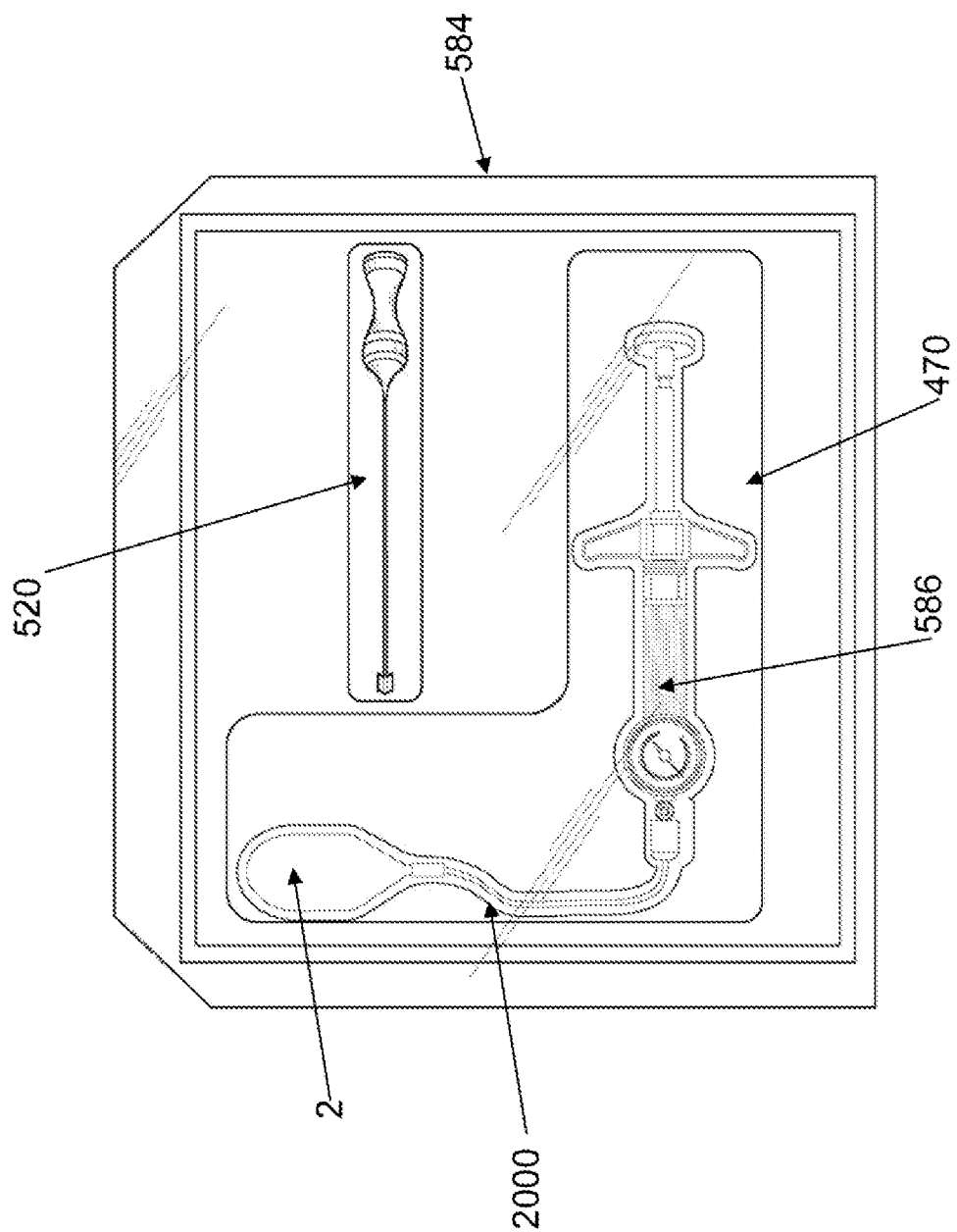

FIG. 177 illustrates that the kit can have the balloon, driving rod, and the inflation syringe. The balloon can be attached to and in fluid communication with a flexible tube. The flexible tube can be attached to and in fluid communication with the inflation syringe. The inflation syringe can be pre-filled with the inflation fluid 586. The kit can be in a sterile package 584.

Figure 178:
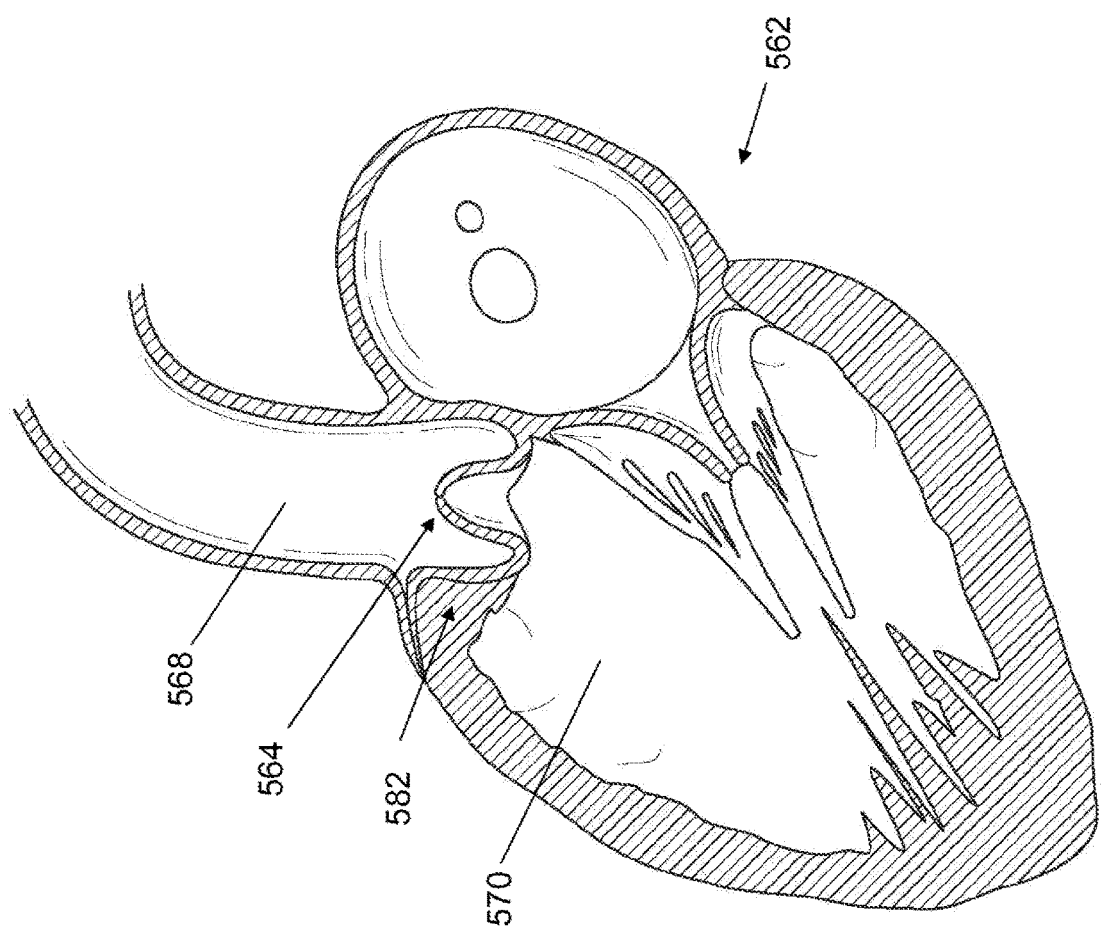

FIG. 178 shows a cross section of the heart 562. The heart 562 has an aorta 568, a left ventricle 570 and an aortic valve 564

FIGS. 179A and 179B and 179C illustrate that a guidewire 572 can be inserted through the aorta 568 and positioned in the left ventricle 570 of the heart 562. The device 2 can be slidably inserted over the guidewire through the aorta 568. The device 2 may be in a deflated state when first placed in the aortic valve 564. The device 2 can be positioned to align along the balloon longitudinal axis with the balloon with the aortic valve leaflets 566. The device 2 can also be rotated about the balloon longitudinal axis to align with the aortic valve 564, for example when cutting apart attached leaflets 566 in a bicuspid aortic valve with a flange, vane, blade, other cutting element described herein, or combinations thereof.

FIG. 179D shows the balloon 20 in an expanded configuration. The device 20 can be non-compliant and open the aortic valve 564 to a precise dimension (for example, about 20 mm or about 24 mm). The balloon 20 can fixedly reconfigure and press the aortic valve leaflets 566 against the outer wall or annulus 582 of the aortic valve 564. The balloon 20 can radially expand the aortic valve annulus 582.

The balloon can have an annular lumen 160, as shown in FIGS. 36A through 40. Natural blood flow through the aortic valve can flow through the annular lumen 160 when the balloon is in an inflated or expanded configuration in the aortic valve. The device can have a device valve. The device valve can open and close, for example depending on the ventricular pressure against the device valve.

A radially expandable implant 156, such as a stent, anchoring annulus or other component of a replacement heart valve, including the replacement valve, or combinations thereof, can be removably attached to the balloon before deployment. The balloon can deploy the radially expandable implant 156 in the aortic valve, for example at the annulus of the aortic valve. The balloon can deliver and deploy a percutaneous aortic valve at the aortic valve annulus.

FIG. 179E illustrates that the balloon can be deflated, contracted and withdrawn from the aortic valve.

FIG. 179F shows the aortic valve in an opened configuration at a larger dimension than before the procedure.

The method described supra can be performed on an aortic, mitral, pulmonary, tricuspid or vascular valve.

FIG. 180A illustrates that the balloon can be positioned in a narrowed, atherosclerotic length of a blood vessel 574 having atherosclerotic plaque 576 on the interior of the vessel wall 578. The vessel 574 can have a vessel lumen 580 through which blood can flow.

FIG. 180B illustrates that the balloon 20 can be inflated and expanded. The balloon 20 can remodel the vessel, pushing the sclerotic plaque radially away from the balloon longitudinal axis. The balloon 20 can deploy a vascular stent to the sclerotic length of the vessel.

FIG. 180C illustrates that the balloon 20 can be deflated, contracted and removed from the narrowed length of the vessel 574. The vessel lumen 574 can remain patent after the balloon is removed, for example restoring blood flow past the treated atherosclerotic length.

The balloon 20 can be implanted in the body semi-permanently or permanently. The balloon 20 can have one, two or more openings for fluid entry and/or exit.

Any elements described herein as singular can be pluralized (i.e., anything described as "one" can be more than one), and plural elements can be used individually. Any species element of a genus element can have the characteristics or elements of any other species element of that genus. The term "comprising" is not meant to be limiting. The above-described configurations, elements or complete assemblies and methods and their elements for carrying out the invention, and variations of aspects of the invention can be combined and modified with each other in any combination.

We claim:

1. Medical inflatable device for use in a biological body including a fluid, the device comprising:
   a balloon having segments that are angularly adjacent to each other and parallel with a longitudinal axis of the device, the balloon including an annular lumen passing through a radial center of the balloon, the annular lumen having a distal port at a distal end of the annular lumen, and a proximal port at a proximal end of the annular lumen for permitting the fluid to flow of the biological body through the annular lumen; and
   a hollow shaft,
   the segments being inflatable by a tube connected to the hollow shaft.

2. The device of claim 1, wherein the segments have a generally circular cross-sectional configuration.

3. The device of claim 1, further comprising an outer wall around the balloon.

4. The device of claim 3, wherein the outer wall comprises reinforcement fibers.

5. The device of claim 4, wherein the reinforcement fibers are arranged at set angles relative to one another.

6. The device of claim 4, wherein at least some of the reinforcement fibers are arranged substantially parallel to the longitudinal axis.

7. The device of claim 4, wherein at least some of the reinforcement fibers are hoop wound around the outer wall.

8. The device of claim 1, further comprising segment joints between the segments.

9. The device of claim 8, wherein the segment joints connect an outer wall of the balloon to an inner wall of the balloon.

10. The device of claim 8, wherein the segment joints are configured to minimize inward radial collapse of the balloon.

11. The device of claim 1, wherein the segments are in fluid isolation from each other along a length of the balloon.

12. The device of claim 1, wherein the segments are in fluid communication with each other along at least a portion of a length of the balloon.

13. The device of claim 1, wherein the walls of the segments further include a radiopaque marker wire.

14. The device of claim 1, wherein the hollow shaft has an outer diameter, and the tube is connected to the hollow shaft radially inwardly of the outer diameter.

15. The device of claim 1, wherein the segments are in an annular configuration, each segment being generally circular in cross-section and in fluid isolation from the other segments.

16. The device of claim 1, wherein the hollow shaft includes an inner lumen and an outer lumen to deliver fluid under pressure to the balloon via the tube.

17. Medical device for use in a biological body including a fluid, the device comprising:
an inflatable balloon having segments that are angularly adjacent to each other and parallel with a longitudinal axis of the device, the balloon surrounding an interior lumen, the interior lumen being an annular lumen passing through a radial center of the balloon, the annular lumen having a distal port at a distal end of the annular lumen, and a proximal port at a proximal end of the annular lumen for permitting the fluid to flow through the annular lumen; and
a hollow shaft located in the interior lumen;
the segments being inflatable by a tube connected to the hollow shaft.

18. The device of claim 17, wherein the hollow shaft extends through the interior lumen to a point distal of the inflatable balloon.

19. Medical device for use in a biological body including a fluid, the device comprising:
an inflatable balloon having segments that are angularly adjacent to each other and parallel with a longitudinal axis of the device, the balloon surrounding an interior lumen, the interior lumen being an annular lumen passing through a radial center of the balloon, the annular lumen having a distal port at a distal end of the annular lumen, and a proximal port at a proximal end of the annular lumen for permitting the fluid to flow through the annular lumen; and
a hollow shaft located in the interior lumen;
wherein the segments are in an annular configuration, each segment being generally circular in cross-section when inflated and in fluid isolation from the other segments.

20. The device of claim 19, further including a tube connected to the hollow shaft for inflating the segments.

21. The device of claim 1, wherein the segments of the balloon are spaced apart from and radially circumscribe the hollow shaft.

* * * * *